(12) United States Patent
Rashal et al.

(10) Patent No.: US 10,202,366 B2
(45) Date of Patent: Feb. 12, 2019

(54) METHODS OF PROMOTING WOUND HEALING USING CRM1 INHIBITORS

(71) Applicant: Karyopharm Therapeutics Inc., Newton, MA (US)

(72) Inventors: Tami Rashal, Ramat Hasharon (IL); Dilara McCauley, Arlington, MA (US); Sharon Shacham, Newton, MA (US); Erkan Baloglu, Stoneham, MA (US)

(73) Assignee: Karyopharm Therapeutics Inc., Newton, MA (US)

( * ) Notice: Subject to any disclaimer, the term of this patent is extended or adjusted under 35 U.S.C. 154(b) by 0 days.

(21) Appl. No.: 14/777,302

(22) PCT Filed: Mar. 14, 2014

(86) PCT No.: PCT/US2014/029322
§ 371 (c)(1),
(2) Date: Sep. 15, 2015

(87) PCT Pub. No.: WO2014/144772
PCT Pub. Date: Sep. 18, 2014

(65) Prior Publication Data
US 2016/0304500 A1    Oct. 20, 2016

Related U.S. Application Data

(60) Provisional application No. 61/793,146, filed on Mar. 15, 2013.

(51) Int. Cl.
| | |
|---|---|
| *C07D 403/12* | (2006.01) |
| *C07D 401/14* | (2006.01) |
| *C07D 405/14* | (2006.01) |
| *C07D 413/14* | (2006.01) |
| *A61K 31/4196* | (2006.01) |
| *C07D 231/12* | (2006.01) |
| *C07D 233/64* | (2006.01) |
| *C07D 401/04* | (2006.01) |
| *C07D 401/06* | (2006.01) |
| *C07D 401/12* | (2006.01) |

(Continued)

(52) U.S. Cl.
CPC ............ *C07D 403/12* (2013.01); *A61K 31/41* (2013.01); *A61K 31/4196* (2013.01); *C07D 207/325* (2013.01); *C07D 207/33* (2013.01); *C07D 213/50* (2013.01); *C07D 231/12* (2013.01); *C07D 233/64* (2013.01); *C07D 249/08* (2013.01); *C07D 257/04* (2013.01); *C07D 401/04* (2013.01); *C07D 401/06* (2013.01); *C07D 401/12* (2013.01); *C07D 401/14* (2013.01); *C07D 403/04* (2013.01); *C07D 403/06* (2013.01); *C07D 403/14* (2013.01); *C07D 405/12* (2013.01); *C07D 405/14* (2013.01); *C07D 409/04* (2013.01); *C07D 409/12* (2013.01); *C07D 413/06* (2013.01); *C07D 413/12* (2013.01); *C07D 413/14* (2013.01); *C07D 417/04* (2013.01); *C07D 417/06* (2013.01); *C07D 417/12* (2013.01); *C07D 487/10* (2013.01)

(58) Field of Classification Search
CPC ................ A61K 31/41; A61K 31/4196; C07D 207/325; C07D 207/33; C07D 213/50; C07D 231/12; C07D 233/64; C07D 249/08; C07D 257/04; C07D 401/04; C07D 401/06; C07D 401/12; C07D 401/14; C07D 403/04; C07D 403/06; C07D 403/12; C07D 403/14; C07D 405/12; C07D 405/14; C07D 409/04; C07D 409/12; C07D 413/06; C07D 413/12; C07D 413/14; C07D 417/04; C07D 417/06; C07D 417/12; C07D 487/10
See application file for complete search history.

(56) References Cited

U.S. PATENT DOCUMENTS

| | | |
|---|---|---|
| 5,153,201 A | 10/1992 | Aono et al. |
| 5,817,677 A | 10/1998 | Linz et al. |

(Continued)

FOREIGN PATENT DOCUMENTS

| | | |
|---|---|---|
| CN | 101309912 A | 11/2008 |
| CN | 101466687 A | 6/2009 |

(Continued)

OTHER PUBLICATIONS

Dorwald, "Side Reactions in Organic Synthesis: A Guide to Successful Synthesis Design" 2005 Wiley-VCH Verlag GmbH & Co. KGaA, Weinheim.*
Orsted et al. (Wound Care Canada, 9, 2, 4-12).*
Final Office Action dated Feb. 27, 2015 for U.S. Appl. No. 13/350,864, "Olefin Containing Nuclear Transport Modulators And Uses Thereof".
Non-Final Office Action dated Jul. 3, 2014 for U.S. Appl. No. 14/219,638 "Hydrazide Containing Nuclear Transport Modulators And Uses Thereof".

(Continued)

*Primary Examiner* — Umamaheswari Ramachandran
(74) *Attorney, Agent, or Firm* — Foley Hoag LLP

(57) ABSTRACT

The invention generally relates to the use of nuclear transport modulators, e.g., CRM1 inhibitors, and more particularly to a compound represented by structural formula I:

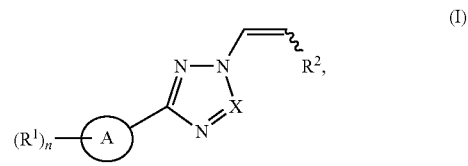

or a pharmaceutically acceptable salt thereof, wherein Ring A, X, $R^1$, $R^2$ and n are as defined and described herein, in a method for promoting wound healing in a subject.

6 Claims, 31 Drawing Sheets

(51) Int. Cl.

| | | |
|---|---|---|
| *C07D 403/04* | (2006.01) | |
| *C07D 403/06* | (2006.01) | |
| *C07D 403/14* | (2006.01) | |
| *C07D 405/12* | (2006.01) | |
| *C07D 409/04* | (2006.01) | |
| *C07D 409/12* | (2006.01) | |
| *C07D 413/06* | (2006.01) | |
| *C07D 413/12* | (2006.01) | |
| *C07D 417/04* | (2006.01) | |
| *C07D 417/06* | (2006.01) | |
| *C07D 417/12* | (2006.01) | |
| *C07D 249/08* | (2006.01) | |
| *C07D 257/04* | (2006.01) | |
| *C07D 487/10* | (2006.01) | |
| *C07D 207/325* | (2006.01) | |
| *C07D 207/33* | (2006.01) | |
| *C07D 213/50* | (2006.01) | |
| *A61K 31/41* | (2006.01) | |

(56) References Cited

U.S. PATENT DOCUMENTS

| | | |
|---|---|---|
| 6,462,049 B1 | 10/2002 | Ogura et al. |
| 7,342,115 B2 | 3/2008 | Hutchison et al. |
| 7,667,041 B2 | 2/2010 | Kimura et al. |
| 7,902,367 B2 | 3/2011 | Nomura et al. |
| 8,273,736 B2 | 9/2012 | Osakada et al. |
| 8,299,102 B2 | 10/2012 | Strobel et al. |
| 8,304,436 B2 | 11/2012 | Strobel et al. |
| 8,513,230 B2 | 8/2013 | Shacham et al. |
| 8,598,168 B2 | 12/2013 | Moradei et al. |
| 8,999,996 B2 | 4/2015 | Sandanayaka et al. |
| 9,079,865 B2 | 7/2015 | Sandanayaka et al. |
| 9,096,543 B2 | 8/2015 | Sandanayaka et al. |
| 9,206,158 B2 | 12/2015 | Sandanayaka et al. |
| 9,266,843 B2 | 2/2016 | Sandanayaka et al. |
| 9,303,000 B2 | 4/2016 | Sandanayaka et al. |
| 9,428,490 B2 | 8/2016 | Sandanayaka et al. |
| 9,550,757 B2 | 1/2017 | Shacham et al. |
| 9,585,874 B2 | 3/2017 | Sandanayaka et al. |
| 9,714,226 B2 | 7/2017 | Sandanayaka et al. |
| 9,738,624 B2 | 8/2017 | Baloglu et al. |
| 9,861,614 B2 | 1/2018 | Sandanayaka et al. |
| 2003/0018025 A1 | 1/2003 | Thurkauf et al. |
| 2009/0221586 A1 | 9/2009 | Okada et al. |
| 2009/0298896 A1 | 12/2009 | Sakuma et al. |
| 2010/0016272 A1 | 1/2010 | Strobel et al. |
| 2010/0056569 A1 | 3/2010 | Nan et al. |
| 2011/0009374 A1* | 1/2011 | Keller .................. A61K 9/0014 514/179 |
| 2011/0275607 A1 | 11/2011 | Shacham et al. |
| 2012/0258986 A1 | 10/2012 | Sandanayaka et al. |
| 2013/0317031 A1 | 11/2013 | Sandanayaka et al. |
| 2014/0155370 A1 | 6/2014 | Shacham et al. |
| 2014/0235653 A1 | 8/2014 | Sandanayaka et al. |
| 2014/0364408 A1 | 12/2014 | Sandanayaka et al. |
| 2015/0018332 A1 | 1/2015 | Sandanayaka et al. |
| 2015/0111893 A1 | 4/2015 | Sandanayaka et al. |
| 2015/0274698 A1* | 10/2015 | Sandanayaka ....... C07D 403/12 514/340 |
| 2016/0145246 A1 | 5/2016 | Sandanayaka et al. |

FOREIGN PATENT DOCUMENTS

| | | |
|---|---|---|
| CN | 103002742 A | 3/2013 |
| EP | 0069513 A2 | 1/1983 |
| EP | 1 939 180 A1 | 7/2008 |
| EP | 1992618 A1 | 11/2008 |
| EP | 2003118 A1 | 12/2008 |
| EP | 2 090 570 A1 | 8/2009 |
| JP | S5841875 A | 3/1983 |
| JP | S62103065 A | 5/1987 |
| JP | H04211089 A | 8/1992 |
| JP | H07118237 A | 5/1995 |
| JP | H11263764 A | 9/1999 |
| JP | 2003/342262 A | 12/2003 |
| JP | 2004168768 A | 6/2004 |
| JP | 2005-255683 A | 9/2005 |
| JP | 2007210929 A | 8/2007 |
| JP | 2009-203238 A | 9/2009 |
| JP | 2009-536615 A | 10/2009 |
| JP | 2009-544696 A | 12/2009 |
| JP | 2010-513341 A | 4/2010 |
| JP | 2010-519337 A | 6/2010 |
| WO | WO-95/30783 A1 | 11/1995 |
| WO | WO-96/16040 A1 | 5/1996 |
| WO | WO-97/15567 A1 | 5/1997 |
| WO | WO-97/37996 A1 | 10/1997 |
| WO | WO-97/48696 A1 | 12/1997 |
| WO | WO-98/25893 A1 | 6/1998 |
| WO | WO-99/50264 A1 | 10/1999 |
| WO | WO-01/62756 A1 | 8/2001 |
| WO | WO-02/26696 A1 | 4/2002 |
| WO | WO-2003/024448 A2 | 3/2003 |
| WO | WO-2004/039365 A1 | 5/2004 |
| WO | WO-2004/039764 A1 | 5/2004 |
| WO | WO-2004/043925 A2 | 5/2004 |
| WO | WO-2004/043951 A1 | 5/2004 |
| WO | WO-2004/076418 A1 | 9/2004 |
| WO | WO-2005/115990 A1 | 12/2005 |
| WO | WO-2006/016637 A1 | 2/2006 |
| WO | WO-2006/019020 A1 | 2/2006 |
| WO | WO-2006/088246 A1 | 8/2006 |
| WO | WO-2007/102580 A1 | 9/2007 |
| WO | WO-2007/147336 A1 | 12/2007 |
| WO | WO-2008/029825 A1 | 3/2008 |
| WO | WO-2008/074413 A2 | 6/2008 |
| WO | WO-2011/069039 A1 | 6/2011 |
| WO | WO-2011/109799 A1 | 9/2011 |
| WO | WO-2012/099807 A1 | 7/2012 |
| WO | WO 2013/019548 * | 2/2013 |
| WO | WO-2013/019561 A1 | 2/2013 |
| WO | WO-2013/020024 A2 | 2/2013 |
| WO | WO-2013/170068 A2 | 11/2013 |
| WO | WO-2014/144772 A1 | 9/2014 |
| WO | WO-2014/152263 A1 | 9/2014 |
| WO | WO-2014/205389 A1 | 12/2014 |
| WO | WO 2014/205393 A1 | 12/2014 |
| WO | WO-2016/025904 A1 | 2/2016 |
| WO | WO-2017/117529 A1 | 7/2017 |
| WO | WO-2017/117535 A1 | 7/2017 |

OTHER PUBLICATIONS

Non-Final Office Action dated May 27, 2014 for U.S. Appl. No. 13/350,864 "Olefin Containing Nuclear Transport Modulators And Uses Thereof".

Non-Final Office Action dated Sep. 21, 2012 for U.S. Appl. No. 13/041,377 "Nuclear Transport Modulators and Uses Thereof".

Non-Final Office Action for U.S. Appl. No. 13/891,044 "Nuclear Transport Modulators And Uses Thereof" dated Oct. 21, 2014.

Non-Final Office Action for U.S. Appl. No. 13/931,372 "Nuclear Transport Modulators And Uses Thereof" dated Feb. 9, 2015.

Non-Final Office Action for U.S. Appl. No. 14/399,868 "Nuclear Transport Modulators And Uses Thereof" dated Feb. 13, 2015.

Non-Final Office Action for U.S. Appl. No. 14/747,394 "Nuclear Transport Modulators and Uses Thereof" dated Apr. 20, 2016.

Notice of Allowability for U.S. Appl. No. 13/041,377 "Nuclear Transport Modulators and Uses Thereof", mailed May 2, 2013.

Notice of Allowability for U.S. Appl. No. 14/219,638 "Hydrazide Containing Nuclear Transport Modulators and Uses Thereof", dated Oct. 10, 2014.

Notice of Allowability for U.S. Appl. No. 14/235,306 "Hydrazide Containing Nuclear Transport Modulators and Uses Thereof", dated Apr. 6, 2015.

Notice of Allowability for U.S. Appl. No. 14/399,668 "Nuclear Transport Modulators and Uses Thereof", dated Sep. 19, 2015.

Notice of Allowance for U.S. Appl. No. 13/891,044 "Nuclear Transport Modulators and Uses Thereof", dated Apr. 7, 2015.

(56) References Cited

OTHER PUBLICATIONS

Notice of Allowance for U.S. Appl. No. 14/735,853 "Nuclear Transport Modulators and Uses Thereof", dated Aug. 4, 2015.
Notice of Allowance for U.S. Appl. No. 14/900,469 dated Apr. 18, 2017.
Notice of Allowance for U.S. Appl. No. 14/940,310 dated Mar. 14, 2017.
Notice of Allowance for U.S. Appl. No. 14/747,394 dated Aug. 30, 2017.
U.S. Appl. No. 14/989,377, filed Jan. 6, 2016, "Nuclear Transport Modulators and Uses Thereof."
Balsamini, "(E)-3-(2-(N-Phenylcarbamoyl)vinyl)pyrrole-2-carboxylic Acid Derivatives. A Novel Class of Glycine Site Antagonists", Journal of Medicinal Chemistry, 41(6):808-820 (Jan. 1, 1998).
Brekhov, Y. et al., "Cyanomethyltetrazoles II reactions of the methylene Fragment", Zhurnal organicheskoi Khimii, 28(9): 1921-1925 (1992).
Buckler, R.T. et al., "Synthesis and Antiinflammatory Activity of Some 1,2,3- and 1,2,4-Triazolerpropionic Acids", Journal of Medicinal Chemistry, 21(12): 1254-1260 (1978).
Burdeska et al., "Anil-Synthese. 23. Mitteilung. Ueber die Herstellung von Styryl- and Stilbenyl-Derivaten des Pyrimidins // Anil synthesis. Part 23. Preparation of styryl and stilbenyl derivatives of pyrimidines," Helv Chim Acta, 64(1): 113-152 (1981).
Cai, X., et al., "Inhibition of Thr-55 phosphorylation restores p53 nuclear localization and sensitizes cancer cells to DNA damage", Proc Nat Acad Sci, 105(44):16958-16963 (Nov. 4, 2008).
Cronshaw, J.M. et al., "The nuclear pore complex: disease associations and functional correlations", Trends Endocrin Metab. 15:34-39 (2004).
Daelemans, D. et al., "A synthetic HIV-1 Rev inhibitor interfering with the CRM1-mediated nuclear export", PNAS, 99(22):14440-14445 (Oct. 29, 2002).
Database PubChem Compound, Database Accession No. 33777540 (May 29, 2009), 3 pages.
Database PubChem Compound, Database Accession No. 33777561 (May 29, 2009), 3 pages.
Database PubChem Compound, Database Accession No. 33777585 (May 29, 2009), 3 pages.
Database PubChem Compound, Database Accession No. 66525271 (Oct. 24, 2012), 3 pages.
Database PubChem Compound, Database Accession No. 66525276 (Oct. 24, 2012), 3 pages.
Database PubChem Compound, Database Accession No. 72062355, Database Registry, RN 940775-13-3 (2007), 11 pages.
Davis, J.R. et al., "Controlling protein compartmentalization to overcome disease" Pharmaceut Res., 24:17-27 (2007).
Extended Search Report for EP Application No. 11751491.9, "Nuclear Transport Modulators And Uses Thereof", dated Dec. 17, 2013., 6 pages.
Extended Search Report for EP Application No. 12736172.3, "Olefin Containing Nuclear Transport Modulators And Uses Thereof", dated May 8, 2014., 3 pages.
Falini, B. et al., "Both carboxy-terminus NES motif and mutated tryptophan(S) are crucial for aberrant nuclear export of nucleophosmin leukemic mutants in NPMc+ AML", Blood Journal, 107(11):4514-4523 (Feb. 8, 2013).
Freundt, E.C. et al., "Molecular Determinants for Subcellular Localization of the Severe Acute Respiratory Syndrome Coronavirus Open Reading Frame 3b Protein", Journal of Virology, 83(13):6631-6640 (Jul. 2009).
Ghildyal, R. et al., "The Respiratory Syncytial Virus Matrix Protein Possesses a Crm1-Mediated Nuclear Export Mechanism", Journal of Virology, 83(11):5353-5362 (Jun. 2009).
Ghosh, C.C. et al., "Analysis of nucleocytoplasmic shuttling of NF kappa B proteins in human leukocytes", Methods Mol. Biol. 457:279-92 (2008).
Golub, T.R. et al., "Molecular Classification of Cancer: Class Discovery and Class Prediction by Gene Expression Monitoring", Science, 286: 531-537 (1999).
Gupta, N. et. al., "Retinal tau pathology in human glaucomas" Can J Ophthalmol. 43(1):53-60 (Feb. 2008).
Hoffman et al., "Synthesis of Vinyl-Functionalized Oxazoles by Olefin Cross-Metathesis", J. Org. Chem. 73: 2400-2403 (2008).
Hoshino, L. et al., "Combined effects of p53 gene therapy and leptomycin B in human esophageal squamous cell carcinoma", Oncology, 75:113-119 (2008).
Huff, J., "HIV Protease: A Novel Chemotherapeutic Target for Aids", Journal of Medicinal Chemistry, 34(8): 2305-2314 (1991).
International Preliminary Report on Patentability for International Application No. PCT/US2011/027328, "Nuclear Transport Modulators And Uses Thereof" dated Sep. 11, 2012, 9 pages.
International Preliminary Report on Patentability for International Application No. PCT/US2012/021406, "Olefin Containing Nuclear Transport Modulators and Uses Thereof" dated Jul. 17, 2013, 4 pages.
International Preliminary Report on Patentability for International Application No. PCT/US2014/043479, dated Dec. 22, 2015, 5 pages.
International Preliminary Report on Patentability for International Application No. PCT/US2014/043484, dated Dec. 22, 2015, 7 pages.
International Preliminary Report on Patentability for International Application No. PCT/US2012/048319, "Hydrazide Containing Nuclear Transport Modulators And Uses Thereof"; dated Feb. 4, 2014, 10 pages.
International Preliminary Report on Patentability for International Application No. PCT/US2012/048368, "Nuclear Transport Modulators And Uses Thereof"; dated Feb. 4, 2014, 10 pages.
International Preliminary Report on Patentability for International Application No. PCT/US2013/040404, "Nuclear Transport Modulators And Uses Thereof"; dated Nov. 11, 2014, 6 pages.
International Search Report and The Written Opinion of the International Searching Authority for International Application No. PCT/US2012/021406, "Olefin Containing Nuclear Transport Modulators And Uses Thereof" dated Apr. 30, 2012., 2 pages.
International Search Report and The Written Opinion of the International Searching Authority for International Application No. PCT/US2012/049470, "Maleimide Compounds and Methods of Treatment," dated Feb. 13, 2013., 27 pages.
International Search Report and The Written Opinion of the International Searching Authority for International Application No. PCT/US2013/040404, "Nuclear Transport Modulators And Uses Thereof"; dated Nov. 18, 2013, 3 pages.
International Search Report and the Written Opinion of the International Searching Authority, or the Declaration for International Application No. PCT/US2014/027136 "Exo Olefin-Containing Nuclear Transport Modulators and Uses Thereof"; dated Jul. 11, 2014, 4 pages.
International Search Report and the Written Opinion of the International Searching Authority, or the Declaration for International Application No. PCT/US2014/029322 "Methods Of Promoting Wound Healing Using CRM1 Inhibitors"; dated May 28, 2014, 4 pages.
International Search Report and the Written Opinion of the International Searching Authority, or the Declaration for International Application No. PCT/US2014/043479 "Nuclear Transport Modulators And Uses Thereof"; dated Sep. 17, 2014, 4 pages.
International Search Report and the Written Opinion of the International Searching Authority, or the Declaration for International Application No. PCT/US2014/043484 "Nuclear Transport Modulators and Uses Thereof"; dated Sep. 2, 2014, 4 pages.
International Search Report and Written Opinion for International Application No. PCT/US2016/069492 dated Feb. 16, 2017, 2 pages.
International Search Report and Written Opinion for International Application No. PCT/US2016/069508 dated May 23, 2017, 18 pages.
International Search Report for International Application No. PCT/US2011/027328, "Nuclear Transport Modulators And Uses Thereof" dated Apr. 29, 2011.

(56) References Cited

OTHER PUBLICATIONS

International Search Report for International Application No. PCT/US2012/048319, "Hydrazide Containing Nuclear Transport Modulators And Uses Thereof" dated Nov. 9, 2012, 6 pages.
International Search Report for International Application No. PCT/US2012/048366, "Nuclear Transport Modulators And Uses Thereof" dated Sep. 21, 2012, 5 pages.
Jiang et al., "Palladium-Catalyzed Alkenylation of 1,2,3-Trizoles with Terminal Conjugated Alkenes by Direct C—H Bond Functionalization," Eur J Org Chem, 7:1227-30 (2010).
Karyagin, A. Yu., Reagents for addressed modification of biopolymers, Russian Chemical Bulletin, 2000, 49(3):540-5.
Kau, T.R. et al., "A chemical genetic screen identifies inhibitors of regulated nuclear export of a Forkhead transcription factor in PTEN-deficient tumor cells", Cancer Cell, pp. 463-476 (2003).
Lain, S. et al., "Accumulating active p53 in the nucleus by inhibition of nuclear export: a novel strategy to promote the p53 tumor suppressor function", Exp Cell Res. 253: 315-324 (1999).
Lain, S. et al., "An inhibitor of nuclear export activates the p53 response and induces the localization of HDM2 and p53 to U1A-positive nuclear bodies associated with the PODs", Exp Cell Res. 248:457-472 (1999).
Lala, P.K. et al., "Role of nitric oxide in tumor progression: Lessons from experimental tumors", Cancer and Metastasis Reviews, 17: 91-106 (1998).
Lapalombella, R. et al., "Selective Inhibitors of nuclear exports show that CRM1/XPO1 is a target in chronic lymphocytic leukemia", Blood, 120(23): 4621-4634 (Nov. 29, 2012).
Li, A. et al., "Upregulation of CRM1 Relates to Neuronal Apoptosis after Traumatic Brain Injury in Adult Rats", J Mol Neurosci, DOI 10.1007/s12031-013-9994-7, Published online Mar. 15, 2013, 11 pages.
Maga et al., "Pharmacophore modeling and molecular docking led to the discovery of inhibitors of human immunodeficiency virus-1 replication targeting the human cellular aspartic acid-glutamic acid-alanine-aspartic acid box polypeptide 3," J Med Chem, 51(21):6635-8 (2008).
Modzelewska-Banachiewicz, B. et al., "Synthesis and biological activity of (Z) and (E) isomers of 3-(3,4-diaryl-1-1,2,4-triazole-5-yl)prop-2-enoic acid" Monatsh Chem. 140:439-444 (2009).
Modzelewska-Banachiewicz, B. et al., "Synthesis and biological activity of new derivatives of 3-(3,4-diaryl-1-1,2,4-triazole-5-yl)propenoic acid" European Journal of Medicinal Chemistry, 39:873-877 (2004).
Monecke, T. et al., "Crystal Structure of the Nuclear Export Receptor CRM1 in Complex with Snurportin1 and RanGTP", Science, 324:1087-1091 (May 22, 2009).
Muller, P.A.J. et al., "Nuclear-Cytosolic Transport of COMMD1 Regulates NF-κB and HIF-1 Activity", Traffic, 10:514-527 (2009).
Mutka, S. et al., "Nuclear export inhibitors (NEIs) as novel cancer therapeutics", 98th AACr Ann. Mtg., 2 pgs (Apr. 14-18, 2007) (Poster).
Nair, V., "Thermally induced skeletal rearrangement in a triazepine," J Heterocyclic Chem, 12(1):183-4 (1975).
Nakahara, J. et al., "Abnormal expression of TIP30 and arrested nucleocytoplasmic transport within oligodendrocyte precursor cells in multiple sclerosis", Journal of Clinical Investigation, 119(1):169-181 (Jan. 2009).
Noske, A., et al., "Expression of the Nuclear Export Protein Chromosomal Region Maintenance/Exportin 1/Xpo1 Is a Prognostic Factor in Human Ovarian Cancer", Cancer, 112(8):1733-1743 (Apr. 15, 2008).
Patani, G.A., et al., "Bioisosterism: A Rational Approach in Drug Design", Chem Rev, 96:3147-3176 (1996).
Procopiou et al., "Inhibitors of Cholesterol Biosynthesis. 2. 3,5-Dihydroxy-7-(N-pyrrolyl)-6-heptenoates, a Novel Series of HMG-CoA Reductase Inhibitors," J Med Chem, 36(23): 3658-3662 (1993).
Quan, M.L. et al., "Design and Synthesis of Isoxazoline Derivatives as Factor Xa Inhibitors", J. Med. Chem. 42: 2760-2773 (1999).
Rawlinson, S.M. et al., "CRM1-mediated Nuclear Export of Dengue Virus RNA Polymerase NS5 Modulates Interleukin-8 Induction and Virus Production", Journal of Biological Chemistry, 284(23):15589-15597 (Jun. 5, 2009).
Registry(STN)[online], Jan. 23, 2008, CAS registered No. 1000508-38-2, 1 page.
Sakamoto et al., "Studies on Pyrimidine Derivatives. XXV. Reaction of Pyrimidinyl Aldehydes and Ketones with Wittig Reagents," Chem Pharm Bull, 30(2): 610-614 (1982).
Sanchez, V. et al., "Nuclear Export of the Human Cytomegalovirus Tegument Protein pp65 Requires Cyclin-Dependent Kinase Activity and the Crm1 Exporter", Journal of Virology, 81(21):11730-11736 (Nov. 2007).
Shaoyong, Ke. et al., "Research Advance of Acylhydrazine Derivatives with Biological Activities", Chinese Journal of Organic Chemistry 30(12): 1820-1830 (2010).
Shasheva, "Reactions of Hydroxyphenyl-Substituted 1,2,4-Triazoles with Electrophylic Reagents", Russian Journal of General Chemistry, 79(10): 2234-2243 (2009).
Sorokin, A.V. et al., "Nucleocytoplasmic Transport of Proteins", Biochemistry, Moscow, 72(13):1439-1457 (2007).
Sun Q., et al., "Nuclear export inhibition through covalent conjugation and hydrolysis of Leptomycin B by CRM1", Proc Nat Acad Sci, 110(4): 1303-1308 (Jan. 22, 2013).
Terry, L.J. et al., "Crossing the Nuclear Envelope: Hierarchical Regulation of Nucleocytoplasmic Transport", Science, 318:1412-1416 (Nov. 30, 2007).
van der Watt, P.J. et al., "The Karyopherin proteins, Crm1 and Karyopherin β1, are overexpressed in cervical cancer and are critical for cancer cet survival and proliferation", Int. J. Cancer, 124:1829-1840 (2009).
Van Neck, T., et al., "Inhibition of the CRM1-mediated nucleocytoplasmic transport by N-azolylacrylates: Structure-activity relationship and mechanism of action", Bioorganic & Medicinal Chemistry 16:9487-9497 (2008).
Walsh, Jr., M.D., et al., Exportin 1 Inhibition Attenuates Nuclear Factor—κB-Dependent Gene Expression, Shock, 29(2):160-166 (2008).
Nagase H., The Practice of Medicinal Chemistry vol. 1, Technomics Inc., 1998, 253 (English translation provided).
Williams, P., et al., "Characterization of a CRM1-Dependent Nuclear Export Signal in the C Terminus of Herpes Simplex Virus Type 1 Tegument Protein UL47", Journal of Virology, 82(21):10946-10952 (Nov. 2008).
Written Opinion of the International Searching Authority for International Application No. PCT/US2011/027328, "Nuclear Transport Modulators and Uses Thereof" (4823.1003-002) dated Apr. 29, 2011, 8 pages.
Written Opinion of the International Searching Authority for International Application No. PCT/US2012/048319, "Hydrazide Containing Nuclear Transport Modulators And Uses Thereof" (4823.1002-006) dated Nov. 9, 2012, 9 pages.
Written Opinion of the International Searching Authority for International Application No. PCT/US2012/048368, "Nuclear Transport Modulators And Uses Thereof" (4823.1001-002) dated Sep. 21, 2012, 11 pages.
Yao, Y., et al., "The expression of CRM1 is associated with prognosis in human osteosarcoma", Oncology Reports, 21:229-235 (2009).
Zimmerman, T.L. et al., "Nuclear Export of Retinoid X Receptor α in Response to Interleukin-1β-mediated Cell Signaling Roles for JNK and SER", The Journal of Biological Chemistry, 281(22):15434-15440 (Jun. 2, 2006).
Final Rejection for U.S. Appl. No. 13/931,372, "Nuclear Transport Modulators and Uses Thereof," dated Oct. 16, 2015.
Final Rejection for U.S. Appl. No. 14/747,394, "Nuclear Transport Modulators and Uses Thereof," dated Feb. 1, 2017.
Non-Final Rejection for U.S. Appl. No. 14/235,342, "Nuclear Transport Modulators and Uses Thereof," dated Aug. 28, 2015.
Non-Final Rejection for U.S. Appl. No. 14/900,469, "Nuclear Transport Modulators and Uses Thereof," dated Nov. 14, 2016.

(56) References Cited

OTHER PUBLICATIONS

Non-Final Rejection for U.S. Appl. No. 14/940,310, "Hydrazide Containing Nuclear Transport Modulators and Uses Thereof," dated Aug. 11, 2016.
Non-Final Rejection for U.S. Appl. No. 15/413,889, "Nuclear Transport Modulators and Uses Thereof," dated Sep. 14, 2017.
Non-Final Rejection for U.S. Appl. No. 15/629,307, "Hydrazide Containing Nuclear Transport Modulators and Uses Thereof," dated Feb. 14, 2018.
Notice of Allowance for U.S. Appl. No. 13/350,864, "Olefin Containing Nuclear Transport Modulators and Uses Thereof," dated Dec. 1, 2015.
Notice of Allowance for U.S. Appl. No. 13/931,372, "Nuclear Transport Modulators and Uses Thereof," dated Sep. 7, 2016.
Notice of Allowance for U.S. Appl. No. 14/235,342, "Nuclear Transport Modulators and Uses Thereof," dated Apr. 25, 2016.
Notice of Allowance for U.S. Appl. No. 14/989,377, "Nuclear Transport Modulators and Uses Thereof," dated Oct. 28, 2016.
Requirement for Restriction/Election for U.S. Appl. No. 13/041,377, "Nuclear Transport Modulators and Uses Thereof," dated Jul. 5, 2012.
Requirement for Restriction/Election for U.S. Appl. No. 13/350,864, "Olefin Containing Nuclear Transport Modulators and Uses Thereof," dated Dec. 19, 2013.
Requirement for Restriction/Election for U.S. Appl. No. 13/931,372, "Nuclear Transport Modulators and Uses Thereof," May 22, 2014.
Requirement for Restriction/Election for U.S. Appl. No. 14/235,342, "Nuclear Transport Modulators and Uses Thereof," Jun. 9, 2015.
Requirement for Restriction/Election for U.S. Appl. No. 15/217,514, "Nuclear Transport Modulators and Uses Thereof," dated Aug. 8, 2017.
Cancer [online], [retrieved on Jul. 6, 2007] Retrieved from the Internet, URL: http://www.nlm.nih.gov/medlineplus/cancer.html (Year: 2007).
Cantu et al., "Using the Selective Inhibitor of Nuclear Export (SINE) Compound KPT-250 to Reduce Critical Circuit Hyperexcitability an Interneuron Cell Loss in the Controlled Cortical Impact (CCI) Model of Traumatic Brain Injury (TBI) (I11.001)," Neurology, 86(16 Supplement): 111.001 (2016).
Cooper et al., "Synthesis of Some 1,2,4-Triazoles and 1,2,4-Triazolines by Reaction of Oxamidrzone Condensation Products with Acetics Anhyride," Journal of Chemical Society Perkin Transactions 1, 15: 1433-1437 (1975).
Haines et al., "Selective Inhibitors of Nuclear Export Inhibitors Avert Progression in Preclinical Models of Inflammatory Demyelination," Nature Neuroscience, 18(4): 511-520 (2015).
International Preliminary Report on Patentability for International Application No. PCT/US2014/029322 dated Sep. 15, 2015.
International Preliminary Report on Patentability for International Application No. PCT/US2015/045395 dated Feb. 21, 2017.
International Search Report and Written Opinion for International Application No. PCT/US2015/045395 dated Jan. 12, 2016.
International Search Report and Written Opinion for International Application No. PCT/US2017/063439 dated Feb. 2, 2018.
Karypoharm Therapeutics, "Karyopharm Presents Date Demonstrating the Potential of Nuclear Export Protein Exportin 1 (XPO1) Inhibition in the Treatment of Traumatic Brain Injury," Apr. 20, 2016, Retrieved from the Internet: http://investors.karyopharm.com/static-files/577eb861-4183-463a-9a5b-d0f1def1629d [retrieved on Jan. 25, 2018].
Kaur et al., "Tyrphostin Induced Growth Inhibition: Correlation with Effect on p210bcr-abl Autokinase Activity in K562 Chronic Myelogenous Leukemia," Anti-Cancer Drugs, 5(2): 213-222 (1994).
Maekawa et al., "Efficient Formation of a Triazole Ring Via Novel Ring-Opening Reaction of (z)-2-Methyl-4-arylmethylene-5(4H)-Oxazolones with Hydrazides," Heterocycles, 75(12): 2959-2971 (2008).
Tamir et al., "KPT-350, a Selective Inhibitor of Nuclear Export (SINE) Compound, Shows Efficacy in the Mouse Pilocapine Model of Temporal Lobe Epilespy," Journal of Neurological Sciences, 381: 87-88 (2017).

\* cited by examiner control vehicle

Compound 4

METHODS OF PROMOTING WOUND HEALING USING CRM1 INHIBITORS

RELATED APPLICATION

This application claims the benefit of U.S. Provisional Application No. 61/793,146, filed Mar. 15, 2013. The entire teachings of the above application are incorporated herein by reference.

BACKGROUND OF THE INVENTION

The wound healing process consists of three overlapping phases. The first phase is an inflammatory phase, which is characterized by homeostasis, platelet aggregation and degranulation. Platelets as the first response, release multiple growth factors to recruit immune cells, epithelial cells, and endothelial cells. The second stage of wound healing is the proliferative phase during which macrophages and granulocytes invade the wound. Infiltrating fibroblasts begin to produce collagen. The principle characteristics of this phase are epithelialization, angiogenesis, granulation tissue formation and collagen production. The third phase is the remodeling phase where matrix formation occurs. The fibroblasts, epithelial cells, and endothelial cells continue to produce collagen and collagenase as well as matrix metalloproteases (MMPs) for remodeling. Collagen crosslinking takes place and the wound undergoes contraction.

Chronic wounds exhibit a different healing profile from normal acute wounds in that they generally remain in an inflamed state for extended periods of time. Non-healing wounds can commonly be observed, for example, amongst people with diabetes, venous stasis disease, and in immobilized patients.

In view of the foregoing, the discovery of compounds that promote wound healing in a subject in, for example, both acute and chronic wound healing situations is desirable.

SUMMARY OF THE INVENTION

The invention generally relates to the use of nuclear transport modulators, e.g., CRM1 inhibitors, for promoting wound healing in a subject. Exemplary wound types include, for example, burn wounds, incised wounds, open wounds, surgical or post surgical wounds, diabetic lesions, thermal burns, chemical burns, radiation burns, pressure sores, bedsores, and conditions related to diabetes or poor circulation.

One embodiment provides a method of promoting wound healing in a subject in need thereof, the method comprising administering to the subject an effective amount of a CRM1 inhibitor.

Another embodiment provides a method of promoting wound healing in a subject in need thereof, the method comprising administering to the subject an effective amount of a compound represented by structural formula I:

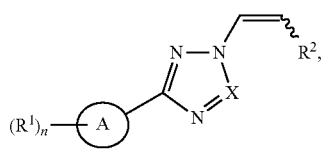

or a pharmaceutically acceptable salt thereof, wherein Ring A, $R^1$, $R^2$ and n are defined herein.

Another embodiment provides a method of promoting wound healing in a subject, the method comprising administering to the subject a therapeutically effective amount of a compound represented by structural formula (IV):

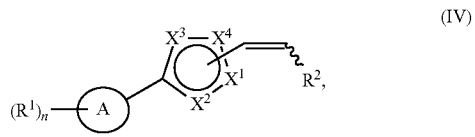

or a pharmaceutically acceptable salt thereof, wherein Ring A, $X^1$, $X^2$, $X^3$, $X^4$, $R^1$, $R^2$ and n are defined herein.

Yet another embodiment provides a method of promoting wound healing in a subject in need thereof, the method comprising administering to the subject a therapeutically effective amount of a CRM1 inhibitor. The wound is selected from the group consisting of a burn wound, an incised wound, an open wound, a surgical or post surgical wound, a diabetic lesion, a thermal burn, a chemical burn, a radiation burn, a pressure sore, a bedsore, and a condition related to diabetes or poor circulation. The CRM1 inhibitor is not leptomycin B.

Another embodiment provides a method of promoting wound healing in a subject in need thereof, the method comprising administering to the subject a therapeutically effective amount of a CRM1 inhibitor, wherein the wound is selected from the group consisting of a non-radiation burn wound, an incised wound, an open wound, a surgical or post surgical wound, a diabetic lesion, a thermal burn, a chemical burn, a pressure sore, a bedsore, and a condition related to diabetes or poor circulation.

Also provided herein are compounds (e.g., a CRM1 inhibitor, a compound represented by structural formula I, II, III, IV or V, or a compound of any one of Tables 1A-1D) for use in promoting wound healing.

The compounds described herein, and their pharmaceutically acceptable salts, can also be used in the manufacture of a medicament for promoting wound healing. Thus, also provided herein is use of a compound described herein, or a pharmaceutically acceptable salt thereof, in the manufacture of a medicament for promoting wound healing.

The compounds described herein promote early wound healing by, for example, stimulating scab formation and preventing wounds from becoming infected, and induce complete wound healing by, for example, preventing wound healing complications associated with abnormal healing of the epidermis and adhesions. Evidence of the beneficial effects of the compounds described herein on wound healing can be found throughout the Exemplification.

BRIEF DESCRIPTION OF THE FIGURES

The foregoing will be apparent from the following more particular description of example embodiments of the invention, as illustrated in the accompanying figures.

For the purposes of the accompanying figures, and the descriptions thereof, Compound 3 refers to Compound C-3 (from Table 1C) in saline; Compound 4 refers to Compound C-3 (from Table 1C) in dimethylsulfoxide (DMSO) at the following concentrations of DMSO in water: 0.1%, 0.02% or 0.0067%; and Compound 5 refers to Compound 129 (from Table 1A) in saline or in DMSO in water.

DETAILED DESCRIPTION OF THE INVENTION

Figure 1A:
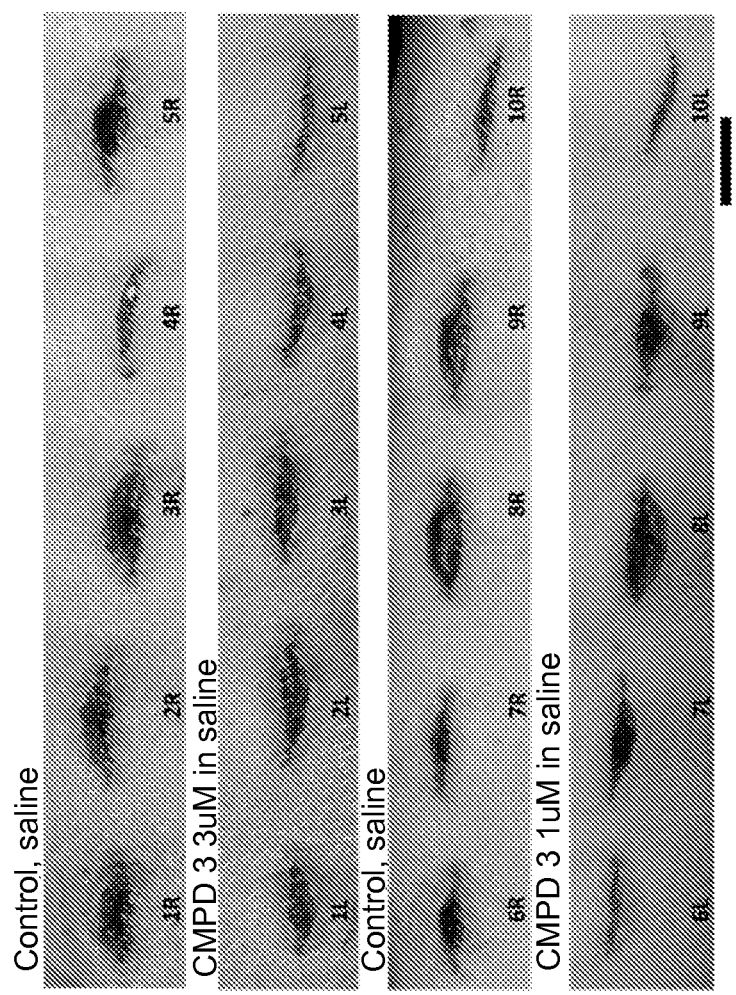
FIG. 1A shows the morphology of wounds treated with saline or with Compound 3 on Day 5 post-wounding in a pig model (the scale bar represents 2.5 cm).

A description of example embodiments of the invention follows.

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

If this is a discrepancy between a structural formula of a compound and the name of a compound, the structural formula should be assumed correct.

Compounds of the present invention may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers or enantiomers, with all possible isomers and mixtures thereof, including optical isomers, being included in the present invention.

The term "aliphatic" or "aliphatic group," as used herein, denotes a monovalent hydrocarbon radical that is straight-chain (i.e., unbranched), branched, or cyclic (including fused, bridged, and spiro-fused polycyclic). An aliphatic group can be saturated or can contain one or more units of unsaturation, but is not aromatic. Unless otherwise specified, aliphatic groups contain 1-6 carbon atoms. However, in some embodiments, an aliphatic group contains 1-10 or 2-8 carbon atoms. In some embodiments, aliphatic groups contain 1-4 carbon atoms and, in yet other embodiments, aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl," as used herein, means a saturated, straight-chain or branched aliphatic group. In one aspect, an alkyl group contains 1-6 or 1-4 carbon atoms. Alkyl includes, but is not limited to, methyl, ethyl, propyl, iso-propyl, n-butyl, sec-butyl, t-butyl, and the like.

The term "alkenyl," as used herein, means a straight-chain or branched aliphatic group having one or more carbon-carbon double bonds (i.e., —CH=CH—). In one aspect, an alkenyl group has from two to four carbon atoms, and includes, for example, and without being limited thereto, ethenyl, 1-propenyl, 1-butenyl and the like. The term "alkenyl" encompasses radicals having carbon-carbon double bonds in the "cis" and "trans" or, alternatively, the "E" and "Z" configurations. If an alkenyl group includes more than one carbon-carbon double bond, each carbon-carbon double bond is independently a cis or trans double bond, or a mixture thereof.

The term "alkynyl," as used herein, means a straight-chain or branched aliphatic radical having one ore more carbon-carbond triple bonds (i.e., —CH≡CH—). In one aspect, an alkyl group has from two to four carbon atoms, and includes, for example, and without being limited thereto, 1-propynyl (propargyl), 1-butynyl and the like.

The terms "cycloaliphatic," "carbocyclyl," "carbocyclo," and "carbocyclic," used alone or as part of a larger moiety, refer to a saturated or partially unsaturated cyclic aliphatic monocyclic or bicyclic ring system, as described herein, having from 3 to 12 members, wherein the aliphatic ring system is optionally substituted as defined above and described herein. In some embodiments, a cycloaliphatic group has 3-6 carbon atoms. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. The terms "cycloaliphatic," "carbocyclyl," "carbocyclo," and "carbocyclic" also include aliphatic rings that are fused to one or more aromatic or nonaromatic rings, such as decahydronaphthyl, tetrahydronaphthyl, decalin, or bicyclo[2.2.2]octane.

The term "cycloalkyl," as used herein, means a saturated cyclic aliphatic monocyclic or bicyclic ring system having from 3-12 members. A cycloalkyl can be optionally substituted as described herein. In some embodiments, a cycloalkyl has 3-6 carbons.

The term "heterocyclyl," as used herein, means a saturated or unsaturated aliphatic ring system having from 3 to 12 members in which at least one carbon atom is replaced with a heteroatom selected from N, S and O. A heterocyclyl can contain one or more rings, which may be attached together in a pendent manner or may be fused. In one aspect, a heterocyclyl is a three- to seven-membered ring system and includes, for example, and without being limited thereto, piperidinyl, piperazinyl, pyrrolidinyl, tetrahydrofuranyl and the like.

The term "heteroatom" means one or more of oxygen, sulfur, nitrogen, phosphorus, or silicon, and includes any oxidized form of nitrogen, sulfur, phosphorus, or silicon; the quaternized form of any basic nitrogen; and a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated," as used herein, means that a moiety has one or more units of unsaturation.

The term "alkoxy," as used herein, means —O-alkyl. "Alkoxy" can include a straight-chained or branched alkyl. In one aspect, "alkoxy" has from one to eight carbon atoms and includes, for example, and without being limited thereto, methoxy, ethoxy, propyloxy, isopropyloxy, t-butoxy and the like.

The term "halo" or "halogen" as used herein means halogen and includes, for example, and without being limited thereto, fluoro, chloro, bromo, iodo and the like, in both radioactive and non-radioactive forms.

The term "haloalkyl," as used herein, means an alkyl group that is substituted with one or more halogen atoms. In some embodiments, haloalkyl refers to a perhalogenated alkyl group. In some embodiments, haloalkyl refers to an alkyl group which is substituted with one or more halogen atoms. Exemplary haloalkyl groups include —$CF_3$, —$CF_2H$, —$CCl_3$, —$CF_2CH_3$, —$CH_2CF_3$, —$CH_2(CF_3)_2$, —$CF_2(CF_3)_2$, and the like. Preferred haloalkyl groups include —$CF_3$ and —$CF_2H$. A particularly preferred haloalkyl group is —$CF_3$.

The term "alkylene," as used herein, means a bivalent branched or unbranched saturated hydrocarbon radical. In one aspect, "alkylene" has one to six carbon atoms, and includes, for example, and without being limited thereto, methylene, ethylene, n-propylene, n-butylene and the like.

The term "alkenylene," as used herein, means a bivalent branched or unbranched hydrocarbon radical having one or more carbon-carbon double bonds (i.e., —CH=CH—). In one aspect, "alkenylene" has two to six carbon atoms, and includes, for example, and without being limited thereto, ethenylene, n-propenylene, n-butenylene and the like.

The term "alkynylene," as used herein, means a bivalent branched or unbranched hydrocarbon radical having one ore more carbon-carbond triple bonds (i.e., —C≡C—). In one aspect, "alkynylene" has two to six carbon atoms, and includes, for example, and without being limited thereto, ethynylene, n-propynylene, n-butynylene and the like.

The term "aryl," alone or in combination, as used herein, means a carbocyclic aromatic system containing one or more rings, which may be attached together in a pendent manner or may be fused. In particular embodiments, aryl is one, two or three rings. In one aspect, the aryl has six to twelve ring atoms. The term "aryl" encompasses aromatic radicals such as phenyl, naphthyl, tetrahydronaphthyl, indanyl, biphenyl, phenanthryl, anthryl and acenaphthyl. An "aryl" group can have 1 to 4 substituents, such as lower alkyl, hydroxyl, halo, haloalkyl, nitro, cyano, alkoxy, lower alkylamino and the like.

The term "heteroaryl," alone or in combination, as used herein, means an aromatic system wherein at least one carbon atom is replaced by a heteroatom selected from N, S and O. A heteroaryl can contain one or more rings, which may be attached together in a pendent manner or may be fused. In particular embodiments, heteroaryl is one, two or three rings. In one aspect, the heteroaryl has five to twelve ring atoms. The term "heteroaryl" encompasses heteroaromatic groups such as triazolyl, imidazolyl, pyrrolyl, pyrazolyl, tetrazolyl, pyridyl, pyrimidinyl, pyrazinyl, pyridazinyl, indolyl, furyl, benzofuryl, thienyl, benzothienyl, quinolyl, oxazolyl, oxadiazolyl, isoxazolyl, and the like. A "heteroaryl" group can have 1 to 4 substituents, such as lower alkyl, hydroxyl, halo, haloalkyl, nitro, cyano, alkoxy, lower alkylamino and the like.

It is understood that substituents and substitution patterns on the compounds of the invention can be selected by one of ordinary skill in the art to provide compounds that are chemically stable and that can be readily synthesized by techniques known in the art, as well as those methods set forth below. In general, the term "substituted," whether preceded by the term "optionally" or not, means that one or more hydrogens of the designated moiety are replaced with a suitable substituent. Unless otherwise indicated, an "optionally substituted group" can have a suitable substituent at each substitutable position of the group and, when more than one position in any given structure may be substituted with more than one substituent selected from a specified group, the substituent can be either the same or different at every position. Alternatively, an "optionally substituted group" can be unsubstitued.

Combinations of substituents envisioned by this invention are preferably those that result in the formation of stable or chemically feasible compounds. If a substituent is itself substituted with more than one group, it is understood that these multiple groups can be on the same carbon atom or on different carbon atoms, as long as a stable structure results. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted group" are independently halogen; haloalkyl; —$(CH_2)_{0-4}R°$; —$(CH_2)_{0-4}R°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —C(S)R°; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —OC(O)$(CH_2)_{0-4}SR$—, SC(S)SR°; —$(CH_2)_{0-4}SC(O)R°$; —$(CH_2)_{0-4}C(O)NR°_2$; —$C(S)NR°_2$; —C(S)SR°; —SC(S)SR°, —$(CH_2)_{0-4}OC(O)NR°_2$; —C(O)N(OR°)R°; —C(O)C(O)R°; —$C(O)CH_2C(O)R°$; —C(NOR°)R°; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —N(OR°)R°; —C(NH)$NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O-$N(R°)_2$, wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of R°, taken together with their intervening atom(s), form a 3-12-membered saturated, partially unsaturated, or aryl monocyclic or bicyclic ring having 0-4 heteroatoms independently selected from nitrogen, oxygen, and sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, —(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents on a saturated carbon atom of an "optionally substituted group" include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, and —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R$^\bullet$, —(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, and —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted group" include —R$^\dagger$, —NR$^\dagger{}_2$, —C(O)R$^\dagger$, —(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, and —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3-12-membered saturated, partially unsaturated, or aryl monocyclic or bicyclic ring having 0-4 heteroatoms independently selected from nitrogen, oxygen, and sulfur.

Suitable substituents on the aliphatic group of R$^\dagger$ are independently halogen, —RR$^\bullet$, —(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds of this invention include salts derived from suitable inorganic and organic acids and bases that are compatible with the treatment of subjects.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable acid addition salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In some embodiments, exemplary inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms.

In some embodiments, acid addition salts of the compounds of formula I are most suitably formed from pharmaceutically acceptable acids, and include, for example, those formed with inorganic acids, e.g., hydrochloric, sulfuric or phosphoric acids and organic acids e.g. succinic, maleic, acetic or fumaric acid.

Other non-pharmaceutically acceptable salts, e.g., oxalates can be used, for example, in the isolation of compounds of formula I for laboratory use, or for subsequent conversion to a pharmaceutically acceptable acid addition salt. Also included within the scope of the invention are base addition salts (such as sodium, potassium and ammonium salts), solvates and hydrates of compounds of the invention. The conversion of a given compound salt to a desired compound salt is achieved by applying standard techniques, well known to one skilled in the art.

A "pharmaceutically acceptable basic addition salt" is any non-toxic organic or inorganic base addition salt of the acid compounds represented by formula I, or any of its intermediates. Illustrative inorganic bases which form suitable salts include, but are not limited thereto, lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this invention. Such compounds are useful, for example, as analytical tools, as probes in biological assays, or as therapeutic agents in accordance with the present invention.

The term "stereoisomers" is a general term for all isomers of an individual molecule that differ only in the orientation of their atoms in space. It includes mirror image isomers (enantiomers), geometric (cis/trans) isomers and isomers of compounds with more than one chiral center that are not mirror images of one another (diastereomers).

The term "treat" or "treating" means to alleviate one or more symptoms, to eliminate the causation of one or more symptoms, either on a temporary or permanent basis, or to prevent or delay the onset of one or more symptoms associated with a disorder or condition. In the case of treating a wound, treating means to promote wound healing.

The term "therapeutically effective amount" means an amount of a compound that is effective in treating or lessening the severity of one or more symptoms of a disorder or condition. In the case of wound healing, a therapeutically effective amount is an amount that promotes healing of a wound.

As used herein, "promoting wound healing" means treating a subject with a wound and achieving healing, either partially or fully, of the wound. Promoting wound healing can mean, e.g., one or more of the following: promoting epidermal closure; promoting migration of the dermis; promoting dermal closure in the dermis; reducing wound healing complications, e.g., hyperplasia of the epidermis and adhesions; reducing wound dehiscence; and promoting proper scab formation.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of being administered to a subject. One example of such a carrier is pharmaceutically acceptable oil typically used for parenteral administration. Pharmaceutically acceptable carriers are well known in the art.

When introducing elements disclosed herein, the articles "a," "an," "the," and "said" are intended to mean that there are one or more of the elements. The terms "comprising," "having" and "including" are intended to be open-ended and mean that there may be additional elements other than the listed elements.

Exemplary Embodiments

A first embodiment is a method for promoting wound healing in a subject in need thereof, the method comprising administering to the subject an effective amount of a CRM1 inhibitor.

In a first aspect of the first embodiment, the CRM1 inhibitor is not leptomycin B.

In a second aspect of the first embodiment, the wound is selected from the group consisting of a burn wound, an incised wound, an open wound, a surgical or post surgical wound, a diabetic lesion, a thermal burn, a chemical burn, a radiation burn, a pressure sore, a bedsore, and a condition related to diabetes or poor circulation; and the CRM1 inhibitor is not leptomycin B.

In a third aspect of the first embodiment, the wound is selected from the group consisting of a non-radiation burn wound, an incised wound, an open wound, a surgical or post surgical wound, a diabetic lesion, a thermal burn, a chemical burn, a pressure sore, a bedsore, and a condition related to diabetes or poor circulation.

In a fourth aspect of the first embodiment, the wound is a diabetic ulcer.

A second embodiment is a method for promoting wound healing in a subject in need thereof, the method comprising administering to the subject an effective amount of a compound represented by structural formula I:

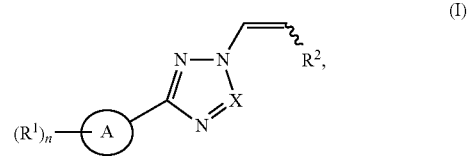

or a pharmaceutically acceptable salt thereof, wherein:
Ring A is phenyl or pyridyl;
X is —N— or —C(H)—;
each $R^1$ is independently selected from halo;

haloalkyl; —$(CH_2)_{1-4}R°$; —$(CH_2)_{0-4}OR°$; —O—$(CH_2)_{0-4}C(O)OR°$; —O—(CH=CH)—$C(O)O$ $R°$; —$(CH_2)_{0-4}CH(OR°)_2$; —$(CH_2)_{0-4}SR°$; —$(CH_2)_{0-4}$-carbocyclyl, which may be substituted with $R°$; —$(CH_2)_{0-4}$-aryl, which may be substituted with $R°$; —$(CH_2)_{0-4}$-heterocyclyl, which may be substituted with $R°$; —$(CH_2)_{0-4}$-heteroaryl, which may be substituted with $R°$; —CH=CH-carbocyclyl, which may be substituted with $R°$; —CH=CH-aryl, which may be substituted with $R°$; —CH=CH-heterocyclyl, which may be substituted with $R°$; —CH=CH-heteroaryl, which may be substituted with $R°$; —$NO_2$; —CN; —$N_3$; —$(CH_2)_{0-4}N(R°)_2$; —$(CH_2)_{0-4}N(R°)C(O)R°$; —$(CH_2)_{0-4}N(R°)C(S)$ $R°$; —$(CH_2)_{0-4}N(R°)C(O)NR°_2$; —$(CH_2)_{0-4}N(R°)C(S)NR°_2$; —$(CH_2)_{0-4}N(R°)C(O)OR°$; —$(CH_2)_{0-4}N(R°)N(R°)C(O)R°$; —$(CH_2)_{0-4}N(R°)N(R°)C(O)NR°_2$; —$(CH_2)_{0-4}N(R°)N(R°)C(O)OR°$; —$(CH_2)_{0-4}C(O)R°$; —$(CH_2)_{0-4}C(S)R°$; —$(CH_2)_{0-4}C(O)OR°$; —$(CH_2)_{0-4}C(O)SR°$; —$(CH_2)_{0-4}OC(O)R°$; —$(CH_2)_{0-4}OC(O)(CH_2)_{0-4}SR°$, —$(CH_2)_{0-4}SC(S)SR°$; —$(CH_2)_{0-4}SC(O)R°$; —$(CH_2)_{0-4}C(O)NR°_2$; —$(CH_2)_{0-4}C(S)NR°_2$; —$(CH_2)_{0-4}C(S)SR°$; —$(CH_2)_{0-4}OC(O)NR°_2$; —$(CH_2)_{0-4}C(O)N(OR°)R°$; —$(CH_2)_{0-4}C(O)C(O)R°$; —$(CH_2)_{0-4}C(O)CH_2C(O)R°$; —$(CH_2)_{0-4}C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$(CH_2)_{0-4}S(O)_2NR°_2$; —$(CH_2)_{0-4}S(O)R°$; —$(CH_2)_{0-4}N(R°)S(O)_2NR°_2$; —$(CH_2)_{0-4}N(R°)S(O)_2R°$; —$(CH_2)_{0-4}N(OR°)R°$; —$(CH_2)_{0-4}C(NH)NR°_2$; —$(CH_2)_{0-4}P(O)_2R°$; —$(CH_2)_{0-4}P(O)R°_2$; —$(CH_2)_{0-4}OP(O)R°_2$; —$(CH_2)_{0-4}OP(O)(OR°)_2$; —$(CH_2)_{0-4}ON(R°)_2$; —$(CH_2)_{0-4}$—O—$(CH_2)_{1-4}$—$N(R°)_2$; —$(CH_2)_{0-4}$—O—$(CH_2)_{0-4}$—$OR°$; and —$(CH_2)_{0-4}C(O)O$—$N(R°)_2$; or two $R^1$, taken together with their intervening atoms, form a 3-12-membered carbocyclyl, aryl, heterocyclyl or heteroaryl, wherein:

each $R°$ is independently hydrogen, $C_{1-6}$ aliphatic, —$CH_2$-carbocyclyl, —$CH_2$-aryl, —$CH_2$-heterocyclyl, —$CH_2$-heteroaryl, —$O(CH_2)_{0-1}$-carbocyclyl, —$O(CH_2)_{0-1}$-aryl, —$O(CH_2)_{0-1}$-heterocyclyl, —$O(CH_2)_{0-1}$-heteroaryl, carbocyclyl, aryl, heterocyclyl or heteroaryl, or two independent occurrences of $R°$, taken together with their intervening atom(s), form a 3-12-membered carbocyclyl, aryl, heterocyclyl or heteroaryl; and each $R°$ and each ring formed from two independent occurrences of $R°$, taken together with their intervening atom(s), are optionally and independently substituted with one or more substituents selected from the group consisting of halo, CN, OH, unsubstituted $C_1$-$C_3$ alkyl, halo-$C_1$-$C_3$ alkyl, —$NH_2$, —$NO_2$, —NH(unsubstituted $C_1$-$C_3$ alkyl), —N(unsubstituted $C_1$-$C_3$ alkyl)$_2$, —O—$C_1$-$C_3$ alkyl, —C(O)OH, —C(O)O-(unsubstituted $C_1$-$C_3$ alkyl), —C(O)-(unsubstituted $C_1$-$C_3$ alkyl), —O-(unsubstituted $C_1$-$C_3$ alkyl), and —S-(unsubstituted $C_1$-$C_3$ alkyl);

$R^2$ is selected from —$C(O)$—O—$R^3$, —$C(O)$—$N(R^5)(R^6)$, —$C(O)$—$N(R^7)$—$N(R^5)(R^6)$, —CN, —$CF_3$, —$S(O)_{1-2}(C_1$-$C_4$ alkyl), and heteroaryl, wherein:

$R^3$ is selected from $C_1$-$C_4$ alkyl, $C_2$-$C_4$ alkenyl, $C_2$-$C_4$ alkynyl, carbocyclyl, aryl, heterocyclyl and heteroaryl;

$R^4$ is selected from —NH—($C_3$-$C_6$ cycloalkyl), —N($C_1$-$C_4$ alkyl)-($C_3$-$C_6$ cycloalkyl), —$C_1$-$C_6$ alkyl, —($C_0$-$C_4$ alkylene)-carbocyclyl, —($C_0$-$C_4$ alkylene)-heterocyclyl, —($C_0$-$C_4$ alkylene)-aryl, and —($C_0$-$C_4$ alkylene)-heteroaryl;

$R^5$ and $R^6$ are each independently selected from hydrogen, $C_1$-$C_4$ alkyl $C_2$-$C_4$ alkenyl, $C_2$-$C_4$ alkynyl, carbocyclyl, aryl, heterocyclyl and heteroaryl; or $R^5$ and $R^6$ are taken together with the nitrogen atom to which they are commonly attached to form a heterocyclyl or heteroaryl;

each $R^7$ is independently hydrogen or $C_1$-$C_4$ alkyl; and n is 0, 1, 2, 3, 4 or 5, wherein, unless otherwise designated, each alkyl, alkenyl, alkynyl, alkylene, carbocyclyl, aryl, cycloalkyl, heterocyclyl and heteroaryl is optionally and independently substituted.

In a first aspect of the second embodiment each $R^7$ is hydrogen. The values for the remaining variables are as defined in the second embodiment.

In a second aspect of the second embodiment, X is —C(H)—. The values for the remaining variables are as defined in the second embodiment, or first aspect thereof.

In a third aspect of the second embodiment, X is —N—. The values for the remaining variables are as defined in the second embodiment, or first or second aspect thereof.

In a fourth aspect of the second embodiment, n is 0, 1 or 2. The values for the remaining variables are as defined in the second embodiment, or first through third aspects thereof.

In a fifth aspect of the second embodiment, each $R^1$ is independently selected from halo, —$C_1$-$C_4$ alkyl, —$C_1$-$C_4$ haloalkyl, and —O—$C_1$-$C_4$ alkyl, or is absent. The values for the remaining variables are as defined in the second embodiment, or first through fourth aspects thereof.

In a sixth aspect of the second embodiment, each $R^1$ is independently selected from —$CF_3$, —Cl and —$OCH_3$, or is absent. The values for the remaining variables are as defined in the second embodiment, or first through fifth aspects thereof.

In a seventh aspect of the second embodiment:

$R^2$ is —$C(O)$—O—$R^3$, and $R^3$ is selected from optionally substituted $C_1C_4$ alkyl and $C_2$-$C_4$ alkenyl; or $R^2$ is —$C(O)$—$N(R^5)(R^6)$, and $R^5$ and $R^6$ are taken together with the nitrogen atom to which they are commonly attached to form an optionally substituted saturated heterocyclyl; or $R^2$ is —$C(O)$—NH—$NH(R^6)$, and $R^6$ is an optionally substituted heteroaryl; or $R^2$ is —$C(O)$—NH—NH—$C(O)$—$R^4$, and $R^4$ is selected from optionally substituted —NH—($C_3$-$C_6$ cycloalkyl), —N($C_1$-$C_4$ alkyl)-($C_3$-$C_6$ cycloalkyl), —$C_1$-$C_6$ alkyl, —($C_0$-$C_4$ alkylene)-heterocyclyl and —($C_0$-$C_4$ alkylene)-heteroaryl; or $R^2$ is optionally substituted $C_5$-$C_6$ heteroaryl. The values for the remaining variables are as defined in the second embodiment, or first through sixth aspects thereof.

In an eighth aspect of the second embodiment:

$R^2$ is —$C(O)$—O—$R^3$, and $R^3$ is selected from ethyl, isopropyl and —$CH_2$-CH=$CH_2$; or $R^2$ is —$C(O)$—$N(R^5)(R^6)$, and $R^5$ and $R^6$ are taken together with the nitrogen atom to which they are commonly attached to form an optionally substituted azetidin-1-yl, pyrrolidin-1-yl, or piperidin-1-yl; or $R^2$ is —$C(O)$—NH—$NH(R^6)$, and $R^6$ is optionally substituted pyridinyl, pyrimidinyl, pyrazinyl or pyridazinyl; or $R^2$ is —$C(O)$—NH—NH—$C(O)$—$R^4$, and $R^4$ is selected from —$C(CH_3)_3$, —NH-cyclopropyl, and optionally substituted —(CH$_2$)$_{0-1}$-pyrazinyl, piperidinyl, —(CH$_2$)$_{0-1}$-morpholinyl, or pyrazolyl; or R$^2$ is optionally substituted oxadiazolyl. The values for the remaining variables are as defined in the second embodiment, or first through seventh aspects thereof R$^2$ is optionally substituted oxadiazolyl. The values for the remaining variables are as defined in the second embodiment, or first through seventh aspects thereof.

In a ninth aspect of the second embodiment, R$^2$ is selected from —C(O)—O—R$^3$, —C(O)—N(R$^5$)(R$^6$), —C(O)—N(R$^7$)—N(R$^5$)(R$^6$), and heteroaryl. The values for the remaining variables are as defined in the second embodiment, or first through eighth aspects thereof.

In a tenth aspect of the second embodiment, Ring A is phenyl. The values for the remaining variables are as defined in the second embodiment, or first through ninth aspects thereof.

In an eleventh aspect of the second embodiment, Ring A is pyridyl. The values for the remaining variables are as defined in the second embodiment, or first through tenth aspects thereof.

In a twelfth aspect of the second embodiment, Ring A is pyrid-2-yl, pyrid-3-yl or pyrid-4-yl. The values for the remaining variables are as defined in the second embodiment, or first through eleventh aspects thereof.

In a thirteenth aspect of the second embodiment, Ring A is pyrid-4-yl. The values for the remaining variables are as defined in the second embodiment, or first through twelfth aspects thereof.

In a fourteenth aspect of the second embodiment, each R$^1$ is independently selected from —CF$_3$, —CN, halo, —OH, C$_1$-C$_3$ alkyl, C$_3$-C$_6$ cycloalkyl, C$_3$-C$_{12}$ heterocycloalkyl, halo-C$_1$-C$_3$ alkyl, —NH$_2$, —NO$_2$, —NH(C$_1$-C$_3$ alkyl), —N(C$_1$-C$_3$ alkyl)(C$_1$-C$_3$ alkyl), —C(O)OH, —C(O)O—(C$_1$-C$_6$ alkyl), —C(O)—(C$_1$-C$_3$ alkyl), —O—(C$_1$-C$_3$ alkyl), —O—(C$_1$-C$_3$ haloalkyl), and —S—(C$_1$-C$_3$ alkyl). The values for the remaining variables are as defined in the second embodiment, or first through thirteenth aspects thereof.

In a fifteenth aspect of the second embodiment:

R$^2$ is —C(O)—O—R$^3$, and R$^3$ is selected from unsubstituted C$_1$-C$_4$ alkyl, C$_1$ alkyl substituted with a 5-6-membered monocyclic heterocyclyl ring having 1-3 heteroatoms independently selected from nitrogen, oxygen and sulfur and C$_2$-C$_4$ alkenyl; or R$^2$ is —C(O)—N(R$^5$)(R$^6$), and R$^5$ and R$^6$ are taken together with the nitrogen atom to which they are commonly attached to form an optionally substituted saturated heterocyclyl; or R$^2$ is —C(O)—NH—NH(R$^6$), and R$^6$ is an optionally substituted heteroaryl; or R$^2$ is —C(O)—NH—NH—C(O)—R$^4$, and R$^4$ is selected from optionally substituted —NH—(C$_3$-C$_6$ cycloalkyl), —N(C$_1$-C$_4$ alkyl)-(C$_3$-C$_6$ cycloalkyl), —C$_1$-C$_6$ alkyl, —(C$_0$-C$_4$ alkylene)-heterocyclyl and —(C$_0$-C$_4$ alkylene)-heteroaryl; or R$^2$ is optionally substituted C$_5$-C$_6$ heteroaryl. The values for the remaining variables are as defined in the second embodiment, or first through fourteenth aspects thereof.

In a third embodiment, the compound is represented by structural formula II:

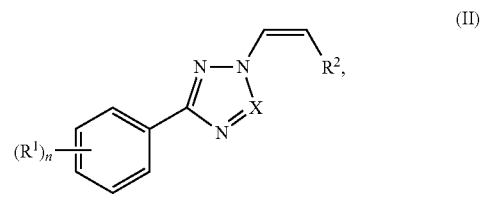

or a pharmaceutically acceptable salt thereof. The values for the variables are as defined in the second embodiment, or any aspect thereof.

In a fourth embodiment, the compound is represented by structural formula III:

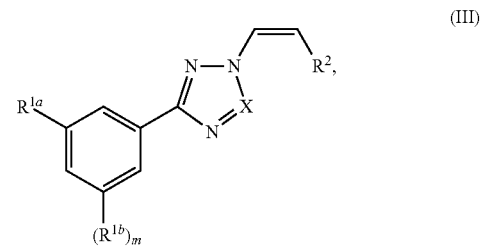

or a pharmaceutically acceptable salt thereof, wherein:

R$^{1a}$ and R$^{1b}$ are each independently selected from halo; haloalkyl; —(CH$_2$)$_{1-4}$R°; —(CH$_2$)$_{0-4}$OR°; —O—(CH$_2$)$_{0-4}$C(O)OR°; —O—(CH═CH)—C(O)O R°; —(CH$_2$)$_{0-4}$CH(OR°)$_2$; —(CH$_2$)$_{0-4}$SR°; —(CH$_2$)$_{0-4}$-carbocyclyl, which may be substituted with R°; —(CH$_2$)$_{0-4}$-aryl, which may be substituted with R°; —(CH$_2$)$_{0-4}$-heterocyclyl, which may be substituted with R°; —(CH$_2$)$_{0-4}$-heteroaryl, which may be substituted with R°; —CH═CH-carbocyclyl, which may be substituted with R°; —CH═CH-aryl, which may be substituted with R°; —CH═CH-heterocyclyl, which may be substituted with R°; —CH═CH-heteroaryl, which may be substituted with R°; —NO$_2$; —CN; —N$_3$; —(CH$_2$)$_{0-4}$N(R°)$_2$; —(CH$_2$)$_{0-4}$N(R°)C(O)R°; —(CH$_2$)$_{0-4}$N(R°)C(S) R°; —(CH$_2$)$_{0-4}$N(R°)C(O)NR°$_2$; —(CH$_2$)$_{0-4}$N(R°)C(S)NR°$_2$; —(CH$_2$)$_{0-4}$N(R°)C(O)OR°; —(CH$_2$)$_{0-4}$N(R°)N(R°)C(O)R°; —(CH$_2$)$_{0-4}$N(R°)N(R°)C(O)NR°$_2$; —(CH$_2$)$_{0-4}$N(R°)N(R°)C(O)OR°; —(CH$_2$)$_{0-4}$C(O)R°; —(CH$_2$)$_{0-4}$C(S)R°; —(CH$_2$)$_{0-4}$C(O)OR°; —(CH$_2$)$_{0-4}$C(O)SR°; —(CH$_2$)$_{0-4}$OC(O)R°; —(CH$_2$)$_{0-4}$OC(O)(CH$_2$)$_{0-4}$SR°, —(CH$_2$)$_{0-4}$SC(S)SR°; —(CH$_2$)$_{0-4}$SC(O)R°; —(CH$_2$)$_{0-4}$C(O)NR°$_2$; —(CH$_2$)$_{0-4}$C(S)NR°$_2$; —(CH$_2$)$_{0-4}$C(S)SR°; —(CH$_2$)$_{0-4}$OC(O)NR°$_2$; —(CH$_2$)$_{0-4}$C(O)N(OR°)R°; —(CH$_2$)$_{0-4}$C(O)C(O)R°: —(CH$_2$)$_{0-4}$C(O)C H$_2$C(O)R°; —(CH$_2$)$_{0-4}$C(NOR°)R°: —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —(CH$_2$)$_{0-4}$S(O)$_2$NR°$_2$; —(CH$_2$)$_{0-4}$S(O)R°; —(CH$_2$)$_{0-4}$N(R°) S(O)$_2$NR°$_2$; —(CH$_2$)$_{0-4}$N(R°)S(O)$_2$R°; —(CH$_2$)$_{0-4}$N(OR°)R°; —(CH$_2$)$_{0-4}$C(NH)NR°$_2$; —(CH$_2$)$_{0-4}$P(O)$_{62}$R°; —(CH$_2$)$_{0-4}$P(O)R°$_2$; —(CH$_2$)$_{0-4}$OP(O)R°$_2$; —(CH$_2$)$_{0-4}$OP(O)(OR°)$_2$; —(CH$_2$)$_{0-4}$ON(R°)$_2$; —(CH$_2$)$_{0-4}$—O—(CH$_2$)$_{1-4}$—N(R°)$_2$; —(CH$_2$)$_{0-4}$—O—(CH$_2$)$_{0-4}$—OR°; and —(CH$_2$)$_{0-4}$C(O)O—N(R°)$_2$; or two R$^1$, taken together with their intervening atoms, form a 3-12-membered carbocyclyl, aryl, heterocyclyl or heteroaryl, wherein:

each R° is independently hydrogen, $C_{1-6}$ aliphatic, —$CH_2$-carbocyclyl, —$CH_2$-aryl, —$CH_2$-heterocyclyl, —$CH_2$-heteroaryl, —O(C$H_2$)$_{0-1}$-carbocyclyl, —O(CH$_2$)$_{0-1}$-aryl, —O(CH$_2$)$_{0-1}$-heterocyclyl, —O(CH$_2$)$_{0-1}$-heteroaryl, carbocyclyl, aryl, heterocyclyl or heteroaryl, or two independent occurrences of R°, taken together with their intervening atom(s), form a 3-12-membered carbocyclyl, aryl, heterocyclyl or heteroaryl; and each R° and each ring formed from two independent occurrences of R°, taken together with their intervening atom(s), are optionally and independently substituted with one or more substituents selected from the group consisting of halo, CN, OH, unsubstituted $C_1$-$C_3$ alkyl, halo-$C_1$-$C_3$ alkyl, —$NH_2$, —$NO_2$, —NH(unsubstituted $C_1$-$C_3$ alkyl), —N(unsubstituted $C_1$-$C_3$ alkyl)$_2$, —O—$C_1$-$C_3$ alkyl, —C(O)OH, —C(O)O-(unsubstituted $C_1$-$C_3$ alkyl), —C(O)-(unsubstituted $C_1$-$C_3$ alkyl), —O-(unsubstituted $C_1$-$C_3$ alkyl), and —S-(unsubstituted $C_1C_3$ alkyl); and m is 0 or 1.

The values for the remaining variables are as defined above for the second embodiment, or first through third, seventh through ninth, or fourteenth aspect thereof.

In a first aspect of the fourth embodiment, $R^{1a}$ is halo or —$C_1$-$C_4$ haloalkyl. The values for the remaining variables are as defined above for the second embodiment, or first through third or seventh through ninth or fourteenth aspect thereof, or the fourth embodiment.

In a second aspect of the fourth embodiment, $R^{1b}$ is —$C_1$-$C_4$ haloalkyl or —O—$C_1$-$C_4$ alkyl, or is absent. The values for the remaining variables are as defined above for the first embodiment, or first through third, seventh through ninth or fourteenth aspect thereof, or the fourth embodiment, or first aspect thereof.

In a third aspect of the fourth embodiment, m is 0. The values for the remaining variables are as defined above for the second embodiment, or first through third, seventh through ninth or fourteenth aspect thereof, or the fourth embodiment, or first or second aspect thereof.

In a fourth aspect of the fourth embodiment, m is 1. The values for the remaining variables are as defined above for the second embodiment, or first through third, seventh through ninth or fourteenth aspect thereof, or the fourth embodiment, or first through third aspects thereof.

In a fifth aspect of the fourth embodiment, $R^{1a}$ and $R^{1b}$ are each independently selected from —$CF_3$, —CN, halo, —OH, $C_1$-$C_3$ alkyl, $C_3$-$C_6$ cycloalkyl, $C_3$-$C_{12}$ heterocycloalkyl, halo-$C_1$-$C_3$ alkyl, —$NH_2$, —$NO_2$, —NH($C_1$-$C_3$ alkyl), —N($C_1$-$C_3$ alkyl)($C_1$-$C_3$ alkyl), —C(O)OH, —C(O)O—($C_1$-$C_6$ alkyl), —C(O)—($C_1$-$C_3$ alkyl), —O—($C_1$-$C_3$ alkyl), —O—($C_1$-$C_3$ haloalkyl), and —S—($C_1$-$C_3$ alkyl). The values for the remaining variables are as defined above for the second embodiment, or first through third, seventh through ninth or fourteenth aspect thereof, or the fourth embodiment, or first through fourth aspects thereof.

In a sixth aspect of the fouth embodiment, $R^{1a}$ and $R^{1b}$ are each —$CF_3$. The values for the remaining variables are as defined above for the second embodiment, or first through third, seventh through ninth or fourteenth aspect thereof, or the fourth embodiment, or first through fifth aspects thereof.

In a seventh aspect of the fourth embodiment:
$R^2$ is —C(O)—O—$R^3$, and $R^3$ is selected from unsubstituted $C_1$-$C_4$ alkyl, $C_1$ alkyl substituted with a 5-6-membered monocyclic heterocyclyl ring having 1-3 heteroatoms independently selected from nitrogen, oxygen and sulfur and $C_2$-$C_4$ alkenyl; or $R^2$ is —C(O)—N($R^5$)($R^6$), and $R^5$ and $R^6$ are taken together with the nitrogen atom to which they are commonly attached to form an optionally substituted saturated heterocyclyl; or $R^2$ is —C(O)—NH—NH($R^6$), and $R^6$ is an optionally substituted heteroaryl; or $R^2$ is —C(O)—NH—NH—C(O)—$R^4$, and $R^4$ is selected from optionally substituted —NH—($C_3$-$C_6$ cycloalkyl), —N($C_1$-$C_4$ alkyl)-($C_3$-$C_6$ cycloalkyl), —$C_1$-$C_6$ alkyl, —($C_0$-$C_4$ alkylene)-heterocyclyl and —($C_0$-$C_4$ alkylene)-heteroaryl; or $R^2$ is optionally substituted $C_5$-$C_6$ heteroaryl. The values for the remaining variables are as defined above for the second embodiment, or first through third, seventh through ninth or fourteenth aspect thereof, or the fourth embodiment, or first through sixth aspects thereof.

In a fifth embodiment of the invention, the compound is represented by structural formula (IV):

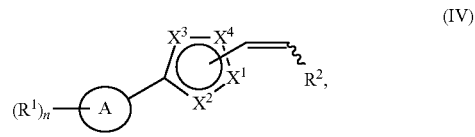

(IV)

or a pharmaceutically acceptable salt therof, wherein:
Ring A is phenyl or pyridyl;
each of $X^1$, $X^2$, $X^3$ and $X^4$, is independently —N—, —N(H)—, —(C)— or —C(H)—, wherein at least one of $X^1$, $X^2$, $X^3$ and $X^4$ is —N— or —NH—;
each $R^1$ is independently selected from halo; haloalkyl; —(CH$_2$)$_{1-4}$R°; —(CH$_2$)$_{0-4}$OR°; —O—(CH$_2$)$_{0-4}$C(O)OR°; —O—(CH=CH)—C(O)OR°; —(CH$_2$)$_{0-4}$CH(OR°)$_2$; —(CH$_2$)$_{0-4}$SR°; —(CH$_2$)$_{0-4}$-carbocyclyl, which may be substituted with R°; —(CH$_2$)$_{0-4}$-aryl, which may be substituted with R°; —(CH$_2$)$_{0-4}$-heterocyclyl, which may be substituted with R°; —(CH$_2$)$_{0-4}$-heteroaryl, which may be substituted with R°; —CH=CH-carbocyclyl, which may be substituted with R°; —CH=CH-aryl, which may be substituted with R°; —CH=CH-heterocyclyl, which may be substituted with R°; —CH=CH-heteroaryl, which may be substituted with R°; —$NO_2$; —CN; —$N_3$; —(CH$_2$)$_{0-4}$N(R°)$_2$; —(CH$_2$)$_{0-4}$N(R°)C(O)R°; —(CH$_2$)$_{0-4}$N(R°)C(S)R°; —(CH$_2$)$_{0-4}$N(R°)C(O)NR°$_2$; —(CH$_2$)$_{0-4}$N(R°)C(S) NR°$_2$; —(CH$_2$)$_{0-4}$N(R°)C(O)OR°; —(CH$_2$)$_{0-4}$N(R°)N(R°)C(O)R°; —(CH$_2$)$_{0-4}$N(R°)N(R°)C(O) NR°$_2$; —(CH$_2$)$_{0-4}$N(R°)N(R°)C(O)O R°; —(CH$_2$)$_{0-4}$C(O)R°; —(CH$_2$)$_{0-4}$C(S)R°; —(CH$_2$)$_{0-4}$C(O)OR°; —(CH$_2$)$_{0-4}$C(O)SR°; —(CH$_2$)$_{0-4}$OC(O)R°; —(CH$_2$)$_{0-4}$OC(O)(CH$_2$)$_{0-4}$SR°; —(CH$_2$)$_{0-4}$SC(S)SR°; —(CH$_2$)$_{0-4}$SC(O)R°; —(CH$_2$)$_{0-4}$C(O)NR°$_2$; —(CH$_2$)$_{0-4}$C(S)NR°$_2$; —(CH$_2$)$_{0-4}$C(S)SR°; —(CH$_2$)$_{0-4}$OC(O)NR°$_2$; —(CH$_2$)$_{0-4}$C(O)N(OR°)R°; —(CH$_2$)$_{0-4}$C(O)C(O)R°: —(CH$_2$)$_{0-4}$C(O)CH$_2$C(O)R°; —(CH$_2$)$_{0-4}$C(NOR°)R°: —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —(CH$_2$)$_{0-4}$S(O)$_2$NR°$_2$; —(CH$_2$)$_{0-4}$S(O)R°; —(CH$_2$)$_{0-4}$N(R°)S(O)$_2$NR°$_2$; —(CH$_2$)$_{0-4}$N(R°)S(O)$_2$R°; —(CH$_2$)$_{0-4}$N(OR°)R°; —(CH$_2$)$_{0-4}$C(NH)NR°$_2$; —(CH$_2$)$_{0-4}$P(O)$_2$R°; —(CH$_2$)$_{0-4}$P(O)R°$_2$; —(CH$_2$)$_{0-4}$OP(O)R°$_2$; —(CH$_2$)$_{0-4}$OP(O)(OR°)$_2$; —(CH$_2$)$_{0-4}$ON (R°)$_2$; —(CH$_2$)$_{0-4}$—O—(CH$_2$)$_{1-4}$—N(R°)$_2$; —(CH$_2$)$_{0-4}$—O—(CH$_2$)$_{0-4}$—OR°; and —(CH$_2$)$_{0-4}$C(O)O—N(R°)$_2$; or two R$^1$, taken together with their intervening atoms, form a 3-12-membered carbocyclyl, aryl, heterocyclyl or heteroaryl, wherein:
each R° is independently hydrogen,
C$_{1-6}$ aliphatic, —CH$_2$-carbocyclyl, —CH$_2$-aryl, —CH$_2$-heterocyclyl, —CH$_2$-heteroaryl, —O(CH$_2$)$_{0-1}$-carbocyclyl, —O(CH$_2$)$_{0-1}$-aryl, —O(CH$_2$)$_{0-1}$-heterocyclyl, —O(CH$_2$)$_{0-1}$-heteroaryl, carbocyclyl, aryl, heterocyclyl or heteroaryl, or two independent occurrences of R°, taken together with their intervening atom(s), form a 3-12-membered carbocyclyl, aryl, heterocyclyl or heteroaryl; and
each R° and each ring formed from two independent occurrences of R°, taken together with their intervening atom(s), are optionally and independently substituted with one or more substituents selected from the group consisting of halo, CN, OH, unsubstituted C$_1$-C$_3$ alkyl, halo-C$_1$-C$_3$ alkyl, —NH$_2$, —NO$_2$, —NH(unsubstituted C$_1$-C$_3$ alkyl), —N(unsubstituted C$_1$-C$_3$ alkyl)$_2$, —O—C$_1$-C$_3$ alkyl, —C(O)OH, —C(O)O-(unsubstituted C$_1$-C$_3$ alkyl), —C(O)-(unsubstituted C$_1$-C$_3$ alkyl), —O-(unsubstituted C$_1$-C$_3$ alkyl), and —S-(unsubstituted C$_1$-C$_3$ alkyl);

R$^2$ is selected from
—C(O)—O—R$^3$, —C(O)—N(R$^5$)(R$^6$), —C(O)—N(R$^7$)—N(R$^5$)(R$^6$), —CN, —CF$_3$, —S(O)$_{1-2}$(C$_1$-C$_4$ alkyl), and heteroaryl, wherein:
R$^3$ is selected from C$_1$-C$_4$ alkyl, C$_2$-C$_4$ alkenyl, C$_2$-C$_4$ alkynyl, carbocyclyl, aryl, heterocyclyl and heleroaryl;
R$^4$ is selected from —NH—(C$_3$-C$_6$ cycloalkyl), —N(C$_1$-C$_4$ alkyl)-(C$_3$-C$_6$ cycloalkyl), —C$_1$-C$_6$ alkyl, —(C$_0$-C$_4$ alkylene)-carbocyclyl, —(C$_0$-C$_4$ alkylene)-heterocyclyl, —(C$_0$-C$_4$ alkylene)-aryl, and —(C$_0$-C$_4$ alkylene)-heteroaryl;
R$^5$ and R$^6$ are each independently selected from hydrogen, C$_1$-C$_4$ alkyl C$_2$-C$_4$ alkenyl, C$_2$-C$_4$ alkynyl, carbocyclyl, aryl, heterocyclyl and heleroaryl; or
R$^5$ and R$^6$ are taken together with the nitrogen atom to which they are commonly attached to form a heterocyclyl or heteroaryl;
each R$^7$ is independently hydrogen or C$_1$-C$_4$ alkyl; and
n is 0, 1, 2, 3, 4 or 5, wherein, unless otherwise designated, each alkyl, alkenyl, alkynyl, alkylene, carbocyclyl, aryl, cycloalkyl, heterocyclyl and heteroaryl is optionally and independently substituted.

In a first aspect of the fifth embodiment, the compound is represented by structural formula (V):

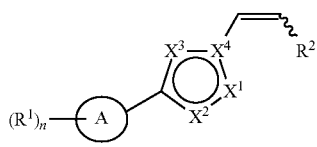

(V)

or a pharmaceutically acceptable salt thereof, wherein X$^4$ is —N— or —C—. The values for the remaining variables are as defined above for the second through fourth embodiments, or any aspect thereof.

In a second aspect of the fifth embodiment, X$^4$ is —C—. The values for the remaining variables are as defined above for the second through fourth embodiments, or any aspect thereof, or the fifth embodiment, or first aspect thereof.

In a third aspect of the fifth embodiment, one of X$^1$, X$^2$ and X$^3$ is —N(H)—, and the remaining two are each —N—. The values for the remaining variables are as defined above for the second through fourth embodiments, or any aspect thereof, or the fifth embodiment, or first or second aspect thereof.

In a fourth aspect of the fifth embodiment, X$^1$ is —N—, X$^2$ is —N(H)—, X$^3$ is —N—, and X$^4$ is —C—. The values for the remaining variables are as defined above for the second through fourth embodiments, or any aspect thereof, or the fifth embodiment, or first through third aspects thereof.

In a fifth aspect of the fifth embodiment, X$^1$ is —N—, X$^2$ is —N—, X$^3$ is —N(H)—, and X$^4$ is —C—. The values for the remaining variables are as defined above for the second through fourth embodiments, or any aspect thereof, or the fifth embodiment, or first through fourth aspects thereof.

In a sixth aspect of the fifth embodiment, X$^4$ is —N—. The values for the remaining variables are as defined above for the second through fourth embodiments, or any aspect thereof, or the fifth embodiment, or first through fifth aspects thereof.

In a seventh aspect of the fifth embodiment, the ring represented by

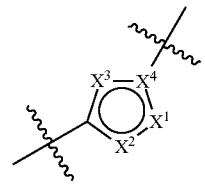

in structural formula (V) is selected from:

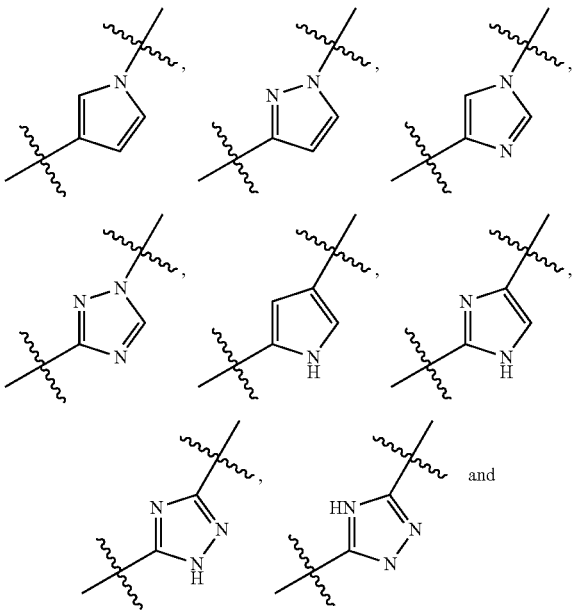

-continued

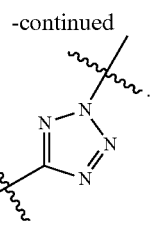

The values for the remaining variables are as defined above for the second through fourth embodiments, or any aspect thereof, or the fifth embodiment, or first through sixth aspects thereof.

In an eighth aspect of the fifth embodiment, the ring represented by

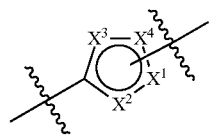

in structural formula (IV) is selected from:

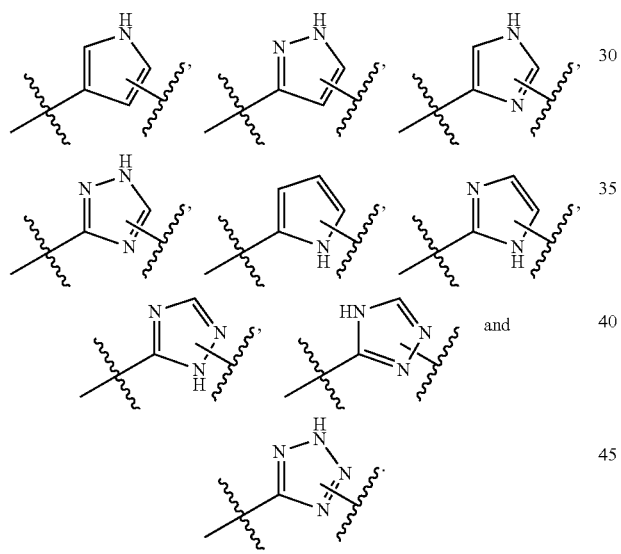

The values for the remaining variables are as defined above for the second through fourth embodiments, or any aspect thereof, or the fifth embodiment, or first through seventh aspects thereof.

In a sixth embodiment of the invention, the compound is represented by structural formula (I), (II), (III), (IV) or (V), or a pharmaceutically acceptable salt thereof, wherein $R^2$ is —C(O)OR$^3$. The values for the remaining variables are as defined above for the second through fifth embodiments, or any aspect thereof.

In a first aspect of the sixth embodiment, $R^3$ —CH(CH$_3$)$_2$. The values for the remaining variables are as defined above for the second through fifth embodiments, or any aspect thereof, or the sixth embodiment.

In a second aspect of the sixth embodiment, $R^3$ is —CH$_2$- (5-6 membered monocyclic heterocyclic ring having 1-3 heteroatoms independently selected from nitrogen, oxygen and sulfur). The values for the remaining variables are as defined above for the second through fifth embodiments, or any aspect thereof, or the sixth embodiment, or first aspect thereof.

In a third aspect of the sixth embodiment, $R^3$ is —CH$_2$-(6 membered monocyclic heterocyclic ring having 1-3 nitrogen atoms). The values for the remaining variables are as defined above for the second through fifth embodiments, or any aspect thereof, or the sixth embodiment, or first or second aspect thereof.

In a fourth aspect of the sixth embodiment, the compound is represented by structural formula (VI):

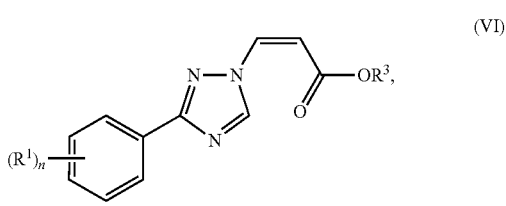

(VI)

or a pharmaceutically acceptable salt thereof, wherein the values for $R^1$, $R^3$ and n are as defined above for the second through fifth embodiments, or any aspect thereof, or the sixth embodiment, or first through third aspects thereof.

In a fifth aspect of the sixth embodiment, the compound is represented by structural formula (VII):

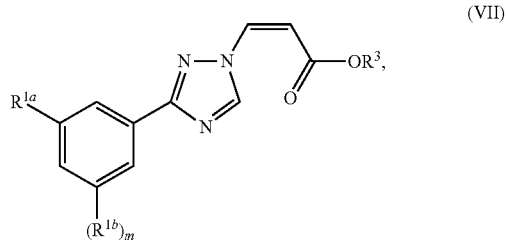

(VII)

or a pharmaceutically acceptable salt thereof, wherein the values for $R^{1a}$, $R^{1b}$, m and $R^3$ are as defined above for the second through fifth embodiments, or any aspect thereof, or the sixth embodiment, or first through fourth aspects thereof.

In a seventh embodiment of the invention, the compound is represented by structural formula (I), (II), (III), (IV) or (V), or a pharmaceutically acceptable salt thereof, wherein $R^2$ is —C(O)—N(R$^5$)(R$^6$). The values for the remaining variables are as defined above for the second through fifth embodiments, or any aspect thereof.

In a first aspect of the seventh embodiment, $R^5$ and $R^6$ are taken together with their intervening atoms to form an optionally substituted 4-8 membered saturated, partially unsaturated, or aromatic heterocyclic ring having 1-3 heteroatoms independently selected from nitrogen, oxygen, and sulfur. The values for the remaining variables are as defined above for the second through fifth embodiments, or any aspect thereof, or the seventh embodiment.

In a second aspect of the seventh embodiment, $R^5$ and $R^6$ are taken together with their intervening atoms to form an optionally substituted 4-8 membered saturated, partially unsaturated, or aromatic heterocyclic ring having 1-3 heteroatoms independently selected from nitrogen, oxygen, and sulfur optionally substituted with one or two substituents independently selected from halo, (C$_1$-C$_3$)haloalkyl, ($C_1$-$C_3$)alkyl, —OH, pyridin-2-yl, —$CH_2$—N($C_1$-$C_3$ alkyl)$_2$, —$CH_2$—NH($C_1$-$C_3$ alkyl), —$CH_2$-$NH_2$, —CN, —$CO_2H$ and —C(O)—O—($C_1$-$C_3$ alkyl). The values for the remaining variables are as defined above for the second through fifth embodiments, or any aspect thereof, or the seventh embodiment, or first aspect thereof.

In a third aspect of the seventh embodiment, the 4-8 membered saturated heterocyclic ring formed by $R^5$, $R^6$ and their intervening atoms is an azetidin-1-yl ring optionally substituted at the 3-position with one or two substituents independently selected from halo, ($C_1$-$C_3$)haloalkyl, ($C_1$-$C_3$) alkyl, —OH, pyridin-2-yl, —$CH_2$—N($C_1$-$C_3$ alkyl)$_2$, —$CH_2$—NH($C_1$-$C_3$ alkyl), —$CH_2$—$NH_2$, —CN, —$CO_2H$ and —C(O)—O—($C_1$-$C_3$ alkyl). The values for the remaining variables are as defined above for the second through fifth embodiments, or any aspect thereof, or the seventh embodiment, or first or second aspect thereof.

In a fourth aspect of the seventh embodiment, the 4-8 membered saturated heterocyclic ring formed by $R^5$, $R^6$ and their intervening atoms is an azetidin-1-yl ring substituted at the 3-position with two fluoro substituents. The values for the remaining variables are as defined above for the second through fifth embodiments, or any aspect thereof, or the seventh embodiment, or first through third aspects thereof.

In a fifth aspect of the seventh embodiment, $R^5$ is hydrogen and $R^6$ is selected

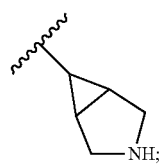 [SMILES: *C1C2CNCC12]

from —$CH_2$-oxazol-5-yl, —$CH_2$-pyrimidin-5-yl, —$CH_2$-(1-methylpyrrolidin-3-yl), or or $R^5$ and $R^6$ are taken together with the nitrogen atom to which they are bound to form

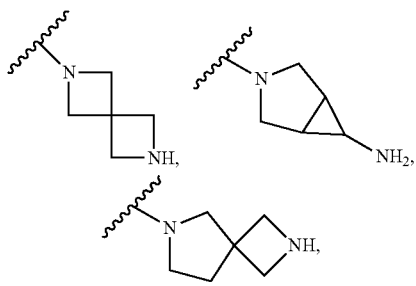

4-hydroxypiperidin-1-yl, pyrrolidiny-1-yl, or azetidin-1-yl, wherein the pyrrolidiny-1-yl and azetidin-1-yl are each optionally and independently substituted at the 3-position with up to two substituents independently selected from fluoro, —$CF_3$, —$CH_3$, —OH, pyridin-2-yl, —$CH_2$—N($CH_3$)$_2$, —$CH_2$—NH—$CH_3$, —$CH_2$—$NH_2$, —CN and —C(O)—O—$CH_3$. The values for the remaining variables are as defined above for the second through fifth embodiments, or any aspect thereof, or the seventh embodiment, or first through fourth aspects thereof.

In a sixth aspect of the seventh embodiment, the compound is represented by structural formula (VIII):

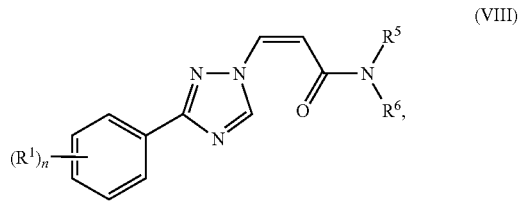

or a pharmaceutically acceptable salt thereof, wherein the values for $R^1$, $R^5$, $R^6$ and n are as defined above for the second through fifth embodiments, or any aspect thereof, or the seventh embodiment, or first through fifth aspects thereof.

In a seventh aspect of the seventh embodiment, the compound is represented by structural formula (IX):

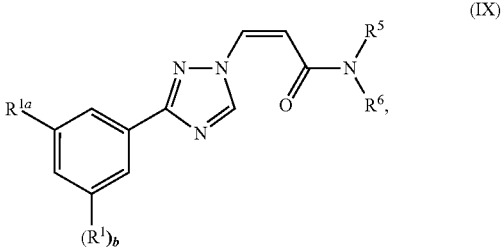

or a pharmaceutically acceptable salt thereof, wherein the values for $R^{1a}$, $R^{1b}$, $R^5$, $R^6$ and m are as defined above for the second through fifth embodiments, or any aspect thereof, or the seventh embodiement, or first through sixth aspects thereof.

In an eighth embodiment of the invention, the compound is represented by structural formula (I), (II), (III), (IV) or (V), or a pharmaceutically acceptable salt thereof, wherein $R^2$ is —C(O)—N($R^7$)—N($R^5$)($R^6$). The values for the remaining variables are as defined above for the second through fifth embodiments, or any aspect thereof.

In a first aspect of the eighth embodiment, $R^2$ is —C(O)—N(H)—N($R^5$)($R^6$) wherein $R^5$ is hydrogen or methyl and $R^6$ is an optionally substituted 5-6-membered heteroaryl; or $R^5$ and $R^6$ are taken together with the nitrogen atom to which they are commonly attached to form an optionally substituted 4-7-membered heterocyclyl. The values for the remaining variables are as defined above for the second through fifth embodiments, or any aspect thereof, or the eighth embodiment.

In a second aspect of the eighth embodiment, $R^2$ is —C(O)—N(H)—N($R^5$)($R^6$) wherein $R^5$ is hydrogen or methyl and $R^6$ is an optionally substituted 5-6-membered heteroaryl having at least one nitrogen atom and, optionally, 1-3 additional heteroatoms selected from nitrogen, oxygen and sulfur; or $R^5$ and $R^6$ are taken together with the nitrogen atom to which they are commonly attached to form an optionally substituted 4-6-membered heterocyclyl. The values for the remaining variables are as defined above for the second through fifth embodiments, or any aspect thereof, or the eighth embodiment, or first aspect thereof.

In a third aspect of the eighth embodiment, $R^2$ is —C(O)—N(H)—N($R^5$)($R^6$) wherein $R^5$ is hydrogen or methyl and $R^6$ is an optionally substituted 5-6-membered heteroaryl having 1-3 nitrogen atoms; or $R^5$ and $R^6$ are taken together with the nitrogen atom to which they are commonly attached to form an optionally substituted 4-6-membered heterocyclyl. The values for the remaining variables are as defined above for the second through fifth embodiments, or any aspect thereof, or the eighth embodiment, or first or second aspect thereof.

In a fourth aspect of the eighth embodiment, $R^2$ is —C(O)—N(H)—N($R^5$)($R^6$) wherein $R^5$ is selected from hydrogen and methyl and $R^6$ is selected from pyridin-2-yl, pyridin-3-yl, pyridin-4-yl, pyrazin-2-yl, and quinoxalin-2-yl, pyrimidin-4-yl, 1,1-dioxotetrahydrothiophen-3-yl and cyclopropyl and is optionally substituted with one or more substituents independently selected from methyl and halogen; or $R^5$ and $R^6$ are taken together with their intervening atoms to form 4-hydroxypiperidin-1-yl, pyrrolidin-1-yl, azepan-1-yl, 4-benzylpiperazin-1-yl, 4-ethylpiperazin-1-yl, 3-hydroxyazetidin-1-yl, or morpholin-4-yl. The values for the remaining variables are as defined above for the second through fifth embodiments, or any aspect thereof, or the eighth embodiment, or first through third aspects thereof.

In a fifth aspect of the eighth embodiment, $R^2$ is —C(O)—N(H)—N($R^5$)($R^6$) wherein $R^5$ is selected from hydrogen and methyl and $R^6$ is selected from pyridin-2-yl, pyridin-4-yl, pyrazin-2-yl and pyrimidin-4-yl and is optionally substituted with a single substituent selected from methyl and chloro; or $R^5$ and $R^6$ are taken together to form 4-hydroxypiperdin-1-yl. The values for the remaining variables are as defined above for the second through fifth embodiments, or any aspect thereof, or the eighth embodiment, or first through fourth aspects thereof.

In a sixth aspect of the eighth embodiment, the compound is represented by structural formula (X):

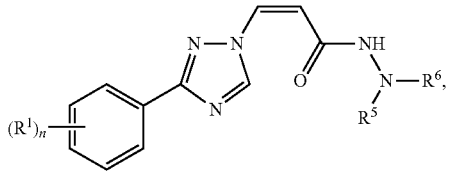

(X)

or a pharmaceutically acceptable salt thereof, wherein the values for $R^1$, $R^5$, $R^6$ and n are as defined above for the second through fifth embodiments, or any aspect thereof, or the eighth embodiment, or first through fifth aspects thereof.

In a seventh aspect of the eighth embodiment, the compound is represented by structural formula (XI):

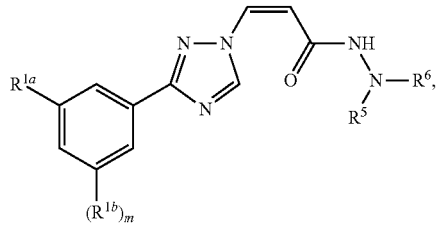

(XI)

or a pharmaceutically acceptable salt thereof, wherein the values for $R^{1a}$, $R^{1b}$, $R^5$, $R^6$ and m are as defined above for the second through fifth embodiments, or any aspect thereof, or the eighth embodiment, or first through sixth aspects thereof.

In a ninth embodiment of the invention, the compound is represented by structural formula (I), (II), (III), (IV) or (V), or a pharmaceutically acceptable salt thereof, wherein $R^2$ is optionally substituted heteroaryl. The values for the remaining variables are as defined above for the second through fifth embodiments, or any aspect thereof.

In a first aspect of the ninth embodiment, $R^2$ is an optionally substituted 5-6 membered heteroaryl ring having at least one nitrogen atom and, optionally, 1-3 additional heteroatoms selected from nitrogen, oxygen and sulfur. The values for the remaining variables are as defined above for the second through fifth embodiments, or any aspect thereof, or the ninth embodiment.

In a second aspect of the ninth embodiment, $R^2$ is an optionally substituted 5-membered heteroaryl ring having at least one nitrogen atom and, optionally, 1-3 additional heteroatoms selected from nitrogen, oxygen and sulfur. The values for the remaining variables are as defined above for the second through fifth embodiments, or any aspect thereof, or the ninth embodiment, or first aspect thereof.

In a third aspect of the ninth embodiment, $R^2$ is an optionally substituted 6-membered heteroaryl ring having at least one nitrogen atom and, optionally, 1-3 additional heteroatoms selected from nitrogen, oxygen and sulfur. The values for the remaining variables are as defined above for the second through fifth embodiments, or any aspect thereof, or the ninth embodiment, or first or second aspect thereof.

In a fourth aspect of the ninth embodiment, $R^2$ is a heteroaryl (e.g., a $C_5$-$C_6$ heteroaryl or a 5-6 membered heteroaryl ring having at least one nitrogen atom and, optionally, 1-3 additional heteroatoms selected from nitrogen, oxygen and sulfur) optionally substituted with one or more substituents selected from the group consisting of ($C_1$-$C_3$)alkyl, ($C_3$-$C_7$)cycloalkyl, ($C_3$-$C_7$)heterocyclyl, cyano, ($C_1$-$C_3$)haloalkyl, halogen, nitro, ($C_1$-$C_3$)haloalkoxy and ($C_1$-$C_3$)alkoxy. The values for the remaining variables are as defined above for the second through fifth embodiments, or any aspect thereof, or the ninth embodiment, or first or second aspect thereof.

Exemplary compounds for use in the methods of the invention are set forth in Tables 1A-1D.

TABLE 1A

| Example | Structure | Name |
|---|---|---|
| 1 | 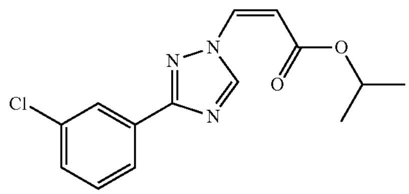 [SMILES: CC(C)OC(=O)/C=C\n1cnc(-c2cccc(Cl)c2)n1] | (Z)-3-[3-(3-Chloro-phenyl)-[1,2,4]-triazolo-1-yl]-acrylic acid isopropyl ester |
| 2 | 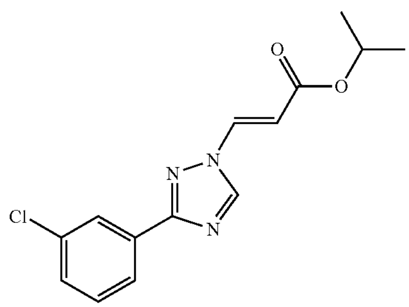 [SMILES: CC(C)OC(=O)/C=C/n1cnc(-c2cccc(Cl)c2)n1] | (E)-3-[3-(3-Chloro-phenyl)-[1,2,4]-triazol-1-yl]-acrylic acid isopropyl ester |
| w3 | 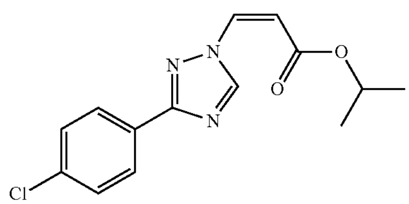 [SMILES: CC(C)OC(=O)/C=C\n1cnc(-c2ccc(Cl)cc2)n1] | (Z)-isopropyl 3-(3-(4-chlorophenyl)-1H-1,2,4-triazol-1-yl)acrylate |
| 4 | 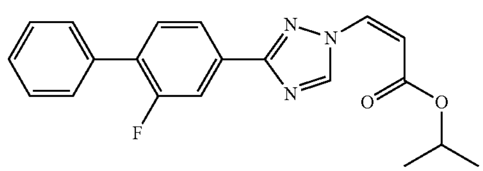 [SMILES: CC(C)OC(=O)/C=C\n1cnc(-c2ccc(-c3ccccc3)c(F)c2)n1] | (Z)-isopropyl 3-(3-(2-fluoro-[1,1'-biphenyl]-4-yl)-1H-1,2,4-triazol-1-yl)acrylate |
| 5 | 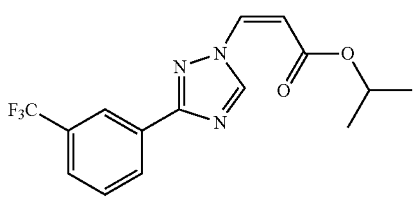 [SMILES: CC(C)OC(=O)/C=C\n1cnc(-c2cccc(C(F)(F)F)c2)n1] | (Z)-isopropyl 3-(3-(3-(trifluoromethyl)phenyl)-1H-1,2,4-triazol-1-yl)acrylate |
| 6 | 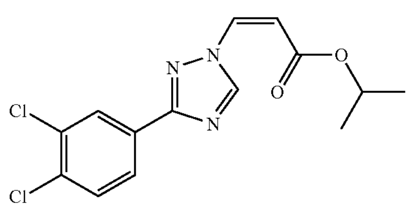 [SMILES: CC(C)OC(=O)/C=C\n1cnc(-c2ccc(Cl)c(Cl)c2)n1] | (Z)-isopropyl 3-(3-(3,4-dichlorophenyl)-1H-1,2,4-triazol-1-yl)acrylate |
| 7 | 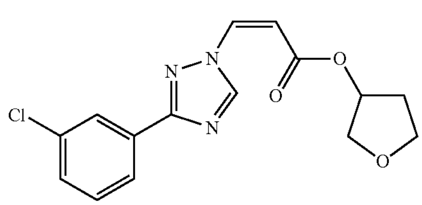 [SMILES: O=C(/C=C\n1cnc(-c2cccc(Cl)c2)n1)OC1CCOC1] | (Z)-tetrahydrofuran-3-yl 3-(3-(3-chlorophenyl)-1H-1,2,4-triazol-1-yl)acrylate |

TABLE 1A-continued

Exemplary Compounds.

| Example | Structure | Name |
|---|---|---|
| 8 | 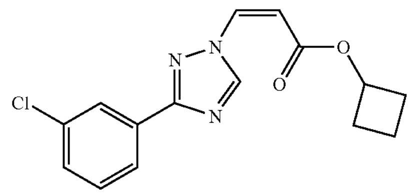 [SMILES: O=C(/C=C\n1cnc(-c2cccc(Cl)c2)n1)OC1CCC1] | (Z)-cyclobutyl 3-(3-(3-chlorophenyl)-1H-1,2,4-triazol-1-yl)acrylate |
| 9 | 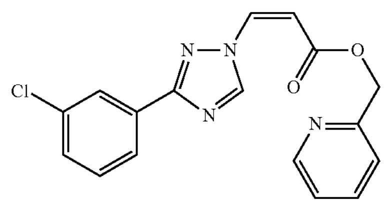 [SMILES: O=C(/C=C\n1cnc(-c2cccc(Cl)c2)n1)OCc1ccccn1] | (Z)-pyridin-2-ylmethyl 3-(3-(3-chlorophenyl)-1H-1,2,4-triazol-1-yl)acrylate |
| 10 | 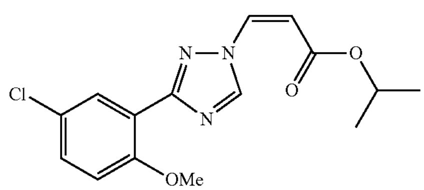 [SMILES: COc1ccc(Cl)cc1-c1ncn(/C=C\C(=O)OC(C)C)n1] | (Z)-isopropyl 3-(3-(5-chloro-2-methoxyphenyl)-1H-1,2,4-triazol-1-yl)acrylate |
| 11 | 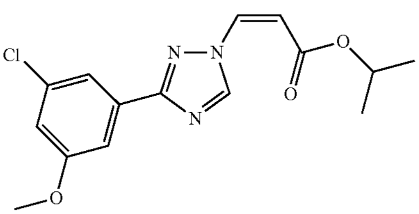 [SMILES: COc1cc(Cl)cc(-c2ncn(/C=C\C(=O)OC(C)C)n2)c1] | (Z)-isopropyl 3-(3-(3-chloro-5-methoxyphenyl)-1H-1,2,4-triazol-1-yl)acrylate |
| 12 | 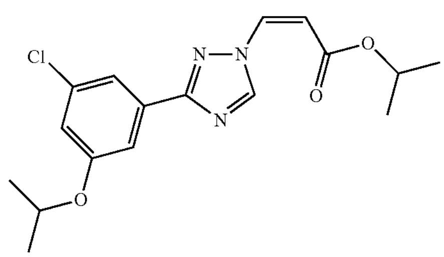 [SMILES: CC(C)OC(=O)/C=C\n1cnc(-c2cc(Cl)cc(OC(C)C)c2)n1] | (Z)-isopropyl 3-(3-(3-chloro-5-isopropoxyphenyl)-1H-1,2,4-triazol-1-yl)acrylate |
| 13 | 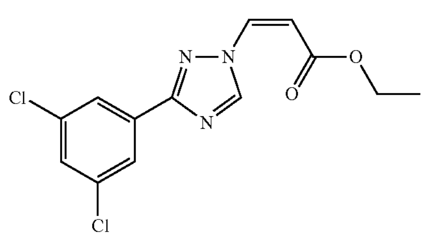 [SMILES: CCOC(=O)/C=C\n1cnc(-c2cc(Cl)cc(Cl)c2)n1] | (Z)-3-[3-(3,5-Dichloro-phenyl)-[1,2,4]triazol-1-yl]-acrylic acid ethyl ester |
| 14 | 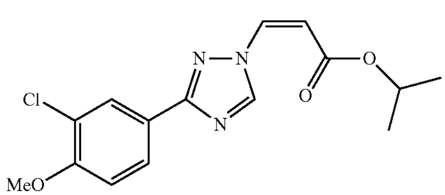 [SMILES: COc1ccc(-c2ncn(/C=C\C(=O)OC(C)C)n2)cc1Cl] | (Z)-isopropyl 3-(3-(3-chloro-4-methoxyphenyl)-1H-1,2,4-triazol-1-yl)acrylate |

TABLE 1A-continued

Exemplary Compounds.

| Example | Structure | Name |
|---|---|---|
| 15 | 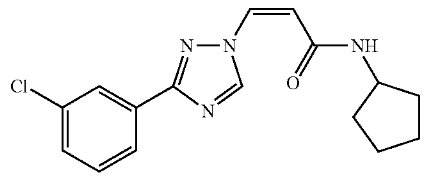 [SMILES: O=C(/C=C\n1cnc(-c2cccc(Cl)c2)n1)NC1CCCC1] | (Z)-3-(3-(3-chlorophenyl)-1H-1,2,4-triazol-1-yl)-N-cyclopentylacrylamide |
| 16 | 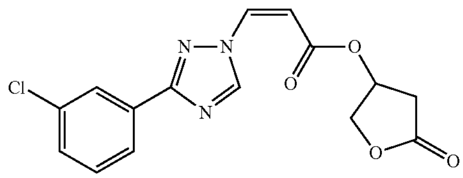 [SMILES: O=C(/C=C\n1cnc(-c2cccc(Cl)c2)n1)OC1COC(=O)C1] | (Z)-5-oxotetrahydrofuran-3-yl 3-(3-(3-chlorophenyl)-1H-1,2,4-triazol-1-yl)acrylate |
| 17 | 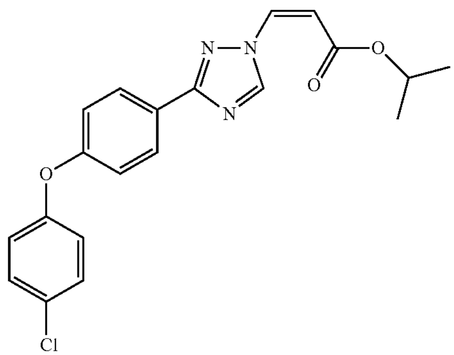 [SMILES: CC(C)OC(=O)/C=C\n1cnc(-c2ccc(Oc3ccc(Cl)cc3)cc2)n1] | (Z)-isopropyl 3-(3-(4-(4-chlorophenoxy)phenyl)-1H-1,2,4-triazol-1-yl)acrylate |
| 18 | 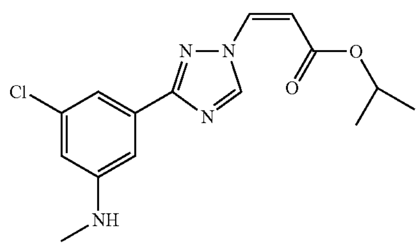 [SMILES: CNc1cc(Cl)cc(-c2ncn(/C=C\C(=O)OC(C)C)n2)c1] | (Z)-isopropyl 3-(3-(3-chloro-5-(methylamino)phenyl)-1H-1,2,4-triazol-1-yl)acrylate |
| 19 | 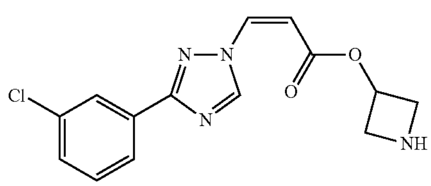 [SMILES: O=C(/C=C\n1cnc(-c2cccc(Cl)c2)n1)OC1CNC1] | (Z)-azetidin-3-yl 3-(3-(3-chlorophenyl)-1H-1,2,4-triazol-1-yl)acrylate |
| 20 | 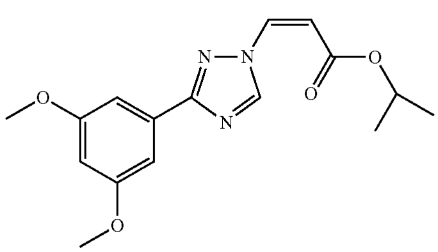 [SMILES: COc1cc(OC)cc(-c2ncn(/C=C\C(=O)OC(C)C)n2)c1] | (Z)-isopropyl 3-(3-(3,5-dimethoxyphenyl)-1H-1,2,4-triazol-1-yl)acrylate |

TABLE 1A-continued

Exemplary Compounds.

| Example | Structure | Name |
|---|---|---|
| 21 | 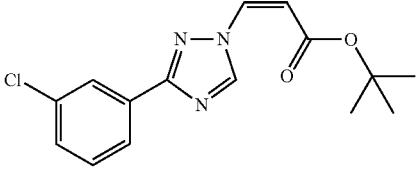 [SMILES: CC(C)(C)OC(=O)/C=C\n1cnc(-c2cccc(Cl)c2)n1] | (Z)-tert-butyl 3-(3-(3-chlorophenyl)-1H-1,2,4-triazol-1-yl)acrylate |
| 22 | 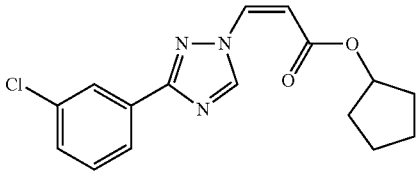 [SMILES: O=C(/C=C\n1cnc(-c2cccc(Cl)c2)n1)OC1CCCC1] | (Z)-cyclopentyl 3-(3-(3-chlorophenyl)-1H-1,2,4-triazol-1-yl)acrylate |
| 23 | 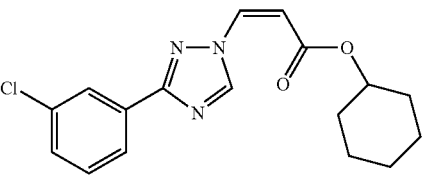 [SMILES: O=C(/C=C\n1cnc(-c2cccc(Cl)c2)n1)OC1CCCCC1] | (Z)-cyclohexyl 3-(3-(3-chlorophenyl)-1H-1,2,4-triazol-1-yl)acrylate |
| 24 | 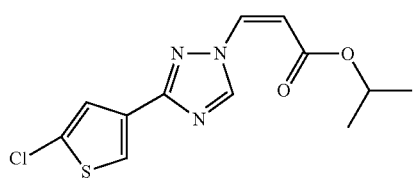 [SMILES: CC(C)OC(=O)/C=C\n1cnc(-c2csc(Cl)c2)n1] | (Z)-isopropyl 3-(3-(5-chorothiophen-3-yl)-1H-1,2,4-triazol-1-yl)acrylate |
| 25 | 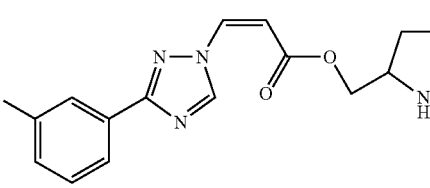 | (Z)-pyrrolidin-2-ylmethyl 3-(3-(3-chlorophenyl)-1H-1,2,4-triazol-1-yl)acrylate |
| 26 | 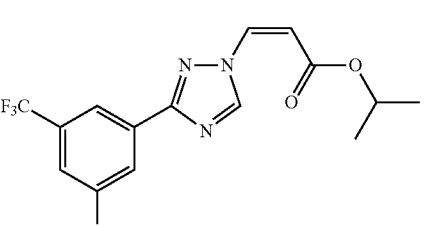 | (Z)-isopropyl 3-(3-(3-methoxy-5-(trifluoromethyl)phenyl)-1H-1,2,4-triazol-1-yl)acrylate |
| 27 | 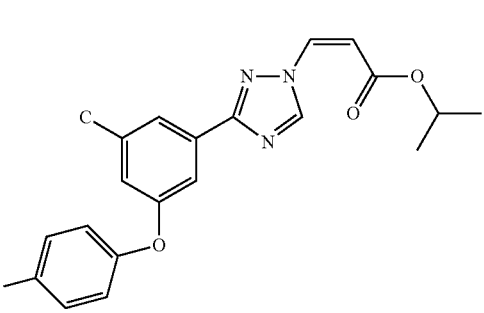 | (Z)-isopropyl 3-(3-(3-chloro 5-(4-chlorophenoxy)phenyl)-1H-1,2,4-triazol-1-yl)acrylate |

TABLE 1A-continued

| Example | Structure | Name |
|---|---|---|
| 28 | 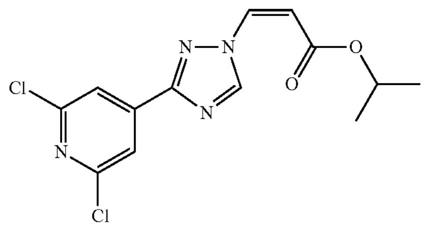 [SMILES: CC(C)OC(=O)/C=C\n1cnc(-c2cc(Cl)nc(Cl)c2)n1] | (Z)-isopropyl 3-(3-(2,6-dichloropyridin-4-yl)-1H-1,2,4-triazol-1-yl)acrylate |
| 29 | 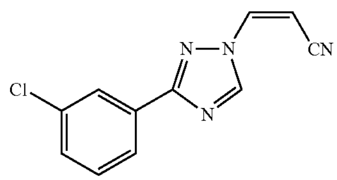 [SMILES: N#C/C=C\n1cnc(-c2cccc(Cl)c2)n1] | (Z)-3-(3-(3-chlorophenyl)-1H-1,2,4-triazol-1-yl)acrylonitrile |
| 30 | 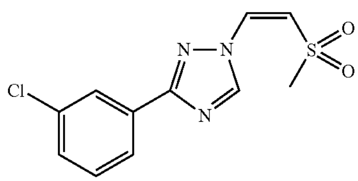 [SMILES: CS(=O)(=O)/C=C\n1cnc(-c2cccc(Cl)c2)n1] | (Z)-3-(3-chlorophenyl)-1-(2-(methylsulfonyl)vinyl)-1H-1,2,4-triazole |
| 31 | 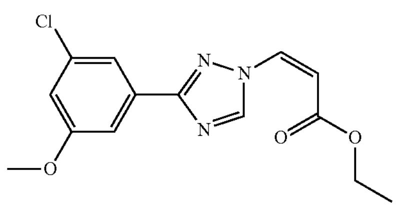 [SMILES: CCOC(=O)/C=C\n1cnc(-c2cc(Cl)cc(OC)c2)n1] | (Z)-ethyl 3-(3-(3-chloro-5-methoxyphenyl)-1H-1,2,4-triazol-1-yl)acrylate |
| 32 | 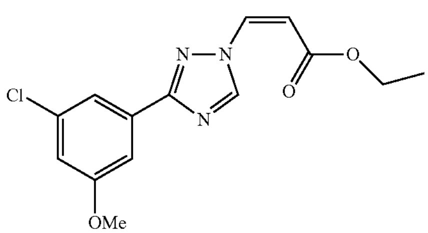 [SMILES: CCOC(=O)/C=C\n1cnc(-c2cc(Cl)cc(OC)c2)n1] | (Z)-methyl 3-(3-(3-chloro-5-methoxyphenyl)-1H-1,2,4-triazol-1-yl)acrylate |
| 33 | 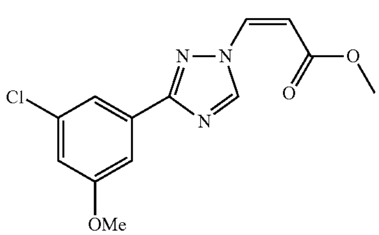 [SMILES: COC(=O)/C=C\n1cnc(-c2cc(Cl)cc(OC)c2)n1] | (Z)-methyl 3-(3-(3-chloro-5-methoxyphenyl)-1H-1,2,4-triazol-1-yl)acrylate |
| 34 | 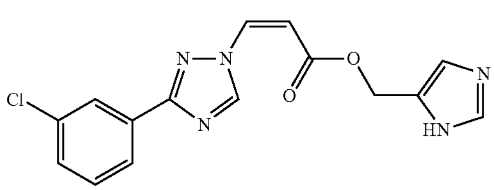 [SMILES: O=C(/C=C\n1cnc(-c2cccc(Cl)c2)n1)OCc1cnc[nH]1] | (Z)-(1H-imidazol-5-yl)methyl 3-(3-(3-chlorophenyl)-1H-1,2,4-triazol-1-yl)acrylate |

TABLE 1A-continued

Exemplary Compounds.

| Example | Structure | Name |
|---|---|---|
| 35 | 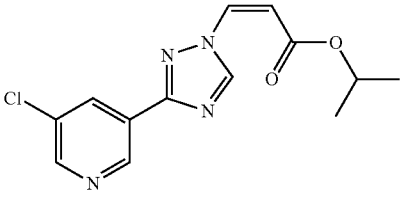 [SMILES: CC(C)OC(=O)/C=C\n1cnc(-c2cncc(Cl)c2)n1] | (Z)-isopropyl 3-(3-(5-chloropyridin-3-yl)-1H-1,2,4-triazol-1-yl)acrylate |
| 36 | 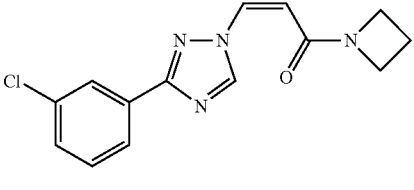 [SMILES: O=C(/C=C\n1cnc(-c2cccc(Cl)c2)n1)N1CCC1] | (Z)-1-(azetidin-1-yl)-3-(3-(3-chlorophenyl)-1H-1,2,4-triazol-1-yl)prop-2-en-1-one |
| 37 | 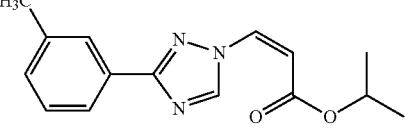 | (Z)-isopropyl 3-(3-(m-tolyl)-1H-triazol-1-yl)acrylate |
| 38 | 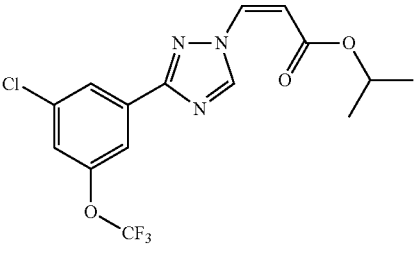 [SMILES: CC(C)OC(=O)/C=C\n1cnc(-c2cc(Cl)cc(OC(F)(F)F)c2)n1] | (Z)-isopropyl 3-(3-(3-chloro-5-(trifluoromethoxy)phenyl)-1H-1,2,4-triazol-1-yl)acrylate |
| 39 | 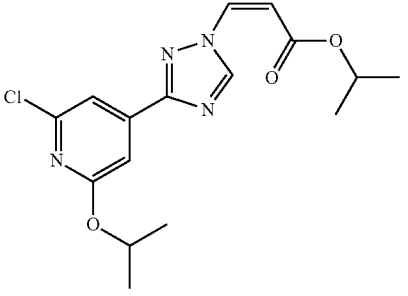 [SMILES: CC(C)OC(=O)/C=C\n1cnc(-c2cc(Cl)nc(OC(C)C)c2)n1] | (Z)-isopropyl 3-(3-(2-chloro-6-isopropoxypyridin-4-yl)-1H-1,2,4-triazol-1-yl)acrylate |
| 40 | 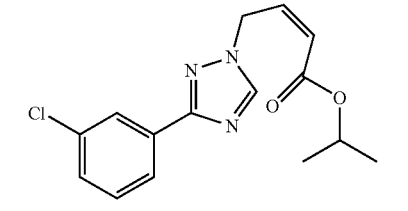 [SMILES: CC(C)OC(=O)/C=C\Cn1cnc(-c2cccc(Cl)c2)n1] | (Z)-isopropyl 4-(3-(3-chlorophenyl)-1H-1,2,4-triazol-1-yl)but-2-enoate |
| 41 | 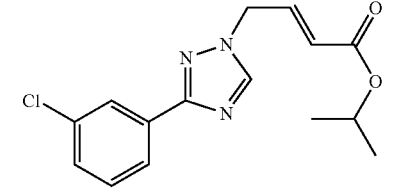 [SMILES: CC(C)OC(=O)/C=C/Cn1cnc(-c2cccc(Cl)c2)n1] | (E)-isopropyl 4-(3-(3-chlorophenyl)-1H-1,2,4-triazol-1-yl)but-2-enoate |

TABLE 1A-continued

Exemplary Compounds.

| Example | Structure | Name |
|---|---|---|
| 42 | 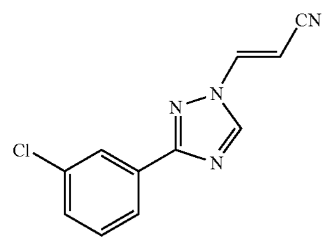 [SMILES: N#C/C=C/n1cnc(-c2cccc(Cl)c2)n1] | (E)-3-(3-(3-chlorophenyl)-1H-1,2,4-triazol-1-yl)acrylonitrile |
| 43 | 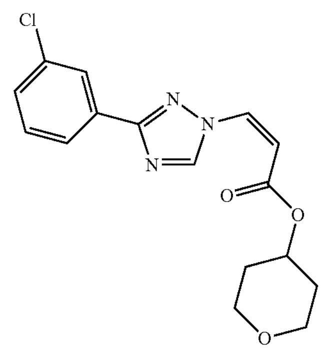 [SMILES: O=C(/C=C\n1cnc(-c2cccc(Cl)c2)n1)OC1CCOCC1] | (Z)-tetrahydro-2H-pyran-4-yl 3-(3-(3-chlorophenyl)-1H-1,2,4-triazol-1-yl)acrylate |
| 44 | 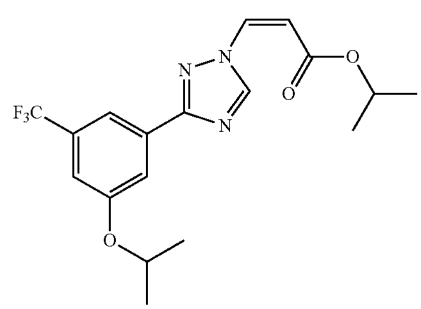 | (Z)-isopropyl 3-(3-(3-isopropoxy-5-(trifluoromethyl)phenyl)-1H-1,2,4-triazol-1-yl)acrylate |
| 45 | 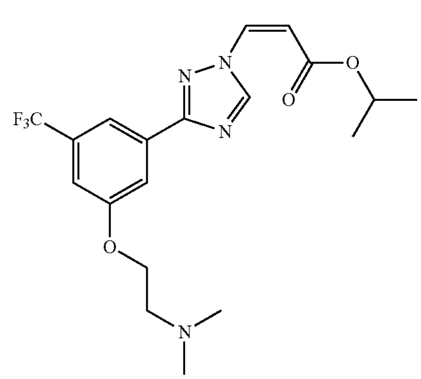 [SMILES: CC(C)OC(=O)/C=C\n1cnc(-c2cc(OCCN(C)C)cc(C(F)(F)F)c2)n1] | (Z)-isopropyl 3-(3-(3-(2-(dimethylamino)ethoxy)-5-(trifluoromethyl)phenyl)-1H-1,2,4-triazol-1-yl)acrylate |

TABLE 1A-continued

Exemplary Compounds.

| Example | Structure | Name |
|---|---|---|
| 46 | 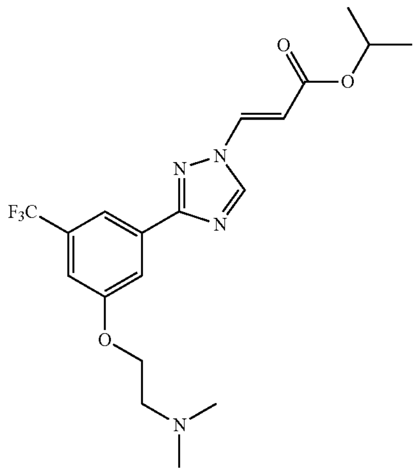 [SMILES: CC(C)OC(=O)/C=C/n1cnc(-c2cc(OCCN(C)C)cc(C(F)(F)F)c2)n1] | (E)-isopropyl 3-(3-(3-(2-(dimethylamino)ethoxy)-5-(trifluoromethyl)phenyl)-1H-1,2,4-triazol-1-yl)acrylate |
| 47 | 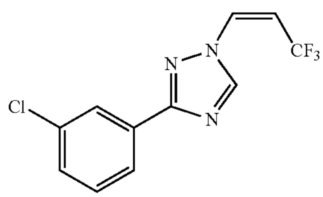 [SMILES: FC(F)(F)/C=C\n1cnc(-c2cccc(Cl)c2)n1] | (Z)-3-(3-chlorophenyl)-1-(3,3,3-trifluoroprop-1-en-1-yl)-1H-1,2,4-triazole |
| 48 | 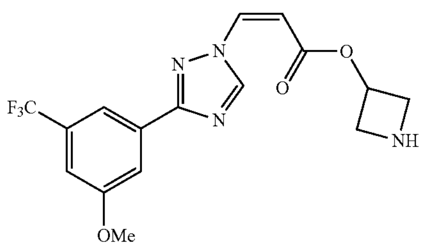 [SMILES: COc1cc(-c2ncn(/C=C\C(=O)OC3CNC3)n2)cc(C(F)(F)F)c1] | (Z)-azetidin-3-yl 3-(3-(3-methoxy-5-(trifluoromethyl)phenyl)-1H-1,2,4-triazol-1-yl)acrylate |
| 49 | 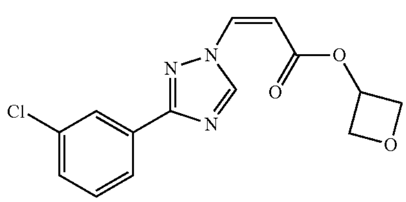 [SMILES: O=C(/C=C\n1cnc(-c2cccc(Cl)c2)n1)OC1COC1] | (Z)-azetidin-3-yl 3-(3-(3-chlorophenyl)-1H-1,2,4-triazol-1-yl)acrylate |
| 50 | 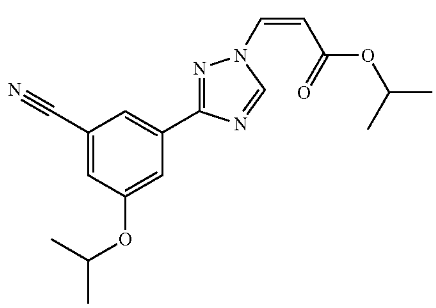 [SMILES: CC(C)OC(=O)/C=C\n1cnc(-c2cc(C#N)cc(OC(C)C)c2)n1] | (Z)-isopropyl 3-(3-(3-cyano-5-isopropoxyphenyl)-1H-1,2,4-triazol-1-yl)acrylate |

TABLE 1A-continued
| Example | Structure | Name |
|---------|-----------|------|
| 51 | 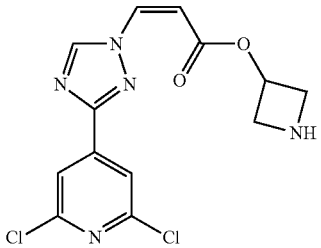 [SMILES: O=C(/C=C\n1cnc(-c2cc(Cl)nc(Cl)c2)n1)OC1CNC1] | (Z)-azetidin-3-yl 3-(3-(2,6-dichloropyridin-4-yl)-1H-1,2,4-triazol-1-yl)acrylate |
| 52 | 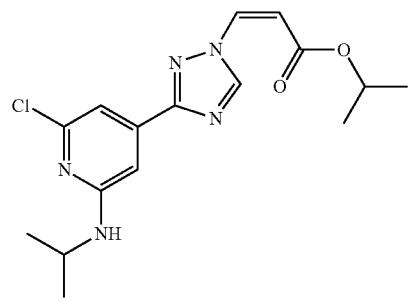 [SMILES: CC(C)Nc1cc(-c2ncn(/C=C\C(=O)OC(C)C)n2)cc(Cl)n1] | (Z)-isopropyl 3-(3-(2-chloro-6-(isopropylamino)pyridin-4-yl)-1H-1,2,4-triazol-1-yl)acrylate |
| 53 | 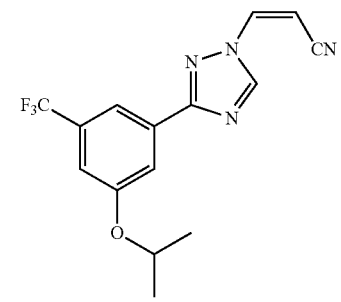 [SMILES: CC(C)Oc1cc(-c2ncn(/C=C\C#N)n2)cc(C(F)(F)F)c1] | (Z)-3-(3-(3-isopropoxy-5-(trifluoromethyl)phenyl)-1H-1,2,4-triazol-1-yl)acrylonitrile |
| 54 | 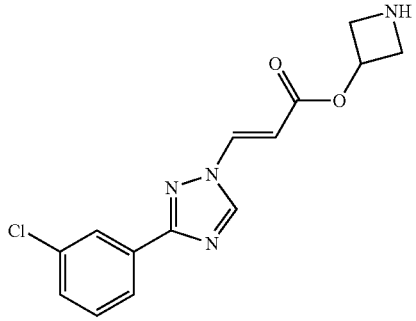 [SMILES: O=C(/C=C/n1cnc(-c2cccc(Cl)c2)n1)OC1CNC1] | (E)-azetidin-3-yl 3-(3-(3-chlorophenyl)-1H-1,2,4-triazol-1-yl)acrylate |

TABLE 1A-continued

| Example | Structure | Name |
|---|---|---|
| 55 | 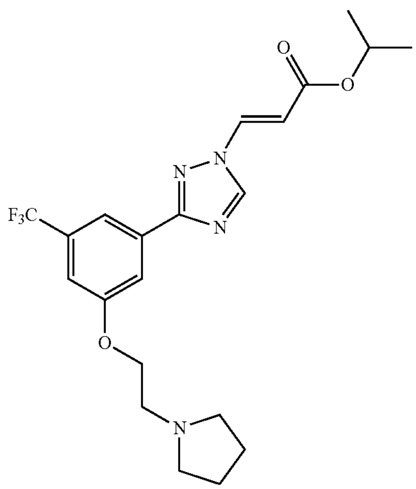 [SMILES: CC(C)OC(=O)/C=C/n1cnc(-c2cc(OCCN3CCCC3)cc(C(F)(F)F)c2)n1] | (E)-isopropyl 3-(3-(3-(2-(pyrrolidin-1-yl)ethoxy)-5-(trifluoromethyl)phenyl)-1H-1,2,4-triazol-1-yl)acrylate |
| 56 | 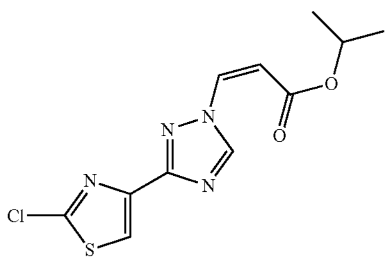 | (Z)-isopropyl 3-(3-(2-chlorothiazol-4-yl)-1H-1,2,4-triazol-1-yl)acrylate |
| 57 | 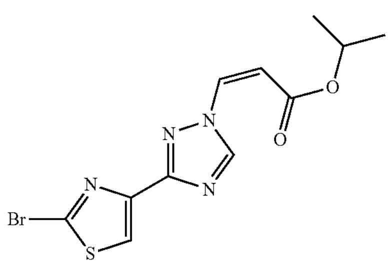 [SMILES: CC(C)OC(=O)/C=C\n1cnc(-c2csc(Cl)n2)n1] | (Z)-isopropyl 3-(3-(2-bromothiazol-4-yl)-1H-1,2,4-triazol-1-yl)acrylate |
| 58 | 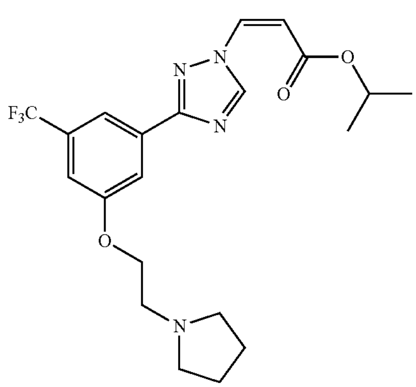 [SMILES: CC(C)OC(=O)/C=C\n1cnc(-c2cc(OCCN3CCCC3)cc(C(F)(F)F)c2)n1] | (Z)-isopropyl 3-(3-(3-(2-(pyrrolidin-1-yl)ethoxy)-5-(trifluoromethyl)phenyl)-1H-1,2,4-triazol-1-yl)acrylate |

TABLE 1A-continued

| Example | Structure | Name |
|---|---|---|
| 59 | 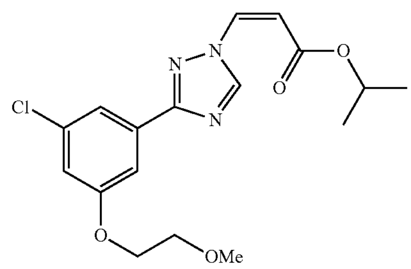 [SMILES: COCCOc1cc(Cl)cc(-c2ncn(/C=C\C(=O)OC(C)C)n2)c1] | (Z)-isopropyl 3-(3-(3-chloro-5-(2-methoxyethoxy)phenyl)-1H-1,2,4-triazol-1-yl)acrylate |
| 60 | 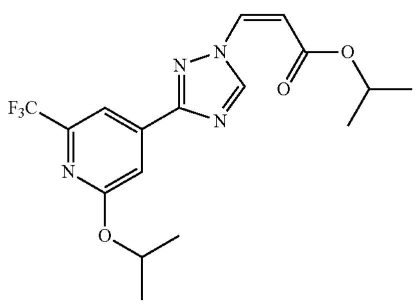 [SMILES: CC(C)OC(=O)/C=C\n1cnc(-c2cc(OC(C)C)nc(C(F)(F)F)c2)n1] | (Z)-isopropyl 3-(3-(2-isopropoxy-6-(trifluoromethyl)pyridin-4-yl)-1H-1,2,4-triazol-1-yl)acrylate |
| 61 | 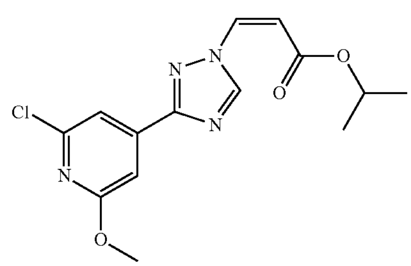 [SMILES: COc1cc(-c2ncn(/C=C\C(=O)OC(C)C)n2)cc(Cl)n1] | (Z)-isopropyl 3-(3-(2-chloro-6-methoxypyridin-4-yl)-1H-1,2,4-triazol-1-yl)acrylate |
| 62 | 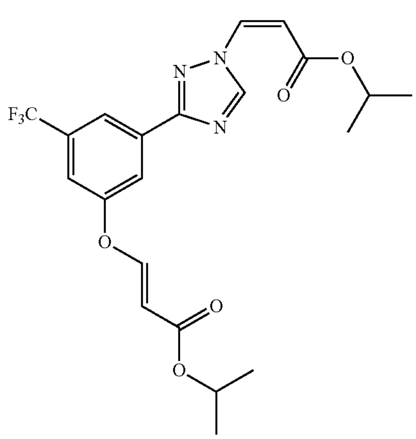 [SMILES: CC(C)OC(=O)/C=C\n1cnc(-c2cc(O/C=C/C(=O)OC(C)C)cc(C(F)(F)F)c2)n1] | (E)-isopropyl 3-(3-(1-((Z)-3-isopropoxy-3-oxoprop-1-en-1-yl)-1H-1,2,4-triazol-3-yl)-5-(trifluoromethyl)phenoxy)acrylate |

TABLE 1A-continued

| Example | Structure | Name |
|---|---|---|
| 63 | 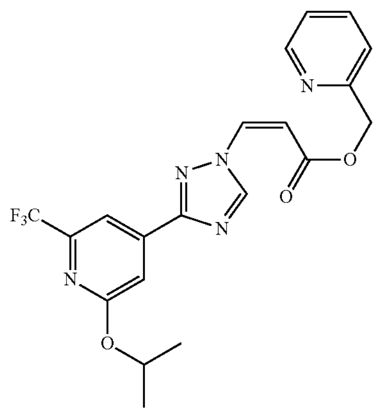 [SMILES: CC(C)Oc1cc(-c2ncn(/C=C\C(=O)OCc3ccccn3)n2)cc(C(F)(F)F)n1] | (Z)-pyridin-2-ylmethyl 3-(3-(2-isopropoxy-6-(trifluoromethyl)pyridin-4-yl)-1H-1,2,4-triazol-1-yl)acrylate |
| 64 | 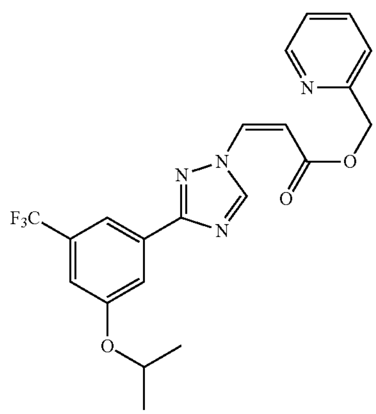 | (Z)-pyridin-2-ylmethyl 3-(3-(3-isopropoxy-5-(trifluoromethyl)phenyl)-1H-1,2,4-triazol-1-yl)acrylate |
| 65 | 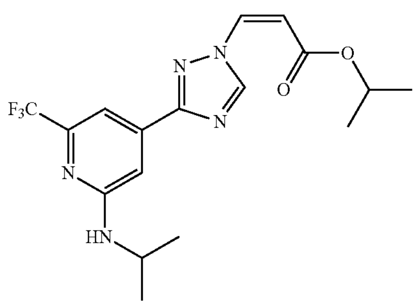 [SMILES: CC(C)Nc1cc(-c2ncn(/C=C\C(=O)OC(C)C)n2)cc(C(F)(F)F)n1] | (Z)-isopropyl 3-(3-(2-(isopropylamino)-6-(trifluoromethyl)pyridin-4-yl)-1H-1,2,4-triazol-1-yl)acrylate |
| 66 | 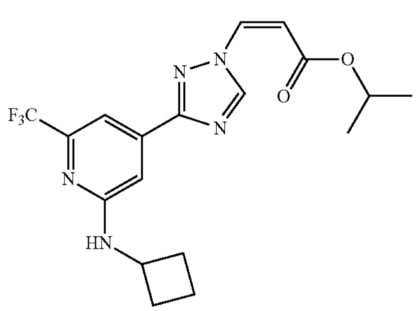 [SMILES: CC(C)OC(=O)/C=C\n1cnc(-c2cc(NC3CCC3)nc(C(F)(F)F)c2)n1] | (Z)-isopropyl 3-(3-(2-(cyclobutylamino)-6-(trifluoromethyl)pyridin-4-yl)-1H-1,2,4-triazol-1-yl)acrylate |

TABLE 1A-continued

Exemplary Compounds.

| Example | Structure | Name |
|---|---|---|
| 67 | 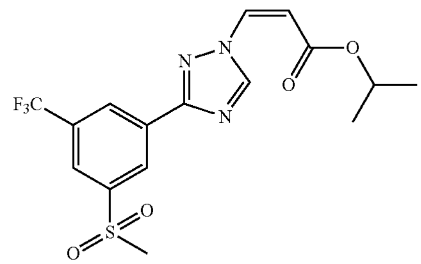 [SMILES: CC(C)OC(=O)/C=C\n1cnc(-c2cc(C(F)(F)F)cc(S(C)(=O)=O)c2)n1] | (Z)-isopropyl 3-(3-(3-(methylsulfonyl)-5-(trifluoromethyl)phenyl)-1H-1,2,4-triazol-1-yl)acrylate |
| 68 | 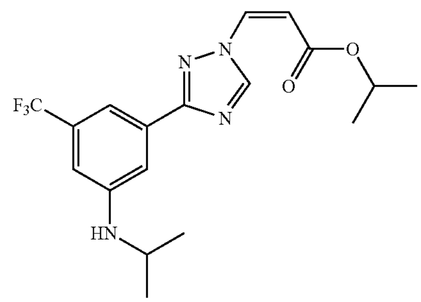 [SMILES: CC(C)Nc1cc(-c2ncn(/C=C\C(=O)OC(C)C)n2)cc(C(F)(F)F)c1] | (Z)-isopropyl 3-(3-(3-(isopropylamino)-5-(trifluoromethyl)phenyl)-1H-1,2,4-triazol-1-yl)acrylate |
| 69 | 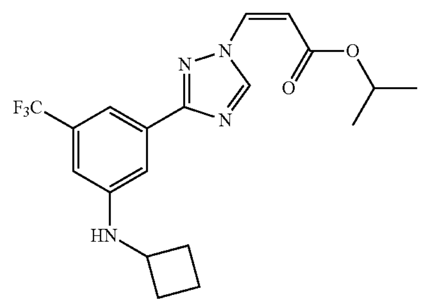 [SMILES: CC(C)OC(=O)/C=C\n1cnc(-c2cc(NC3CCC3)cc(C(F)(F)F)c2)n1] | (Z)-isopropyl 3-(3-(3-(cyclobutylamino)-5-(trifluoromethyl)phenyl)-1H-1,2,4-triazol-1-yl)acrylate |
| 70 | 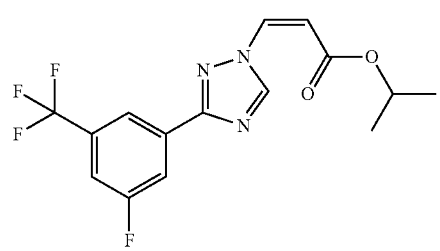 [SMILES: CC(C)OC(=O)/C=C\n1cnc(-c2cc(F)cc(C(F)(F)F)c2)n1] | (Z)-isopropyl 3-(3-(3-fluoro-5-(trifluoromethyl)phenyl)-1H-1,2,4-triazol-1-yl)acrylate |
| 71 | 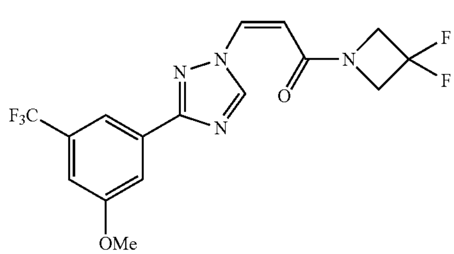 [SMILES: COc1cc(-c2ncn(/C=C\C(=O)N3CC(F)(F)C3)n2)cc(C(F)(F)F)c1] | (Z)-1-(3,3-difluoroazetidin-1-yl)-3-(3-(3-methoxy-5-(trifluoromethyl)phenyl)-1H-1,2,4-triazol-1-yl)prop-2-en-1-one |
| 72 | 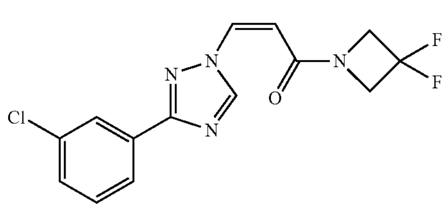 [SMILES: O=C(/C=C\n1cnc(-c2cccc(Cl)c2)n1)N1CC(F)(F)C1] | (Z)-3-(3-(3-chlorophenyl)-1H-1,2,4-triazol-1-yl)-1-(3,3-difluoroazetidin-1-yl)prop-2-en-1-one |

TABLE 1A-continued

Exemplary Compounds.

| Example | Structure | Name |
|---|---|---|
| 73 | 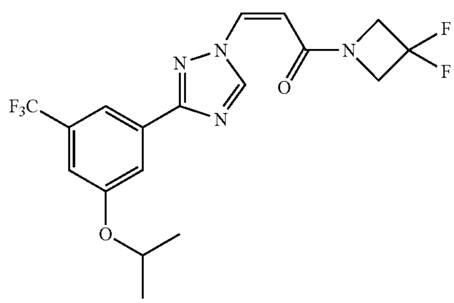 [SMILES: CC(C)Oc1cc(-c2ncn(/C=C\C(=O)N3CC(F)(F)C3)n2)cc(C(F)(F)F)c1] | (Z)-1-(3,3-difluoroazetidin-1-yl)-3-(3-(3-isopropoxy-5-(trifluoromethyl)phenyl)-1H-1,2,4-triazol-1-yl)prop-2-en-1-one |
| 74 | 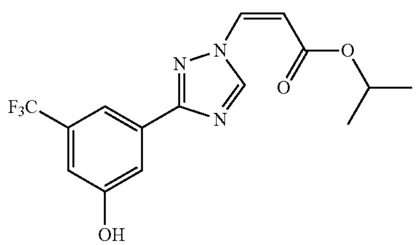 [SMILES: CC(C)OC(=O)/C=C\n1cnc(-c2cc(O)cc(C(F)(F)F)c2)n1] | (Z)-isopropyl 3-(3-(3-hydroxy-5-(trifluoromethyl)phenyl)-1H-1,2,4-triazol-1-yl)acrylate |
| 75 | 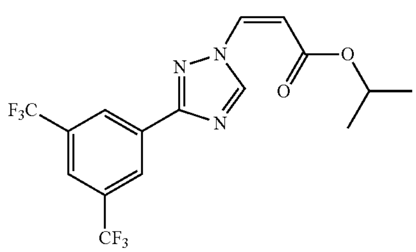 [SMILES: CC(C)OC(=O)/C=C\n1cnc(-c2cc(C(F)(F)F)cc(C(F)(F)F)c2)n1] | (Z)-isopropyl 3-(3-(3,5-bis(trifluoromethyl)phenyl)-1H-1,2,4-triazol-1-yl)acrylate |
| 76 | 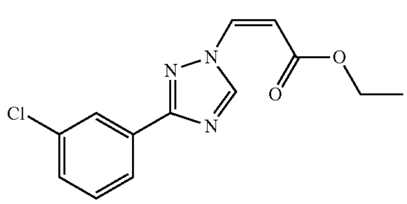 [SMILES: CCOC(=O)/C=C\n1cnc(-c2cccc(Cl)c2)n1] | (Z)-3-[3-(3-Chloro-phenyl)-[1,2,4]-triazol-1-yl]-acrylic acid ethyl ester |
| 77 | 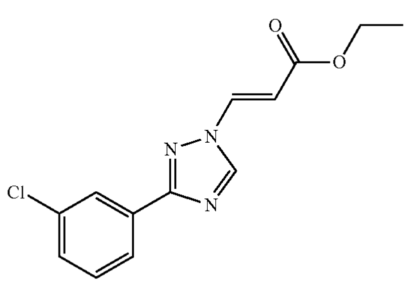 [SMILES: CCOC(=O)/C=C/n1cnc(-c2cccc(Cl)c2)n1] | (E)-3-[3-(3-Chloro-phenyl)-[1,2,4]-triazol-1-yl]-acrylic acid ethyl ester |

TABLE 1A-continued

Exemplary Compounds.

| Example | Structure | Name |
|---|---|---|
| 78 | 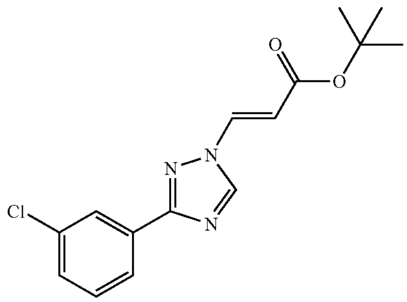 [SMILES: CC(C)(C)OC(=O)/C=C/n1cnc(-c2cccc(Cl)c2)n1] | (E)-3-[3-(3-Chloro-phenyl)-[1,2,4]-triazol-1-yl]-acrylic acid tert-butyl ester |
| 79 | 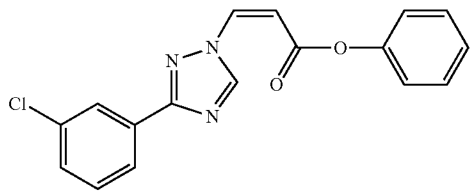 [SMILES: O=C(/C=C\n1cnc(-c2cccc(Cl)c2)n1)Oc1ccccc1] | (Z)-3-[3-(3-Chloro-phenyl)-[1,2,4]triazol-1-yl]-acrylic acid phenyl ester |
| 80 | 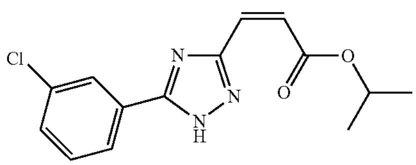 [SMILES: CC(C)OC(=O)/C=C\c1n[nH]c(-c2cccc(Cl)c2)n1] | (Z)-3-[5-(3-Chloro-phenyl)-1H-[1,2,4]triazol-3-yl]-acrylic acid isopropyl ester |
| 81 | 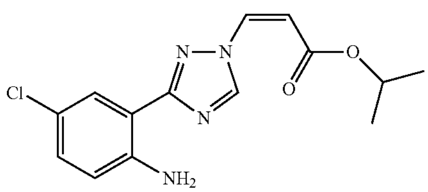 [SMILES: CC(C)OC(=O)/C=C\n1cnc(-c2cc(Cl)ccc2N)n1] | 3-[3-(2-Amino-5-chloro-phenyl)-[1,2,4]triazol-1-yl]-acrylic acid isopropyl ester |
| 82 | 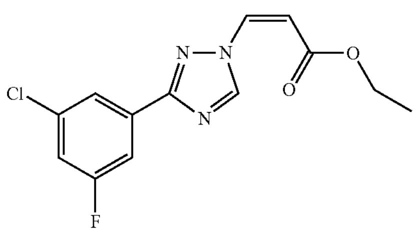 [SMILES: CCOC(=O)/C=C\n1cnc(-c2cc(F)cc(Cl)c2)n1] | 3-[3-(3-Chloro-5-fluoro-phenyl)-[1,2,4]triazol-1-yl]-acrylic acid ethyl ester |
| 83 | 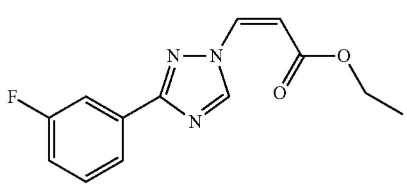 [SMILES: CCOC(=O)/C=C\n1cnc(-c2cccc(F)c2)n1] | 3-[3-(3-Fluoro-phenyl)-[1,2,4]triazol-1-yl]-acrylic acid ethyl ester |
| 84 | 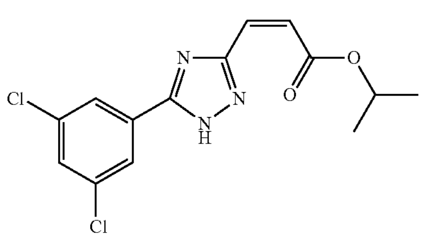 [SMILES: CC(C)OC(=O)/C=C\c1n[nH]c(-c2cc(Cl)cc(Cl)c2)n1] | (Z)-isopropyl 3-(5-(3,5-dichlorophenyl)-1H-1,2,4-triazol-3-yl)acrylic |

TABLE 1A-continued

Exemplary Compounds.

| Example | Structure | Name |
|---|---|---|
| 85 | 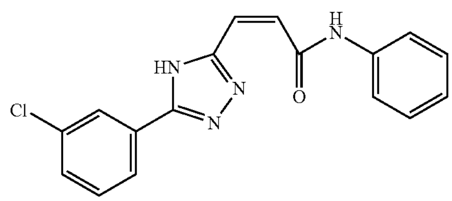 [SMILES: O=C(/C=C\c1nnc(-c2cccc(Cl)c2)[nH]1)Nc1ccccc1] | (Z)-3-(5-(3-chlorophenyl)-4H-1,2,4-triazol-3-yl)-N-phenylacrylamide |
| 86 | 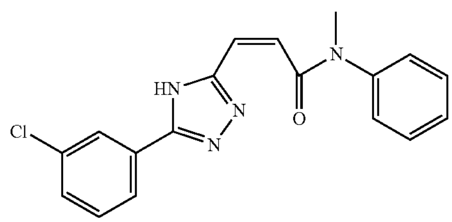 [SMILES: CN(C(=O)/C=C\c1nnc(-c2cccc(Cl)c2)[nH]1)c1ccccc1] | (Z)-3-(5-(3-chlorophenyl)-4H-1,2,4-triazol-3-yl)-N-methyl-N-phenylacrylamide |
| 87 | 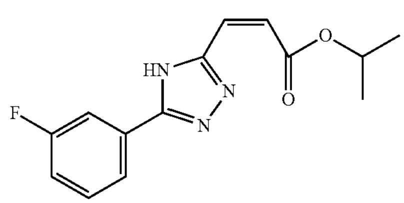 [SMILES: CC(C)OC(=O)/C=C\c1nnc(-c2cccc(F)c2)[nH]1] | (Z)-isopropyl 3-(5-(3-fluorophenyl)-4H-1,2,4-triazol-3-yl)acrylate |
| 88 | 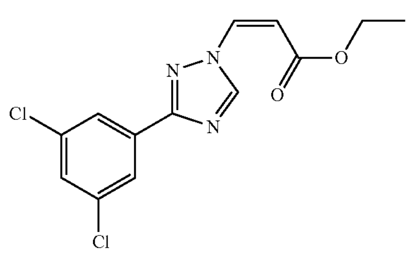 [SMILES: CCOC(=O)/C=C\n1cnc(-c2cc(Cl)cc(Cl)c2)n1] | (Z)-ethyl 3-(3-(3,5-dichlorophenyl)-1H-1,2,4-triazol-1-yl)acrylate |
| 89 | 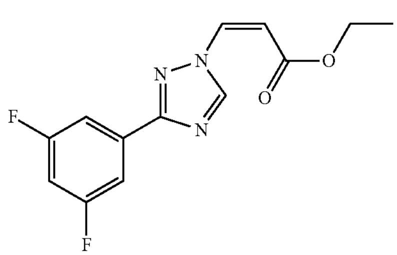 [SMILES: CCOC(=O)/C=C\n1cnc(-c2cc(F)cc(F)c2)n1] | (Z)-ethyl 3-(3-(3,5-difluorophenyl)-1H-1,2,4-triazol-1-yl)acrylate |

TABLE 1A-continued

Exemplary Compounds.

| Example | Structure | Name |
| --- | --- | --- |
| 90 | 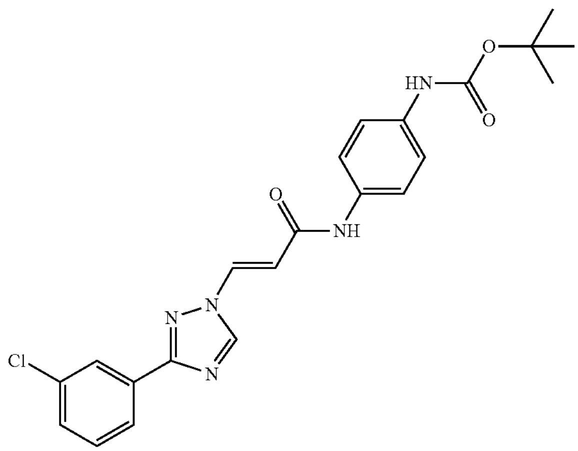 [SMILES: CC(C)(C)OC(=O)Nc1ccc(NC(=O)/C=C/n2cnc(-c3cccc(Cl)c3)n2)cc1] | (E)-tert-butyl (4-(3-(3-(3-chlorophenyl)-1H-1,2,4-triazol-1-yl)acrylamido)phenyl)carbamate |
| 92 | 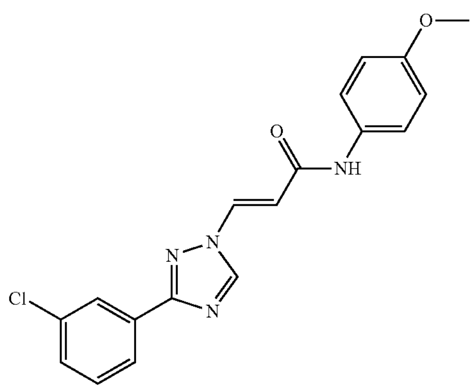 [SMILES: COc1ccc(NC(=O)/C=C/n2cnc(-c3cccc(Cl)c3)n2)cc1] | (E)-3-(3-(3-chlorophenyl)-1H-1,2,4-triazol-1-yl)-N-(4-methoxyphenyl)acrylamide |
| 93 | 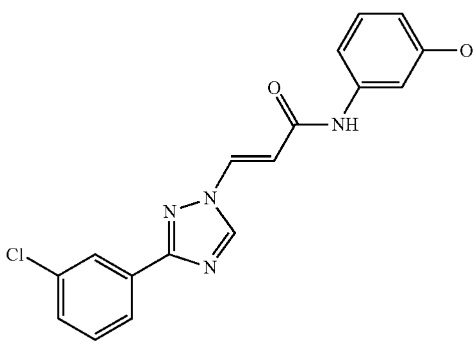 [SMILES: O=C(/C=C/n1cnc(-c2cccc(Cl)c2)n1)Nc1cccc(O)c1] | (E)-N-(3 Chloro-phenyl)-3-[3-(3-chloro-phenyl)-[1,2,4]-triazol-1-yl]-acryl amide |
| 94 | 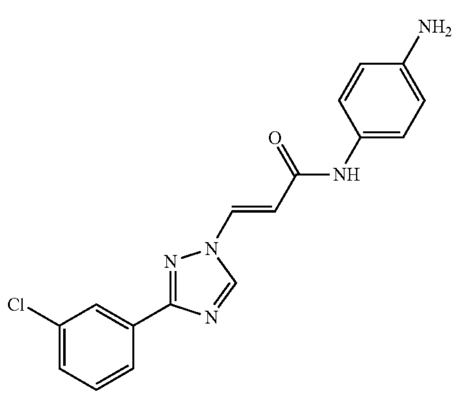 [SMILES: Nc1ccc(NC(=O)/C=C/n2cnc(-c3cccc(Cl)c3)n2)cc1] | (E)-N-(4-Amino-phenyl)-3-[3-(3-chloro-phenyl)-[1,2,4]-triazol-1-yl]-acryl amide |

TABLE 1A-continued

Exemplary Compounds.

| Example | Structure | Name |
|---|---|---|
| 95 | 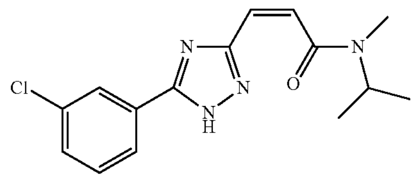 [SMILES: CC(C)N(C)C(=O)/C=C\c1n[nH]c(-c2cccc(Cl)c2)n1] | 3-[5-(3-Chloro-phenyl)-1H-[1,2,4]triazol-3-yl]-N-isopropyl-N-methyl-acrylamide |
| 96 | 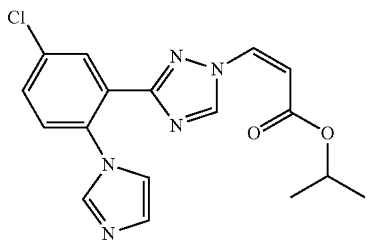 [SMILES: CC(C)OC(=O)/C=C\n1cnc(-c2cc(Cl)ccc2-n2ccnc2)n1] | (Z)-isopropyl 3-(3-(5-chloro-2-(1H-imidazol-1-yl)phenyl)-1H-1,2,4-triazol-1-yl)acrylate |
| 97 | 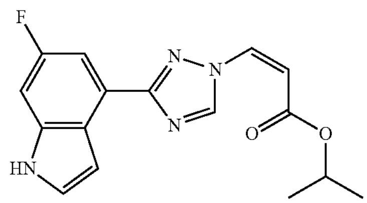 [SMILES: CC(C)OC(=O)/C=C\n1cnc(-c2cc(F)cc3[nH]ccc23)n1] | (Z)-isopropyl 3-(3-(6-fluoro-1H-indol-4-yl)-1H-1,2,4-triazol-1-yl)acrylate |
| 98 | 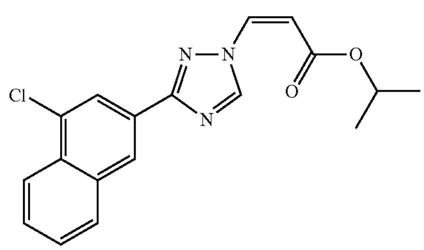 [SMILES: CC(C)OC(=O)/C=C\n1cnc(-c2cc(Cl)c3ccccc3c2)n1] | (Z)-isopropyl 3-(3-(4-chloronaphthalen-2-yl)-1H-1,2,4-triazol-1-yl)acrylate |
| 99 | 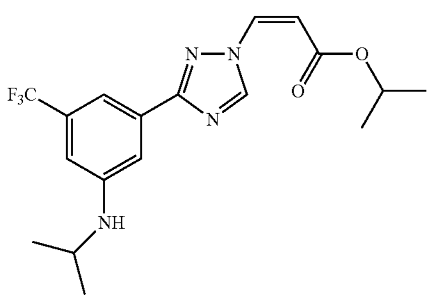 [SMILES: CC(C)Nc1cc(-c2ncn(/C=C\C(=O)OC(C)C)n2)cc(C(F)(F)F)c1] | (Z)-isopropyl 3-(3-(3-(isopropylamino)-5-(trifluoromethyl)phenyl)-1H-1,2,4-triazol-1-yl)acrylate |
| 100 | 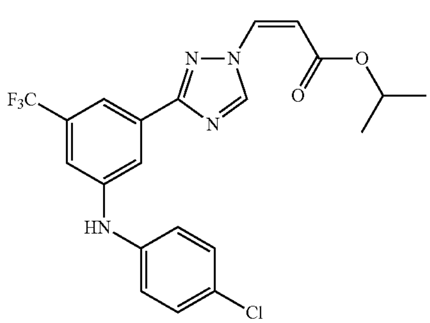 [SMILES: CC(C)OC(=O)/C=C\n1cnc(-c2cc(Nc3ccc(Cl)cc3)cc(C(F)(F)F)c2)n1] | (Z)-isopropyl 3-(3-(3-((4-chlorophenyl)amino)-5-(trifluoromethyl)phenyl)-1H-1,2,4-triazol-1-yl)acrylate |

TABLE 1A-continued

Exemplary Compounds.

| Example | Structure | Name |
|---|---|---|
| 101 | 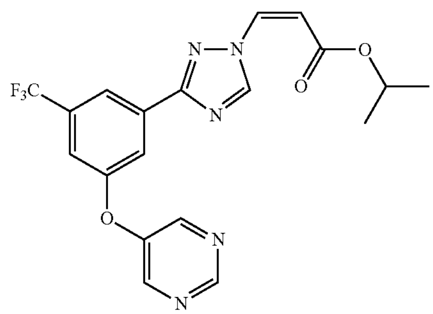 [SMILES: CC(C)OC(=O)/C=C\n1cnc(-c2cc(Oc3cncnc3)cc(C(F)(F)F)c2)n1] | (Z)-isopropyl 3-(3-(3-(pyrimidin-5-yloxy)-5-(trifluoromethyl)phenyl)-1H-1,2,4-triazol-1-yl)acrylate |
| 102 | 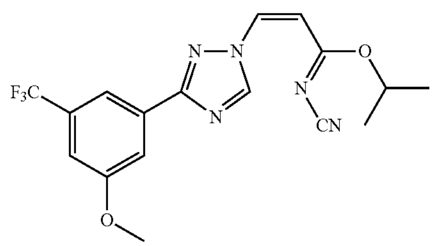 [SMILES: COc1cc(-c2ncn(/C=C\C(=N\C#N)OC(C)C)n2)cc(C(F)(F)F)c1] | (1Z,2Z)-isopropyl N-cyano-3-(3-(3-methoxy-5-(trifluoromethyl)phenyl)-1H-1,2,4-triazol-1-yl)acrylamide |
| 103 | 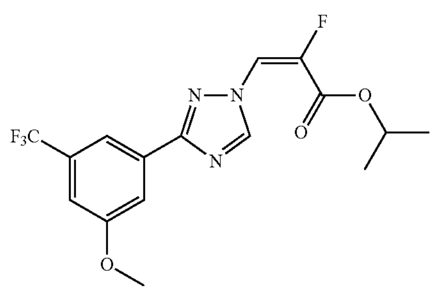 [SMILES: COc1cc(-c2ncn(/C=C(/F)C(=O)OC(C)C)n2)cc(C(F)(F)F)c1] | (E)-isopropyl 2-fluoro-3-(3-(3-methoxy-5-(trifluoromethyl)phenyl)-1H-1,2,4-triazol-1-yl)acrylate |
| 104 | 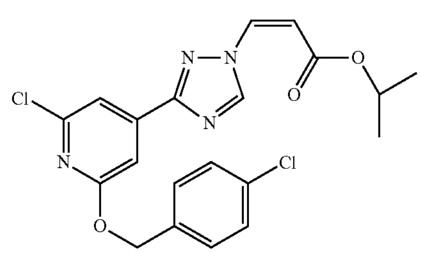 [SMILES: CC(C)OC(=O)/C=C\n1cnc(-c2cc(Cl)nc(OCc3ccc(Cl)cc3)c2)n1] | (Z)-isopropyl 3-(3-(2-chloro-6-((4-chlorobenzyl)oxy)pyridin-4-yl)-1H-1,2,4-triazol-1-yl)acrylate |
| 105 | 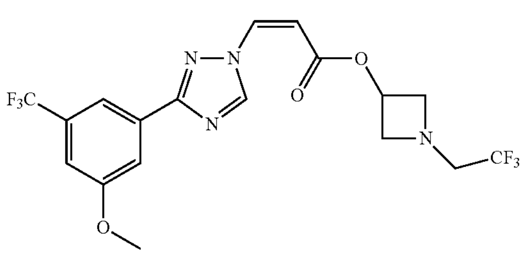 [SMILES: COc1cc(-c2ncn(/C=C\C(=O)OC3CN(CC(F)(F)F)C3)n2)cc(C(F)(F)F)c1] | (Z)-1-(2,2,2-trifluoroethyl)azetidin-3-yl 3-(3-(3-methoxy-5-(trifluoromethyl)phenyl)-1H-1,2,4-triazol-1-yl)acrylate |

TABLE 1A-continued

| Example | Structure | Name |
|---|---|---|
| 106 | 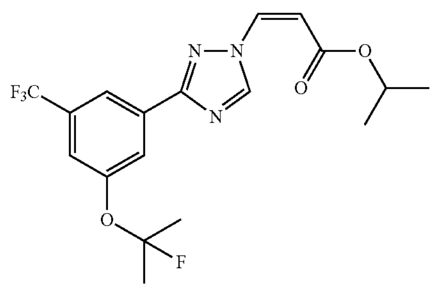 [SMILES: CC(C)OC(=O)/C=C\n1cnc(-c2cc(OC(C)(C)F)cc(C(F)(F)F)c2)n1] | (Z)-isopropyl 3-(3-((2-fluoropropan-2-yl)oxy)-5-(trifluoromethyl)phenyl)-1H-1,2,4-triazol-1-yl)acrylate |
| 107 | 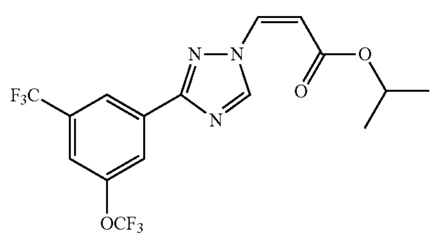 [SMILES: CC(C)OC(=O)/C=C\n1cnc(-c2cc(OC(F)(F)F)cc(C(F)(F)F)c2)n1] | (Z)-isopropyl 3-(3-(3-(trifluoromethoxy)-5-(trifluoromethyl)phenyl)-1H-1,2,4-triazol-1-yl)acrylate |
| 108 | 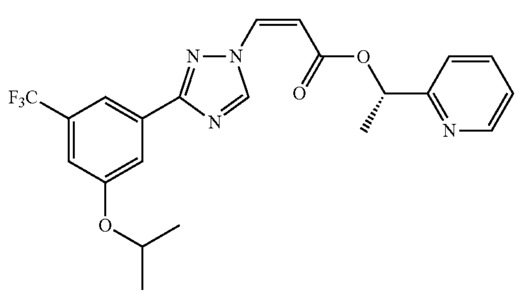 [SMILES: CC(C)Oc1cc(-c2ncn(/C=C\C(=O)O[C@@H](C)c3ccccn3)n2)cc(C(F)(F)F)c1] | (S,Z)-1-(pyridin-2-yl)ethyl 3-(3-(3-isopropoxy-5-(trifluoromethyl)phenyl)-1H-1,2,4-triazol-1-yl)acrylate |
| 109 | 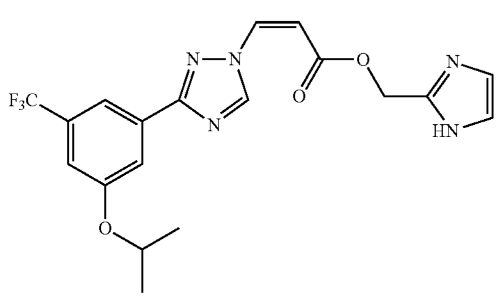 [SMILES: CC(C)Oc1cc(-c2ncn(/C=C\C(=O)OCc3ncc[nH]3)n2)cc(C(F)(F)F)c1] | (Z)-(1H-imidazol-2-yl)methyl 3-(3-(3-isopropoxy-5-(trifluoromethyl)phenyl)-1H-1,2,4-triazol-1-yl)acrylate |
| 110 | 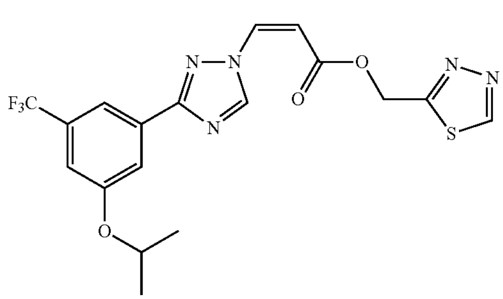 [SMILES: CC(C)Oc1cc(-c2ncn(/C=C\C(=O)OCc3nncs3)n2)cc(C(F)(F)F)c1] | (Z)-(1,3,4-thiadiazol-2-yl)methyl 3-(3-(3-isopropoxy-5-(trifluoromethyl)phenyl)-1H-1,2,4-triazol-1-yl)acrylate |

TABLE 1A-continued

Exemplary Compounds.

| Example | Structure | Name |
|---|---|---|
| 111 | 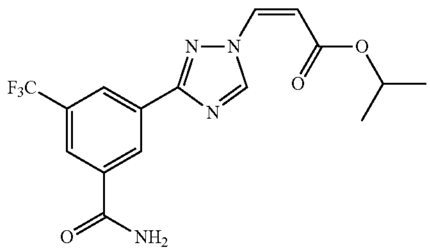 [SMILES: CC(C)OC(=O)/C=C\n1cnc(-c2cc(C(N)=O)cc(C(F)(F)F)c2)n1] | (Z)-isopropyl 3-(3-(3-carbamoyl-5-(trifluoromethyl)phenyl)-1H-1,2,4-triazol-1-yl)acrylate |
| 112 | 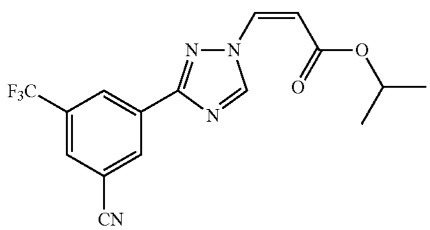 [SMILES: CC(C)OC(=O)/C=C\n1cnc(-c2cc(C#N)cc(C(F)(F)F)c2)n1] | (Z)-isopropyl 3-(3-(3-cyano-5-(trifluoromethyl)phenyl)-1H-1,2,4-triazol-1-yl)acrylate |
| 113 | 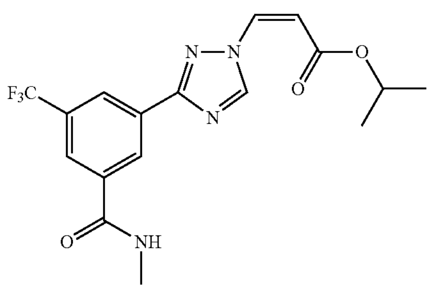 [SMILES: CNC(=O)c1cc(-c2ncn(/C=C\C(=O)OC(C)C)n2)cc(C(F)(F)F)c1] | (Z)-isopropyl 3-(3-(3-(methylcarbamoyl)-5-(trifluoromethyl)phenyl)-1H-1,2,4-triazol-1-yl)acrylate |
| 114 | 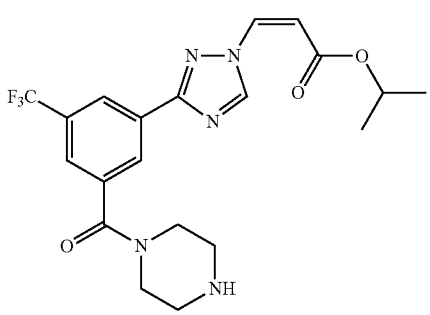 [SMILES: CC(C)OC(=O)/C=C\n1cnc(-c2cc(C(=O)N3CCNCC3)cc(C(F)(F)F)c2)n1] | (Z)-isopropyl 3-(3-(3-(piperazine-1-carbonyl)-5-(trifluoromethyl)phenyl)-1H-1,2,4-triazol-1-yl)acrylate |
| 115 | 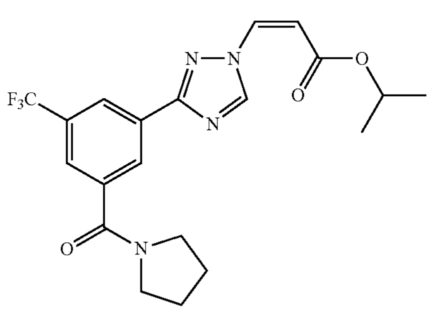 [SMILES: CC(C)OC(=O)/C=C\n1cnc(-c2cc(C(=O)N3CCCC3)cc(C(F)(F)F)c2)n1] | (Z)-isopropyl 3-(3-(3-(pyrrolidine-1-carbonyl)-5-(trifluoromethyl)phenyl)-1H-1,2,4-triazol-1-yl)acrylate |

TABLE 1A-continued

| Example | Structure | Name |
|---|---|---|
| 116 | 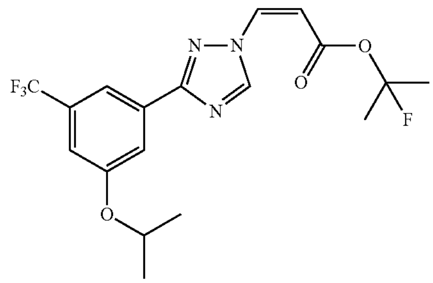 [SMILES: CC(C)Oc1cc(-c2ncn(/C=C\C(=O)OC(C)(C)F)n2)cc(C(F)(F)F)c1] | (Z)-2-fluoropropan-2-yl 3-(3-(3-isopropoxy-5-(trifluoromethyl)phenyl)-1H-1,2,4-triazol-1-yl)acrylate |
| 117 | 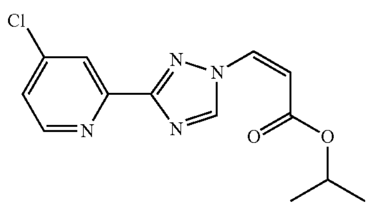 [SMILES: CC(C)OC(=O)/C=C\n1cnc(-c2cc(Cl)ccn2)n1] | (Z)-isopropyl 3-(3-(4-chloropyridin-2-yl)-1H-1,2,4-triazol-1-yl)acrylate |
| 118 | 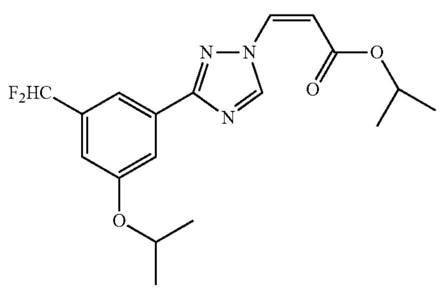 [SMILES: CC(C)OC(=O)/C=C\n1cnc(-c2cc(OC(C)C)cc(C(F)F)c2)n1] | (Z)-isopropyl 3-(3-(3-(difluoromethyl)-5-isopropoxyphenyl)-1H-1,2,4-triazol-1-yl)acrylate |
| 119 | 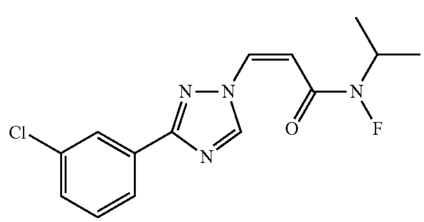 [SMILES: CC(C)N(F)C(=O)/C=C\n1cnc(-c2cccc(Cl)c2)n1] | (Z)-3-(3-(3-chlorophenyl)-1H-1,2,4-triazol-1-yl)-N-fluoro-N-isopropylacrylamide |
| 120 | 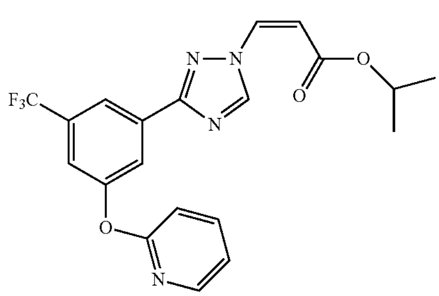 [SMILES: CC(C)OC(=O)/C=C\n1cnc(-c2cc(Oc3ccccn3)cc(C(F)(F)F)c2)n1] | (Z)-isopropyl 3-(3-(3-(pyridin-2-yloxy)-5-(trifluoromethyl)phenyl)-1H-1,2,4-triazol-1-yl)acrylate |
| 121 | 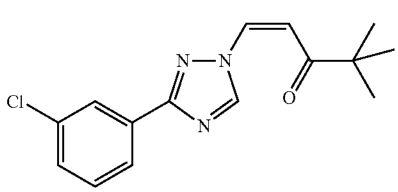 [SMILES: CC(C)(C)C(=O)/C=C\n1cnc(-c2cccc(Cl)c2)n1] | (Z)-1-(3-(3-chlorophenyl)-1H-1,2,4-triazol-1-yl)-4,4-dimethylpent-1-en-3-one |

TABLE 1A-continued

Exemplary Compounds.

| Example | Structure | Name |
|---|---|---|
| 122 | 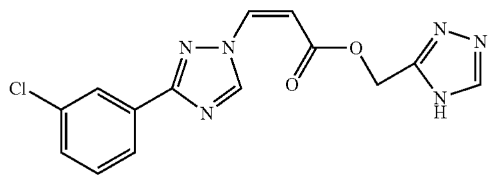 [SMILES: O=C(/C=C\n1cnc(-c2cccc(Cl)c2)n1)OCc1nnc[nH]1] | (Z)-(4H-1,2,4-triazol-3-yl)methyl 3-(3-(3-chlorophenyl)-1H-1,2,4-triazol-1-yl)acrylate |
| 123 | 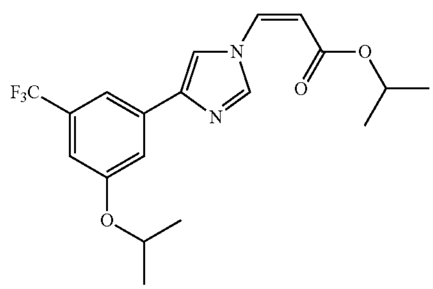 [SMILES: CC(C)OC(=O)/C=C\n1cnc(-c2cc(OC(C)C)cc(C(F)(F)F)c2)c1] | (Z)-isopropyl 3-(4-(3-isopropoxy-5-(trifluoromethyl)phenyl)-1H-imidazol-1-yl)acrylate |
| 124 | 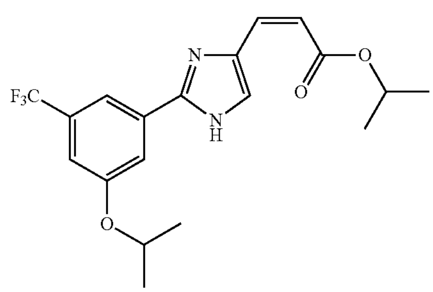 [SMILES: CC(C)OC(=O)/C=C\c1c[nH]c(-c2cc(OC(C)C)cc(C(F)(F)F)c2)n1] | (Z)-isopropyl 3-(2-(3-isopropoxy-5-(trifluoromethyl)phenyl)-1H-imidazol-4-yl)acrylate |
| 125 | 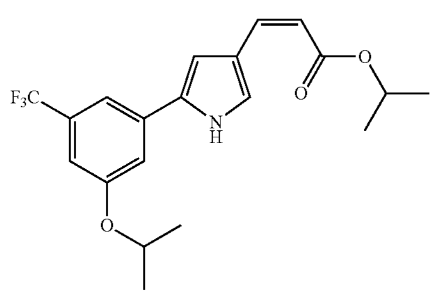 [SMILES: CC(C)OC(=O)/C=C\c1c[nH]c(-c2cc(OC(C)C)cc(C(F)(F)F)c2)c1] | (Z)-isopropyl 3-(5-(3-isopropoxy-5-(trifluoromethyl)phenyl)-1H-pyrrol-3-yl)acrylate |
| 126 | 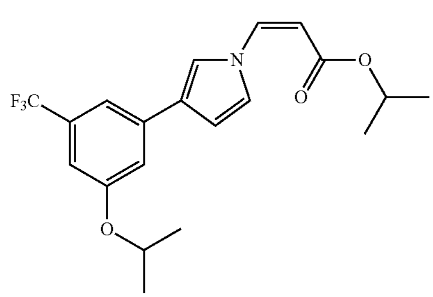 [SMILES: CC(C)OC(=O)/C=C\n1ccc(-c2cc(OC(C)C)cc(C(F)(F)F)c2)c1] | (Z)-isopropyl 3-(3-(3-isopropoxy-5-(trifluoromethyl)phenyl)-1H-pyrrol-1-yl)acrylate |

TABLE 1A-continued

Exemplary Compounds.

| Example | Structure | Name |
|---|---|---|
| 127 | 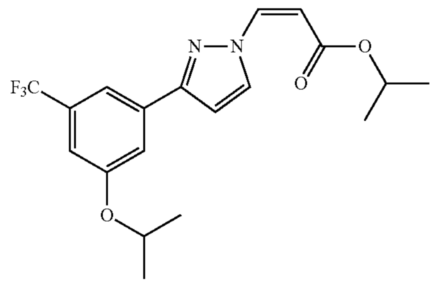 [SMILES: CC(C)OC(=O)/C=C\n1ccc(-c2cc(OC(C)C)cc(C(F)(F)F)c2)n1] | (Z)-isopropyl 3-(3-(3-isopropoxy-5-(trifluoromethyl)phenyl)-1H-pyrazol-1-yl)acrylate |
| 128 | 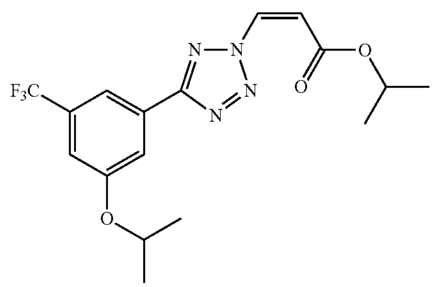 [SMILES: CC(C)OC(=O)/C=C\n1nnc(-c2cc(OC(C)C)cc(C(F)(F)F)c2)n1] | (Z)-isopropyl 3-(5-(3-isopropoxy-5-(trifluoromethyl)phenyl)-2H-tetrazol-2-yl)acrylate |
| 129 | 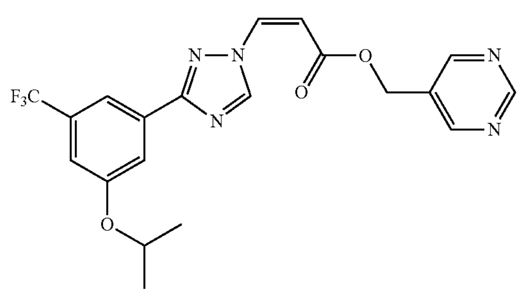 [SMILES: CC(C)Oc1cc(-c2ncn(/C=C\C(=O)OCc3cncnc3)n2)cc(C(F)(F)F)c1] | (Z)-pyrimidin-5-ylmethyl 3-(3-(3-isopropoxy-5-(trifluoromethyl)phenyl)-1H-1,2,4-triazol-1-yl)acrylate |
| 130 | 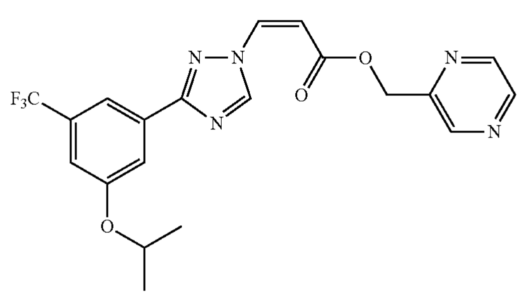 [SMILES: CC(C)Oc1cc(-c2ncn(/C=C\C(=O)OCc3cnccn3)n2)cc(C(F)(F)F)c1] | pyrazin-2-ylmethyl (Z)-3-(3-(3-isopropoxy-5-(trifluoromethyl)phenyl)-1H-1,2,4-triazol-1-yl)acrylate |

Methods of making compounds disclosed in Table 1A and compounds of formula (I) wherein $R^2$ is —C(O)—O—$R^3$ are disclosed, for example, in International Application No. PCT/US2011/027328, the entire contents of which are incorporated herein by reference.

TABLE 1B

| Compound | Structure | Name |
|---|---|---|
| B-1 | 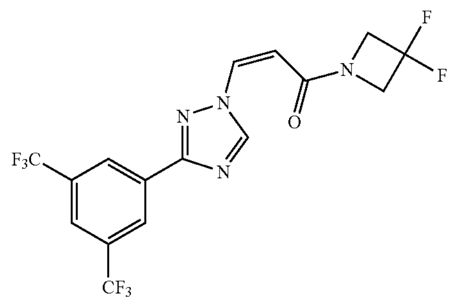 [SMILES: O=C(/C=C\n1cnc(-c2cc(C(F)(F)F)cc(C(F)(F)F)c2)n1)N1CC(F)(F)C1] | (Z)-3-(3-(3,5-bis(trifluoromethyl)phenyl)-1H-1,2,4-triazol-1-yl)-1-(3,3-difluoroazetidin-1-yl)prop-2-en-1-one |
| B-2 | 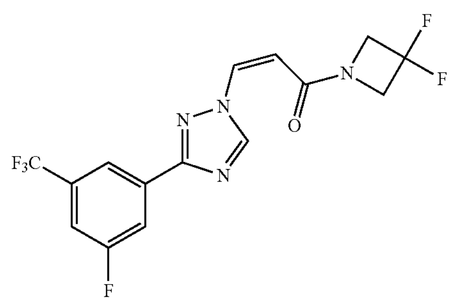 [SMILES: O=C(/C=C\n1cnc(-c2cc(F)cc(C(F)(F)F)c2)n1)N1CC(F)(F)C1] | (Z)-1-(3,3-difluoroazetidin-1-yl)-3-(3-(3-fluoro-5-(trifluoromethyl)phenyl)-1H-1,2,4-triazol-1-yl)prop-2-en-1-one |
| B-3 | 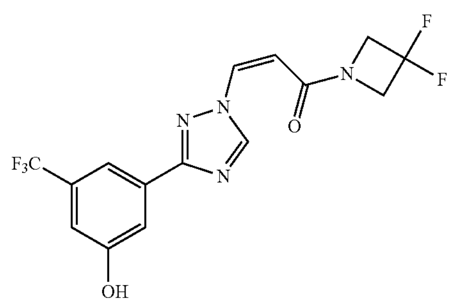 [SMILES: O=C(/C=C\n1cnc(-c2cc(O)cc(C(F)(F)F)c2)n1)N1CC(F)(F)C1] | (Z)-1-(3,3-difluoroazetidin-1-yl)-3-(3-(3-hydroxy-5-(trifluoromethyl)phenyl)-1H-1,2,4-triazol-1-yl)prop-2-en-1-one |
| B-4 | 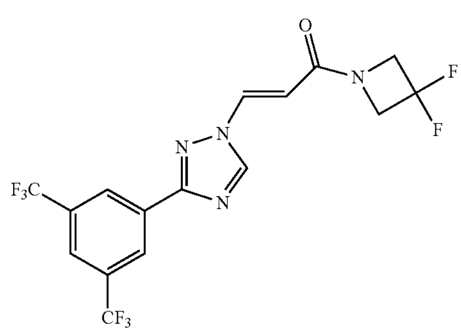 [SMILES: O=C(/C=C/n1cnc(-c2cc(C(F)(F)F)cc(C(F)(F)F)c2)n1)N1CC(F)(F)C1] | (E)-3-(3-(3,5-bis(trifluoromethyl)phenyl)-1H-1,2,4-triazol-1-yl)-1-(3,3-difluoroazetidin-1-yl)prop-2-en-1-one |
| B-5 | 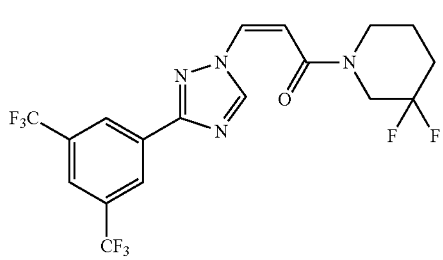 [SMILES: O=C(/C=C\n1cnc(-c2cc(C(F)(F)F)cc(C(F)(F)F)c2)n1)N1CCCC(F)(F)C1] | (Z)-3-(3-(3,5-bis(trifluoromethyl)phenyl)-1H-1,2,4-triazol-1-yl)-1-(3,3-difluoropiperidin-1-yl)prop-2-en-1-one |

TABLE 1B-continued

Exemplary Compounds.

| Compound | Structure | Name |
|---|---|---|
| B-6 | 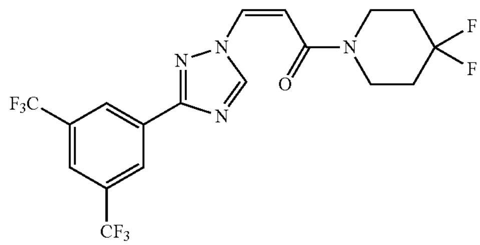 [SMILES: O=C(/C=C\n1cnc(-c2cc(C(F)(F)F)cc(C(F)(F)F)c2)n1)N1CCC(F)(F)CC1] | (Z)-3-(3-(3,5-bis(trifluoromethyl)phenyl)-1H-1,2,4-triazol-1-yl)-1-(4,4-difluoropiperidin-1-yl)prop-2-en-1-one |
| B-7 | 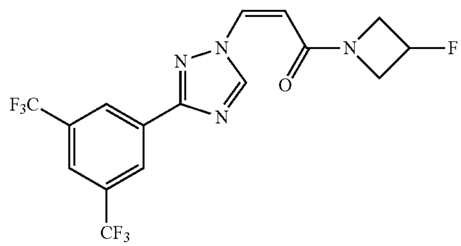 [SMILES: O=C(/C=C\n1cnc(-c2cc(C(F)(F)F)cc(C(F)(F)F)c2)n1)N1CC(F)C1] | (Z)-3-(3-(3,5-bis(trifluoromethyl)phenyl)-1H-1,2,4-triazol-1-yl)-1-(3-fluoroazetidin-1-yl)prop-2-en-1-one |
| B-8 | 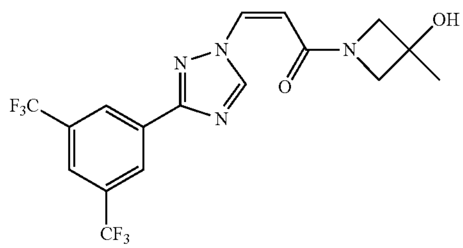 [SMILES: CC1(O)CN(C(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-1-(3-hydroxy-3-methylazetidin-1-yl)prop-2-en-1-one |
| B-9 | 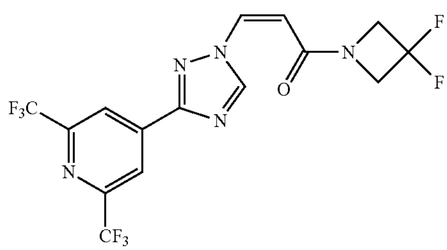 [SMILES: O=C(/C=C\n1cnc(-c2cc(C(F)(F)F)nc(C(F)(F)F)c2)n1)N1CC(F)(F)C1] | (Z)-3-(3-(2,6-bis(trifluoromethyl)pyridin-4-yl)-1H-1,2,4-triazol-1-yl)-1-(3,3-difluoroazetidin-1-yl)prop-2-en-1-one |
| B-10 | 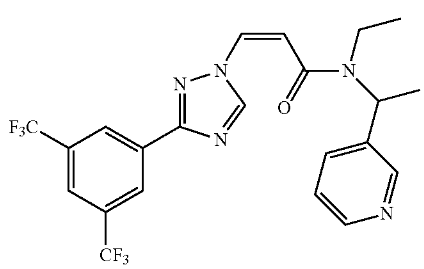 [SMILES: CCN(C(=O)/C=C\n1cnc(-c2cc(C(F)(F)F)cc(C(F)(F)F)c2)n1)C(C)c1cccnc1] | (Z)-3-(3-(3,5-bis(trifluoromethyl)phenyl)-1H-1,2,4-triazol-1-yl)-N-ethyl-N-(1-(pyridin-3-yl)ethyl)acrylamide |
| B-11 | 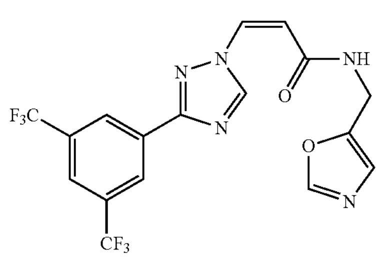 [SMILES: O=C(/C=C\n1cnc(-c2cc(C(F)(F)F)cc(C(F)(F)F)c2)n1)NCc1cnco1] | (Z)-3-(3-(3,5-bis(trifluoromethyl)phenyl)-1H-1,2,4-triazol-1-yl)-N-(oxazol-5-ylmethyl)acrylamide |

TABLE 1B-continued

Exemplary Compounds.

| Compound | Structure | Name |
|---|---|---|
| B-12 | 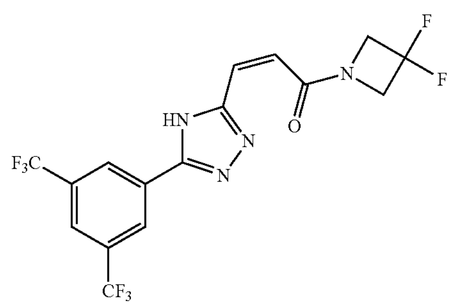 [SMILES: O=C(/C=C\c1nnc(-c2cc(C(F)(F)F)cc(C(F)(F)F)c2)[nH]1)N1CC(F)(F)C1] | (Z)-3-(5-(3,5-bis(trifluoromethyl)phenyl)-4H-1,2,4-triazol-3-yl)-1-(3,3-difluoroazetidin-1-yl)prop-2-en-1-one |
| B-13 | 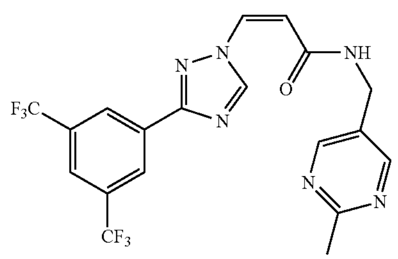 [SMILES: Cc1ncc(CNC(=O)/C=C\n2cnc(-c3cc(C(F)(F)F)cc(C(F)(F)F)c3)n2)cn1] | (Z)-3-(3-(3,5-bis(trifluoromethyl)phenyl)-1H-1,2,4-triazol-1-yl)-N-((2-methylpyrimidin-5-yl)methyl)acrylamide |
| B-14 | 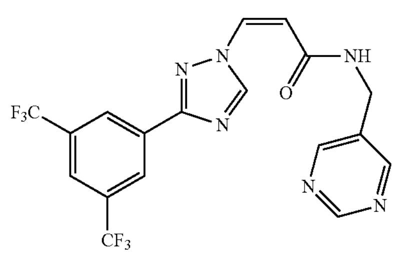 [SMILES: O=C(/C=C\n1cnc(-c2cc(C(F)(F)F)cc(C(F)(F)F)c2)n1)NCc1cncnc1] | (Z)-3-(3-(3,5-bis(trifluoromethyl)phenyl)-1H-1,2,4-triazol-1-yl)-N-(pyrimidin-5-ylmethyl)acrylamide |
| B-15 | 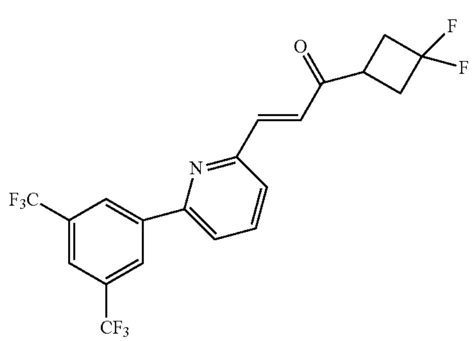 [SMILES: O=C(/C=C/c1cccc(-c2cc(C(F)(F)F)cc(C(F)(F)F)c2)n1)C1CC(F)(F)C1] | (E)-3-(6-(3,5-bis(trifluoromethyl)phenyl)pyridin-2-yl)-1-(3,3-difluorocyclobutyl)prop-2-en-1-one |
| B-16 | 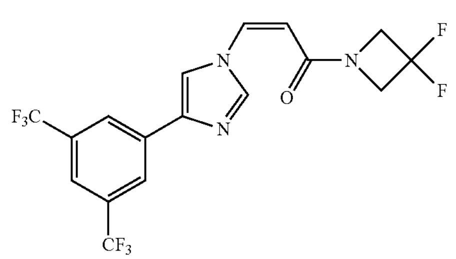 [SMILES: O=C(/C=C\n1cnc(-c2cc(C(F)(F)F)cc(C(F)(F)F)c2)c1)N1CC(F)(F)C1] | (Z)-3-(4-(3,5-bis(trifluoromethyl)phenyl)-1H-imidazol-1-yl)-1-(3,3-difluoroazetidin-1-yl)prop-2-en-1-one |

TABLE 1B-continued

Exemplary Compounds.

| Compound | Structure | Name |
|---|---|---|
| B-17 | 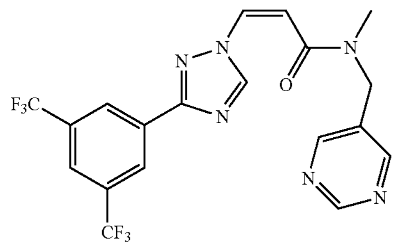 [SMILES: CN(Cc1cncnc1)C(=O)/C=C\n1cnc(-c2cc(C(F)(F)F)cc(C(F)(F)F)c2)n1] | (Z)-3-(3-(3,5-bis(trifluoromethyl)phenyl)-1H-1,2,4-triazol-1-yl)-N-methyl-N-(pyrimidin-5-ylmethyl)acrylamide |
| B-18 | 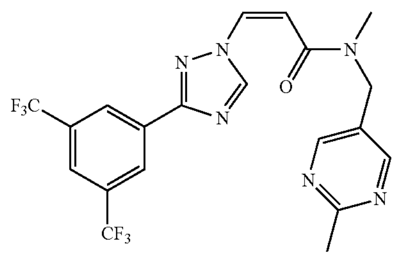 [SMILES: Cc1ncc(CN(C)C(=O)/C=C\n2cnc(-c3cc(C(F)(F)F)cc(C(F)(F)F)c3)n2)cn1] | (Z)-3-(3-(3,5-bis(trifluoromethyl)phenyl)-1H-1,2,4-triazol-1-yl)-N-methyl-N-((2 methylpyrimidin-5-yl)methyl)acrylamide |
| B-19 | 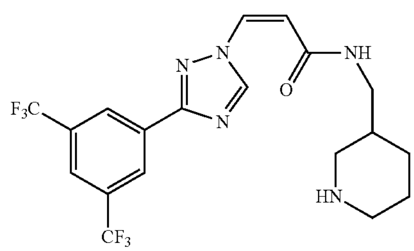 [SMILES: O=C(/C=C\n1cnc(-c2cc(C(F)(F)F)cc(C(F)(F)F)c2)n1)NCC1CCCNC1] | (Z)-3-(3-(3,5-bis(trifluoromethyl)phenyl)-1H-1,2,4-triazol-1-yl)-N-(piperidin-3-ylmethyl)acrylamide |
| B-20 | 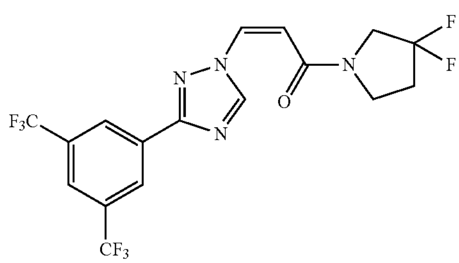 [SMILES: O=C(/C=C\n1cnc(-c2cc(C(F)(F)F)cc(C(F)(F)F)c2)n1)N1CCC(F)(F)C1] | (Z)-3-(3-(3,5-bis(trifluoromethyl)phenyl)-1H-1,2,4-triazol-1-yl)-1-(3,3-difluoropyrrolidin-1-yl)prop-2-en-1-one |
| B-21 | 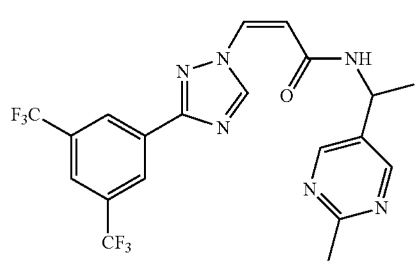 [SMILES: Cc1ncc(C(C)NC(=O)/C=C\n2cnc(-c3cc(C(F)(F)F)cc(C(F)(F)F)c3)n2)cn1] | (Z)-3-(3-(3,5-bis(trifluoromethyl)phenyl)-1H-1,2,4-triazol-1-yl)-N-(1-(2-methylpyrimidin-5-yl)ethyl)acrylamide |
| B-22 | 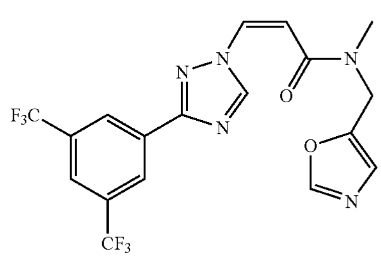 [SMILES: CN(Cc1cnco1)C(=O)/C=C\n1cnc(-c2cc(C(F)(F)F)cc(C(F)(F)F)c2)n1] | (Z)-3-(3-(3,5-bis(trifluoromethyl)phenyl)-1H-1,2,4-triazol-1-yl)-N-methyl-N-(oxazol-5-ylmethyl)acrylamide |

TABLE 1B-continued

Exemplary Compounds.

| Compound | Structure | Name |
|---|---|---|
| B-23 | 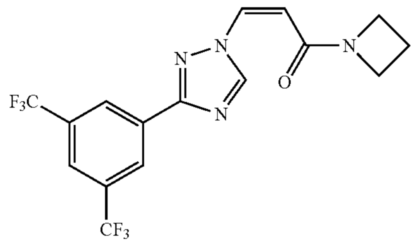 [SMILES: O=C(/C=C\n1cnc(-c2cc(C(F)(F)F)cc(C(F)(F)F)c2)n1)N1CCC1] | (Z)-1-(azetidin-1-yl)-3-(3-(3,5-bis(trifluoromethyl)phenyl)-1H-1,2,4-triazol-1-yl)prop-2-en-1-one |
| B-24 | 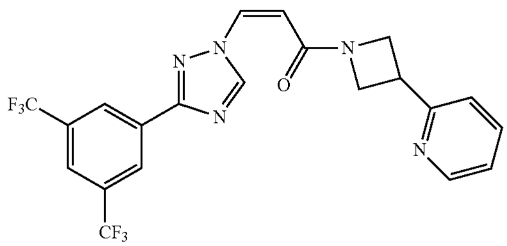 [SMILES: O=C(/C=C\n1cnc(-c2cc(C(F)(F)F)cc(C(F)(F)F)c2)n1)N1CC(c2ccccn2)C1] | (Z)-3-(3-(3,5-bis(trifluoromethyl)phenyl)-1H-1,2,4-triazol-1-yl)-1-(3-(pyridin-2-yl)azetidin-1-yl)prop-2-en-1-one |
| B-25 | 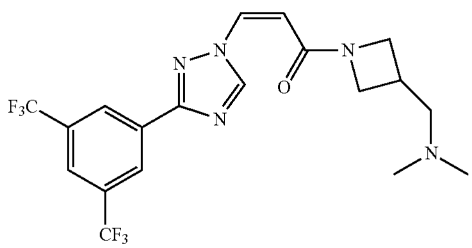 [SMILES: CN(C)CC1CN(C(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-1-(3-((dimethylamino)methyl)azetidin-1-yl)prop-2-en-1-one |
| B-26 | 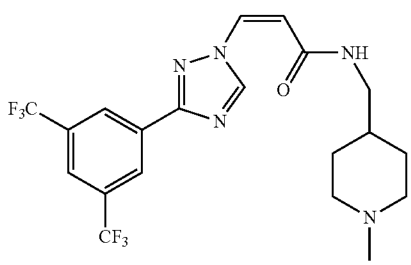 [SMILES: CN1CCC(CNC(=O)/C=C\n2cnc(-c3cc(C(F)(F)F)cc(C(F)(F)F)c3)n2)CC1] | (Z)-3-(3-(3,5-bis(trifluoromethyl)phenyl)-1H-1,2,4-triazol-1-yl)-N-((1-methylpiperidin-4-yl)methyl)acrylamide |
| B-27 | 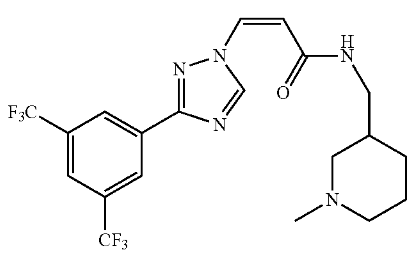 [SMILES: CN1CCCC(CNC(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-N-((1-methylpiperidin-3-yl)methyl)acrylamide |
| B-28 | 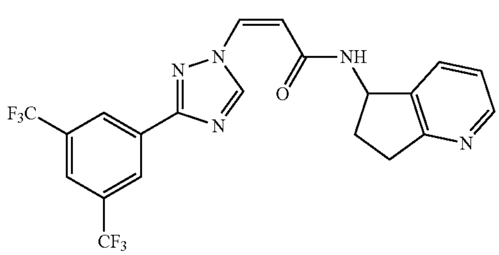 [SMILES: O=C(/C=C\n1cnc(-c2cc(C(F)(F)F)cc(C(F)(F)F)c2)n1)NC1CCc2ncccc21] | (Z)-3-(3-(3,5-bis(trifluoromethyl)phenyl)-1H-1,2,4-triazol-1-yl)-N-(6,7-dihydro-5H-cyclopenta[b]pyridin-5-yl)acrylamide |

TABLE 1B-continued

Exemplary Compounds.

| Compound | Structure | Name |
|---|---|---|
| B-29 | 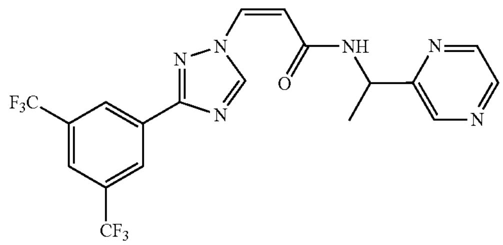 [SMILES: CC(NC(=O)/C=C\n1cnc(-c2cc(C(F)(F)F)cc(C(F)(F)F)c2)n1)c1cnccn1] | (Z)-3-(3-(3,5-bis(trifluoromethyl)phenyl)-1H-1,2,4-triazol-1-yl)-N-(1-(pyrazin-2-yl)ethyl)acrylamide |
| B-30 | 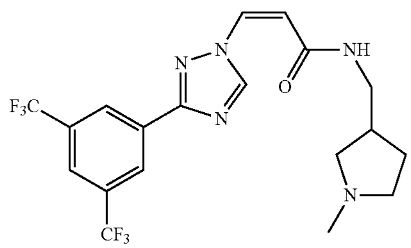 [SMILES: CN1CCC(CNC(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-N-((1-methylpyrrolidin-3-yl)methyl)acrylamide |
| B-31 | 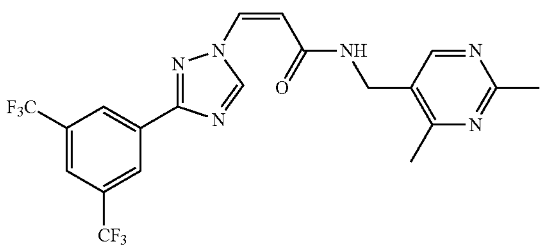 [SMILES: Cc1ncc(CNC(=O)/C=C\n2cnc(-c3cc(C(F)(F)F)cc(C(F)(F)F)c3)n2)c(C)n1] | (Z)-3-(3-(3,5-bis(trifluoromethyl)phenyl)-1H-1,2,4-triazol-1-yl)-N-((2,4-dimethylpyrimidin-5-yl)methyl)acrylamide |
| B-32 | 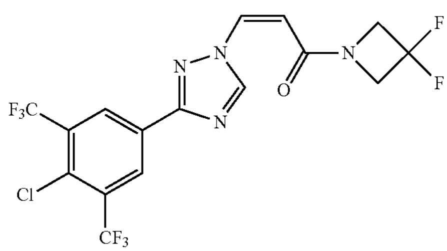 [SMILES: O=C(/C=C\n1cnc(-c2cc(C(F)(F)F)c(Cl)c(C(F)(F)F)c2)n1)N1CC(F)(F)C1] | (Z)-3-(3-(4-chloro-3,5-bis(trifluoromethyl)phenyl)-1H-1,2,4-triazol-1-yl)-1-(3,3-difluoroazetidin-1-yl)prop-2-en-1-one |
| B-33 | 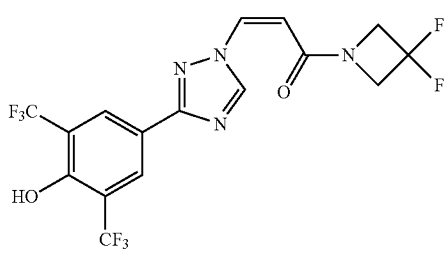 | (Z)-1-(3,3-difluoroazetidin-1-yl)-3-(3-(4-hydroxy-3,5-bis(trifluoromethyl)phenyl)-1H-1,2,4-triazol-1-yl)prop-2-en-1-one |
| B-34 | 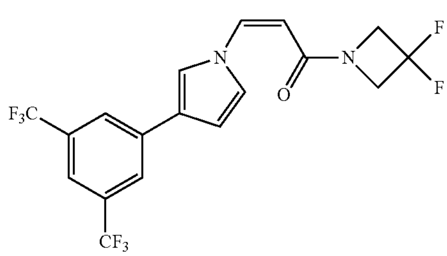 [SMILES: O=C(/C=C\n1ccc(-c2cc(C(F)(F)F)cc(C(F)(F)F)c2)c1)N1CC(F)(F)C1] | (Z)-3-(3-(3,5-bis(trifluoromethyl)phenyl)-1H-pyrrol-1-yl)-1-(3,3-difluoroazetidin-1-yl)prop-2-en-1-one |

TABLE 1B-continued

Exemplary Compounds.

| Compound | Structure | Name |
|---|---|---|
| B-35 | 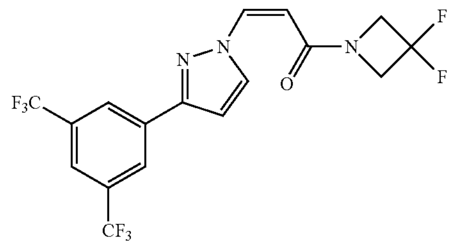 [SMILES: O=C(/C=C\n1ccc(-c2cc(C(F)(F)F)cc(C(F)(F)F)c2)n1)N1CC(F)(F)C1] | (Z)-3-(3-(3,5-bis(trifluoromethyl)phenyl)-1H-pyrazol-1-yl)-1-(3,3-difluoroazetidin-1-yl)prop-2-en-1-one |
| B-36 | 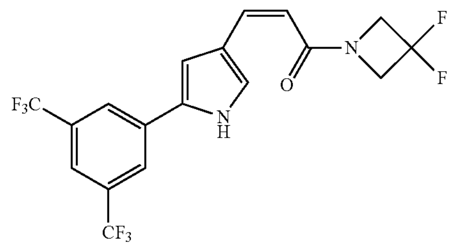 [SMILES: O=C(/C=C\c1c[nH]c(-c2cc(C(F)(F)F)cc(C(F)(F)F)c2)c1)N1CC(F)(F)C1] | (Z)-3-(5-(3,5-bis(trifluoromethyl)phenyl)-1H-pyrrol-3-yl)-1-(3,3-difluoroazetidin-1-yl)prop-2-en-1-one |
| B-37 | 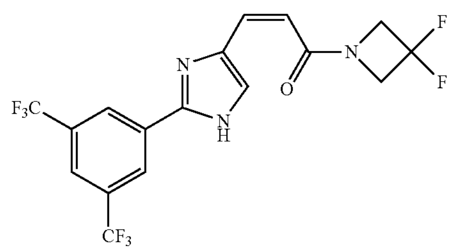 [SMILES: O=C(/C=C\c1c[nH]c(-c2cc(C(F)(F)F)cc(C(F)(F)F)c2)n1)N1CC(F)(F)C1] | (Z)-3-(2-(3,5-bis(trifluoromethyl)phenyl)-1H-imidazol-4-yl)-1-(3,3-difluoroazetidin-1-yl)prop-2-en-1-one |
| B-38 | 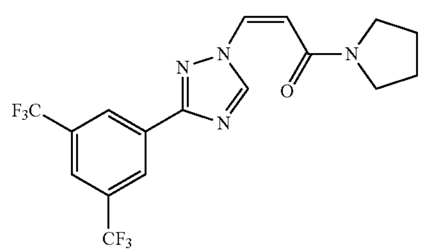 [SMILES: O=C(/C=C\n1cnc(-c2cc(C(F)(F)F)cc(C(F)(F)F)c2)n1)N1CCCC1] | (Z)-3-(3-(3,5-bis(trifluoromethyl)phenyl)-1H-1,2,4-triazol-1-yl)-1-(pyrrolidin-1-yl)prop-2-en-1-one |
| B-39 | 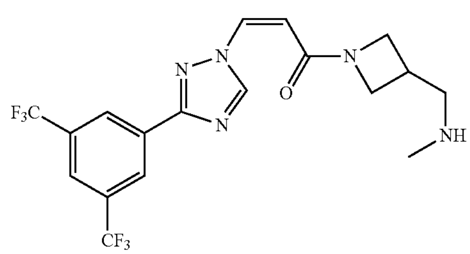 [SMILES: CNCC1CN(C(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-1-(3-((methylamino)methyl)azetidin-1-yl)prop-2-en-1-one |
| B-40 | 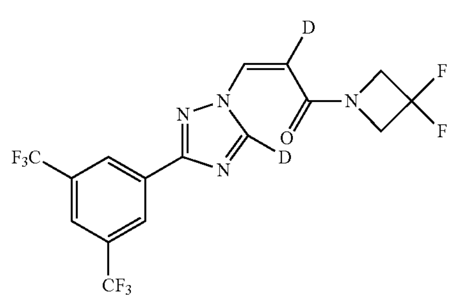 [SMILES: [2H]/C(=C/n1nc(-c2cc(C(F)(F)F)cc(C(F)(F)F)c2)nc1[2H])C(=O)N1CC(F)(F)C1] | D2-(Z)-3-(3-(3,5-bis(trifluoromethyl)phenyl)-1H-1,2,4-triazol-1-yl)-1-(3,3-difluoroazetidin-1-yl)prop-2-en-1-one |

TABLE 1B-continued

| Compound | Structure | Name |
|---|---|---|
| B-41 | 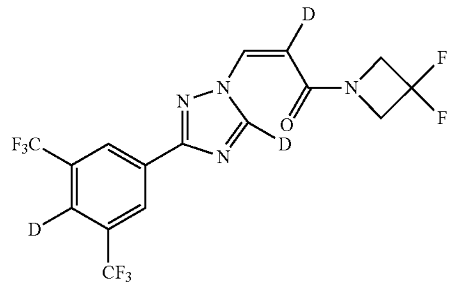 [SMILES: [2H]/C(=C/n1nc(-c2cc(C(F)(F)F)c([2H])c(C(F)(F)F)c2)nc1[2H])C(=O)N1CC(F)(F)C1] | D3-(Z)-3-(3-(3,5-bis(trifluoromethyl)phenyl)-1H-1,2,4-triazol-1-yl)-1-(3,3-difluoroazetidin-1-yl)prop-2-en-1-one |
| B-42 | 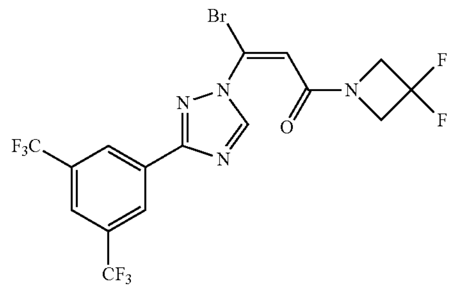 [SMILES: O=C(/C=C(/Br)n1cnc(-c2cc(C(F)(F)F)cc(C(F)(F)F)c2)n1)N1CC(F)(F)C1] | (E)-3-(3-(3,5-bis(trifluoromethyl)phenyl)-1H-1,2,4-triazol-1-yl)-3-bromo-1-(3,3-difluoroazetidin-1-yl)prop-2-en-1-one |
| B-43 | 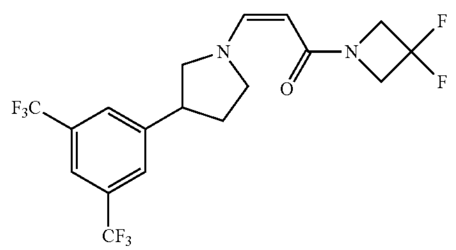 [SMILES: O=C(/C=C\N1CCC(c2cc(C(F)(F)F)cc(C(F)(F)F)c2)C1)N1CC(F)(F)C1] | 3-(3-(3,5-bis(trifluoromethyl)phenyl)pyrrolidin-1-yl)-1-(3,3-difluoroazetidin-1-yl)propan-1-one |
| B-44 | 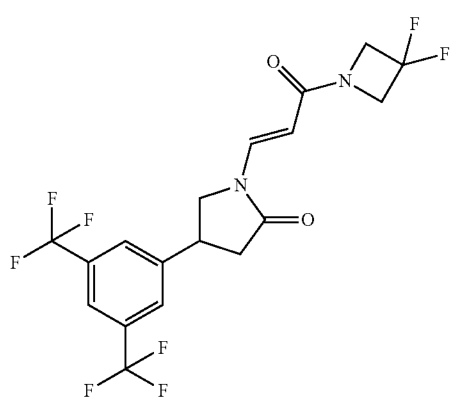 [SMILES: O=C1CC(c2cc(C(F)(F)F)cc(C(F)(F)F)c2)CN1/C=C/C(=O)N1CC(F)(F)C1] | (E)-4-(3,5-bis(trifluoromethyl)phenyl)-1-(3-(3,3-difluoroazetidin-1-yl)-3-oxoprop-1-en-1-yl)pyrrolidin-2-one |
| B-45 | 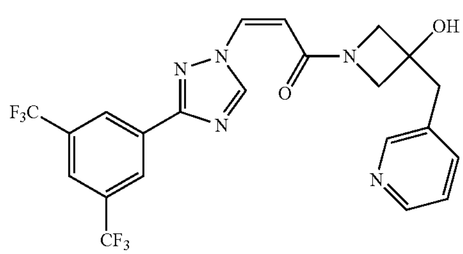 [SMILES: O=C(/C=C\n1cnc(-c2cc(C(F)(F)F)cc(C(F)(F)F)c2)n1)N1CC(O)(Cc2cccnc2)C1] | (Z)-3-(3-(3,5-bis(trifluoromethyl)phenyl)-1H-1,2,4-triazol-1-yl)-1-(3-hydroxy-3-(pyridin-3-ylmethyl)azetidin-1-yl)prop-2-en-1-one |

TABLE 1B-continued

Exemplary Compounds.

| Compound | Structure | Name |
|---|---|---|
| B-46 | 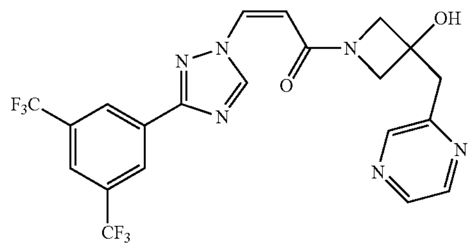 [SMILES: O=C(/C=C\n1cnc(-c2cc(C(F)(F)F)cc(C(F)(F)F)c2)n1)N1CC(O)(Cc2cnccn2)C1] | (Z)-3-(3-(3,5-bis(trifluoromethyl)phenyl)-1H-1,2,4-triazol-1-yl)-1-(3-hydroxy-3-(pyrazin-2-ylmethyl)azetidin-1-yl)prop-2-en-1-one |
| B-47 | 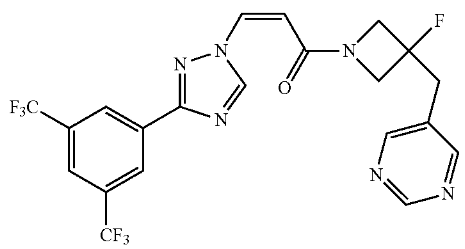 [SMILES: O=C(/C=C\n1cnc(-c2cc(C(F)(F)F)cc(C(F)(F)F)c2)n1)N1CC(F)(Cc2cncnc2)C1] | (Z)-3-(3-(3,5-bis(trifluoromethyl)phenyl)-1H-1,2,4-triazol-1-yl)-1-(3-fluoro-3-(pyrimidin-5-ylmethyl)azetidin-1-yl)prop-2-en-1-one |
| B-48 | 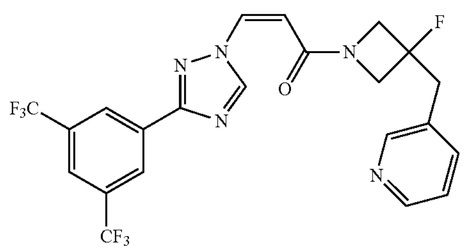 [SMILES: O=C(/C=C\n1cnc(-c2cc(C(F)(F)F)cc(C(F)(F)F)c2)n1)N1CC(F)(Cc2cccnc2)C1] | (Z)-3-(3-(3,5-bis(trifluoromethyl)phenyl)-1H-1,2,4-triazol-1-yl)-1-(3-fluoro-3-(pyridin-3-ylmethyl)azetidin-1-yl)prop-2-en-1-one |
| B-49 | 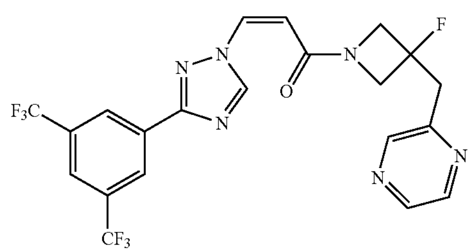 [SMILES: O=C(/C=C\n1cnc(-c2cc(C(F)(F)F)cc(C(F)(F)F)c2)n1)N1CC(F)(Cc2cnccn2)C1] | (Z)-3-(3-(3,5-bis(trifluoromethyl)phenyl)-1H-1,2,4-triazol-1-yl)-1-(3-fluoro-3-(pyrazin-2-ylmethyl)azetidin-1-yl)prop-2-en-1-one |
| B-50 | 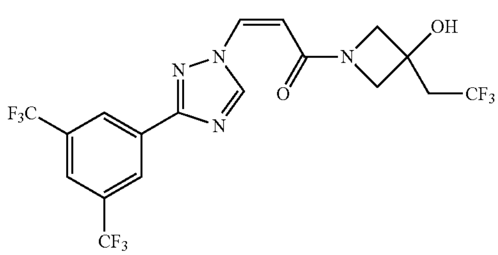 [SMILES: O=C(/C=C\n1cnc(-c2cc(C(F)(F)F)cc(C(F)(F)F)c2)n1)N1CC(O)(CC(F)(F)F)C1] | (Z)-3-(3-(3,5-bis(trifluoromethyl)phenyl)-1H-1,2,4-triazol-1-yl)-1-(3-hydroxy-3-(2,2,2-trifluoroethyl)azetidin-1-yl)prop-2-en-1-one |
| B-51 | 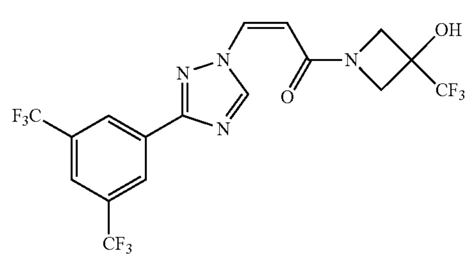 [SMILES: O=C(/C=C\n1cnc(-c2cc(C(F)(F)F)cc(C(F)(F)F)c2)n1)N1CC(O)(C(F)(F)F)C1] | (Z)-3-(3-(3,5-bis(trifluoromethyl)phenyl)-1H-1,2,4-triazol-1-yl)-1-(3-hydroxy-3-(trifluoromethyl)azetidin-1-yl)prop-2-en-1-one |

TABLE 1B-continued

Exemplary Compounds.

| Compound | Structure | Name |
|---|---|---|
| B-52 | 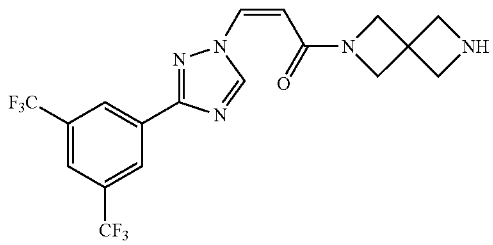 [SMILES: O=C(/C=C\n1cnc(-c2cc(C(F)(F)F)cc(C(F)(F)F)c2)n1)N1CC2(CNC2)C1] | (Z)-3-(3-(3,5-bis(trifluoromethyl)phenyl)-1H-1,2,4-triazol-1-yl)-1-(2,6-diazaspiro[3.3]heptan-2-yl)prop-2-en-1-one |
| B-53 | 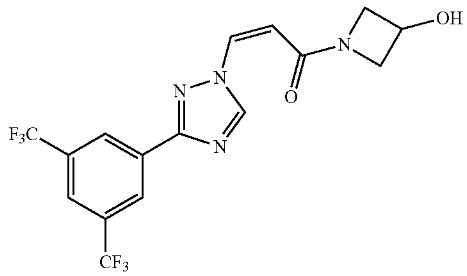 [SMILES: O=C(/C=C\n1cnc(-c2cc(C(F)(F)F)cc(C(F)(F)F)c2)n1)N1CC(O)C1] | (Z)-1-(3-(3-(3,5-bis(trifluoromethyl)phenyl)-1H-1,2,4-triazol-1-yl)acryloyl)azetidine-3-carbonitrile |
| B-54 | 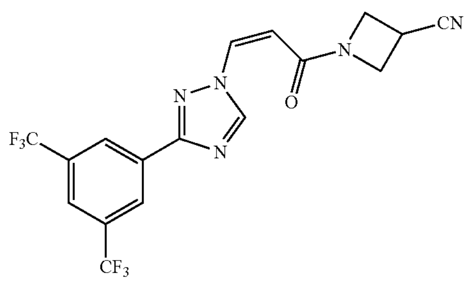 [SMILES: N#CC1CN(C(=O)/C=C\n2cnc(-c3cc(C(F)(F)F)cc(C(F)(F)F)c3)n2)C1] | (Z)-1-(3-(3-(3,5-bis(trifluoromethyl)phenyl)-1H-1,2,4-triazol-1-yl)acryloyl)azetidine-3-carbonitrile |
| B-55 | 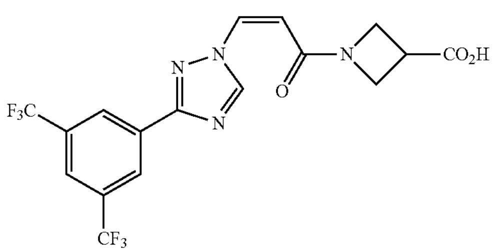 [SMILES: O=C(O)C1CN(C(=O)/C=C\n2cnc(-c3cc(C(F)(F)F)cc(C(F)(F)F)c3)n2)C1] | (Z)-1-(3-(3-(3,5-bis(trifluoromethyl)phenyl)-1H-1,2,4-triazol-1-yl)acryloyl)azetidine 3-carboxylic acid |
| B-56 | 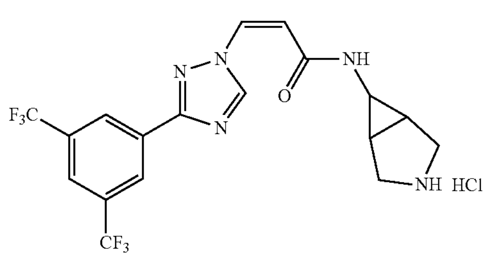 [SMILES: O=C(/C=C\n1cnc(-c2cc(C(F)(F)F)cc(C(F)(F)F)c2)n1)NC1C2CNCC21 ; Cl] | (Z)-N-(3-azabicyclo[3.1.0]hexan-6-yl)-3-(3-(3,5-bis(trifluoromethyl)phenyl)-1H-1,2,4-triazol-1-yl)acrylamide |
| B-57 | 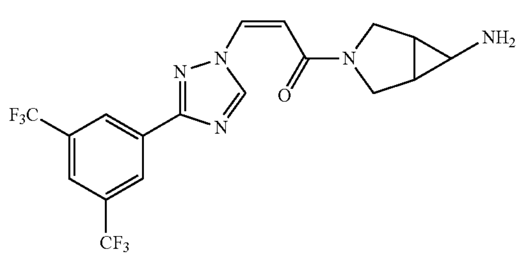 [SMILES: NC1C2CN(C(=O)/C=C\n3cnc(-c4cc(C(F)(F)F)cc(C(F)(F)F)c4)n3)CC12] | (Z)-N-(3-aminobicyclo[3.1.0]hexan-6-yl)-3-(3-(3,5-bis(trifluoromethyl)phenyl)-1H-1,2,4-triazol-1-yl)acrylamide |

TABLE 1B-continued

| Compound | Structure | Name |
|---|---|---|
| B-58 | 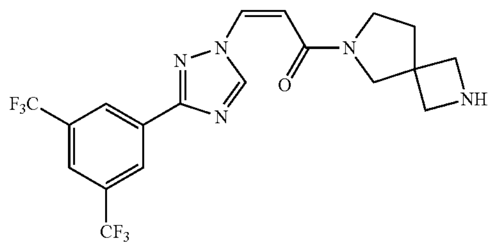 [SMILES: O=C(/C=C\n1cnc(-c2cc(C(F)(F)F)cc(C(F)(F)F)c2)n1)N1CCC2(CNC2)C1] | (Z)-N-(2,6-diazaspiro[3.4]octan-6-ylmethyl)-3-(3-(3,5-bis(trifluoromethyl)phenyl)-1H-1,2,4-triazol-1-yl)acrylamide |
| B-59 | 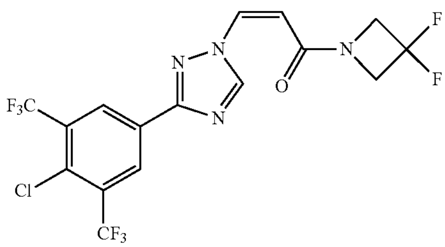 [SMILES: O=C(/C=C\n1cnc(-c2cc(C(F)(F)F)c(Cl)c(C(F)(F)F)c2)n1)N1CC(F)(F)C1] | (Z)-3-(3-(4-chloro-3,5-bis(trifluoromethyl)phenyl)-1H-1,2,4-triazol-1-yl)-1-(3,3-difluoroazetidin-1-yl)prop-2-en-1-one |
| B-60 | 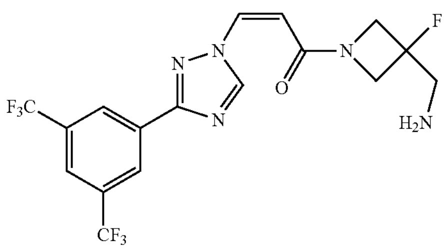 [SMILES: NCC1(F)CN(C(=O)/C=C\n2cnc(-c3cc(C(F)(F)F)cc(C(F)(F)F)c3)n2)C1] | (Z)-1-(3-(aminomethyl)-3-fluoroazetidin-1-yl)-3-(3-(3,5-bis(trifluoromethyl)phenyl)-1H-1,2,4-triazol-1-yl)prop-2-en-1-one |
| B-61 | 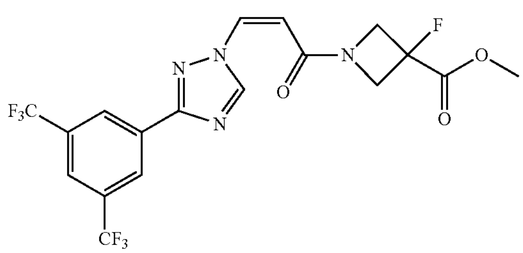 [SMILES: COC(=O)C1(F)CN(C(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-1-(3-fluoro-3-(2-methoxyacetyl)azetidin-1-yl)prop-2-en-1-one |
| B-62 | 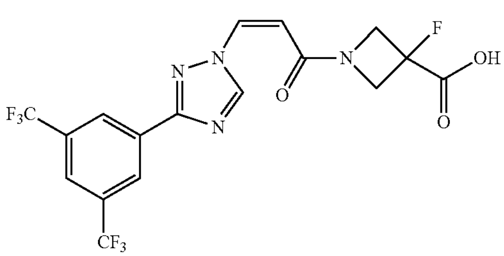 [SMILES: O=C(/C=C\n1cnc(-c2cc(C(F)(F)F)cc(C(F)(F)F)c2)n1)N1CC(F)(C(=O)O)C1] | (Z)-3-(3-(3,5-bis(trifluoromethyl)phenyl)-1H-1,2,4-triazol-1-yl)-1-(3-fluoro-3-(2-hydroxyacetyl)azetidin-1-yl)prop-2-en-1-one |

TABLE 1B-continued

Exemplary Compounds.

| Compound | Structure | Name |
|---|---|---|
| B-63 | 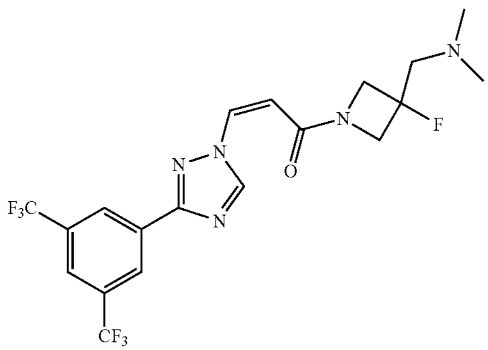 [SMILES: CN(C)CC1(F)CN(C(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-1-(3-((dimethylamino)methyl)-3-fluoroazetidin-1-yl)prop-2-en-1-one |
| B-64 | 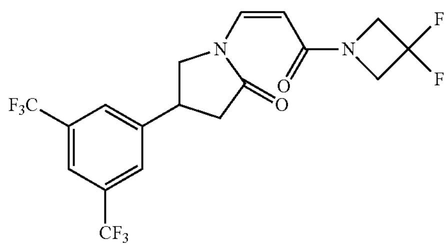 [SMILES: O=C1CC(c2cc(C(F)(F)F)cc(C(F)(F)F)c2)CN1/C=C\C(=O)N1CC(F)(F)C1] | (Z)-4-(3,5-bis(trifluoromethyl)phenyl)-1-(3-(3,3-difluoroazetidin-1-yl)-3-oxoprop-1-en-1-yl)pyrrolidin-2-one |
| B-65 | 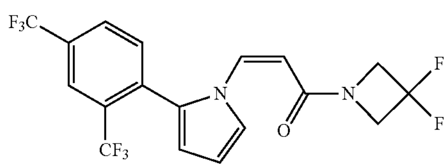 [SMILES: O=C(/C=C\n1cccc1-c1ccc(C(F)(F)F)cc1C(F)(F)F)N1CC(F)(F)C1] | (Z)-3-(2-(2,4-bis(trifluoromethyl)phenyl)-1H-pyrrol-1-yl)-1-(3,3-difluoroazetidin-1-yl)prop-2-en-1-one |
| B-66 | 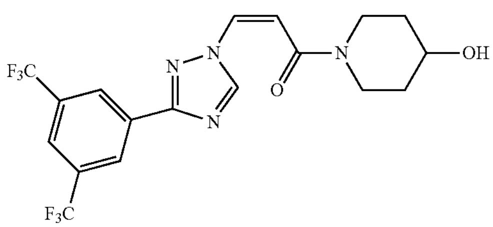 [SMILES: O=C(/C=C\n1cnc(-c2cc(C(F)(F)F)cc(C(F)(F)F)c2)n1)N1CCC(O)CC1] | (Z)-3-(3-(3,5-bis(trifluoromethyl)phenyl)-1H-1,2,4-triazol-1-yl)-1-(4-hydroxypiperidin-1-yl)prop-2-en-1-one |
| B-67 | 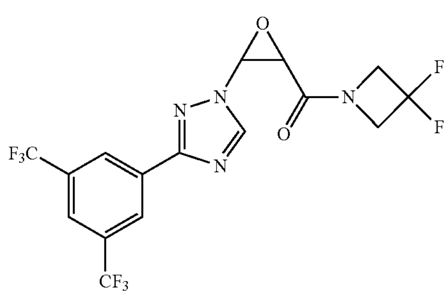 [SMILES: O=C(C1OC1n1cnc(-c2cc(C(F)(F)F)cc(C(F)(F)F)c2)n1)N1CC(F)(F)C1] | (3-(3-(3,5-bis(trifluoromethyl)phenyl)-1H-1,2,4-triazol-1-yl)oxiran-2-yl)(3,3-difluoroazetidin-1-yl)methanone |
| B-68 | 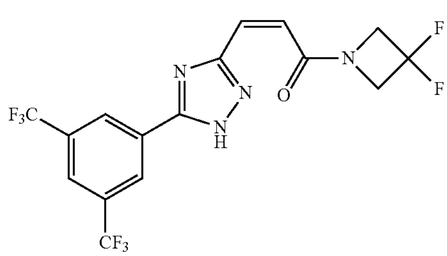 [SMILES: O=C(/C=C\c1n[nH]c(-c2cc(C(F)(F)F)cc(C(F)(F)F)c2)n1)N1CC(F)(F)C1] | (Z)-3-(5-(3,5-bis(trifluoromethyl)phenyl)-1H-1,2,4-triazol-3-yl)-1-(3,3-difluoroazetidin-1-yl)prop-2-en-1-one |

TABLE 1B-continued

Exemplary Compounds.

| Compound | Structure | Name |
|---|---|---|
| B-69 | 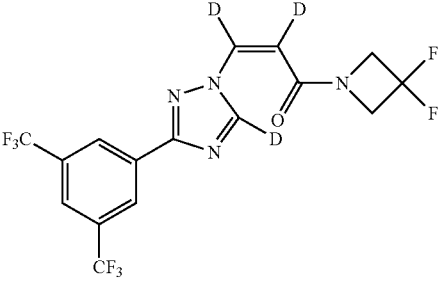 [SMILES: [2H]/C(C(=O)N1CC(F)(F)C1)=C(\[2H])n1nc(-c2cc(C(F)(F)F)cc(C(F)(F)F)c2)nc1[2H]] | D3-(Z)-3-(3-(3,5-bis(trifluoromethyl)phenyl)-1H-1,2,4-triazol-1-yl)-1-(3,3-difluoroazetidin-1-yl)prop-2-en-1-one |

Methods of making the compounds of Table 1B and compounds of formula (I) wherein $R^2$ is —C(O)—N($R^5$)($R^6$) are disclosed, for example, in International Application No. PCT/US2012/048368, the entire contents of which are incorporated herein by reference.

TABLE 1C

Exemplary Compounds.

| Cmpd. No. | Structure |
|---|---|
| C-3 | 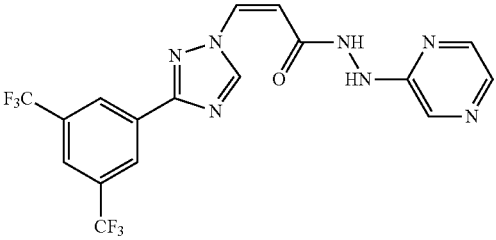 [SMILES: O=C(/C=C\n1cnc(-c2cc(C(F)(F)F)cc(C(F)(F)F)c2)n1)NNc1cnccn1] |
| C-4 | 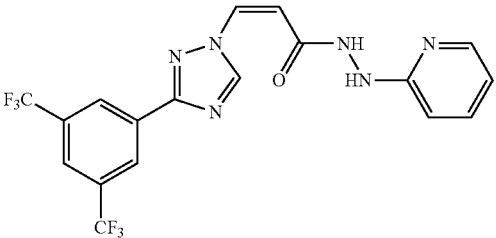 [SMILES: O=C(/C=C\n1cnc(-c2cc(C(F)(F)F)cc(C(F)(F)F)c2)n1)NNc1ccccn1] |
| C-5 | 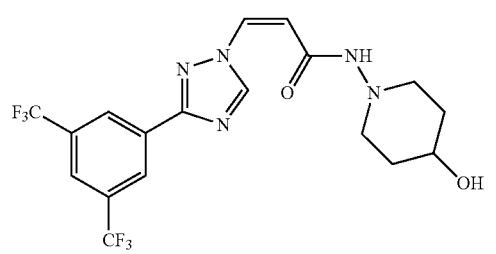 [SMILES: O=C(/C=C\n1cnc(-c2cc(C(F)(F)F)cc(C(F)(F)F)c2)n1)NN1CCC(O)CC1] |

TABLE 1C-continued

Exemplary Compounds.

| Cmpd. No. | Structure |
|---|---|
| C-6 | 3-[3,5-bis(trifluoromethyl)phenyl]-1,2,4-triazol-1-yl acrylamide with N-pyrrolidinyl group |
| C-7 | 3-[3,5-bis(trifluoromethyl)phenyl]-1,2,4-triazol-1-yl acrylohydrazide with N-methyl-N'-(pyridin-2-yl) group |
| C-8 | 3-[3,5-bis(trifluoromethyl)phenyl]-1,2,4-triazol-1-yl acrylohydrazide with N-methyl-N'-(pyrazin-2-yl) group |
| C-9 | 3-[3,5-bis(trifluoromethyl)phenyl]-1,2,4-triazol-1-yl acrylohydrazide with N-methyl-N'-(3-methylpyridin-2-yl) group |
| C-10 | 3-[3,5-bis(trifluoromethyl)phenyl]-1,2,4-triazol-1-yl acrylohydrazide with N'-(5-methylpyridin-2-yl) group |
| C-11 | 3-[3,5-bis(trifluoromethyl)phenyl]-1,2,4-triazol-1-yl acrylohydrazide with N-methyl-N'-(pyridin-3-yl) group |

TABLE 1C-continued

Exemplary Compounds.

| Cmpd. No. | Structure |
|---|---|
| C-12 | 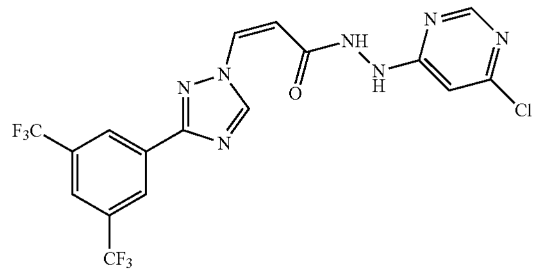 [SMILES: O=C(/C=C\n1cnc(-c2cc(C(F)(F)F)cc(C(F)(F)F)c2)n1)NNc1cc(Cl)ncn1] |
| C-13 | 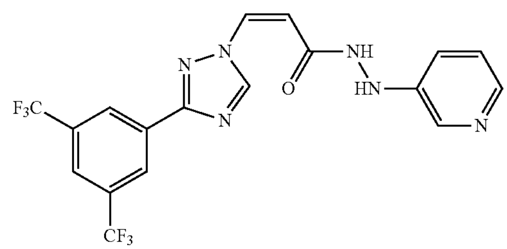 [SMILES: O=C(/C=C\n1cnc(-c2cc(C(F)(F)F)cc(C(F)(F)F)c2)n1)NNc1cccnc1] |
| C-14 | 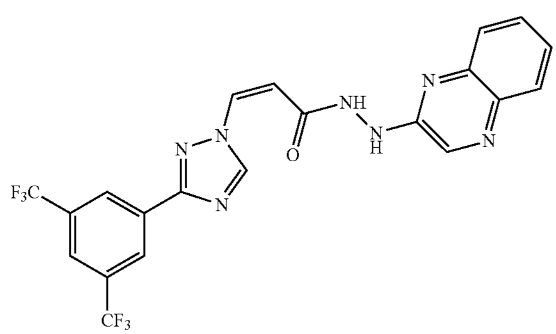 [SMILES: O=C(/C=C\n1cnc(-c2cc(C(F)(F)F)cc(C(F)(F)F)c2)n1)NNc1cnc2ccccc2n1] |
| C-15 | 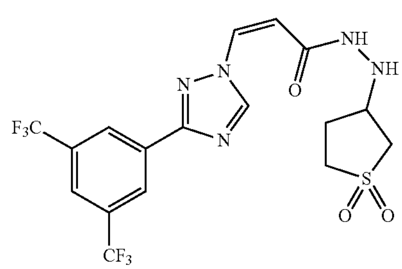 [SMILES: O=C(/C=C\n1cnc(-c2cc(C(F)(F)F)cc(C(F)(F)F)c2)n1)NNC1CCS(=O)(=O)C1] |
| C-16 | 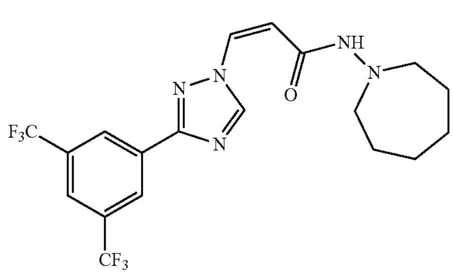 [SMILES: O=C(/C=C\n1cnc(-c2cc(C(F)(F)F)cc(C(F)(F)F)c2)n1)NN1CCCCCC1] |

TABLE 1C-continued

Exemplary Compounds.

| Cmpd. No. | Structure |
|---|---|
| C-17 | 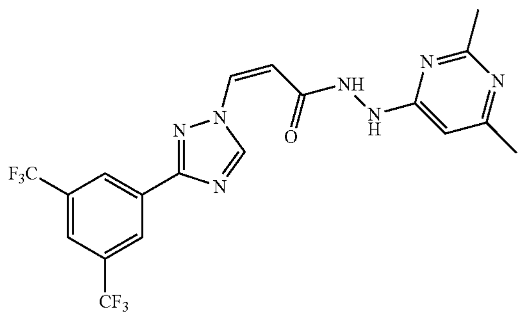 [SMILES: Cc1cc(NNC(=O)/C=C\n2cnc(-c3cc(C(F)(F)F)cc(C(F)(F)F)c3)n2)nc(C)n1] |
| C-18 | 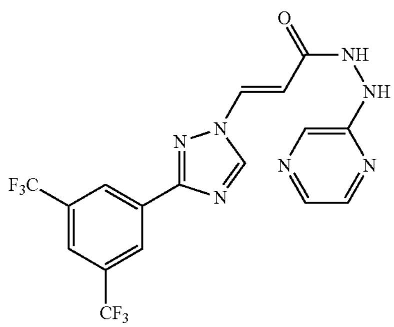 [SMILES: O=C(/C=C/n1cnc(-c2cc(C(F)(F)F)cc(C(F)(F)F)c2)n1)NNc1cnccn1] |
| C-19 | 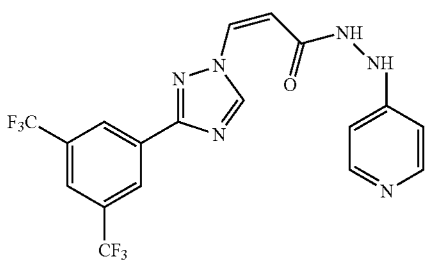 [SMILES: O=C(/C=C\n1cnc(-c2cc(C(F)(F)F)cc(C(F)(F)F)c2)n1)NNc1ccncc1] |
| C-20 | 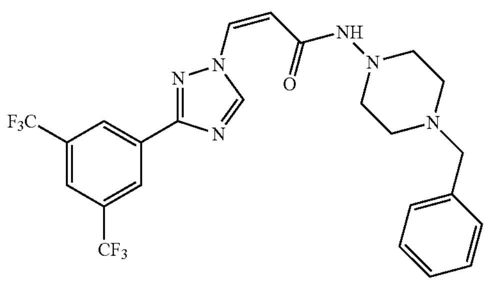 [SMILES: O=C(/C=C\n1cnc(-c2cc(C(F)(F)F)cc(C(F)(F)F)c2)n1)NN1CCN(Cc2ccccc2)CC1] |
| C-21 | 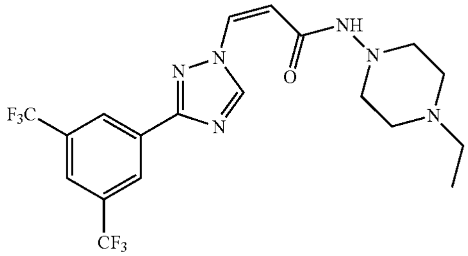 [SMILES: CCN1CCN(NC(=O)/C=C\n2cnc(-c3cc(C(F)(F)F)cc(C(F)(F)F)c3)n2)CC1] |

TABLE 1C-continued
Exemplary Compounds.
| Cmpd. No. | Structure |
|---|---|
| C-22 | 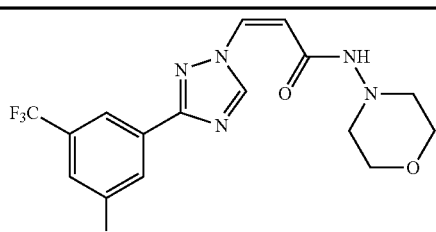 |
| C-23 | 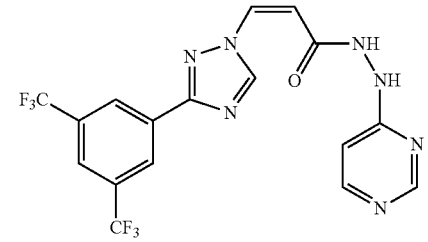 [SMILES: O=C(/C=C\n1cnc(-c2cc(C(F)(F)F)cc(C(F)(F)F)c2)n1)NNc1ccncn1] |
| C-24 | 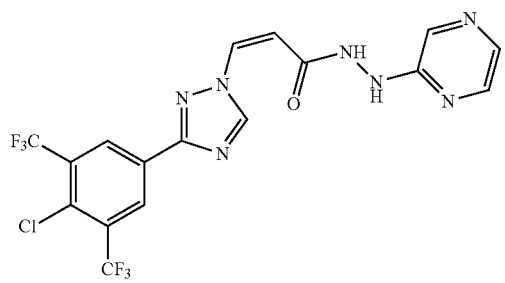 [SMILES: O=C(/C=C\n1cnc(-c2cc(C(F)(F)F)c(Cl)c(C(F)(F)F)c2)n1)NNc1cnccn1] |
| C-25 | 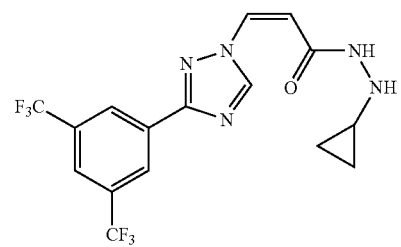 [SMILES: O=C(/C=C\n1cnc(-c2cc(C(F)(F)F)cc(C(F)(F)F)c2)n1)NNC1CC1] |
| C-26 | 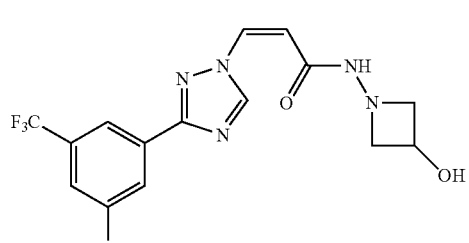 |
Methods of making the compounds of Table 1C and compounds of formula (I) wherein $R^2$ is —C(O)—N($R^7$)—N($R^5$)($R^6$) are disclosed, for example, in International Application No. PCT/US2012/048319, the entire contents of which are incorporated herein by reference.

TABLE 1D

| Exemplary Compounds. | | |
|---|---|---|
| Compound | Structure | Name |
| D-1 | | (Z)-2-(2-(3-(3-methoxy-5-(trifluoromethyl)phenyl)-1H-1,2,4-triazol-1-yl)vinyl)-1,3,4-oxadiazole |
| D-2 | | (Z)-2-(2-(3-(3-methoxy-5-(trifluoromethyl)phenyl)-1H-1,2,4-triazol-1-yl)vinyl)-5-methyl-1,3,4-oxadiazole |
| D-3 | | (Z)-2-isopropyl-5-(2-(3-(3-methoxy-5-(trifluoromethyl)phenyl)-1H-1,2,4-triazol-1-yl)vinyl)-1,3,4-oxadiazole |
| D-4 | | (Z)-2-cyclopentyl-5-(2-(3-(3-methoxy-5-(trifluoromethyl)phenyl)-1H-1,2,4-triazol-1-yl)vinyl)-1,3,4-oxadiazole |
| D-5 | | (Z)-2-(azetidin-3-yl)-5-(2-(3-(3-methoxy-5-(trifluoromethyl)phenyl)-1H-1,2,4-triazol-1-yl)vinyl)-1,3,4-oxadiazole |
| D-6 | | (Z)-1-(5-(2-(3-(3-methoxy-5-(trifluoromethyl)phenyl)-1H-1,2,4-triazol-1-yl)vinyl)-1,3,4-oxadiazol-2-yl)-N,N-dimethylmethanamine |

TABLE 1D-continued

Exemplary Compounds.

| Compound | Structure | Name |
|---|---|---|
| D-7 | 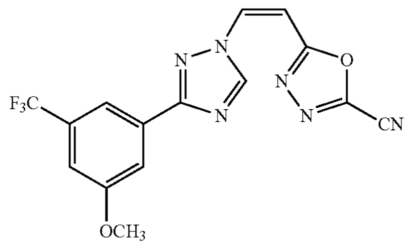 [SMILES: COc1cc(-c2ncn(/C=C\c3nnc(C#N)o3)n2)cc(C(F)(F)F)c1] | (Z)-5-(2-(3-(3-methoxy-5-(trifluoromethyl)phenyl)-1H-1,2,4-triazol-1-yl)vinyl)-1,3,4-oxadiazole-2-carbonitrile |
| D-8 | 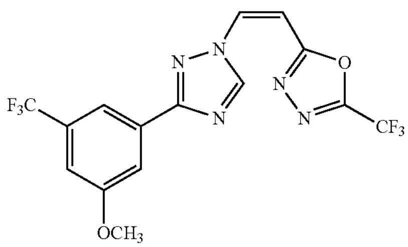 [SMILES: COc1cc(-c2ncn(/C=C\c3nnc(C(F)(F)F)o3)n2)cc(C(F)(F)F)c1] | (Z)-2-(2-(3-(3-methoxy-5-(trifluoromethyl)phenyl)-1H-1,2,4-triazol-1-yl)vinyl)-5-(trifluoromethyl)-1,3,4-oxadiazole |
| D-9 | 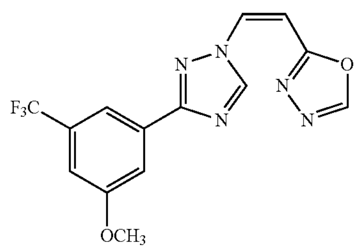 [SMILES: COc1cc(-c2ncn(/C=C\c3nnco3)n2)cc(C(F)(F)F)c1] | (Z)-2-(2-(3-(2-methoxy-6-(trifluoromethyl)pyridin-4-yl)-1H-1,2,4-triazol-1-yl)vinyl)-1,3,4-oxadiazole |
| D-10 | 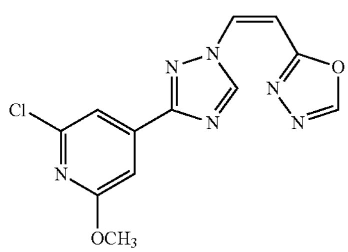 [SMILES: COc1cc(-c2ncn(/C=C\c3nnco3)n2)cc(Cl)n1] | (Z)-2-(2-(3-(2-chloro-6-methoxypyridin-4-yl)-1H-1,2,4-triazol-1-yl)vinyl)-1,3,4-oxadiazole |
| D-11 | 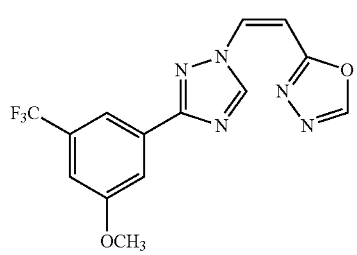 [SMILES: COc1cc(-c2ncn(/C=C\c3nnco3)n2)cc(C(F)(F)F)c1] | (Z)-5-(2-(3-(3-methoxy-5-(trifluoromethyl)phenyl)-1H-1,2,4-triazol-1-yl)vinyl)-1,2,4-oxadiazole |
| D-12 | 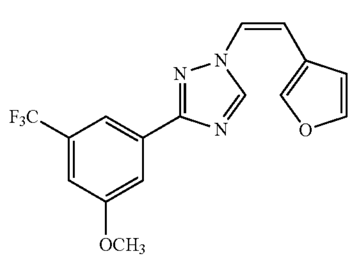 [SMILES: COc1cc(-c2ncn(/C=C\c3ccoc3)n2)cc(C(F)(F)F)c1] | (Z)-4-(2-(3-(3-methoxy-5-(trifluoromethyl)phenyl)-1H-1,2,4-triazol-1-yl)vinyl)oxazole |

TABLE 1D-continued

Exemplary Compounds.

| Compound | Structure | Name |
|---|---|---|
| D-13 | 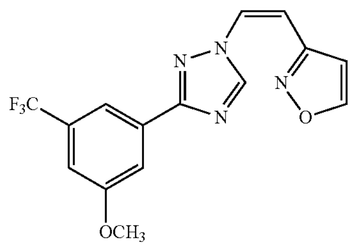 [SMILES: COc1cc(-c2ncn(/C=C\c3ccon3)n2)cc(C(F)(F)F)c1] | (Z)-3-(2-(3-(3-methoxy-5-(trifluoromethyl)phenyl)-1H-1,2,4-triazol-1-yl)vinyl)isoxazole |
| D-14 | 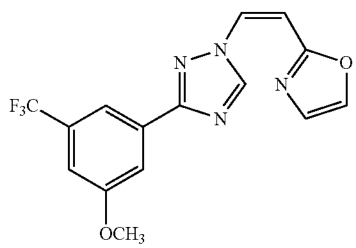 | (Z)-2-(2-(3-(3-methoxy-5-(trifluoromethyl)phenyl)-1H-1,2,4-triazol-1-yl)vinyl)oxazole |
| D-15 | 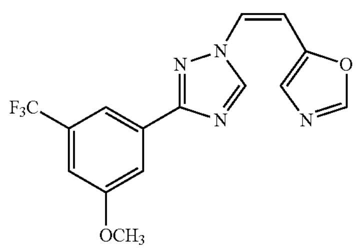 | (Z)-5-(2-(3-(3-methoxy-5-(trifluoromethyl)phenyl)-1H-1,2,4-triazol-1-yl)vinyl)oxazole |
| D-16 | 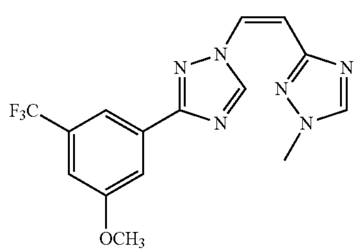 [SMILES: COc1cc(-c2ncn(/C=C\c3ncn(C)n3)n2)cc(C(F)(F)F)c1] | (Z)-3-(3-methoxy-5-(trifluoromethyl)phenyl)-1-(2-(1-methyl-1H-1,2,4-triazol-3-yl)vinyl)-1H-1,2,4-triazole |
| D-17 | 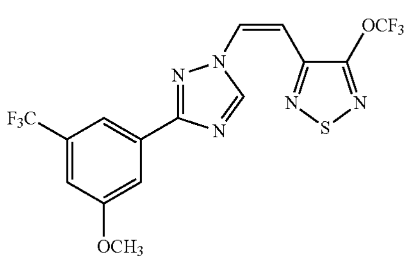 [SMILES: COc1cc(-c2ncn(/C=C\c3nsnc3OC(F)(F)F)n2)cc(C(F)(F)F)c1] | (Z)-3-(2-(3-(3-methoxy-5-(trifluoromethyl)phenyl)-1H-1,2,4-triazol-1-yl)vinyl)-4-(trifluoromethoxy)-1,2,5-thiadiazole |
| D-18 | 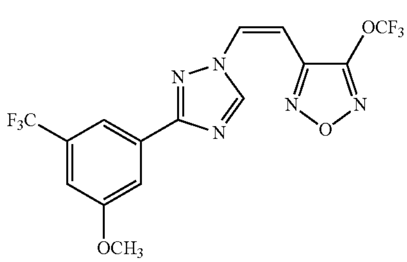 [SMILES: COc1cc(-c2ncn(/C=C\c3nonc3OC(F)(F)F)n2)cc(C(F)(F)F)c1] | (Z)-3-(2-(3-(3-methoxy-5-(trifluoromethyl)phenyl)-1H-1,2,4-triazol-1-yl)vinyl)-4-(trifluoromethoxy)-1,2,5-oxadiazole |

TABLE 1D-continued

Exemplary Compounds.

| Compound | Structure | Name |
|---|---|---|
| D-19 | 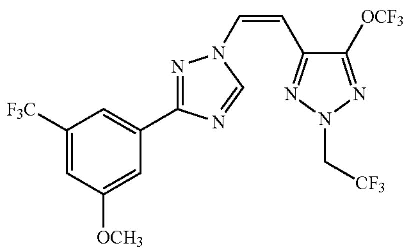 [SMILES: COc1cc(-c2ncn(/C=C\c3nn(CC(F)(F)F)nc3OC(F)(F)F)n2)cc(C(F)(F)F)c1] | (Z)-4-(2-(3-(3-methoxy-5-(trifluoromethyl)phenyl)-1H-1,2,4-triazol-1-yl)vinyl)-2-(2,2,2-trifluoroethyl)-5-(trifluoromethoxy)-2H-1,2,3-triazole |
| D-20 | 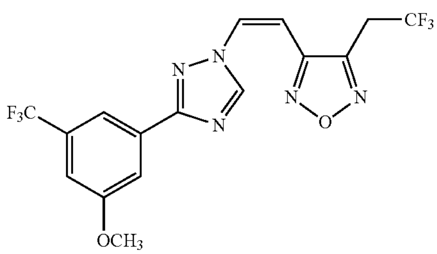 [SMILES: COc1cc(-c2ncn(/C=C\c3nonc3CC(F)(F)F)n2)cc(C(F)(F)F)c1] | (Z)-3-(2-(3-(3-methoxy-5-(trifluoromethyl)phenyl)-1H-1,2,4-triazol-1-yl)vinyl)-4-(2,2,2-trifluoroethyl)-1,2,5-oxadiazole |
| D-21 | 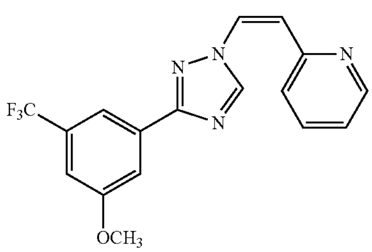 [SMILES: COc1cc(-c2ncn(/C=C\c3ccccn3)n2)cc(C(F)(F)F)c1] | (Z)-2-(2-(3-(3-methoxy-5-(trifluoromethyl)phenyl)-1H-1,2,4-triazol-1-yl)vinyl)pyridine |
| D-22 | 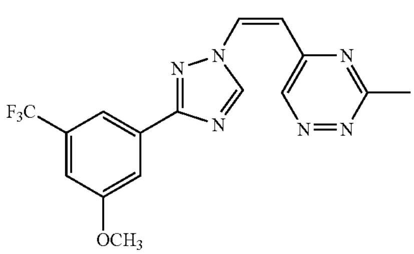 [SMILES: COc1cc(-c2ncn(/C=C\c3cnnc(C)n3)n2)cc(C(F)(F)F)c1] | (Z)-5-(2-(3-(3-methoxy-5-(trifluoromethyl)phenyl)-1H-1,2,4-triazol-1-yl)vinyl)-3-methyl-1,2,4-triazine |
| D-23 | 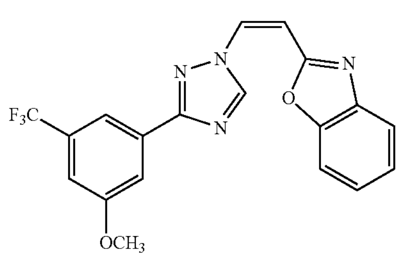 [SMILES: COc1cc(-c2ncn(/C=C\c3nc4ccccc4o3)n2)cc(C(F)(F)F)c1] | (Z)-2-(2-(3-(3-methoxy-5-(trifluoromethy)phenyl)-1H-1,2,4-triazol-1-yl)vinyl)benzo[d]oxazole |
| D-24 | 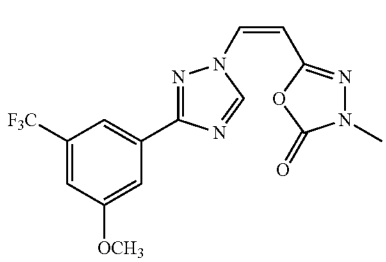 [SMILES: COc1cc(-c2ncn(/C=C\c3nn(C)c(=O)o3)n2)cc(C(F)(F)F)c1] | (Z)-5-(2-(3-(3-methoxy-5-(trifluoromethyl)phenyl)-1H-1,2,4-triazol-1-yl)vinyl)-3-methyl-1,3,4-oxadiazol-2(3H)-one |

TABLE 1D-continued

Exemplary Compounds.

| Compound | Structure | Name |
|---|---|---|
| D-25 | 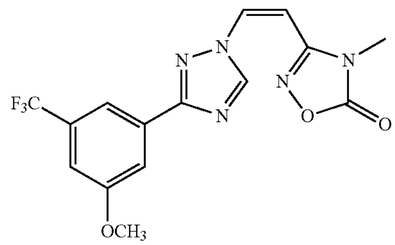 [SMILES: COc1cc(-c2ncn(/C=C\c3noc(=O)n3C)n2)cc(C(F)(F)F)c1] | (Z)-3-(2-(3-(3-methoxy-5-(trifluoromethyl)phenyl)-1H-1,2,4-triazol-1-yl)vinyl)-4-methyl-1,2,4-oxadiazol-5(4H)-one |
| D-26 | 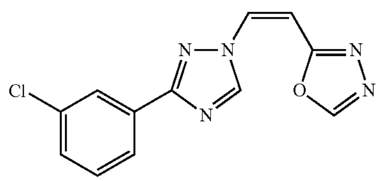 [SMILES: Clc1cccc(-c2ncn(/C=C\c3nnco3)n2)c1] | (Z)-2-(2-(3-(3-chlorophenyl)-1H-1,2,4-triazol-1-yl)vinyl)-1,3,4-oxadiazole |
| D-27 | 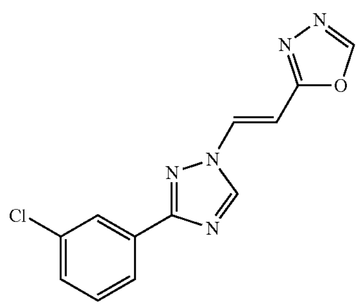 [SMILES: Clc1cccc(-c2ncn(/C=C/c3nnco3)n2)c1] | (E)-2-(2-(3-(3-methoxy-5-(trifluoromethyl)phenyl)-1H-1,2,4-triazol-1-yl)vinyl)-1,3,4-oxadiazole |
| D-28 | 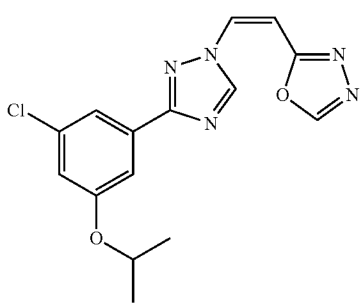 [SMILES: CC(C)Oc1cc(Cl)cc(-c2ncn(/C=C\c3nnco3)n2)c1] | (Z)-2-(2-(3-(3-chloro-5-isopropoxyphenyl)-1H-1,2,4-triazol-1-yl)vinyl)-1,3,4-oxadiazole |
| D-29 | 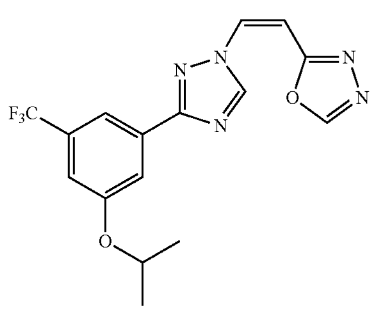 [SMILES: CC(C)Oc1cc(-c2ncn(/C=C\c3nnco3)n2)cc(C(F)(F)F)c1] | (Z)-2-(2-(3-(3-isopropoxy-5-(trifluoromethyl)phenyl)-1H-1,2,4-triazol-1-yl)vinyl)-1,3,4-oxadiazole |

TABLE 1D-continued

Exemplary Compounds.

| Compound | Structure | Name |
|---|---|---|
| D-30 | 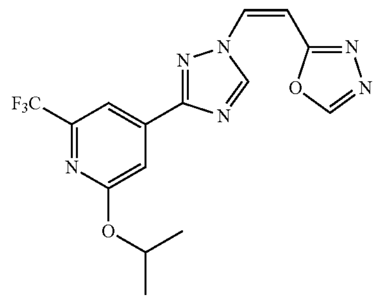 [SMILES: CC(C)Oc1cc(-c2ncn(/C=C\c3nnco3)n2)cc(C(F)(F)F)n1] | (Z)-2-(2-(3-(2-isopropoxy-6-(trifluoromethyl)pyridin-4-yl)-1H-1,2,4-triazol-1-yl)vinyl)-1,3,4-oxadiazole |
| D-31 | 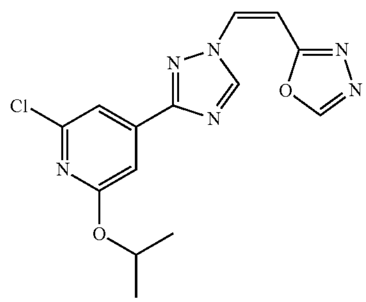 | (Z)-2-(2-(3-(2-chloro-6-isopropoxypyridin-4-yl)-1H-1,2,4-triazol-1-yl)vinyl)-1,3,4-oxadiazole |
| D-32 | 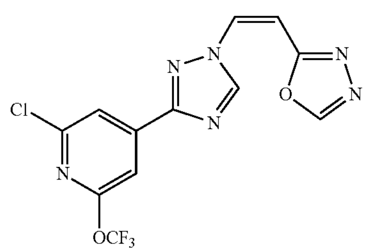 [SMILES: FC(F)(F)Oc1cc(-c2ncn(/C=C\c3nnco3)n2)cc(Cl)n1] | (Z)-2-(2-(3-(2-chloro-6-(trifluoromethoxy)pyridin-4-yl)-1H-1,2,4-triazol-1-yl)vinyl)-1,3,4-oxadiazole |
| D-33 | 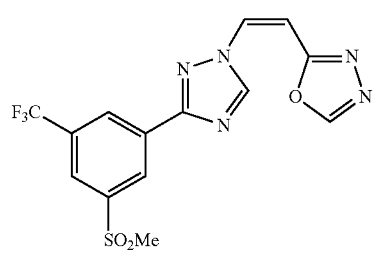 [SMILES: CS(=O)(=O)c1cc(-c2ncn(/C=C\c3nnco3)n2)cc(C(F)(F)F)c1] | (Z)-2-(2-(3-(3-(methylsulfonyl)-5-(trifluoromethyl)phenyl)-1H-1,2,4-triazol-1-yl)vinyl)-1,3,4-oxadiazole |
| D-34 | 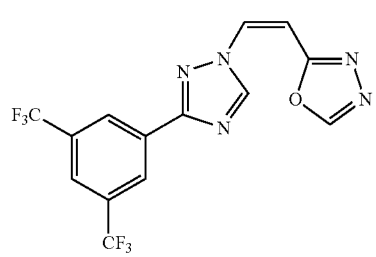 [SMILES: FC(F)(F)c1cc(-c2ncn(/C=C\c3nnco3)n2)cc(C(F)(F)F)c1] | (Z)-2-(2-(3-(3,5-bis(trifluoromethyl)phenyl)-1H-1,2,4-triazol-1-yl)vinyl)-1,3,4-oxadiazole |

TABLE 1D-continued

Exemplary Compounds.

| Compound | Structure | Name |
|---|---|---|
| D-35 | 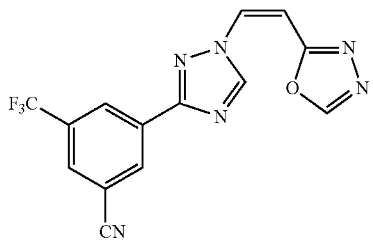 [SMILES: N#Cc1cc(-c2ncn(/C=C\c3nnco3)n2)cc(C(F)(F)F)c1] | (Z)-3-(1-(2-(1,3,4-oxadiazol-2-yl)vinyl)-1H-1,2,4-triazol-3-yl)-5-(trifluoromethyl)benzonitrile |
| D-36 | 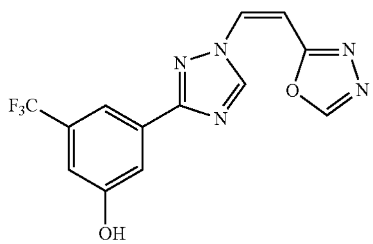 [SMILES: Oc1cc(-c2ncn(/C=C\c3nnco3)n2)cc(C(F)(F)F)c1] | (Z)-3-(1-(2-(1,3,4-oxadiazol-2-yl)vinyl)-1H-1,2,4-triazol-3-yl)-5-(trifluoromethyl)phenol |
| D-37 | 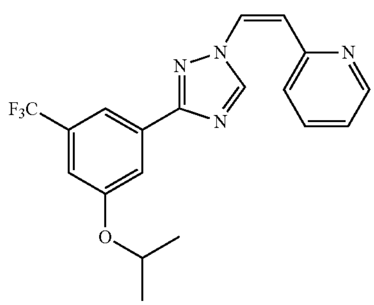 [SMILES: CC(C)Oc1cc(-c2ncn(/C=C\c3ccccn3)n2)cc(C(F)(F)F)c1] | (Z)-2-(2-(3-(3-isopropoxy-5-(trifluoromethyl)phenyl)-1H-1,2,4-triazol-1-yl)vinyl)pyridine |
| D-38 | 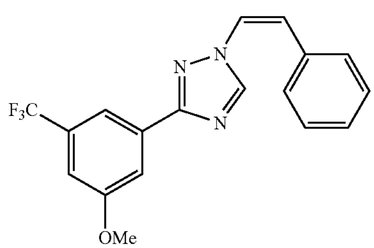 [SMILES: COc1cc(-c2ncn(/C=C\c3ccccc3)n2)cc(C(F)(F)F)c1] | (Z)-3-(3-methoxy-5-(trifluoromethyl)phenyl)-1-styryl-1H-1,2,4-triazole |
| D-39 | 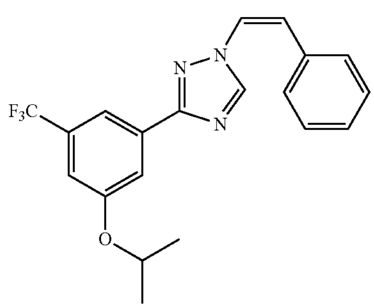 [SMILES: CC(C)Oc1cc(-c2ncn(/C=C\c3ccccc3)n2)cc(C(F)(F)F)c1] | (Z)-3-(3-isopropoxy-5-(trifluoromethyl)phenyl)-1-styryl-1H-1,2,4-triazole |

Methods of making the compounds of Table 1D and compounds of formula (I) wherein $R^2$ is heteroaryl are disclosed, for example, in International Application No. PCT/US2012/021406, the entire contents of which are incorporated herein by reference.

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit CRM1, in a biological sample or in a subject. In certain embodiments, a composition of this invention is formulated for administration to a subject in need of such composition. The term "subject", as used herein, means an animal. In some embodiments, the animal is a mammal. In certain embodiments, the subject is a veterinary subject (i.e., a non-human mammal subject), such as a pig or a horse. In some embodiments, the subject is a dog. In other embodiments, the subject is a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Other pharmaceutically acceptable carriers, adjuvants or vehicles include water, saline and dimethylsulfoxide, as well as other hydrophobic or hydrophilic solvents.

Pharmaceutically acceptable compositions of the present invention may be formulated to provide dry wound care (e.g., formulated for oral administration or administration as a topical cream) or to provide moist wound care (e.g., liquid formulations).

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or intraperitoneally. Preferably, the compounds and compositions described herein are administered orally or topically.

The term "parenteral," as used herein includes subcutaneous, intravenous, intramuscular, intraocular, intravitreal, intra-articular, intra-synovial, intrasternal, intrathecal, intra-hepatic, intraperitoneal intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Alternatively, pharmaceutically acceptable compositions of this invention may be administered in the form of suppositories for rectal administration.

Pharmaceutically acceptable compositions of this invention may also be administered topically, especially when the target of treatment includes areas or organs readily accessible by topical application, including the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For ophthalmic use, provided pharmaceutically acceptable compositions may be formulated as micronized suspensions or in an ointment such as petrolatum.

Pharmaceutically acceptable compositions of this invention may also be administered by nasal aerosol or inhalation.

In some embodiments, pharmaceutically acceptable compositions of this invention are formulated for intra-peritoneal administration.

The amount of compounds of the present invention that may be combined with the carrier materials to produce a composition in a single dosage form will vary depending upon the host treated and the particular mode of administration. In one embodiment, provided compositions should be formulated so that a dosage of between 0.01-100 mg/kg body weight/day of the inhibitor can be administered to a subject receiving these compositions. In another embodiment, the dosage is from about 0.5 to about 100 mg/kg of body weight, or between 1 mg and 1000 mg/dose, every 4 to 120 hours, or according to the requirements of the particular drug. Typically, the pharmaceutical compositions of this invention will be administered from about 1 to about 6 times per day.

In some embodiments, the compound is formulated for oral administration at a dosage of approximately 5 mg/kg to approximately 10 mg/kg, preferably at a dosage of approximately 7.5 mg/kg.

In some embodiments, the compound is formulated for topical administration at a concentration of approximately 0.3 µM to approximately 10 µM.

It should also be understood that a specific dosage and treatment regimen for any particular subject will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Wound Healing

Wounds are a type of condition characterized by cell or tissue damage. Wound healing is a dynamic pathway that optimally leads to restoration of tissue integrity and function. The wound healing process consists of three overlapping phases. The first phase is an inflammatory phase, which is characterized by homeostasis, platelet aggregation and degranulation. Platelets as the first response, release multiple growth factors to recruit immune cells, epithelial cells, and endothelial cells. The inflammatory phase typically occurs over days 0-5. The second stage of wound healing is the proliferative phase during which macrophages and granulocytes invade the wound. Infiltrating fibroblasts begin to produce collagen. The principle characteristics of this phase are epithelialization, angiogenesis, granulation tissue formation and collagen production. The proliferative phase typically occurs over days 3-14. The third phase is the remodeling phase where matrix formation occurs. The fibroblasts, epithelial cells, and endothelial cells continue to produce collagen and collagenase as well as matrix metalloproteases (MMPs) for remodeling. Collagen crosslinking takes place and the wound undergoes contraction. The remodeling phase typically occurs from day 7 to one year.

Compounds and compositions described herein can be used for promoting wound healing (e.g., promoting or accelerating wound closure and/or wound healing, mitigating scar fibrosis of the tissue of and/or around the wound, inhibiting apoptosis of cells surrounding or proximate to the wound). Thus, in certain embodiments, the present invention provides a method for promoting wound healing in a subject, comprising administering to the subject a therapeutically effective amount of a compound (e.g., a CRM1 inhibitor), or pharmaceutically acceptable salt or composition thereof. The method need not achieve complete healing or closure of the wound; it is sufficient for the method to promote any degree of wound closure. In this respect, the method can be employed alone or as an adjunct to other methods for healing wounded tissue.

The compounds and compositions described herein can be used to treat wounds during the inflammatory (or early) phase, during the proliferative (or middle) wound healing phase, and/or during the remodeling (or late) wound healing phase.

In some embodiments, the subject in need of wound healing is a human or an animal, for example, a dog, a cat, a horse, a pig, or a rodent, such as a mouse.

In some embodiments, the compounds and compositions described herein useful for wound healing are administered topically, for example, proximate to the wound site, or systemically.

More specifically, a therapeutically effective amount of a compound or composition described herein can be administered (optionally in combination with other agents) to the wound site by coating the wound or applying a bandage, packing material, stitches, etc., that are coated or treated with the compound or composition described herein. As such, the compounds and compositions described herein can be formulated for topical administration to treat surface wounds. Topical formulations include those for delivery via the mouth (buccal) and to the skin such that a layer of skin (i.e., the epidermis, dermis, and/or subcutaneous layer) is contacted with the compound or composition described herein. Topical delivery systems may be used to administer topical formulations of the compounds and compositions described herein.

Alternatively, the compounds and compositions described herein can be administered at or near the wound site by, for example, injection of a solution, injection of an extended release formulation, or introduction of a biodegradable implant comprising the compound or composition described herein.

The compounds and compositions described herein can be used to treat acute wounds or chronic wounds. A chronic wound results when the normal reparative process is interrupted. Chronic wounds can develop from acute injuries as a result of unrecognized persistent infections or inadequate primary treatment. In most cases however, chronic lesions are the end stage of progressive tissue breakdown owing to venous, arterial, or metabolic vascular disease, pressure sores, radiation damage, or tumors.

In chronic wounds, healing does not occur for a variety of reasons, including improper circulation in diabetic ulcers, significant necrosis, such as in burns, and infections. In these chronic wounds, viability or the recovery phase is often the rate-limiting step. The cells are no longer viable and, thus, initial recovery phase is prolonged by unfavorable wound bed environment.

Chronic wounds include, but are not limited to the following: chronic ischemic skin lesions; scleroderma ulcers; arterial ulcers; diabetic foot ulcers; pressure ulcers; venous ulcers; non-healing lower extremity wounds; ulcers due to inflammatory conditions; and/or long-standing wounds. Other examples of chronic wounds include chronic ulcers, diabetic wounds, wounds caused by diabetic neuropathy, venous insufficiencies, and arterial insufficiencies, and pressure wounds and cold and warm burns. Yet other examples of chronic wounds include chronic ulcers, diabetic wounds, wounds caused by diabetic neuropathy, venous insufficiencies, arterial insufficiencies, and pressure wounds.

Acute wounds include, but are not limited to, post-surgical wounds, lacerations, hemorrhoids and fissures.

In a particular embodiment, the compounds and compositions described herein can be used for diabetic wound healing or accelerating healing of leg and foot ulcers secondary to diabetes or ischemia in a subject.

In one embodiment, the wound is a surface wound. In another embodiment, the wound is a surgical wound (e.g., abdominal or gastrointestinal surgical wound). In a further embodiment, the wound is a burn. In yet another embodiment, the wound is the result of radiation exposure.

The compounds and compositions described herein can also be used for diabetic wound healing, gastrointestinal wound healing, or healing of an adhesion due, for example, to an operation.

The compounds and compositions described herein can also be used to heal wounds that are secondary to another disease. For example, in inflammatory skin diseases, such as psoriasis and dermatitis, there are numerous incidents of skin lesions that are secondary to the disease, and are caused by deep cracking of the skin, or scratching of the skin. The compounds and compositions described herein can be used to heal wounds that are secondary to these diseases, for example, inflammatory skin diseases, such as psoriasis and dermatitis.

In a further embodiment, the wound is an internal wound. In a specific aspect, the internal wound is a chronic wound. In another specific aspect, the wound is a vascular wound. In yet another specific aspect, the internal wound is an ulcer. Examples of internal wounds include, but are not limited to, fistulas and internal wounds associated with cosmetic surgery, internal indications, Crohn's disease, ulcerative colitis, internal surgical sutures and skeletal fixation. Other examples of internal wounds include, but are not limited to, fistulas and internal wounds associated with cosmetic surgery, internal indications, internal surgical sutures and skeletal fixation.

Examples of wounds include, but are not limited to, abrasions, avulsions, blowing wounds (i.e., open pneumothorax), burn wounds, contusions, gunshot wounds, incised wounds, open wounds, penetrating wounds, perforating wounds, puncture wounds, séton wounds, stab wounds, surgical wounds, subcutaneous wounds, diabetic lesions, or tangential wounds. Additional examples of wounds that can be treated by the compounds and compositions described herein include acute conditions or wounds, such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies; trauma -induced injuries including cuts, incisions, excoriations; injuries sustained from accidents; post-surgical injuries, as well as chronic conditions, such as pressure sores, bedsores, conditions related to diabetes and poor circulation, and all types of acne. In addition, the wound can include dermatitis, such as impetigo, intertrigo, folliculitis and eczema, wounds following dental surgery; periodontal disease; wounds following trauma; and tumor -associated wounds. Yet other examples of wounds include animal bites, arterial disease, insect stings and bites, bone infections, compromised skin/muscle grafts, gangrene, skin tears or lacerations, skin aging, surgical incisions, including slow or non-healing surgical wounds, intracerebral hemorrhage, aneurysm, dermal asthenia, and post-operation infections.

In preferred embodiments, the wound is selected from the group consisting of a burn wound, an incised wound, an open wound, a surgical or post surgical wound, a diabetic lesion, a thermal burn, a chemical burn, a radiation burn, a pressure sore, a bedsore, and a condition related to diabetes or poor circulation. In more preferred embodiments, the wound is selected from the group consisting of an incised wound, an open wound, a surgical or post surgical wound, a diabetic lesion, a pressure sore, a bedsore, and a condition or wound related to diabetes or poor circulation.

In some embodiments, the wound is selected from the group consisting of a non -radiation burn wound, an incised wound, an open wound, a surgical or post surgical wound, a diabetic lesion, a thermal burn, a chemical burn, a pressure sore, a bedsore, and a condition related to diabetes or poor circulation. In some embodiments, the wound is selected from the group consisting of an incised wound, an open wound, a surgical or post surgical wound, a diabetic lesion, a pressure sore, a bedsore, and a condition related to diabetes or poor circulation.

In some embodiments, the wound is not a burn.

In some embodiments, the wound is not a wound associated with eczema, atopic dermatitis, contact dermatitis, urticaria, scleroderma, psoriasis, and dermatosis with acute inflammatory components. For example, the wound is not a wound associated with psoriasis.

The present disclosure also relates to methods and compositions of reducing scar formation during wound healing in a subject. The compounds and compositions described herein can be administered directly to the wound or to cells proximate the wound at an amount effective to reduce scar formation in and/or around the wound. Thus, in some embodiments, a method of reducing scar formation during wound healing in a subject is provided, the method comprising administering to the subject a therapeutically effective amount of a compound described herein (e.g., a CRM1 inhibitor), or a pharmaceutically acceptable salt thereof.

The wound can include any injury to any portion of the body of a subject. According to embodiments, methods are provided to ameliorate, reduce, or decrease the formation of scars in a subject that has suffered a burn injury. According to preferred embodiments, methods are provided to treat, reduce the occurrence of, or reduce the probability of developing hypertrophic scars in a subject that has suffered an acute or chronic wound or injury.

The activity of a compound utilized in this invention as an inhibitor of CRM1 may be assayed in vitro, in vivo or in a cell line. Detailed conditions for assaying a compound utilized in this invention as an inhibitor of CRM1 are set forth in the Examples section below, and in International Application Nos. PCT/US2011/027328; PCT/US2012/048368; PCT/US2012/048319; and PCT/US2012/021406. The activity of many of the compounds in Tables 1A-1D in assays designed to measure CRM1 inhibitory activity can also be found in International Application Nos. PCT/US2011/027328; PCT/US2012/048368; PCT/US2012/048319; and PCT/US2012/021406.

Other Uses of Compounds and Pharmaceutically Acceptable Compositions

Compounds and compositions described herein, in particular Compounds 129 and 130 in Table 1A, are generally useful for the inhibition of CRM1 and are therefore useful for treating one or more disorders associated with activity of CRM1. Thus, in certain embodiments, the present invention provides a method for treating a CRM1-mediated disorder comprising the step of administering to a patient in need thereof a therapeutically effective amount of a compound of the present invention (e.g., Compound 129 or 130 in Table 1A), or pharmaceutically acceptable composition thereof The compounds and compositions described herein can also be administered to cells in culture, e.g. in vitro or ex vivo, or to a subject, e.g., in vivo, to treat, prevent, and/or diagnose a variety of disorders, including those described herein below.

As used herein, the term "CRM1-mediated" disorder or condition, as used herein, means any disease or other deleterious condition in which CRM1 is known to play a role. Accordingly, another embodiment of the present invention relates to treating or lessening the severity of one or more diseases in which CRM1 is known to play a role. In some embodiments, the present invention provides methods of treating a disease associated with expression or activity of p53, p73, p21, pRB, p27, IκB, NFκB, c-Abl, FOXO proteins, COX -2, or an HDAC (histone deacetylases) in a subject comprising administering to the patient a therapeutically effective amount of a compound described herein. In another embodiment, the present invention relates to a method of treating or lessening the severity of a disease or condition selected from a proliferative disorder (e.g., cancer), an inflammatory disorder, an autoimmune disorder, a viral infection, an ophthalmological disorder or a neurodegenerative disorder wherein said method comprises administering to a patient in need thereof a compound or composition according to the present invention. In a more specific embodiment, the present invention relates to a method of treating or lessening the severity of cancer. Specific examples of the above disorders are set forth in detail below.

Cancers treatable by the compounds of this invention include, but are not limited to, hematologic malignancies (leukemias, lymphomas, myelomas including multiple myeloma, myelodysplastic and myeloproliferative syndromes) and solid tumors (carcinomas such as prostate, breast, lung, colon, pancreatic, renal, ovarian as well as soft tissue and osteosarcomas, and stromal tumors). Breast cancer (BC) can include basal-like breast cancer (BLBC), triple negative breast cancer (TNBC) and breast cancer that is both BLBC and TNBC. In addition, breast cancer can include invasive or non-invasive ductal or lobular carcinoma, tubular, medullary, mucinous, papillary, cribriform carcinoma of the breast, male breast cancer, recurrent or metastatic breast cancer, phyllodes tumor of the breast and Paget's disease of the nipple.

Inflammatory disorders treatable by the compounds of this invention include, but are not limited to, multiple sclerosis, rheumatoid arthritis, degenerative joint disease, systemic lupus, systemic sclerosis, vasculitis syndromes (small, medium and large vessel), atherosclerosis, inflammatory bowel disease, irritable bowel syndrome, Crohn's disease, mucous colitis, ulcerative colitis, gastritis, sepsis, psoriasis and other dermatological inflammatory disorders (such as eczema, atopic dermatitis, contact dermatitis, urticaria, scleroderma, and dermatosis with acute inflammatory components, pemphigus, pemphigoid, allergic dermatitis), and urticarial syndromes.

Viral diseases treatable by the compounds of this invention include, but are not limited to, acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster. Viral diseases treatable by the compounds of this invention also include chronic viral infections, including hepatitis B and hepatitis C.

Exemplary ophthalmology disorders include, but are not limited to, macular edema (diabetic and nondiabetic macular edema), aged related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epitheliitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency or cataract.

Neurodegenerative diseases treatable by a compound of Formula I include, but are not limited to, Parkinson's, Alzheimer's, and Huntington's, and Amyotrophic lateral sclerosis (ALS/Lou Gehrig's Disease).

Compounds and compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, polycystic kidney disorder (PKD) and other renal disorders.

Compounds and compositions described herein may also be used to treat disorders related to food intake such as obesity and hyperphagia.

In another embodiment, a compound or composition described herein may be used to treat or prevent allergies and respiratory disorders, including asthma, bronchitis, pulmonary fibrosis, allergic rhinitis, oxygen toxicity, emphysema, chronic bronchitis, acute respiratory distress syndrome, and any chronic obstructive pulmonary disease (COPD).

In some embodiments, the disorder or condition associated with CRM1 activity is muscular dystrophy, arthritis, for example, osteoarthritis and rheumatoid arthritis, ankylosing spondilitis, traumatic brain injury, spinal cord injury, sepsis, rheumatic disease, cancer atherosclerosis, type 1 diabetes, type 2 diabetes, leptospiriosis renal disease, glaucoma, retinal disease, ageing, headache, pain, complex regional pain syndrome, cardiac hypertrophy, musclewasting, catabolic disorders, obesity, fetal growth retardation, hypercholesterolemia, heart disease, chronic heart failure, ischemia/reperfusion, stroke, cerebral aneurysm, angina pectoris, pulmonary disease, cystic fibrosis, acid-induced lung injury, pulmonary hypertension, asthma, chronic obstructive pulmonary disease, Sjogren's syndrome, hyaline membrane disease, kidney disease, glomerular disease, alcoholic liver disease, gut diseases, peritoneal endometriosis, skin diseases, nasal sinusitis, mesothelioma, anhidrotic ecodermal dysplasia-ID, behcet's disease, incontinentia pigmenti, tuberculosis, asthma, crohn's disease, colitis, ocular allergy, appendicitis, paget's disease, pancreatitis, periodonitis, endometriosis, inflammatory bowel disease, inflammatory lung disease, silica-induced diseases, sleep apnea, AIDS, HIV-1, autoimmune diseases, antiphospholipid syndrome, lupus, lupus nephritis, familial mediterranean fever, hereditary periodic fever syndrome, psychosocial stress diseases, neuropathological diseases, familial amyloidotic polyneuropathy, inflammatory neuropathy, parkinson's disease, multiple sclerosis, alzheimer's disease, amyotropic lateral sclerosis, huntington's disease, cataracts, or hearing loss.

In other embodiments, the disorder or condition associated with CRM1 activity is head injury, uveitis, inflammatory pain, allergen induced asthma, non-allergen induced asthma, glomerular nephritis, ulcerative colitis, necrotizing enterocolitis, hyperimmunoglobulinemia D with recurrent fever (HIDS), TNF receptor associated periodic syndrome (TRAPS), cryopyrin-associated periodic syndromes, Muckle-Wells syndrome (urticaria deafness amyloidosis), familial cold urticaria, neonatal onset multisystem inflammatory disease (NOMID), periodic fever, aphthous stomatitis, pharyngitis and adenitis (PFAPA syndrome), Blau syndrome, pyogenic sterile arthritis, pyoderma gangrenosum,acne (PAPA), deficiency of the interleukin-1-receptor antagonist (DIRA), subarachnoid hemorrhage, polycystic kidney disease, transplant, organ transplant, tissue transplant, myelodysplastic syndrome, irritant-induced inflammation, plant irritant-induced inflammation, poison ivy/urushiol oil-induced inflammation, chemical irritant-induced inflammation, bee sting-induced inflammation, insect bite-induced inflammation, sunburn, burns, dermatitis, endotoxemia, lung injury, acute respiratory distress syndrome, alcoholic hepatitis, or kidney injury caused by parasitic infections.

In further aspects, the present invention provides a use of a compound described herein for the manufacture of a medicament for the treatment of a disease associated with expression or activity of p53, p73, p21, pRB, p27, IκB, NFκB, c-Abl, FOXO proteins, COX -2 or an HDAC in a subject. In some embodiments, the present invention provides a use of a compound described herein in the manufacture of a medicament for the treatment of any of cancer and/or neoplastic disorders, angiogenesis, autoimmune disorders, inflammatory disorders and/or diseases, epigenetics, hormonal disorders and/or diseases, viral diseases, neurodegenerative disorders and/or diseases, wounds, and ophthalmologic disorders.

In some embodiments, the present invention provides a method for inhibiting CRM1 in a biological sample comprising contacting the biological sample with, or administering to the patient, a therapeutically effective amount of a pharmaceutically acceptable salt of a compound of the invention, or pharmaceutically acceptable composition thereof.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders, e.g., tumors arising from prostate, brain, bone, colon, lung, breast, ovarian, and liver origin, hematopoietic neoplastic disorders, e.g., leukemias, lymphomas, myeloma and other malignant plasma cell disorders, and metastatic tumors. Prevalent cancers include: breast, prostate, colon, lung, liver, and pancreatic cancers. Treatment with the compound can be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof, as well as in familial cancer syndromes such as Li Fraumeni Syndrome, Familial Breast-Ovarian Cancer (BRCA1 or BRAC2 mutations) Syndromes, and others. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the National Cancer Institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS- Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non- Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes;

Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non- Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T- Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

Further exemplary cancers include diffuse large B-cell lymphoma (DLBCL) and mantle cell lymphoma (MCL).

Metastases of the aforementioned cancers can also be treated or prevented in accordance with the methods described herein.

Combination Therapies

In some embodiments, a compound described herein is administered together with an additional "second" therapeutic agent or treatment. The choice of second therapeutic agent may be made from any agent that is typically used in a monotherapy to treat the indicated disease or condition. As used herein, the term "administered together" and related terms refers to the simultaneous or sequential administration of therapeutic agents in accordance with this invention. For example, a therapeutically effective amount of a compound of the present invention may be administered with a therapeutically effective amount of another therapeutic agent simultaneously or sequentially in separate unit dosage forms or together in a single unit dosage form. Accordingly, the present invention provides a single unit dosage form comprising a compound of the invention, an additional therapeutic agent, and a pharmaceutically acceptable carrier, adjuvant, or vehicle.

In one embodiment of the invention, where a second therapeutic agent is administered to a subject, the therapeutically effective amount of the compound of this invention is less than its therapeutically effective amount would be where the second therapeutic agent is not administered. In another embodiment, the therapeutically effective amount of the second therapeutic agent is less than its therapeutically effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art. The additional agents may be administered separately, as part of a multiple dose regimen, from the compounds of this invention. Alternatively, those agents may be part of a single dosage form, mixed together with the compounds of this invention in a single composition.

Cancer Combination Therapies

In some embodiments, a compound described herein is administered together with an additional cancer treatment. Exemplary additional cancer treatments include, for example: chemotherapy, targeted therapies such as antibody therapies, kinase inhibitors, immunotherapy, and hormonal therapy, epigenetic therapy, proteosome inhibitors, and anti -angiogenic therapies. Examples of each of these treatments are provided below. As used herein, the term "combination," "combined," and related terms refer to the simultaneous or sequential administration of therapeutic agents in accordance with this invention. For example, a therapeutically effective amount of a compound of the present invention can be administered with a therapeutically effective amount of another therapeutic agent simultaneously or sequentially in separate unit dosage forms or together in a single unit dosage form. Accordingly, the present invention provides a single unit dosage form comprising a compound of the invention, an additional therapeutic agent, and a pharmaceutically acceptable carrier, adjuvant, or vehicle.

The amount of both a compound of the invention and additional therapeutic agent (in those compositions which comprise an additional therapeutic agent as described above) that can be combined with the carrier materials to produce a single dosage form will vary depending upon the host treated and the particular mode of administration. Preferably, compositions of this invention should be formulated so that a dosage of between 0.01-100 mg/kg body weight/day of a compound of the invention can be administered.

Chemotherapy

In some embodiments, a compound described herein is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, Bendamustin, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, therapeutically effective amounts of chemotherapy agents (including combination chemotherapy) can be used in combination with a therapeutically effective amount of a compound described herein.

Targeted Therapy

Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (Herceptin®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, a therapeutically effective amount of targeted therapy can be used in combination with a therapeutically effective amount of a compound described herein, e.g., Gleevec (Vignari and Wang 2001).

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Angiogenesis

Compounds and methods described herein may be used to treat or prevent a disease or disorder associated with angiogenesis. Diseases associated with angiogenesis include cancer, cardiovascular disease and macular degeneration.

Angiogenesis is the physiological process involving the growth of new blood vessels from pre-existing vessels. Angiogenesis is a normal and vital process in growth and development, as well as in wound healing and in granulation tissue. However, it is also a fundamental step in the transition of tumors from a dormant state to a malignant one. Angiogenesis may be a target for combating diseases characterized by either poor vascularisation or abnormal vasculature.

Application of specific compounds that may inhibit or induce the creation of new blood vessels in the body may help combat such diseases. The presence of blood vessels where there should be none may affect the mechanical properties of a tissue, increasing the likelihood of failure. The absence of blood vessels in a repairing or otherwise metabolically active tissue may inhibit repair or other essential functions. Several diseases, such as ischemic chronic wounds, are the result of failure or insufficient blood vessel formation and may be treated by a local expansion of blood vessels, thus bringing new nutrients to the site, facilitating repair. Other diseases, such as age-related macular degeneration, may be created by a local expansion of blood vessels, interfering with normal physiological processes.

Vascular endothelial growth factor (VEGF) has been demonstrated to be a major contributor to angiogenesis, increasing the number of capillaries in a given network. Upregulation of VEGF is a major component of the physiological response to exercise and its role in angiogenesis is suspected to be a possible treatment in vascular injuries. In vitro studies clearly demonstrate that VEGF is a potent stimulator of angiogenesis because, in the presence of this growth factor, plated endothelial cells will proliferate and migrate, eventually forming tube structures resembling capillaries.

Tumors induce blood vessel growth (angiogenesis) by secreting various growth factors (e.g., VEGF). Growth factors such as bFGF and VEGF can induce capillary growth into the tumor, which some researchers suspect supply required nutrients, allowing for tumor expansion.

Angiogenesis represents an excellent therapeutic target for the treatment of cardiovascular disease. It is a potent, physiological process that underlies the natural manner in which our bodies respond to a diminution of blood supply to vital organs, namely the production of new collateral vessels to overcome the ischemic insult.

Overexpression of VEGF causes increased permeability in blood vessels in addition to stimulating angiogenesis. In wet macular degeneration, VEGF causes proliferation of capillaries into the retina. Since the increase in angiogenesis also causes edema, blood and other retinal fluids leak into the retina, causing loss of vision.

Anti-angiogenic therapy can include kinase inhibitors targeting vascular endothelial growth factor (VEGF) such as sunitinib, sorafenib, or monoclonal antibodies or receptor "decoys" to VEGF or VEGF receptor including bevacizumab or VEGF-Trap, or thalidomide or its analogs (lenalidomide, pomalidomide), or agents targeting non-VEGF angiogenic targets such as fibroblast growth factor (FGF), angiopoietins, or angiostatin or endostatin.

Epigenetics

Compounds and methods described herein may be used to treat or prevent a disease or disorder associated with epigenetics. Epigenetics is the study of heritable changes in phenotype or gene expression caused by mechanisms other than changes in the underlying DNA sequence. One example of epigenetic changes in eukaryotic biology is the process of cellular differentiation. During morphogenesis, stem cells become the various cell lines of the embryo which in turn become fully differentiated cells. In other words, a single fertilized egg cell changes into the many cell types including neurons, muscle cells, epithelium, blood vessels etc. as it continues to divide. It does so by activating some genes while inhibiting others.

Epigenetic changes are preserved when cells divide. Most epigenetic changes only occur within the course of one individual organism's lifetime, but, if a mutation in the DNA has been caused in sperm or egg cell that results in fertilization, then some epigenetic changes are inherited from one generation to the next. Specific epigenetic processes include paramutation, bookmarking, imprinting, gene silencing, X chromosome inactivation, position effect, reprogramming, transvection, maternal effects, the progress of carcinogenesis, many effects of teratogens, regulation of histone modifications and heterochromatin, and technical limitations affecting parthenogenesis and cloning.

Exemplary diseases associated with epigenetics include ATR-syndrome, fragile X-syndrome, ICF syndrome, Angelman's syndrome, Prader-Wills syndrome, BWS, Rett syndrome, α-thalassaemia, cancer, leukemia, Rubinstein-Taybi syndrome and Coffin-Lowry syndrome.

The first human disease to be linked to epigenetics was cancer. Researchers found that diseased tissue from patients with colorectal cancer had less DNA methylation than normal tissue from the same patients. Because methylated genes are typically turned off, loss of DNA methylation can cause abnormally high gene activation by altering the arrangement of chromatin. On the other hand, too much methylation can undo the work of protective tumor suppressor genes.

DNA methylation occurs at CpG sites, and a majority of CpG cytosines are methylated in mammals. However, there are stretches of DNA near promoter regions that have higher concentrations of CpG sites (known as CpG islands) that are free of methylation in normal cells. These CpG islands become excessively methylated in cancer cells, thereby causing genes that should not be silenced to turn off. This abnormality is the trademark epigenetic change that occurs in tumors and happens early in the development of cancer. Hypermethylation of CpG islands can cause tumors by shutting off tumor-suppressor genes. In fact, these types of changes may be more common in human cancer than DNA sequence mutations.

Furthermore, although epigenetic changes do not alter the sequence of DNA, they can cause mutations. About half of the genes that cause familial or inherited forms of cancer are turned off by methylation. Most of these genes normally suppress tumor formation and help repair DNA, including O6-methylguanine-DNA methyltransferase (MGMT), MLH1 cyclin-dependent kinase inhibitor 2B (CDKN2B), and RASSF1A. For example, hypermethylation of the promoter of MGMT causes the number of G-to-A mutations to increase.

Hypermethylation can also lead to instability of microsatellites, which are repeated sequences of DNA. Microsatellites are common in normal individuals, and they usually consist of repeats of the dinucleotide CA. Too much methylation of the promoter of the DNA repair gene MLH1 can make a microsatellite unstable and lengthen or shorten it. Microsatellite instability has been linked to many cancers, including colorectal, endometrial, ovarian, and gastric cancers.

Fragile X syndrome is the most frequently inherited mental disability, particularly in males. Both sexes can be affected by this condition, but because males only have one X chromosome, one fragile X will impact them more severely. Indeed, fragile X syndrome occurs in approximately 1 in 4,000 males and 1 in 8,000 females. People with this syndrome have severe intellectual disabilities, delayed verbal development, and "autistic-like" behavior.

Fragile X syndrome gets its name from the way the part of the X chromosome that contains the gene abnormality looks under a microscope; it usually appears as if it is hanging by a thread and easily breakable. The syndrome is caused by an abnormality in the FMR1 (fragile X mental retardation 1) gene. People who do not have fragile X syndrome have 6 to 50 repeats of the trinucleotide CGG in their FMR1 gene. However, individuals with over 200 repeats have a full mutation, and they usually show symptoms of the syndrome. Too many CGGs cause the CpG islands at the promoter region of the FMR1 gene to become methylated; normally, they are not. This methylation turns the gene off, stopping the FMR1 gene from producing an important protein called fragile X mental retardation protein. Loss of this specific protein causes fragile X syndrome. Although a lot of attention has been given to the CGG expansion mutation as the cause of fragile X, the epigenetic change associated with FMR1 methylation is the real syndrome culprit.

Fragile X syndrome is not the only disorder associated with mental retardation that involves epigenetic changes. Other such conditions include Rubenstein-Taybi, Coffin-Lowry, Prader-Willi, Angelman, Beckwith-Wiedemann, ATR-X, and Rett syndromes.

Epigenetic therapies include inhibitors of enzymes controlling epigenetic modifications, specifically DNA methyltransferases and histone deacetylases, which have shown promising anti-tumorigenic effects for some malignancies, as well as antisense oligonucleotides and siRNA.

Immunotherapy

In some embodiments, a compound described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, prostate cancer vaccine Provenge, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus -tumor effect. In some embodiments, therapeutically effective amounts of immunotherapy agents can be used in combination with a therapeutically effective amount of a compound described herein, or a pharmaceutically acceptable salt or composition thereof.

Hormonal Therapy

In some embodiments, a compound described herein is administered with a hormonal therapy. The growth of some cancers can be inhibited by providing or blocking certain hormones. Common examples of hormone-sensitive tumors include certain types of breast and prostate cancers, as well as certain types of leukemia which respond to certain retinoids/retinoic acids. Removing or blocking estrogen or testosterone is often an important additional treatment. In certain cancers, administration of hormone agonists, such as progestogens may be therapeutically beneficial. In some embodiments, therapeutically effective amounts of hormonal therapy agents can be used in combination with a therapeutically effective amount of a compound described herein.

Hormonal therapy agents include the administration of hormone agonists or hormone antagonists and include retinoids/retinoic acid, compounds that inhibit estrogen or testosterone, as well as administration of progestogens.

Inflammation and Autoimmune Disease

The compounds and methods described herein may be used to treat or prevent a disease or disorder associated with inflammation, particularly in humans and other mammals. A compound described herein may be administered prior to the onset of, at, or after the initiation of inflammation. When used prophylactically, the compounds are preferably provided in advance of any inflammatory response or symptom. Administration of the compounds can prevent or attenuate inflammatory responses or symptoms. Exemplary inflammatory conditions include, for example, multiple sclerosis, rheumatoid arthritis, psoriatic arthritis, degenerative joint disease, spondouloarthropathies, other seronegative inflammatory arthridities, polymyalgia rheumatica, various vasculidities (e.g., giant cell arteritis, ANCA+ vasculitis), gouty arthritis, systemic lupus erythematosus, juvenile arthritis, juvenile rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, schleroderma, psoriasis, and dermatosis with acute inflammatory components.

In another embodiment, a compound or method described herein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, a compound or method described herein may be used to treat autoimmune diseases and/or inflammation associated with autoimmune diseases, such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In a particular embodiment, the compounds described herein can be used to treat multiple sclerosis.

Combination Therapy

In certain embodiments, a therapeutically effective amount of a compound described herein may be administered alone or in combination with therapeutically effective amounts of other compounds useful for treating or preventing inflammation. Exemplary anti-inflammatory agents include, for example, steroids (e.g., Cortisol, cortisone, fludrocortisone, prednisone, 6[alpha]-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other compound is drotrecogin alfa.

Further examples of anti-inflammatory agents include, for example, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, [alpha]-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, caiprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, cropropamide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocoitolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydro cortamate, hydrocortisone, hydrocortisone acetate, hydrocortisone succinate, hydrocortisone hemisuccinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p -lactophenetide, lefetamine, levallorphan, levorphanol, levophenacylmorphan, lofentanil, lonazolac, lornoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide,norlevorphanol, normethadone, normorphine, norpipanone, olsalazine, opium, oxaceprol, oxametacine, oxaprozin, oxycodone, oxymorphone, oxyphenbutazone, papaveretum, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o -acetic acid, salicylic acid, salicylsulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In one embodiment, a compound described herein may be administered with a selective COX-2 inhibitor for treating or preventing inflammation. Exemplary selective COX-2 inhibitors include, for example, deracoxib, parecoxib, celecoxib, valdecoxib, rofecoxib, etoricoxib, and lumiracoxib.

In some embodiments, a provided compound is administered in combination with an anthracycline or a Topo II inhibitor. In certain embodiments, a provided compound is administered in combination with Doxorubicin (Dox). In certain embodiments, a provided compound is administered in combination with bortezomib (and more broadly including carfilzomib). It was surprisingly found that a provided compound in combination with Dox or bortezomib resulted in a synergystic effect (i.e., more than additive).

Viral Infections

Compounds and methods described herein may be used to treat or prevent a disease or disorder associated with a viral infection, particularly in humans and other mammals. A therapeutically effective amount of a compound described herein may be administered prior to the onset of, at, or after the initiation of viral infection. When used prophylactically, the compounds are preferably provided in advance of any viral infection or symptom thereof.

Exemplary viral diseases include acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster.

Exemplary viral pathogens include Adenovirus, Coxsackievirus, Dengue virus, Encephalitis Virus, Epstein-Barr virus, Hepatitis A virus, Hepatitis B virus, Hepatitis C virus, Herpes simplex virus type 1, Herpes simplex virus type 2, cytomegalovirus, Human herpesvirus type 8, Human immunodeficiency virus, Influenza virus, measles virus, Mumps virus, Human papillomavirus, Parainfluenza virus, Poliovirus, Rabies virus, Respiratory syncytial virus, Rubella virus, Varicella-zoster virus, West Nile virus, Dungee, and Yellow fever virus. Viral pathogens may also include viruses that cause resistant viral infections.

Antiviral drugs are a class of medications used specifically for treating viral infections. Antiviral action generally falls into one of three mechanisms: interference with the ability of a virus to infiltrate a target cell (e.g., amantadine, rimantadine and pleconaril), inhibition of the synthesis of virus (e.g., nucleoside analogues, e.g., acyclovir and zidovudine (AZT), and inhibition of the release of virus (e.g., zanamivir and oseltamivir).

Ophthalmology

Compounds and methods described herein may be used to treat or prevent an ophthamology disorder. Exemplary ophthamology disorders include macular edema (diabetic and nondiabetic macular edema), age related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency and cataract.

Other ophthalmology disorders treatable using the compounds and methods described herein include proliferative vitreoretinopathy and chronic retinal detachment.

Inflammatory eye diseases are also treatable using the compounds and methods described herein.

Neurodegenerative Disease

Neurodegeneration is the umbrella term for the progressive loss of structure or function of neurons, including death of neurons. Many neurodegenerative diseases including Parkinson's, Alzheimer's, and Huntington's occur as a result of neurodegenerative processes. As research progresses, many similarities appear which relate these diseases to one another on a sub-cellular level. Discovering these similarities offers hope for therapeutic advances that could ameliorate many diseases simultaneously. There are many parallels between different neurodegenerative disorders including atypical protein assemblies as well as induced cell death.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus.

Huntington's disease causes astrogliosis and loss of medium spiny neurons. Areas of the brain are affected according to their structure and the types of neurons they contain, reducing in size as they cumulatively lose cells. The areas affected are mainly in the striatum, but also the frontal and temporal cortices. The striatum's subthalamic nuclei send control signals to the globus pallidus, which initiates and modulates motion. The weaker signals from subthalamic nuclei thus cause reduced initiation and modulation of movement, resulting in the characteristic movements of the disorder. Exemplary treatments for Huntington's disease include tetrabenazine, neuroleptics, benzodiazepines, amantadine, remacemide, valproic acid, selective serotonin reuptake inhibitors (SSRIs), mirtazapine and antipsychotics.

The mechanism by which the brain cells in Parkinson's are lost may consist of an abnormal accumulation of the protein alpha-synuclein bound to ubiquitin in the damaged cells. The alpha-synuclein-ubiquitin complex cannot be directed to the proteosome. This protein accumulation forms proteinaceous cytoplasmic inclusions called Lewy bodies. The latest research on pathogenesis of disease has shown that the death of dopaminergic neurons by alpha-synuclein is due to a defect in the machinery that transports proteins between two major cellular organelles—the endoplasmic reticulum (ER) and the Golgi apparatus. Certain proteins like Rab1 may reverse this defect caused by alpha-synuclein in animal models. Exemplary Parkinson's disease therapies include levodopa, dopamine agonists such as include bromocriptine, pergolide, pramipexole, ropinirole, piribedil, cabergoline, apomorphine and lisuride, dopa decarboxylate inhibitors, MAO-B inhibitors such as selegilene and rasagilene, anticholinergics and amantadine.

Amyotrophic lateral sclerosis (ALS/Lou Gehrig's Disease) is a disease in which motor neurons are selectively targeted for degeneration. Exemplary ALS therapies include riluzole, baclofen, diazepam, trihexyphenidyl and amitriptyline. Other exemplary neurodegenerative therapeutics include antisense oligonucleotides and stem cells.

Combination Radiation Therapy

Compounds and compositions described herein are useful as radiosensitizers. Therefore, therapeutically effective amounts of compounds and compositions described herein can be administered in combination with a therapeutically effective amount of radiation therapy. Radiation therapy is the medical use of high-energy radiation (e.g., x-rays, gamma rays, charged particles) to shrink tumors and kill malignant cells, and is generally used as part of cancer treatment. Radiation therapy kills malignant cells by damaging their DNA.

Radiation therapy can be delivered to a patient in several ways. For example, radiation can be delivered from an external source, such as a machine outside the patient's body, as in external beam radiation therapy. External beam radiation therapy for the treatment of cancer uses a radiation source that is external to the patient, typically either a radioisotope, such as $^{60}$Co, $^{137}$Cs, or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue can be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also can be reduced by tightly collimating the radiation beam to the general cross section of the tumor taken perpendicular to the axis of the radiation beam. Numerous systems exist for producing such a circumferential collimation, some of which use multiple sliding shutters which, piecewise, can generate a radioopaque mask of arbitrary outline.

For administration of external beam radiation, the amount can be at least about 1 Gray (Gy) fractions at least once every other day to a treatment volume. In a particular embodiment, the radiation is administered in at least about 2 Gray (Gy) fractions at least once per day to a treatment volume. In another particular embodiment, the radiation is administered in at least about 2 Gray (Gy) fractions at least once per day to a treatment volume for five consecutive days per week. In another particular embodiment, radiation is administered in 10 Gy fractions every other day, three times per week to a treatment volume. In another particular embodiment, a total of at least about 20 Gy is administered to a patient in need thereof. In another particular embodiment, at least about 30 Gy is administered to a patient in need thereof. In another particular embodiment, at least about 40 Gy is administered to a patient in need thereof.

Typically, the patient receives external beam therapy four or five times a week. An entire course of treatment usually lasts from one to seven weeks depending on the type of cancer and the goal of treatment. For example, a patient can receive a dose of 2 Gy/day over 30 days.

Internal radiation therapy is localized radiation therapy, meaning the radiation source is placed at the site of the tumor or affected area. Internal radiation therapy can be delivered by placing a radiation source inside or next to the area requiring treatment. Internal radiation therapy is also called brachytherapy. Brachytherapy includes intercavitary treatment and interstitial treatment. In intracavitary treatment, containers that hold radioactive sources are put in or near the tumor. The sources are put into the body cavities. In interstitial treatment, the radioactive sources alone are put into the tumor. These radioactive sources can stay in the patient permanently. Typically, the radioactive sources are removed from the patient after several days. The radioactive sources are in containers.

There are a number of methods for administration of a radiopharmaceutical agent. For example, the radiopharmaceutical agent can be administered by targeted delivery or by systemic delivery of targeted radioactive conjugates, such as a radiolabeled antibody, a radiolabeled peptide and a liposome delivery system. In one particular embodiment of targeted delivery, the radiolabelled pharmaceutical agent can be a radiolabelled antibody. See, for example, Ballangrud A. M., et al. *Cancer Res.*, 2001; 61:2008-2014 and Goldenber, D. M. *J. Nucl. Med.*, 2002; 43(5):693-713, the contents of which are incorporated by reference herein.

In another particular embodiment of targeted delivery, the radiopharmaceutical agent can be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. See, for example, Emfietzoglou D, Kostarelos K, Sgouros G. An analytical dosimetry study for the use of radionuclide-liposome conjugates in internal radiotherapy. J Nucl Med 2001; 42:499-504, the contents of which are incorporated by reference herein.

In yet another particular embodiment of targeted delivery, the radiolabeled pharmaceutical agent can be a radiolabeled peptide. See, for example, Weiner R E, Thakur M L. Radiolabeled peptides in the diagnosis and therapy of oncological diseases. Appl Radiat Isot 2002 Nov; 57(5):749-63, the contents of which are incorporated by reference herein.

In addition to targeted delivery, bracytherapy can be used to deliver the radiopharmaceutical agent to the target site. Brachytherapy is a technique that puts the radiation sources as close as possible to the tumor site. Often the source is inserted directly into the tumor. The radioactive sources can be in the form of wires, seeds or rods. Generally, cesium, iridium or iodine are used.

Systemic radiation therapy is another type of radiation therapy and involves the use of radioactive substances in the blood. Systemic radiation therapy is a form of targeted therapy. In systemic radiation therapy, a patient typically ingests or receives an injection of a radioactive substance, such as radioactive iodine or a radioactive substance bound to a monoclonal antibody.

A "radiopharmaceutical agent," as defined herein, refers to a pharmaceutical agent which contains at least one radiation-emitting radioisotope. Radiopharmaceutical agents are routinely used in nuclear medicine for the diagnosis and/or therapy of various diseases. The radiolabelled pharmaceutical agent, for example, a radiolabelled antibody, contains a radioisotope (RI) which serves as the radiation source. As contemplated herein, the term "radioisotope" includes metallic and non-metallic radioisotopes. The radioisotope is chosen based on the medical application of the radiolabeled pharmaceutical agents. When the radioisotope is a metallic radioisotope, a chelator is typically employed to bind the metallic radioisotope to the rest of the molecule.

When the radioisotope is a non-metallic radioisotope, the non-metallic radioisotope is typically linked directly, or via a linker, to the rest of the molecule.

As used herein, a "metallic radioisotope" is any suitable metallic radioisotope useful in a therapeutic or diagnostic procedure in vivo or in vitro. Suitable metallic radioisotopes include, but are not limited to: Actinium-225, Antimony-124, Antimony-125, Arsenic-74, Barium-103, Barium-140, Beryllium-7, Bismuth-206, Bismuth-207, Bismuth212, Bismuth213, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-60, Copper-62, Copper-64, Copper-67, Erbium-169, Europium-152, Gallium-64, Gallium-67, Gallium-68, Gadolinium153, Gadolinium-157 Gold-195, Gold-199, Hafnium-175, Hafnium-175-181, Holmium-166, Indium-110, Indium -111, Iridium-192, Iron 55, Iron-59, Krypton85, Lead-203, Lead-210, Lutetium-177, Manganese-54, Mercury-197, Mercury203, Molybdenum-99, Neodymium-147, Neptunium -237, Nickel-63, Niobium95, Osmium-185+191, Palladium-103, Palladium-109, Platinum -195m, Praseodymium-143, Promethium-147, Promethium-149, Protactinium-233, Radium -226, Rhenium-186, Rhenium-188, Rubidium-86, Ruthenium-97, Ruthenium-103, Ruthenium-105, Ruthenium-106, Samarium-153, Scandium-44, Scandium-46, Scandium-47, Selenium-75, Silver-110m, Silver-111, Sodium-22, Strontium-85, Strontium-89, Strontium -90, Sulfur-35, Tantalum-182, Technetium-99m, Tellurium-125, Tellurium-132, Thallium -204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, Zirconium-89, and Zirconium-95.

As used herein, a "non-metallic radioisotope" is any suitable nonmetallic radioisotope (non-metallic radioisotope) useful in a therapeutic or diagnostic procedure in vivo or in vitro. Suitable non-metallic radioisotopes include, but are not limited to: Iodine -131, Iodine-125, Iodine-123, Phosphorus-32, Astatine-211, Fluorine-18, Carbon-11, Oxygen -15, Bromine-76, and Nitrogen-13.

Identifying the most appropriate isotope for radiotherapy requires weighing a variety of factors. These include tumor uptake and retention, blood clearance, rate of radiation delivery, half-life and specific activity of the radioisotope, and the feasibility of large-scale production of the radioisotope in an economical fashion. The key point for a therapeutic radiopharmaceutical is to deliver the requisite amount of radiation dose to the tumor cells and to achieve a cytotoxic or tumoricidal effect while not causing unmanageable side-effects.

It is preferred that the physical half-life of the therapeutic radioisotope be similar to the biological half-life of the radiopharmaceutical at the tumor site. For example, if the half-life of the radioisotope is too short, much of the decay will have occurred before the radiopharmaceutical has reached maximum target/background ratio. On the other hand, too long a half-life could cause unnecessary radiation dose to normal tissues. Ideally, the radioisotope should have a long enough half-life to attain a minimum dose rate and to irradiate all the cells during the most radiation sensitive phases of the cell cycle. In addition, the half-life of a radioisotope has to be long enough to allow adequate time for manufacturing, release, and transportation.

Other practical considerations in selecting a radioisotope for a given application in tumor therapy are availability and quality. The purity has to be sufficient and reproducible, as trace amounts of impurities can affect the radiolabeling and radiochemical purity of the radiopharmaceutical.

The target receptor sites in tumors are typically limited in number. As such, it is preferred that the radioisotope have high specific activity. The specific activity depends primarily on the production method. Trace metal contaminants must be minimized as they often compete with the radioisotope for the chelator and their metal complexes compete for receptor binding with the radiolabeled chelated agent.

The type of radiation that is suitable for use in the methods of the present invention can vary. For example, radiation can be electromagnetic or particulate in nature. Electromagnetic radiation useful in the practice of this invention includes, but is not limited to, x-rays and gamma rays. Particulate radiation useful in the practice of this invention includes, but is not limited to, electron beams (beta particles), protons beams, neutron beams, alpha particles, and negative pi mesons. The radiation can be delivered using conventional radiological treatment apparatus and methods, and by intraoperative and stereotactic methods. Additional discussion regarding radiation treatments suitable for use in the practice of this invention can be found throughout Steven A. Leibel et al., Textbook of Radiation Oncology (1998) (publ. W. B. Saunders Company), and particularly in Chapters 13 and 14. Radiation can also be delivered by other methods such as targeted delivery, for example by radioactive "seeds," or by systemic delivery of targeted radioactive conjugates. J. Padawer et al., Combined Treatment with Radioestradiol lucanthone in Mouse C3HBA Mammary Adenocarcinoma and with Estradiol lucanthone in an Estrogen Bioassay, Int. J. Radiat. Oncol. Biol. Phys. 7:347-357 (1981). Other radiation delivery methods can be used in the practice of this invention.

For tumor therapy, both a and n-particle emitters have been investigated. Alpha particles are particularly good cytotoxic agents because they dissipate a large amount of energy within one or two cell diameters. The n-particle emitters have relatively long penetration range (2-12 mm in the tissue) depending on the energy level. The long-range penetration is particularly important for solid tumors that have heterogeneous blood flow and/or receptor expression. The β-particle emitters yield a more homogeneous dose distribution even when they are heterogeneously distributed within the target tissue.

In a particular embodiment, therapeutically effective amounts of the compounds and compositions described herein are administered in combination with a therapeutically effective amount of radiation therapy to treat cancer (e.g., lung cancer, such as non-small cell lung cancer). The amount of radiation necessary can be determined by one of skill in the art based on known doses for a particular type of cancer. See, for example, Cancer Medicine $5^{th}$ ed., Edited by R. C. Bast et al., July 2000, B C Decker.

EXEMPLIFICATION

For the purposes of Examples 1-9, and their associated figures, Compound 3 refers to Compound C-3 (from Table 1C) in saline; Compound 4 refers to Compound C-3 (from Table 1C) in dimethylsulfoxide (DMSO) at the following concentrations of DMSO in water: 0.1%, 0.02% or 0.0067%; and Compound 5 refers to Compound 129 (from Table 1A) in saline or in DMSO in water.

Materials

Mice—C57BL/6J mice, males, aged 6-8 weeks, SPF, obtained from Harlan Laboratories LTD. Mice were kept in sterile individual ventilated cages (IVC) with food and water available ad libitum, 12 h/12 h cycles of darkness and light, controlled temperature of 19-21° C., controlled humidity of 40-60%, positive air pressure inside animal's room, and health report control every 3 months, which was performed on selected sentinels.

Pigs—sus scrofa domestica, Domestic swine (mainly Landrace X large White), female, approximately 60 Kg, 4-5 months old, Lahav Institute of Animal Research, Kibbutz Lahav, Israel. Pigs were kept in clean non-SPF environment, tap water ad libitum directly from public source, food according to recommendation of standard growth tables under supervision of veterinarian.

ISOFLURANE 99.9% for inhalation, lot 6027962, Abbot Laboratories Ltd, England

Water—water for injection, batch 11481012, B. Braun Melsungen AG, Germany

Saline—0.9% sodium chloride for injection, batch 12224012, B. Braun Melsungen AG, Germany DMSO—dimethyl sulfoxide, D2650, Sigma-Aldrich Inc., U.S.

PLURONIC® F-68

PVP K-29/32

EXAMPLE 1

Evaluation of the Effects of Systemic Administration and Topical Application of Test Compounds on C57Bl Mice Skin Wounds The effect of a test compound on skin wound healing can be studied in a mouse longitudinal full thickness skin incision wound model. Upon arrival, animals are identified by ear tags, weighed and left to acclimate for several days before initiation of the experiment. On the day of wounding, mice are weighed and divided into 6 experimental groups with 6 animals per group, in accordance to weight differences stratified randomization. Prior to the surgical procedure, mice are anesthetized with isoflurane and the back of the animals is shaved. Full thickness longitudinal incisions of 20 mm each are performed using a standard scalpel blade on the backs of the animals (parallel to the backbone). Three hours after wounding, due to skin elasticity and activity of the animals, the incisions take on elliptical shapes. At this stage, the widest area of the wound is measured to establish a baseline wound width. Wound healing evaluation is made by measuring the widest area of the wound. Treatment groups consist of oral gavage or topical groups. During the experiment, wounds are photo-documented and morphological analysis is performed. At the end of the experiment, 8 days post wounding, mice are sacrificed, wound widths are measured and biopsies of the wound area are collected and subjected to analysis.

Wounds that are smaller in size, and have scabs that are lighter, thinner and homogenous without cracks, indicate a later stage of wound healing. Wounds that appear larger in size and are covered with thick cracked scabs that expose non-healed wound area both at the edges and in the middle of the wounds, can be seen as reddish and pink areas, and indicate less extensive wound healing.

Morphological analysis is the primary parameter utilized in wound healing assessment in preclinical studies on animals and in clinical treatments of human wounds.

EXAMPLE 2

Evaluation of the Effects of Topical Application of Compound 3 on Pig Skin Wounds For the purposes of this example, and its associated figures, Compound 3 refers to Compound C-3 (from Table 1C) in saline.

The effects of Compound 3 on skin wound healing were studied in a pig longitudinal full thickness skin incision wound model. Upon arrival, animals were identified by ear tags, weighed and left to acclimate for several days before initiation of the experiment. Three days prior to the surgery, pigs were transferred to the hospitalization facility for acclimation. Twelve hours prior to the procedure, food was withheld. On the day of surgery the pig was anesthetized using ketamine, xylazin, diazepam and isoflurane. The hair on the dorsum thorax and abdomen was carefully cut using an Oster® clipper machine (blade size 30) and 20 individual regions of 4 $cm^2$ each were marked in two rows (10 regions per row). Ten pairs of 25 mm±3 mm full thickness longitudinal skin incisions were made using #11 scalpel blade, 4 cm from either side of the dorsum midline. The incisions were 8 mm to 20 mm deep. Variations in wound size are due to differences in skin thickness and the anatomy of the area.

Following the surgical procedure, wounds were divided into experimental groups and treated daily by topical application on the wound area and on wound edges in accordance with the study groups described in Table 2A. Treatment area consisted of a surface of skin up to a distance of 2 cm from the wound center. Dosing solutions were applied gradually on each wound using a pipette, until the entire treatment volume (1 mL of saline or Compound 3) was absorbed by tissue. Alternatively, wound treatment was performed using a gauze pad, which had been soaked in 2 mL of the dosing solution and applied on the wound for 1 minute or, when placed on a scab, until the scab and the wound edges completely absorbed the treatment. Approximately, 1 mL of the solution is delivered to the wound. Absorption is considered complete when liquid no longer moves out of the wound.

TABLE 2A

Initial Study Groups

| Group | Number of wounds | Test Article | Dose | Route of Administration | Schedule |
|---|---|---|---|---|---|
| 1 | 5 front wounds on the right side | Control saline | 1 mL | Topical | Daily |
| 2 | 5 rear wounds on the right side | Control saline | 1 mL | Topical | Daily |
| 3 | 5 front wounds on the left side | Compound 3 | 3 µM | Topical | Daily |
| 4 | 5 rear wounds on the left side | Compound 3 | 1 µM | Topical | Daily |

Several hours after wounding, due to skin elasticity and activity of the animals, the incisions took on elliptical shapes. Wound width and length were measured at 5 day post-wounding. Initial wound measurements were not performed because, following initial skin incision, ellipitical wounds are formed within 12-24 hours after wounding and continue to increase in size for at least 3-5 days. From day 5, wound size in the pig model is stabilized. At this stage, the widest area of the wound was measured to establish a baseline wound width. Wound healing evaluation was made by measuring the widest area of the wound. During the experiment, wounds were photo-documented and morphological analysis was performed.

On day 5 post-wounding, pigs were anaesthetized and photo-documentation of the wounds was performed using FinePix S700 camera. FIG. 1A shows the wound morphology of the wounds on day 5 post-wounding. All wounds treated with Compound 3 and their appropriate controls are presented in a way that allows paired comparison of wounds on the same anatomical location. The scale bar in FIG. 1A=approximately 2.5 cm. N=20 wounds.

On day 5 post-wounding, wound measurements were taken and wound morphology data was measured. Wound width and wound length data is depicted in Table 2B. Wound morphology data is depicted in Table 2C. Scab status was scored as: (+) formed, (−) not formed/open wound and (+/−) partially formed/wound still secreting. Swelling were scored as mild (+), moderate (++) and servere (+++). Wounds with only minor, non-significant swellings were scored as (+/−). Secretions were scored as mild (+), moderate (++) and severe (+++). Wounds with only minor, non-significant secretions were scored as (+/−).

TABLE 2B

Wound Measurement Data Day 5 Post-wounding.

| Treatment | Group | Width (mm) | Length (mm) |
|---|---|---|---|
| | Group 1 | | |
| 3 µM CMPD 3 in saline | L1 | 7.3 | 30.77 |
| | L2 | 7.4 | 30.32 |
| | L3 | 6.4 | 31.21 |
| | L4 | 5.8 | 28.25 |
| | L5 | 4.98 | 30.59 |
| | Average | 6.4 | 30.2 |
| | SD | 0.9 | 1.0 |
| | Group 2 | | |
| 1 µM CMPD 3 in saline | L1 | 8.4 | 40.78 |
| | L2 | 14.11 | 37.00 |
| | L3 | 10.60 | 29.16 |
| | L4 | 5.90 | 30.06 |
| | L5 | 3.10 | 27.70 |
| | Average | 8.4 | 32.9 |
| | SD | 3.8 | 5.1 |
| | Group 3 | | |
| Control Saline | R1 | 10.48 | 32.93 |
| | R2 | 10.49 | 34.65 |
| | R3 | 11.18 | 31.43 |
| | R4 | 5.53 | 30.42 |
| | R5 | 10.06 | 36.25 |
| | Average | 9.5 | 33.1 |
| | SD | 2.0 | 2.1 |
| | Group 4 | | |
| Control Saline | R1 | 8.88 | 33.93 |
| | R2 | 14.17 | 35.53 |
| | R3 | 11.20 | 35.82 |
| | R4 | 8.60 | 33.78 |
| | R5 | 2.80 | 29.06 |
| | Average | 9.1 | 33.6 |
| | SD | 3.7 | 2.4 |

TABLE 2C

Wound Morphology Data Day 5 Post-wounding.

| Treatment | Wound Pair | Swelling | Scab | Secretion | Treatment | Swelling | Scab | Secretion |
|---|---|---|---|---|---|---|---|---|
| 3 µM CMPD 3 in saline | 1 | + | + | − | Saline | ++ | − | + |
| | 2 | + | + | +/− | | ++ | − | + |
| | 3 | + | + | − | | ++ | − | + |
| | 4 | + | + | − | | + | + | − |
| | 5 | + | + | − | | ++ | − | + |
| 1 µM CMPD 3 in saline | 1 | ++ | +/− | − | Saline | ++ | +/− | + |
| | 2 | ++ | +/− | − | | ++ | − | ++ |
| | 3 | + | +/− | +/− | | ++ | − | ++ |
| | 4 | − | + | +/− | | + | +/− | + |
| | 5 | − | + | − | | − | + | − |

At the end of the experiment (12 days after wounding), pigs were sacrificed by administration of anesthetic and KC1. Wound morphology was assessed, wound length and wound width were measured and biopsies of wound area were harvested and fixed using 4% paraformaldehyde for further analysis. Following fixation, wound biopsies were photo-documented using high resolution digital camera FinePix 5700 and biopsies of the wound area subjected to histopathological analysis. Assessment of wound healing was performed in a paired manner in which each wound treated with Compound 3 was directly compared to the control wound at the same anatomical location on the other side of the dorsum midline. This paired assessment of healing is crucial in terms of objective assessment and objective comparison of treated wounds to non-treated because of variability associated with a degree of vascularization and blood circulation in the skin at different areas of the pig's back. Wounds located in the front area near the neck display far better healing properties than wounds located on the rear back. Compound treatment wounds were designated as T1, T2, T3 and T4 and vehicle treated control wounds were designated as C1, C2, C3 and C4. Total number of wounds was twenty.

Wound measurement data from day 12 post-wounding are depicted in Table 2C. A summary of the histological assessment of wounds from day 12 post-wounding is presented in Table 2D. Wounds were scored according to the wound healing histological index. A binary assessment was made for all parameters. The data is shown as a percentage of wounds that meet each wound healing assessment parameter. Healing of the dermis was considered advanced when both edges of the dermis were observed in the same microscope field (x40). The same methodology was employed to assess healing of adipose tissue.

TABLE 2C

Wound Measurement Data Day 12 Post-wounding.

| Treatment | Group | Width (mm) | Length (mm) |
|---|---|---|---|
| | Group 1 | | |
| 3 µM CMPD 3 in saline | L1 | 5.6 | 18.9 |
| | L2 | 5.6 | 22.8 |
| | L3 | 7.3 | 19.5 |
| | L4 | 4.9 | 21.2 |
| | L5 | 4 | 19.7 |
| | Average | 5.48 | 20.42 |
| | SD | 1.1 | 1.4 |
| | Group 2 | | |
| 1 µM CMPD 3 in saline | L1 | 5.2 | 22.3 |
| | L2 | 12.8 | 26.7 |
| | L3 | 4.3 | 23.2 |
| | L4 | 4.5 | 22 |
| | L5 | 2.6 | 19.6 |
| | Average | 5.88 | 22.76 |
| | SD | 3.6 | 2.3 |
| | Group 3 | | |
| Control Saline | R1 | 11.9 | 24.3 |
| | R2 | 10.3 | 26 |
| | R3 | 10.5 | 22 |
| | R4 | 6.5 | 22.5 |
| | R5 | 9.4 | 23.2 |
| | Average | 9.72 | 23.6 |
| | SD | 1.8 | 1.4 |
| | Group 4 | | |
| Control Saline | R1 | 8.3 | 21.7 |
| | R2 | 13.8 | 24.3 |
| | R3 | 10.4 | 27.5 |
| | R4 | 7.8 | 30.5 |
| | R5 | 2.7 | 19.8 |
| | Average | 8.6 | 24.8 |
| | SD | 3.6 | 3.9 |

TABLE 2D

Histological Assessment of Wounds Day 12 Post-wounding.

| Wound No. | Treatment | Epidermal Closure | Epidermal Migration | Epidermal Hyperplasia | Dermal Healing | Adipose Tissue Healing | Abscesses | Adhesion |
|---|---|---|---|---|---|---|---|---|
| L1 | CMPD 3 | + | +/+ | −/− | + | + | −/+ | − |
| L2 | 3 µM in | + | +/+ | +/+ | + | + | + | − |
| L3 | Saline, | + | +/+ | −/− | + | + | −/+ | − |
| L4 | topical | − | +/+ | −/− | + | + | + | − |
| L5 | daily | + | +/+ | +/+ | + | + | + | − |
| L6 | CMPD 3 | − | −/− | +/+ | + | − | + | + |
| L7 | 1 µM in | − | −/− | +/− | − | − | + | + |
| L8 | Saline, | + | +/+ | −/− | + | − | − | − |
| L9 | topical | + | +/+ | −/− | + | + | − | − |
| L10 | daily | + | +/+ | −/− | + | + | − | − |
|  | Positive events/group | 7 | 16 | 7 | 9 | 7 | 6 | 2 |
|  | Percent/group | 70 | 80 | 35 | 90 | 70 | 60 | 20 |
| R1 | Control | − | −/− | +/+ | − | + | + | − |
| R2 | Saline | − | +/+ | −/+ | + | − | + | − |
| R3 | Topical | − | −/− | +/+ | − | − | + | + |
| R4 | daily | + | +/+ | −/− | + | + | + | + |
| R5 |  | − | −/− | +/+ | − | − | + | + |
| R6 |  | + | +/+ | +/+ | − | − | + | + |
| R7 |  | − | −/− | +/+ | − | − | + | + |
| R8 |  | − | −/− | +/+ | − | − | + | + |
| R9 |  | + | +/+ | −/− | − | − | + | + |
| R10 |  | + | +/+ | −/− | + | − | + | + |
|  | Positive events/group | 4 | 10 | 13 | 3 | 2 | 10 | 8 |
|  | Percent/group | 40 | 50 | 65 | 30 | 20 | 100 | 80 |

Dosing solutions were prepared fresh on each day of dosing. Compound 3 was supplied as a lyophilized powder and further reconstituted in injectable 0.9% sodium chloride to make a 3 mg/mL stock suspension. The stock suspension was further diluted with injectable 0.9% sodium chloride to final concentrations of 3 µM and 1 µM for topical application.

Figure 1B:
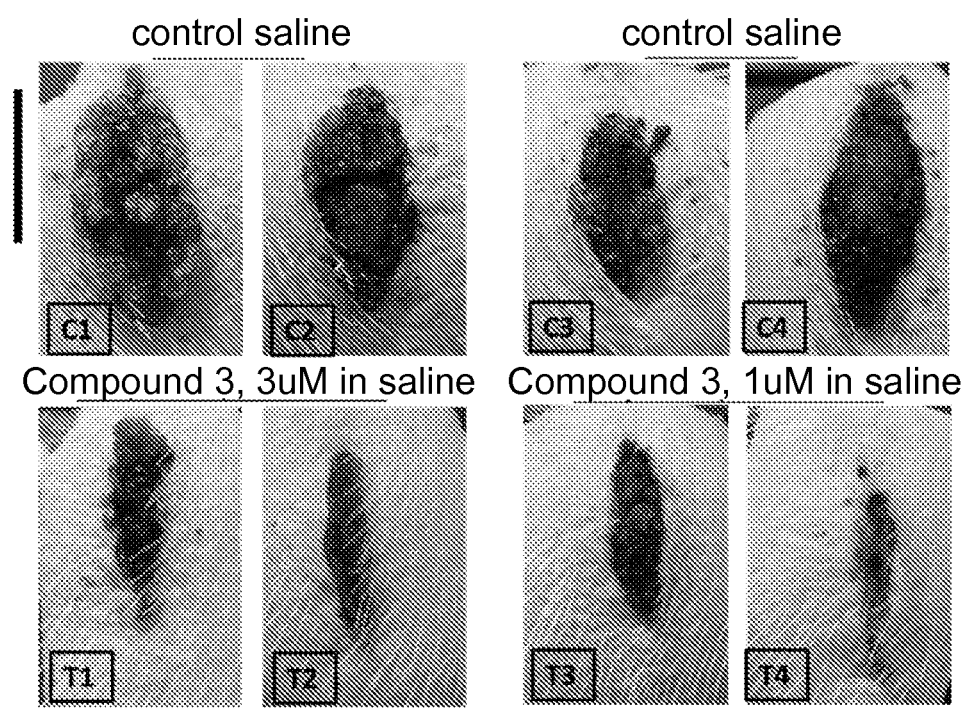
FIG. 1B shows the morphology of wounds treated with saline or with Compound 3 on Day 12 post-wounding in pigs (the black scale bar represents 2 cm).

FIG. 1B shows that all wounds treated with Compound 3 displayed accelerated and superior wound healing compared to wounds treated with saline. Compound 3 treated wounds appeared significantly smaller in size. Scab formation and morphology in Compound 3 treated wounds were homogenous, thinner and had a much more uniformly organized scab surface, indicating that wound healing underneath the scab was more progressive without incidents of oozing, bleeding or secretion from the wound. In control (saline treated) wounds, all morphological parameters indicated delayed wound healing. Scabs in control wounds were highly heterogeneous, cracked and displayed dark colored areas, indicating numerous incidents of exudation, oozing and bleeding during the course of the wound healing process. The best comparison of wound healing in compound versus vehicle treated groups can be seen in T4 and its paired control wound C4 in FIG. 1B. T4 is a wound with an already detached scab and the wound area showed advanced healing with newly formed epidermis accompanied with only minor areas of non-healed tissue (observed as dark spots).

Biopsies from Compound 3-treated wounds on day 12 post-wounding displayed accelerated wound healing compared to wounds treated with saline vehicle alone. Treatment of wounds with Compound 3 enhanced all measured epidermal healing histological parameters and improved and/or accelerated healing processes at the wound gap at day 12 post-wounding. Given all the data, it can be concluded that Compound 3 enhances wound healing.

EXAMPLE 3

Evaluation of the Effects of Topical Application of Compound 3 on Early Wound Healing Processes in Pigs For the purposes of this example, and its associated figures, Compound 3 refers to Compound C-3 (from Table 1C) in saline.

The effects of Compound 3 on early wound healing were studied in a wound model of longitudinal full thickness skin incision in pigs, as outlined in Example 2. Five pairs of 2.5 cm longitudinal full thickness incisions were performed on the frontal section of the back of anaesthetized pigs using #11 scalpel blades, 4 cm from either side of the dorsum midline. Within several hours post-procedure, the longitudinal incision became an elliptical wound.

Wounds were divided into experimental groups and treated daily by topical application on the wound area (including edges and on skin area near the wound). Treatment phase started 24 hours following wounding. Dosing solutions were applied gradually on each wound using a pipette, until the entire treatment volume was absorbed by tissue (1 mL of saline or Compound 3).

On day 5, the state of wound healing and morphology was assessed according to the following parameters: bleeding, oozing, swelling, inflammation, pus secretion and scab formation. Assessment was performed in a paired manner in which each wound treated with Compound 3 was directly compared to the control wound at the same anatomical location on the other side of the dorsum midline.

TABLE 3

Initial Study Groups

| Group | Number of wounds | Test Article | Dose | Route of Administration | Schedule |
|---|---|---|---|---|---|
| 1 | 5 | Control saline | 1 mL | Topical | Daily |
| 2 | 5 | Compound 3 | 3 µM | Topical | Daily |

Dosing solutions were prepared fresh on each day of dosing. Compound 3 was supplied as a lyophilized powder and reconstituted in 0.9% sodium chloride to a 3 mg/mL stock suspension. This stock suspension was further diluted with 0.9% sodium chloride for the preparation of the final 3 µM topical solution.

Figure 2:
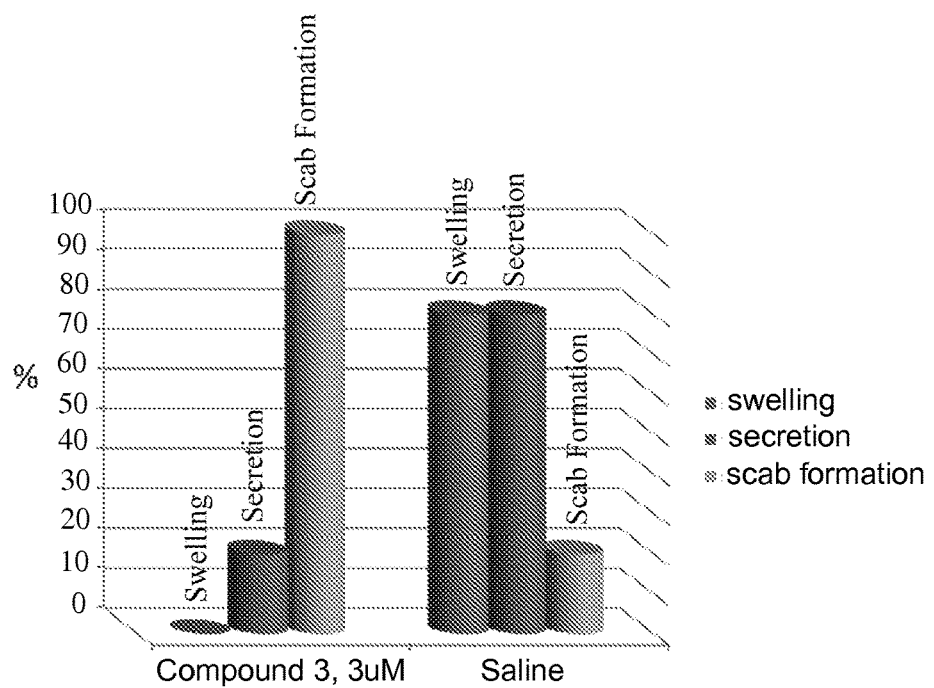
FIG. 2 shows the results of a morphological wound healing assessment of wounds treated with saline or with Compound 3 conducted on Day 5 of treatment.

FIG. 2 shows the results of a morphological wound healing assessment on Day 5 of treatment. Swelling was examined, scored according to the severity in each wound and documented as mild, moderate or severe. Wounds that exhibited moderate and severe swelling are presented as a percentage of total wounds in experimental group. Secretion was examined and scored in a binary mode: a wound that exhibited minimal secretion was considered positive and, a wound without any detectable secretion was considered negative for this parameter. Wounds that exhibited secretions (positive for this parameter) are presented as a percentage of total wounds in experimental group. A scab was considered completely formed when a continuous layer of a hard, dry, reddish, dark yellow or brown formation covered the entire wound area and was strongly attached to the wound bed and, therefore, provided a continuous and strong barrier between the external environment and the wounded tissues. Scab formation was examined and scored in a binary mode: wounds which exhibited a completely formed scab which was dry and strong were considered as positive and wounds without a scab or with scabs at an earlier stage were considered as negative for this parameter. Wounds with a completely formed scab are presented as a percentage of total wounds per group.

FIG. 2 is a graph of the swelling, secretion and scab formation. Swelling and secretion are part of excessive inflammatory response that might delay tissue repair and induce unaesthetic scarring. FIG. 2 depicts that treatment with Compound 3 attenuated the inflammatory response. No abnormal swelling and minimal secretion were observed in the wounds treated with Compound 3. In contrast, high levels of secretion and swelling, indicative of an excessive inflammatory response were observed in saline treated wounds. In wounds treated with Compound 3, 100% scab formation was achieved, whereas in saline treated wounds only 20% of wounds displayed scabbing.

Compound 3 prevented excessive inflammation, promoted early wound healing by stimulating scab formation and preventing wounds from becoming infected.

EXAMPLE 4

Evaluation of the Effects of Topical Application of Compound 4 on Early Wound Healing on Pig Skin and on Irritations and Itching Associated with Damaged or Wounded Skin For the purposes of this example, and its associated figures, Compound 4 refers to Compound C-3 (from Table 1C) in dimethylsulfoxide (DMSO) at the following concentrations of DMSO in water: 0.1%, 0.02% or 0.0067%.

The effect of Compound 4 on skin wound healing was studied in a longitudinal full thickness skin incision wound model in pigs, as described in Example 2. Three days prior to surgery, pigs were transferred to the hospitalization facility for acclimation. Twelve hours prior to the surgical procedure, food was withheld. On the day of surgery, the pigs were anesthetized using ketamine, xylazin, diazepam and isoflurane. The hair on the dorsum thorax and abdomen was cut using Oster® clipper machine (blade size 30). Ten pairs of 4 cm$^2$ each sections were marked, and 2.5 cm full thickness longitudinal skin incisions were made using #11 scalpel blade, on either side of the dorsum midline.

Following surgical procedure, wounds were divided into experimental groups and were treated daily by topical application on the wound area (including edges and on skin area near the wound up to a distance of 2 cm from the wound in all directions). Dosing solutions were applied gradually on each wound using a pipette, until the entire treatment volume was absorbed by tissue (1 mL of vehicle or Compound 4).

Within several hours post-procedure, the longitudinal incision became an elliptical wound due to skin elasticity and activity of the animals. During the experiment, wounds were photo-documented and morphological analysis was performed. Assessment of wound healing was performed in a paired manner in which each wound treated with Compound 4 was directly compared to the control wound at the same anatomical location on the other side of the dorsum midline. During the first 5 days following wounding, wound morphology and animal behavior were recorded. Photo-documentation of the results is presented in FIG. 3.

TABLE 4

Initial Study Groups

| Group | Number of wounds | Test Article | Dose | Route of Administration | Schedule |
|---|---|---|---|---|---|
| 1 | 5 front wounds on the right side | 0.02% DMSO in water | 1 mL | Topical | Daily |
| 2 | 5 rear wounds on the right side | 0.067% DMSO in water | 1 mL | Topical | Daily |
| 3 | 5 front wounds on the left side | Compound 4 in 0.02% DMSO | 3 µM | Topical | Daily |
| 4 | 5 rear wounds on the left side | Compound 4 0.067% DMSO | 1 µM | Topical | Daily |

Dosing solutions were prepared fresh on each day of dosing. Compound 4 was supplied as a lyophilized powder and dissolved in 100% DMSO to a stock concentration of 15 mM. Further dilutions in injectable water were performed to achieve a final concentration of 3 µM and 1 µM for topical application.

Figure 3:
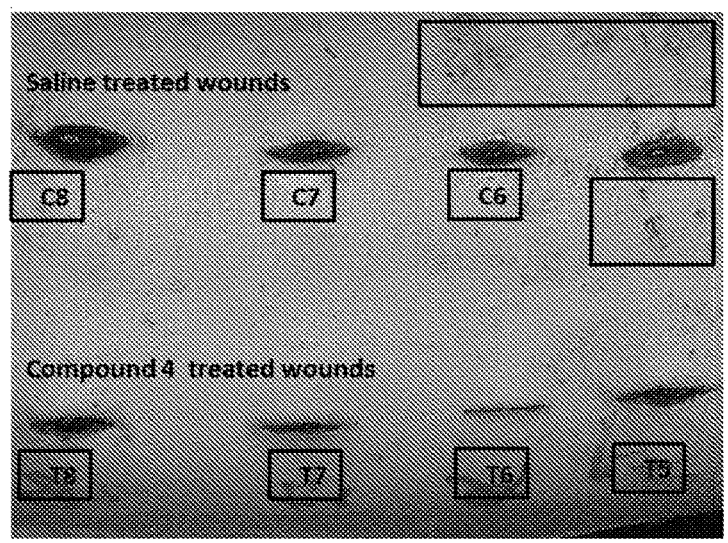
FIG. 3 shows the morphology of saline-treated and Compound 4-treated pig wounds on Day 5 post wounding.

FIG. 3 shows morphology of pig wounds on day 5 post wounding. As part of the daily morphological assessment, photo-documentation of the wounds was performed using a digital high resolution camera FinePix S700. Four representative wound pairs out of the ten are shown. Compound treatment wounds were designated as T5, T6, T7 and T8 and vehicle treated control wounds were designated as C5, C6, C7 and C8. Areas of the skin where signs of scratching were observed are highlighted with black rectangles. Control wound C5 was not marked to allow more clear observation of scratching signs. There were a total of 20 wound.

All wounds treated with Compound 4, (bottom row of the picture shown in FIG. 3) were smaller than their paired control wound in the top row. Moreover, compound 4 treated wounds appeared dry, and wounds T7 and T6 were almost closed. Wounds treated with vehicle (0.02% DMSO in water and 0.067% DMSO in water) were widely open and moist and even contained exudate (wounds C6 and C5).

In addition to the wound status, areas of irritated and scratched skin can be observed, as highlighted by black rectangle in FIG. 3. Irritation and scratching of the pig's lateral area on the side of control wounds was observed at every monitoring session. During the entire experimental phase, pigs only scratched the side treated with DMSO.

Usually, the scratching did not cause damage to the wounds or interfere with the wound healing process because the wound was inflicted on the back near the dorsum midline, such that it was hard and almost impossible for the animal to reach the wounds. However, scratches and some superficial abrasions were seen on the pig's side near the wounds treated with vehicle, indicating that the scratching behavior was due to itching of control wounds. Since no scratching was observed on the side on which wounds were treated with Compound 4, it is possible that Compound 4 has a cooling effect on damaged skin, and thereby prevents itching and scratching.

Wideness, swelling and secretions were prominent only in control, DMSO treated wounds. Compound 4 treated wounds were smaller in size and non-secreting. Compound 4 promoted wound healing and reduced the inflammatory response and, as a result, animals did not scratch the Compound 4 treated wound areas.

EXAMPLE 5

Evaluation of the Effects of Compounds 3, 4 and 5 on Itching and Scratching Associated with Skin Healing in Pigs and Mice For the purposes of this example, and its associated figures, Compound 3 refers to Compound C-3 (from Table 1C) in saline; Compound 4 refers to Compound C-3 (from Table 1C) in dimethylsulfoxide (DMSO) at the following concentrations of DMSO in water: 0.1%, 0.02% or 0.0067%; and Compound 5 refers to Compound 129 (from Table 1A) in saline or in DMSO in water.

In the skin wound studies described herein in mice or pigs, the behavior of the animals was also observed, and attempts to remove scars, signs of discomfort, and scratching of the wound area were quantified. In pigs, scratching of the wounds resulted in obvious signs on the skin such as abrasions. Abnormal behavior and abnormal displays of scratching and signs of pain from all the performed studies (mice and 3 pigs) were analyzed. In these studies, treatment was performed using compounds 3, 4 or 5, and their respective vehicle controls.

Monitoring of healing parameters associated with wound healing and signs of skin irritations and other skin conditions was performed at the wounds and the surrounding treated skin in both mice and pigs. Additionally, throughout the treatment phase, animal behavior was monitored for signs of discomfort and pain; and signs of scratching and tampering with the wounds and the skin. Compounds 3, 4 and 5 exhibited a soothing and calming effect, thereby preventing tampering with the wounds in mice and attempts of scratching in the pigs. Control mice were predisposed to tampering with the wounds and extensive scratching was observed in 3 pigs that only scratched the side of the body where the wounds were treated with vehicle. In all pig experiments, 100% of the pigs scratched the side with the wounds treated with vehicle. In contrast, no scratching signs were observed on the sides of pigs where wounds were treated with Compound 3 or Compound 4.

In mice, treatment with Compounds 3, 4, or 5 reduced the incidence of tampering with wounds in comparison to the vehicle treated mice (DMSO in water, saline, PVP/pluronic or water).

In mice, tampering with wounds usually resulted in the removal of the scab and bleeding or damage to the newly formed tissue on the wound bed that was strongly attached to the scab. The vast majority of such incidents happened in vehicle treated groups (about 20-30% in all experiments).

According to the summary of skin conditions and animal behavior, it can be concluded that treatment of wounds with Compound 3, 4, or 5 prevented tampering with wounds in mice and prevented attempts of scratching in pigs, possibly, due to some soothing and calming effects of the treatment compounds on wounded and irritated skin.

EXAMPLE 6

Dose Response of Compound 4 and Compound 5 on Skin Wound Healing in Mice

For the purposes of this example, and its associated figures, Compound 4 refers to Compound C-3 (from Table 1C) in dimethylsulfoxide (DMSO) at the following concentrations of DMSO in water: 0.1%, 0.02% or 0.0067%; and Compound 5 refers to Compound 129 (from Table 1A) in saline or in DMSO in water. Topical application of Compounds 4 and 5 was performed in accordance with Example 1.

The effects of Compound 4 and Compound 5 on skin wound healing was studied in mice longitudinal full thickness skin incision wound model. Upon arrival, animals were identified by ear tags, weighed and left to acclimate for several days before initiation of the experiment. On the day of wounding, mice were weighed and divided into 7 experimental groups (N=6 or N=7), in accordance to weight differences stratified randomization. The vehicle group received 0.1% DMSO in water while the positive control group was treated with an aqueous 0.6% w/v Pluronic® F-68 and 0.6% w/v PVP K-29/32. Prior to the surgical procedure, mice were anesthetized with isoflurane and the hair on the back of the animals was trimmed. Full thickness longitudinal incisions of 20 mm were performed using a standard scalpel blade on the backs of the animals (parallel to the backbone). Three hours after wounding, due to skin elasticity and activity of the animals, the incisions took elliptical shapes. At this stage, the widest area of the wound was measured. This measurement is referred to as baseline wound width. Wound healing evaluation was made by measuring the widest area of the wound.

Treatment of wounds was performed by topical application (daily) of dosing solutions 0.2 mL directly on wounds. Wound care was a combination of dry and moist wound care. This is because after each daily treatment, wounds were soaked with aqueous dosing solutions. During these 3-5 hours, wound care can be considered as performed in a moist environment.

TABLE 5

Initial Study Groups

| Group | Number of mice | Test Article | Dose | Route of Administration | Schedule |
|---|---|---|---|---|---|
| 1 | 7 | 0.1% DMSO in water | 0.2 mL | Topical | Daily |
| 2 | 6 | Compound 4 in 0.1% DMSO | 9 µM | Topical | Daily |
| 3 | 6 | Compound 4 in 0.1% DMSO | 3 µM | Topical | Daily |
| 4 | 6 | Compound 4 in 0.1% DMSO | 1 µM | Topical | Daily |
| 5 | 6 | Compound 4 in 0.1% DMSO | 0.3 µM | Topical | Daily |
| 6 | 6 | Compound 5 in 0.1% DMSO | 9 µM | Topical | Daily |
| 7 | 6 | Compound 5 in 0.1% DMSO | 3 µM | Topical | Daily |
| 8 | 6 | Compound 5 in 0.1% DMSO | 1 µM | Topical | Daily |
| 9 | 6 | Compound 5 in 0.1% DMSO | 0.3 µM | Topical | Daily |
| 10 | 7 | Control aqueous 0.6% w/v Pluronic® F-68 and 0.6% w/v PVP K-29/32 | 0.2 mL | Topical | Daily |

Dosing solutions were prepared fresh on each day of dosing. Compound 3 and Compound 4 were supplied as lyophilized powder and reconstituted in 0.1% DMSO in water to 3 mg/mL stock suspensions. These stock suspensions were further diluted with 0.1% DMSO in water to prepare the final topical solution. Wounds in control groups were topically treated with 0.1% DMSO in water, or aqueous 0.6% w/v Pluronic® F-68 and 0.6% w/v PVP K-29/32 solution.

Figure 4A:
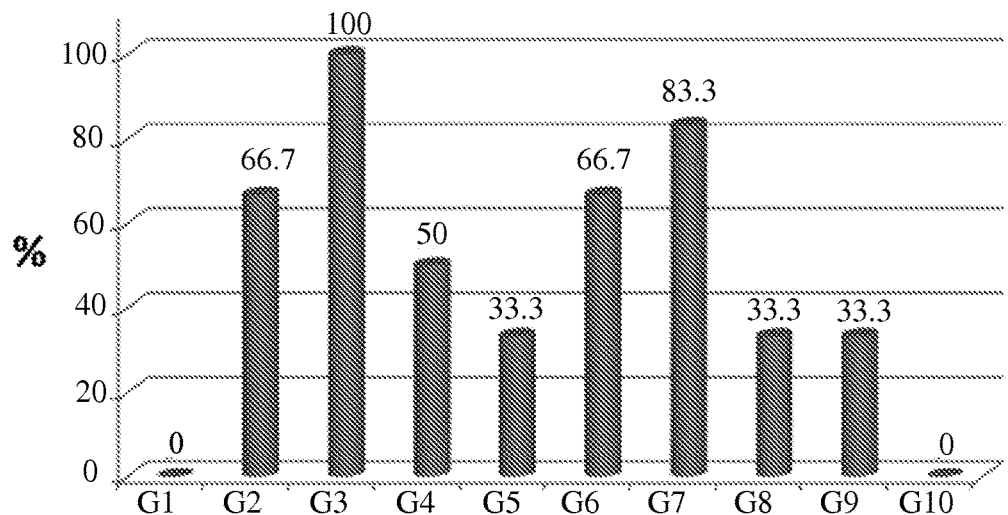
FIG. 4A shows the results of a histological assessment of advanced dermal closure on Day 8 (G1—vehicle control 0.1% DMSO in water; G2, G3, G4 and G5—Compound 4 at concentrations of 9 μM, 3 μM, 1 μM and 0.1 μM, respectively; G6, G7, G8 and G9—Compound 5 at concentrations of 9 μM, 3 μM, 1 μM and 0.1 μM, respectively; G10—positive control group aqueous 0.6% w/v Pluronic® F-68 and 0.6% w/v PVP K-29/32).
Figure 4B:
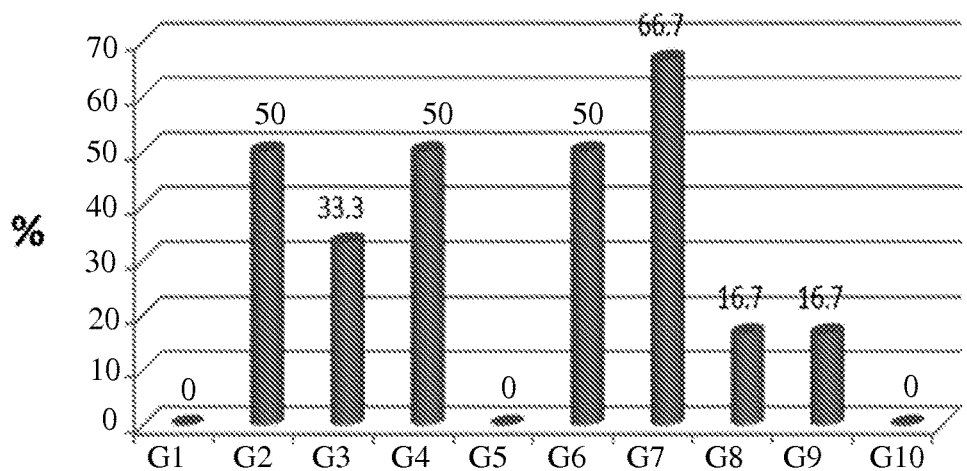
FIG. 4B shows the results of a histological assessment of advanced epidermal closure on Day 8 (G1—vehicle control 0.1% DMSO in water; G2, G3, G4 and G5—Compound 4 at concentrations of 9 μM, 3 μM, 1 μM and 0.1 μM, respectively; G6, G7, G8 and G9—Compound 5 at concentrations of 9 μM, 3 μM, 1 μM and 0.1 μM, respectively; G10—positive control group aqueous 0.6% w/v Pluronic® F-68 and 0.6% w/v PVP K-29/32).
Figure 4C:
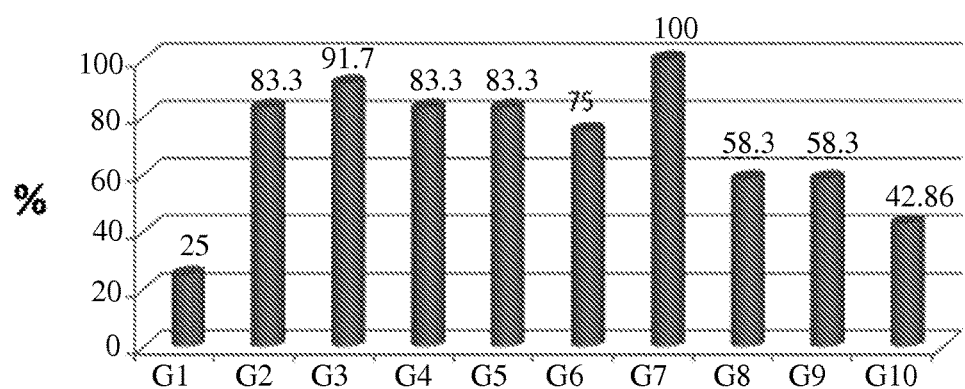
FIG. 4C shows the results of a histological assessment of advanced epidermal migration on Day 8 (G1—vehicle control 0.1% DMSO in water; G2, G3, G4 and G5—Compound 4 at concentrations of 9 μM, 3 μM, 1 μM and 0.1 μM, respectively; G6, G7, G8 and G9—Compound 5 at concentrations of 9 μM, 3 μM, 1 μM and 0.1 μM, respectively; G10—positive control group aqueous 0.6% w/v Pluronic® F-68 and 0.6% w/v PVP K-29/32).

At the end of the experiment, 8 days post wounding, mice were sacrificed by inhalation of $CO_2$, wound widths were measured and biopsies of the wound area were collected and subjected to histological analysis. The biopsies were fixed using 4% paraformaldehyde. Following fixation of the entire wound area, a dissection of 5 mm of the widest area of the wound was performed and these specimens were subjected to paraffin embedding. Paraffin blocks were prepared utilizing standard procedures of graduate dehydration and paraffin embedding of tissues. Thereafter histological sections were prepared and tissues were stained with hematoxylin and eosin (H&E) stain. H&E stained slides were examined and assessment of wound healing efficacy was performed, summarized and graphed as shown in FIGS. 4A-4C. The x-axis of FIGS. 4A-4C presents experimental groups as follows: G1—vehicle control 0.1% DMSO in water; G2, G3, G4 and G5—Compound 4 at concentrations of 9 µM, 3 µM, 1 µM and 0.1 µM, respectively; G6, G7, G8 and G9—Compound 5 at concentrations of 9 µM, 3 µM, 1 µM and 0.1 µM, respectively; G10—positive control group aqueous 0.6% w/v Pluronic® F-68 and 0.6% w/v PVP K-29/32.

FIG. 4A shows the results of a histological assessment of advanced dermal closure on Day 8. Dermal healing was assessed by the examination of eosin stained healthy dermis and the newly formed dermis edges at the wound gap. Wounds with both dermal edges observed in 100× magnification field of the microscope (BX41 Olympus or Axiovert 25, Zeiss) were considered positive for the advanced dermal closure healing parameter. The number of wounds with advanced dermal closure was presented as a percent of total wounds in experimental groups.

FIG. 4B shows the results of a histological assessment of advanced epidermal closure on Day 8. Epidermal closure was assessed using H&E staining by analyzing histological section at the widest area of the wound. Wounds that exhibited the presence of a continuous layer of epidermis covering the entire wound gap and wounds with the most advanced migration of the epidermal edges observed in the microscope field at 400× magnification were considered positive to advanced epidermal closure parameter. The results are presented as a percent of total per experimental group.

FIG. 4C shows the results of a histological assessment of advanced epidermal migration on Day 8. Epidermal migration is assessed using H&E staining by analyzing condensed hematoxylin stained newly formed epidermis at both wound edges. The epidermal edge was considered migratory when newly formed epidermal edge covered about 20-30% of the wound gap. Migratory epidermal edges in the groups were counted and presented as a percent of total number of epidermal edges (twice the number of wounds in the group). Both epidermal edges were considered migratory in wounds that exhibited complete or advanced epidermal closure. A total of 62 wounds were made in 62 mice.

Histological assessment of the effects of Compound 4 and Compound 5 on dermal closure indicated that both compounds induced dermal healing. Only animals treated with Compound 4 and Compound 5 displayed advanced healing stages. No dermal closures were observed in the control groups (G1 and G10).

Epidermal healing was assessed by the examination of epidermal closure (FIG. 4B) and epidermal migration (FIG. 4C). The results indicate that Compound 4 and Compound 5 enhance epidermal healing in a dose-dependent manner. Skin treated with Compounds 4 and 5 also displayed a higher degree of epidermal migration in comparison to the control groups.

All wounds were completely open in control groups and displayed no epidermal closure (0% epidermal closure). However, the epidermis was closed or almost closed in 50% or 67% of the wounds in Compound 4 and Compound 5 treated groups (G2, G4, G6, and G7).

Treatment with Compound 4 and Compound 5 accelerated healing processes in the epidermis and dermis in a dose dependent manner. Significant epidermal closure, migration in the epidermis, and dermal closure in the dermis were observed with Compound 4 and Compound 5 treated wounds.

EXAMPLE 7

Treatment of Wounds with Compound 4 and Compound 5 Prevents Wound Healing Complications, Such as Hyperplasia of the Epidermis and Adhesions For the purposes of this example, and its associated figures, Compound 4 refers to Compound C-3 (from Table 1C) in dimethylsulfoxide (DMSO) at the following concentrations of DMSO in water: 0.1%, 0.02% or 0.0067%; and Compound 5 refers to Compound 129 (from Table 1A) in saline or in DMSO in water.

The effects of Compound 4 and Compound 5 on skin wound healing were studied in a mice longitudinal full thickness skin incision wound model. Upon arrival, animals were identified by ear tags, weighed and left to acclimate for several days before initiation of the experiment. On the day of wounding, the mice were weighed and divided into experimental groups. Each experimental group had either 6 or 7 animals in accordance to weight differences, and animals were randomly divided into groups. The two control groups consisted of a vehicle group (0.1% DMSO in water) and a positive control group (aqueous 0.6% w/v Pluronic® F-68 and 0.6% w/v PVP K-29/32.

Prior to the surgical procedure, mice were anesthetized with isoflurane, and the backs of the animals were shaved. Full thickness longitudinal incisions of 20 mm were performed using a scalpel blade on the backs (parallel to backbone) of the animals. Three hours after wounding, due to skin elasticity and activity of the animals, the incisions took on elliptical shapes. At this stage, the widest area of the wounds was measured. This measurement was used as the baseline wound width. Wound healing evaluation was made by measuring the widest area of the wound. Treatment of wounds was performed by topical daily application of 0.2 mL of Compound 4 or 5 directly on the wounds. Wound care process was partially in a moist environment—after each daily treatment, wounds were wet for some time. At the end of the experiment, 8 days post wounding, mice were sacrificed, wound widths were measured and biopsies of the wound area were collected and subjected to histological analysis.

TABLE 6

Initial Study Groups

| Group | Number of mice | Test Article | Dose | Route of Administration | Schedule |
|---|---|---|---|---|---|
| 1 | 7 | 0.1% DMSO in water | 0.2 mL | Topical | Daily |
| 2 | 6 | Compound 4 in 0.1% DMSO | 3 µM | Topical | Daily |
| 3 | 6 | Compound 5 in 0.1% DMSO | 3 µM | Topical | Daily |
| 4 | 6 | Compound 5 in 0.1% DMSO | 1 µM | Topical | Daily |
| 5 | 7 | Control aqueous 0.6% w/v Pluronic ® F-68 and 0.6% w/v PVP K-29/32 | 0.2 mL | Topical | Daily |

Dosing solutions were prepared fresh on each dosing day. Compound 4 and Compound 5 were supplied as lyophilized powders and reconstituted in 0.1% DMSO in water to a 3 mg/mL stock suspension, which was subsequently diluted with 0.1% DMSO in water to achieve a working concentration for topical application. Wounds in control groups were topically treated with 0.1% DMSO in water or aqueous 0.6% w/v Pluronic® F-68 and 0.6% w/v PVP K-29/32.

Figure 5A:
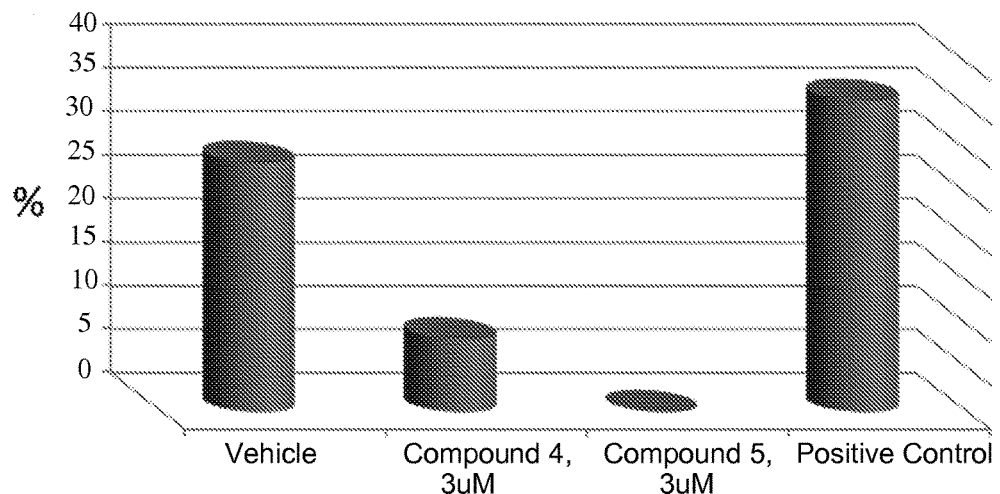
FIG. 5A shows the results of a histological assessment of hyperplasia of the epidermis of wounds treated with 0.1% DMSO in water (vehicle), 3 μM Compound 4, 3 μM Compound 5 or aqueous 0.6% w/v PLURONIC® F-68 and 0.6% w/v PVP K-29/32 (positive control) conducted on Day 8.
Figure 5B:
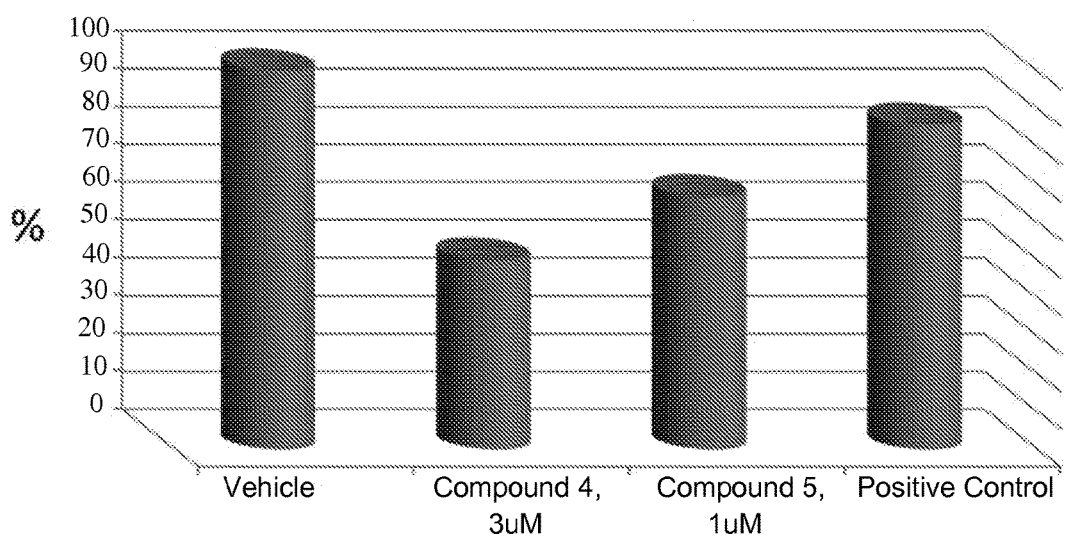
FIG. 5B shows the results of a histological assessment of adhesions at the wound gap of wounds treated with 0.1% DMSO in water (vehicle), 3 μM Compound 4, 1 μM Compound 5 or aqueous 0.6% w/v PLURONIC® F-68 and 0.6% w/v PVP K-29/32 (positive control) conducted on Day 8.

At the end of treatment phase, on day 8 post-wounding, mice were sacrificed by inhalation of $CO_2$ and biopsies of the wound area were harvested. Fixation of wound tissues was performed using 4% paraformaldehyde. Following fixation of the entire wound area, a dissection of 5 mm of the widest area of the wound was performed and was subjected to paraffin embedding. Paraffin blocks were prepared using standard procedures of graduate dehydration. Thereafter, histological sections were prepared and tissues were stained with hematoxylin and eosin (H&E). Wound healing parameters were assessed and graphed. The results are shown in FIGS. 5A and 5B. The x-axis in FIGS. 5A and 5B presents experimental groups treated as follows: vehicle control 0.1% DMSO in water, Compound 4 at a concentration of 3 µM, Compound 5 at a concentration of 3 µM (FIG. 5A) or 1 µM (FIG. 5B), and aqueous 0.6% w/v Pluronic® F-68 and 0.6% w/v PVP K-29/32 as a positive control.

FIG. 5A shows the results of a histological assessment of hyperplasia of the epidermis on Day 8. Non-migratory and hyperplastic epidermal edges in the group were counted, and are presented as a percent of total number of epidermal edges (twice the number of wounds in the group). Hyperplastic epidermal edges were assessed using H&E staining by analyzing condensed hematoxylin stained areas of the epidermis. When the epidermal edge appeared thicker than normal epidermis in a healthy skin area and when such an epidermal edge did not exhibit migration toward sealing the wound gap, it was considered to be hyperplastic and non-migratory.

FIG. 5B shows the results of a histological assessment of adhesions at the wound gap on Day 8. Adhesions were assessed by analyzing cellular and tissue structures at the wound gap. The wound adhesions were scored on a mild, moderate or severe scale. A negative score was considered when there was a clot at the wound gap or normal granulation tissue was replaced by other tissue, such as skeletal muscles or extensive lymphoid tissues. Several adhesions or abnormal granulation occupying more than 40% of the wound gap area were considered as severe. Adhesion was considered mild when it was non-significant and did not interfere with normal skin tissue renewal. Wounds with severe adhesions were calculated as a percent of total wounds per experimental group and graphed as shown. A total of 32 wounds (64 epidermal edges) were made in 32 mice.

The effects of Compound 4 and Compound 5 on wound healing complications in epidermis and dermis were studied using H&E histological staining. Results obtained following assessment of hyperplasia of epidermal edges clearly showed that Compound 4 and Compound 5 prevent hyperplasia of the epidermis (FIG. 5A). 30% of the epidermal edges were hyperplastic in both control groups while only 8% of epidermal edges displayed this complication in the Compound 4 treated group. Moreover, in wounds treated with Compound 5, complications in epidermal healing were not observed. All epidermal edges were migratory and displayed appropriate migration toward sealing of the wound gap.

One of the most important wound healing complications is hyperplasia of the epidermis. As a response to the stress signals associated with wounding, proliferation of cells in the basal layer of the epidermis occurs to compensate for skin loss. Normally, in uneventful wound healing, epidermal cells initiate migration toward sealing the wound gap soon after proliferation. When migration does not occur or is slowed down, for example, in skin complications caused by hyperglycemia in diabetic wounds, epidermal hyperplasia becomes prominent, and may cause even more complications in wound healing. In acute open wounds, as in the model employed in this experiment, or in acute sutured wounds, such as post-surgical wounds, a decline in epidermal healing associated with hyperplasia of epidermal edges increases risk for contamination and other wound healing complications such as wound dehiscence, fluid draining from the wound, or tissue protruding from the wound. Compound 4 and Compound 5 induced accelerated wound healing and reduced events related to slow or problematic healing.

Figure 6A:
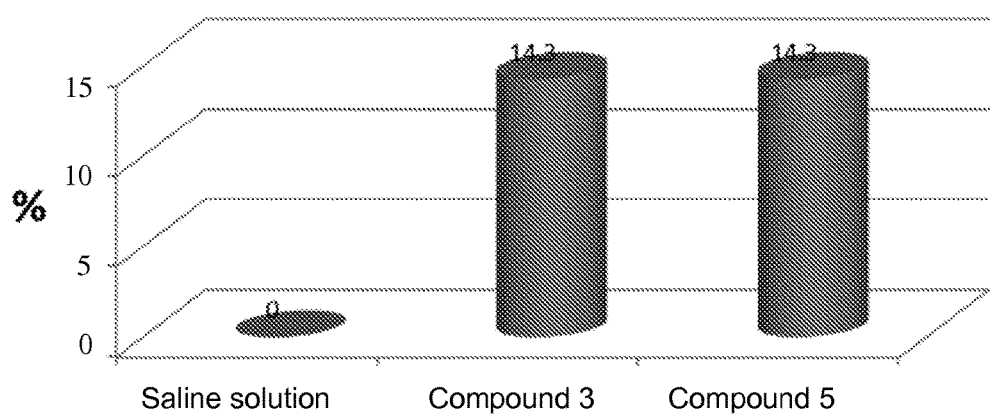
FIG. 6A shows the results of a histological assessment of advanced epidermal closure of wounds treated with saline solution, 3 μM Compound 3 or 3 μM Compound 5 conducted on Day 8.
Figure 6B:
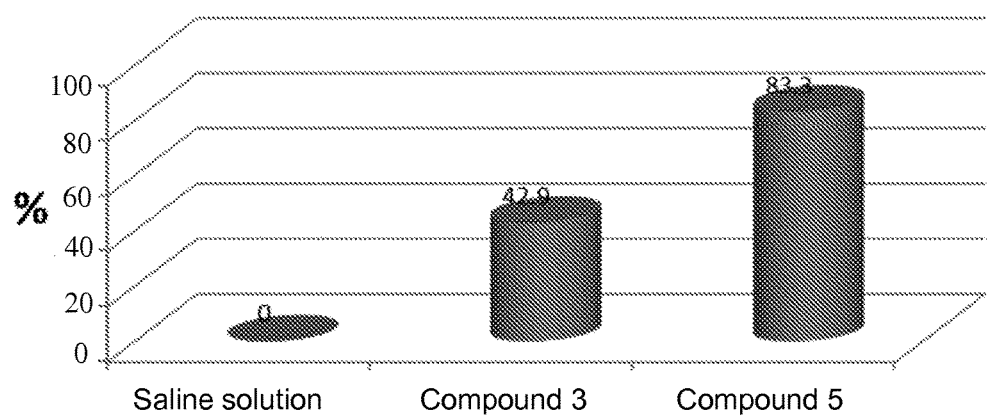
FIG. 6B shows the results of a histological assessment of advanced dermal closure of wounds treated with saline solution, 3 μM Compound 3 or 3 μM Compound 5 conducted on Day 8.

In an effective wound healing process, the primary blood clot undergoes gradual changes in order to form granulation tissue at the wound gap, which, following remodeling, eventually becomes newly formed skin tissue with fully restored functions. When adhesion of non-skin related tissues occurs in the wound gap, granulation tissue does not form properly and, as a result, final tissue remodeling is limited. This may cause further limitations in the functions of healed skin. In wounds treated with Compound 4 and Compound 5, there were fewer adhesions at the wound gap (FIG. 6B). Severe and moderate adhesions were observed in 100% of the wounds in the vehicle control animals and 87% of wounds displayed significant adhesions in positive controls. In contrast, 50% and 67% of wounds treated with Compound 4 and Compound 5, respectively, showed adhesions.

Treatment with Compound 4 and Compound 5 decreases or prevents hyperplasia of epidermal edges, thereby preventing wound healing complications associated with abnormal healing of the epidermis. In addition, treatment of wounds with Compound 4 and Compound 5 decreases adhesions of non-related tissues to the wound gap, thereby promoting more organized skin tissue healing and remodeling.

EXAMPLE 8

Treatment of Wounds with Compound 3 and Compound 5 in a Saline-Based Formulation Improves Wound Healing and Prevents Severe Adhesions For the purposes of this example, and its associated figures, Compound 3 refers to Compound C-3 (from Table 1C) in saline; and Compound 5 refers to Compound 129 (from Table 1A) in saline or in DMSO in water.

The effects of Compound 3 and Compound 5 on skin wound healing were studied in a mouse longitudinal full thickness skin incision wound model. Upon arrival, animals were identified by ear tags, weighed and left to acclimate for several days before initiation of the experiment. On the day of wounding, mice were weighed and divided into experimental groups. Surgical procedures were performed on 7-8 weeks old C57BL male mice anesthetized with Isoflurane. Prior to surgical procedure, mice were anesthetized with isoflurane and the fur was cut. Full thickness longitudinal incisions of 20 mm were performed using a standard scalpel blade on the backs of the animals (parallel to the backbone). Three hours after wounding, due to skin elasticity and activity of the animals, the incisions took on elliptical shapes. At this stage, the widest area of the wound was measured. This measurement is referred to as baseline wound width. Wound healing evaluation was made by measuring the widest area of the wound. Treatment of wounds was performed by a daily application of a topical 0.2 mL solution directly on the wound. The wound care process was conducted partially in a moist environment because after each daily treatment, wounds were wet for some time (3-5 hours). At the end of the experiment, 8 days post wounding, mice were sacrificed, wound widths were measured and biopsies of the wound area were collected and subjected to histological analysis.

TABLE 7

Initial Study Groups

| Group | Number of mice | Test Article | Dose | Route of Administration | Schedule |
|---|---|---|---|---|---|
| 1 | 5 | Saline | 0.2 mL | Topical | Daily |
| 2 | 7 | Compound 4 in saline | 3 uM | Topical | Daily |
| 3 | 7 | Compound 5 in saline | 3 uM | Topical | Daily |

Dosing solutions were prepared fresh on each dosing day. Compound 4 and Compound 5 were supplied as lyophilized powders and reconstituted in saline to make 3 mg/mL stock suspensions which were subsequently diluted with saline to achieve a working concentration of 3 µM for topical application. Wounds in control groups were topically treated with saline.

At the end of the treatment phase, 8 days post-wounding, mice were sacrificed by inhalation of $CO_2$ and biopsies of wound area were harvested. Fixation of wound tissues was performed using 4% paraformaldehyde. Following fixation of the entire wound area, a dissection of 5 mm of the widest area of the wound was performed and the dissected area was subjected to paraffin embedding. Paraffin blocks were prepared using standard procedures of graduate dehydration. Thereafter histological sections were prepared and tissues were stained with hematoxylin and eosin (H&E). Wound healing parameters were assessed and graphed. The x-axis in FIGS. 6A-6D presents experimental groups treated as following: vehicle control saline, 3 µM of Compound 3 in saline and 3 µM of Compound 5 in saline.

FIGS. 6A-6D show the results of a histological assessment of wound healing on Day 8 post-wounding, as measured by assessing advanced epidemeral closure, advanced granulation tissue and severe adhesions at the wound gap. A total N=19 wounds (38 epidermal edges) was performed in 19 mice.

Epidermal closure was assessed using H&E staining by analyzing histological sections at the widest area of the wound. Wounds which exhibited the presence of a continuous layer of epidermis covering the entire wound gap, and wounds with the most advanced migration of the epidermal edges when both edges were observed in the microscope field at 400× magnification were considered positive for the advanced epidermal closure parameter. The results are presented as a percent of total per experimental group in FIG. 6A.

Dermal healing was assessed by the examination of eosin stained healthy dermis and the newly formed dermis edges at the wound gap. Wounds with both dermal edges observed in 100× magnification field of the microscope (BX41 Olympus or Axiovert 25, Zeiss) were considered positive for the advanced dermal closure healing parameter. The number of wounds with advanced dermal closures is presented as a percent of total wounds in experimental groups in FIG. 6B.

Figure 6C:
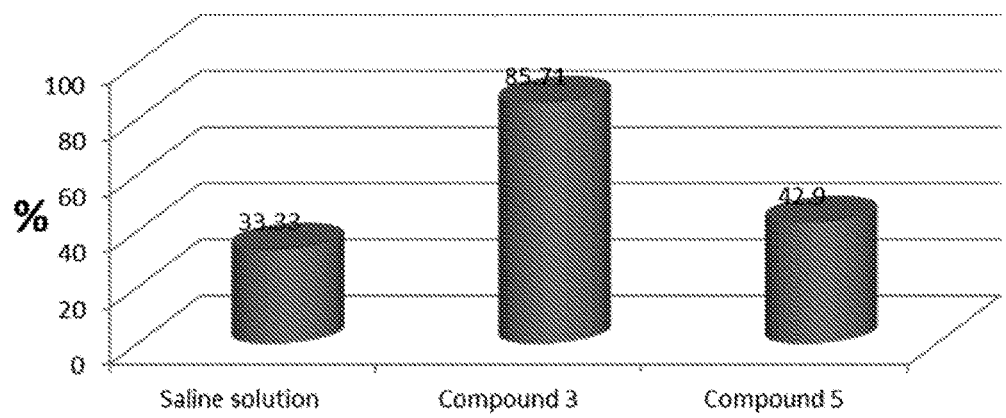
FIGS. 6C shows the results of a histological assessment of advanced granulation tissue of wounds treated with saline solution, 3 μM Compound 3 or 3 μM Compound 5 conducted on Day 8.

Granulation tissue was assessed utilizing H&E staining. When the primary fibrin clot was replaced by fibrous connective tissue containing adipocytes, new capillaries and an infiltrate containing lymphoid cells, macrophages, and plasma cells the granulation tissue was considered early. Early granulation tissue replaced by tissue with a high abundance of fibroblasts and collagen fibers was considered advanced. Overall, areas of advanced granulation tissue at the wound gap were documented as percent of the total wound gap area. A wound gap displaying advanced granulation tissue formation covering 40% of the wound gap was considered positive for this parameter. Results were calculated as a percent of total wounds per group and graphed as shown in FIG. 6C.

Adhesions were assessed by analyzing cellular and tissue structures at the wound gap. The wound adhesions were scored on a mild, moderate or severe scale. A negative score was considered when there was a clot at the wound gap or normal granulation tissue was replaced by other tissue, such as skeletal muscles or extensive lymphoid tissues. Several adhesions or abnormal granulation occupying more than 40% of the wound gap area were considered as severe. Adhesion was considered mild when it was non-significant and didn't interfere with normal skin tissue renewal. Wounds with severe adhesions were calculated as a percent of total wounds per experimental group and graphed as shown in FIG. 6D.

On day 8 post-wounding, wounds treated with Compound 3 and Compound 5 were at an advanced stage of wound healing, whereas wounds in control group, treated with saline, were at a relatively early stage of wound healing. All of the parameters analyzed in FIGS. 6A-6D showed low efficacy of wound healing in control wounds in comparison to treatment with Compound 3 and 5: 0% of advanced dermal closure in control versus 43% and 83% in Compound 3 and Compound 5 treated groups, respectively (FIG. 6B); 0% of advanced epidermal closure in control versus 14% in both treated groups (FIG. 6A); 33% of advanced granulation tissue in control versus 86% and 43% in Compound 3 and Compound 5 treated groups (FIG. 6C), respectively.

Figure 6D:
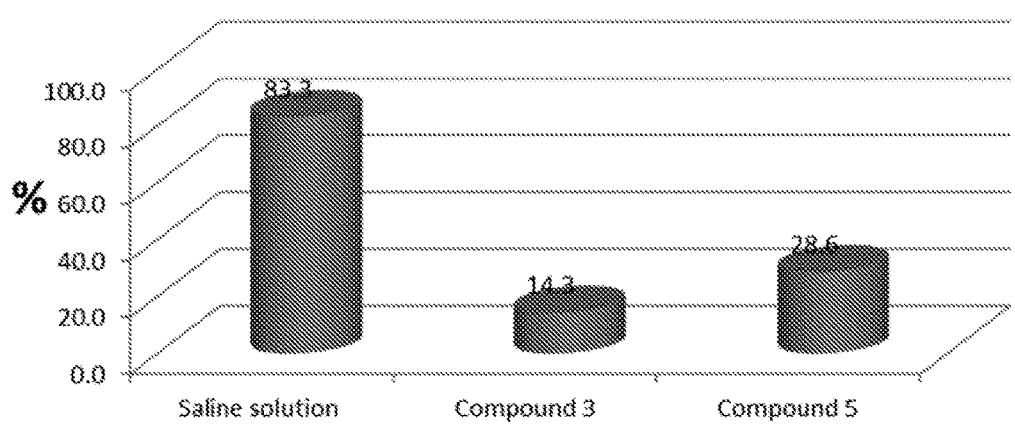
FIG. 6D shows the results of a histological assessment of severe adhesions at the wound gap of wounds treated with saline solution, 3 μM Compound 3 or 3 μM Compound 5 conducted on Day 8.

Low levels of wound healing in control groups were accompanied by a high abundance of severe adhesions at the wound gap—83% of wounds in the control group displayed severe adhesions (FIG. 6D). Much fewer adhesions occurred in treated wounds—only 14% of wounds treated with Compound 3 and 29% of wounds treated with Compound 5 were positive for this parameter.

Treatment with Compound 3 and Compound 5 accelerated healing in the epidermis and dermis, and stimulated advanced granulation tissue formation at the wound gap. In addition, treatment of wounds with Compound 3 and Compound 5 significantly decreased adhesions of non-related tissues to the wound gap.

EXAMPLE 9

Evaluation of the Effects of Topical Application of Compound 4 on Healing Processes and Scarring in the Late Stages of Wound Healing on Pig Skin For the purposes of this example, and its associated figures, Compound 4 refers to Compound C-3 (from Table 1C) in dimethylsulfoxide (DMSO) (e.g., 0.1%, 0.02%, 0.0067% DMSO in water).

The effects of Compound 4 on late stages of skin wound healing was studied in a pig wound model of longitudinal full thickness incision. On the day of surgery, the pig was anesthetized using ketamine, xylazin, diazepam and isoflurane. The hair on the dorsum thorax and abdomen was cut and 10 pairs of 2.5 cm full thickness longitudinal skin incisions were performed using a #11 scalpel blade, 4 cm from either side of the dorsum midline. Following the surgical procedure, wounds were divided into experimental groups and treated daily by topical application on the wound area and on wound edges including treatment of skin near the wound area up to a distance of 2 cm from the wound in all directions,. Dosing solutions were applied gradually on each wound using a pipette, until the entire treatment volume (1 ml of vehicle or Compound 4) was absorbed by the tissue. The skin near the wound was treated with gauze soaked in Compound 4 or vehicle solutions.

During the experiment, wounds were photo-documented and morphological analysis was performed. At the end of the treatment phase (day 19 post-wounding), pigs were sacrificed by dosing of anesthetic and KCl. Morphology of the wounds was examined, wounds were photo-documented and biopsies of wound area were harvested for fixation and further morphological and histological analysis.

TABLE 8

Initial Study Groups

| Group | Number of wounds | Test Article | Dose | Route of Administration | Schedule |
| --- | --- | --- | --- | --- | --- |
| 1 | 5 front wounds on the right side | 0.02% DMSO in water | 1 mL | Topical | Daily |
| 2 | 5 rear wounds on the right side | 0.067% DMSO in water | 1 mL | Topical | Daily |
| 3 | 5 front wounds on the left side | Compound 4 in 0.02% DMSO | 3 µM | Topical | Daily |
| 4 | 5 rear wounds on the left side | Compound 4 0.067% DMSO | 1 µM | Topical | Daily |

Dosing solutions were prepared fresh on each day of dosing. Compound 4 was supplied as a lyophilized powder and dissolved in 100% DMSO to prepare a stock solution of 15 mM Compound 4. Subsequently, dilutions in injectable water were performed to achieve final concentrations of 3 µM and 1 µM for topical application.

At the end of the treatment phase (day 19 post-wounding), the assessment of wound healing was performed. Due to low variability in each treatment group, the mean of Compound 4 treatment groups (1 and 3 µM in 0.02 and 0.067% DMSO) or control treatment groups (0.02 and 0.067% DMSO) was reported.

Figure 7A:
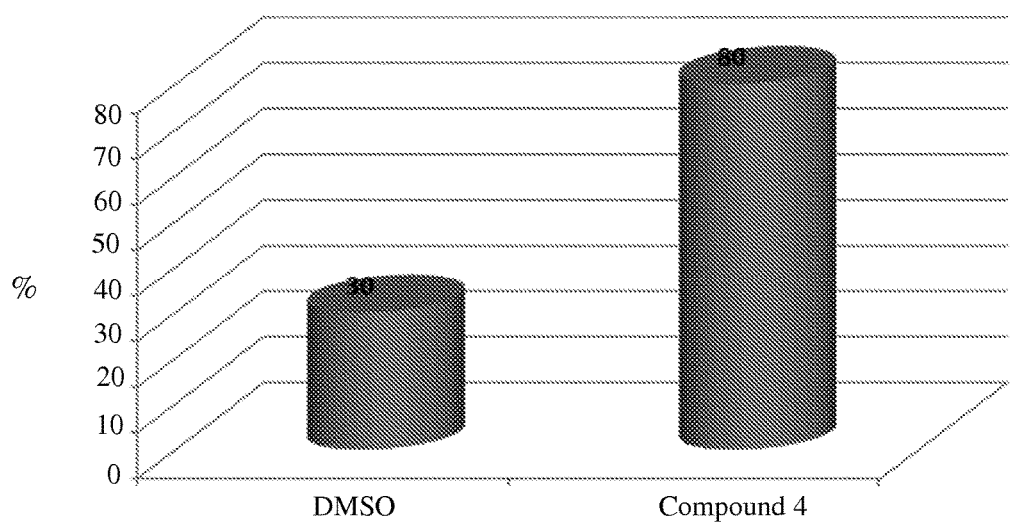
FIG. 7A shows the results of a morphological assessment of complete wound healing of wounds treated with DMSO in water or Compound 4 conducted on Day 19.
Figure 7B:
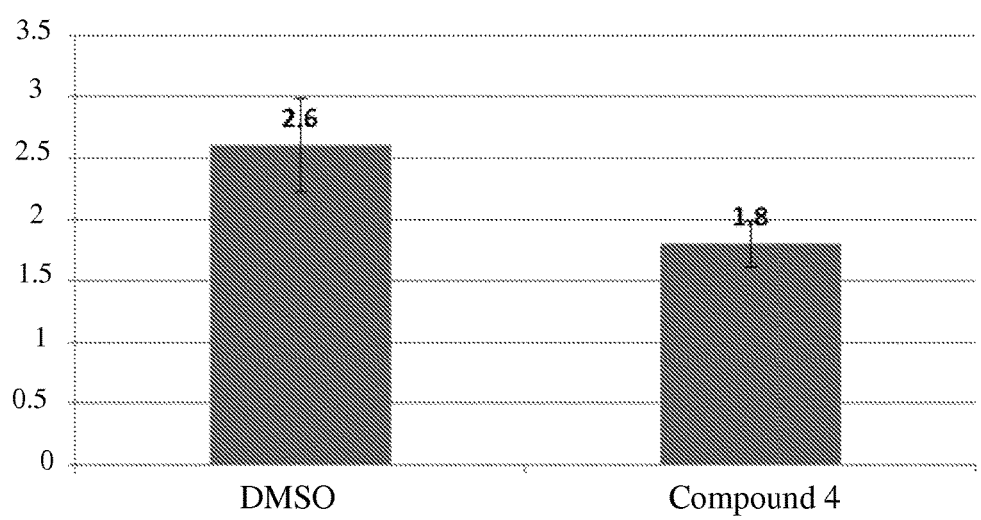
FIG. 7B shows the results of a morphological assessment of scar width (mm) of wounds treated with DMSO in water or Compound 4 conducted on Day 19.

FIG. 7A reports the fully healed wounds as a percent of total wounds per group. FIG. 7B reports the average width of scars in the wounds that healed completely and exhibited full scab detachment. Scars were measured (mm) and the average width of scars and standard deviation were calculated and graphed as shown. A total of 20 wounds was performed.

Figure 8:
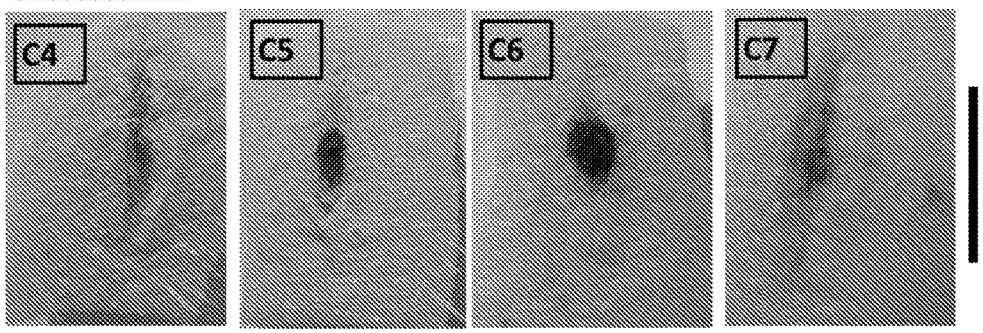
FIG. 8 is reproductions of photographs, and shows the morphology of pig wounds treated with DMSO in water (Control, vehicle) or Compound 4 on Day 19 post-wounding.
Figure 8:
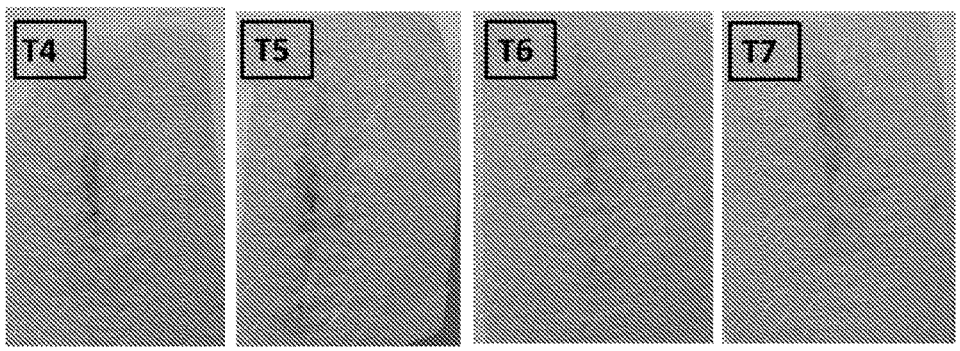

At the end of the treatment phase (day 19 post-wounding), pigs were sacrificed by an overdose of anesthetic and KCl and biopsies of wound area were harvested. Fixation of wound biopsies was performed using 4% paraformaldehyde. Following fixation, wound biopsies were photo-documented using a digital camera FinePix S700 at the highest resolution. Four representative wounds out of 10 wounds are shown in FIG. 8. Compound treatment wounds were designated as T4, T5, T6 and T7 and vehicle treated control wounds were designated as C4, C5, C6, C7. A total of 20 wounds was performed. The black bar in FIG. 8 represents a 2 cm scale.

The results show that by day 19 post-wounding, 80% of wounds treated with Compound 4 displayed complete healing. In contrast, only 30% of wounds displayed complete healing in the control group (FIG. 7A). Further assessment of healing was measured by the reduction in the width of scars. Wounds treated with Compound 4 displayed smaller scars in a statistically significant manner (FIG. 7B). Comparison of wound pictures taken using the highest available resolution indicated that Compound 4 treated groups exhibited faster and improved healing, as well as smaller, less noticeable scars (FIG. 8).

Treatment with Compound 4 stimulated healing of later stages of wound healing and induced complete wound healing when compared to vehicle treated group. Leftover scars following Compound 4 treatment were smaller in size and less noticeable.

EXAMPLE 10

Synthesis of Pyrimidin-5-Ylmethyl (Z)-3-(3-(3-Isopropoxy-5-(Trifluoromethyl)Phenyl)-1H-1,2,4-Triazol-1-Yl)Acrylate (Compound 129 in Table 1A).

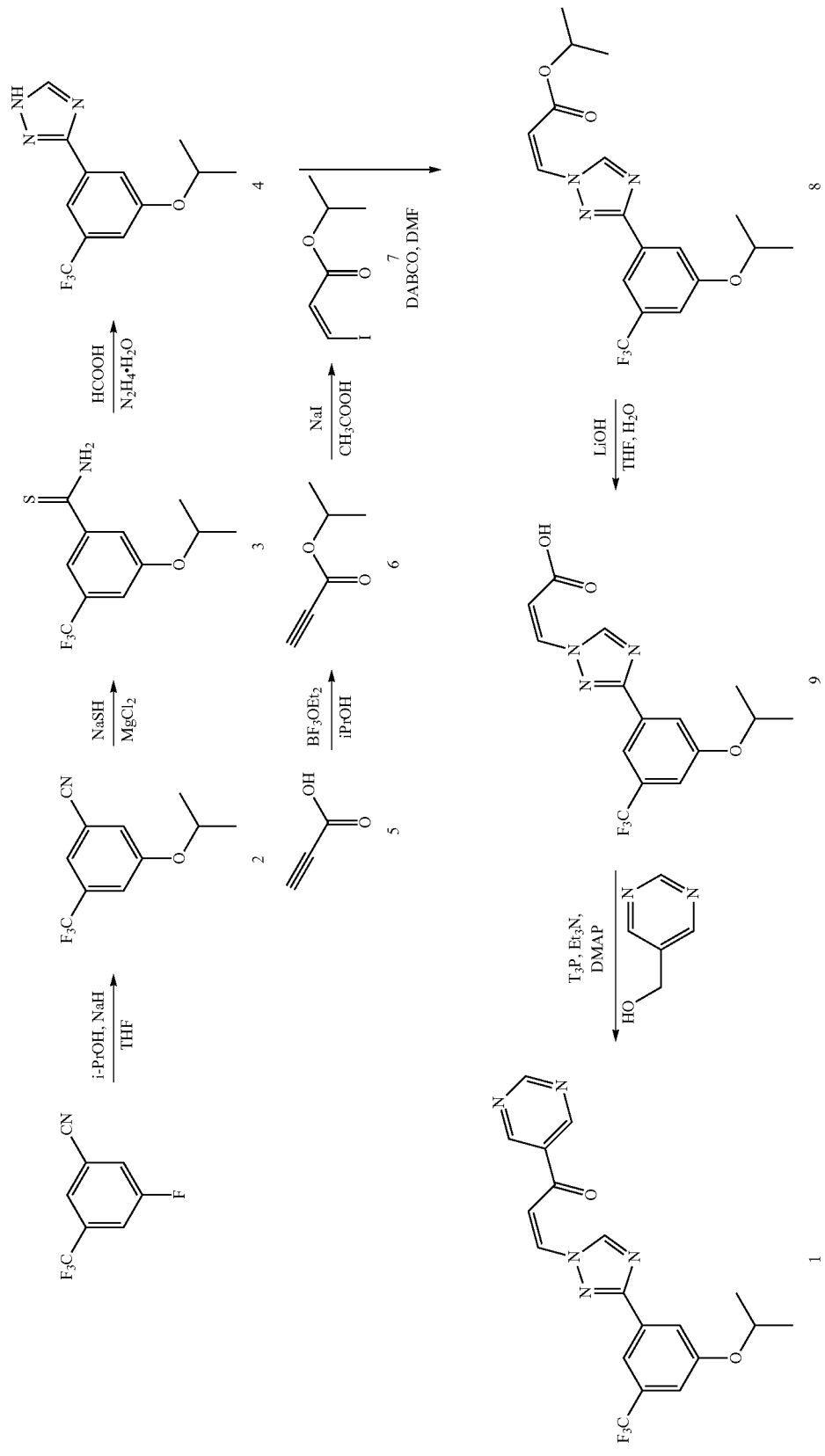

Isopropyl alcohol (90 mL) was added in tetrahydrofuran (THF) (2.5 L) under nitrogen atmosphere and cooled to −30 °C. 60% NaH (50.76 g, 1160 mmol) was added in small portions over 30 minutes and stirred at 0° C. for 1 hour. 3-fluoro-5-(trifluoromethyl) benzonitrile (200 g, 1060 mmol) was added dropwise at 0° C. and stirred at room temperature for 3 hours. The reaction mixture was transferred into iced water and extracted with ethyl acetate (3×1 L). The combined organic layers were concentrated under reduced pressure to afford of 3-isopropoxy-5-(trifluoromethyl)benzonitrile (2 in Scheme 1), which was used without further purification in the following step (Crude yield: 250 g).

3-Isopropoxy-5-(trifluoromethyl)benzonitrile (2 in Scheme 1) (2200 g, 9390 mmol) was dissolved in dimethylformamide (DMF) (20 L). Sodium hydrosulphide hydrate (1420 g, 1879 mmol) and magnesium chloride hexahydrate (2143 g, 1033 mmol) were added, and the reaction mixture was stirred at room temperature for 1 hour. The reaction mixture was transferred into iced water and extracted with ethyl acetate (3×5 L). The combined organic layers were concentrated under reduced pressure to afford 2900 g of 3-isopropoxy-5-(trifluoromethyl)benzothioamide (3 in Scheme 1) which was used without further purification in the following step.

3-Isopropoxy-5-(trifluoromethyl) benzothioamide (3 in Scheme 1) (1000 g, 378 mmol) was dissolved in DMF and hydrazine hydrate monohydrate (204.14 mL) was added dropwise. The reaction mixture was stirred at room temperature for 1.5 hours, the formic acid (3 L) was added dropwise over 45 minutes and heated at 80° C. for 4 hours. The reaction mixture was allowed to cool to room temperature, transferred into iced water, and extracted with ethyl acetate (3×3 L). The combined organic layers were concentrated under reduced pressure and crystallized from hexanes to give 3-(3-isopropoxy-5-(trifluoromethyl)phenyl)-1H-1,2,4-triazole (4 in Scheme 1). Yield (48.33%). $^1$H NMR (400 MHz, CDCl$_3$) δ8.46 (s, 1H), 7.93 (s, 1H), 7.82 (s, 1H), 7.20 (s, 1H), 4.67-4.73 (m, 1H), 1.41 (d, J=6 Hz, 6H).

Propiolic acid (5 in Scheme 1) (1000 g, 1 equiv.) was added in i-PrOH (8 L, 8 Vol.). BF$_3$-etherate (4.54 kg, 2.0 equiv.) was added slowly at 25° C. over a period of 30 minutes. The temperature of the reaction mixture was gradually increased up to 90° C. and stirred at that temperature for 3 hours. Gas chromatography (GC) monitoring after 3 hours showed the completion of the reaction. The reaction mixture was cooled to room temperature, quenched with 20 L of ice cold water and stirred for 30 minutes. 10 L of dichloromethane was added to the reaction mixture and stirred for an additional 30 minutes. The organic layer was separated and the aqueous layer was re-extracted with 5 L of dichloromethane. The combined organic layers were washed with 10 L of brine, dried over anhydrous sodium sulfate, and concentrated under reduced pressure at 35-40° C. (product is volatile) to yield isopropyl propiolate (6 in Scheme 1) as a brown liquid (1.32 kg, 81.25%). Purity 89.67% (GC); $^1$H NMR (300 MHz, CDCl3) δ: 1.22 (d, 6H, J=6.6 Hz), 2.85 (s, 1H), 4.98-5.05 (m, 1H).

Isopropyl propiolate (6 in Scheme 1) (1000 g, 1 equiv.) was added in acetic acid (3.7 L, 3.7 Vol.) at 25° C., and the reaction mixture was stirred for 10 minutes. Sodium iodide (2.138 kg, 1.6 Vol.) was added (a dark brown colour was observed) while stirring. The temperature was increased to 110° C. and the reaction was maintained at that temperature for 1.5 hours. GC monitoring showed the completion of the reaction after 1.5 hours. The reaction mixture was cooled to room temperature, quenched with ice cold water (18.75 L, 18.75 V) and stirred for 30 minutes. Methyl tert-butyl ether (MTBE) (5 L) was added to the reaction mixture and stirred for another 30 minutes. The organic layer was separated and the aqueous layer was re-extracted with MTBE (5 L). The combined organic layers was washed with NaHCO$_3$ (2×10 L), NaHSO$_3$ (2×5 L) and brine (5.2 L, 5.2 V), dried over sodium sulfate and concentrated under reduced pressure at 35° C. to yield (Z)-isopropyl 3-iodoacrylate (7 in Scheme 1) as a brown liquid (1.49 kg, 70%). Purity 87.34% (GC); $^1$H NMR (300 MHz, CDCl3) δ: 1.28 (d, 6H, J=6.3 Hz), 5.08-5.131 (m, 1H), 6.83 (d, 1H, J=8.7 Hz), 7.38 (d, 1H, J=8.7 Hz).

3-(3-Isopropoxy-5-(trifluoromethyl)phenyl)-1H-1,2,4-triazole (4 in Scheme 1) (600 g, 1.0 eq.) was added in DMF (3.0 L). 1,4-Diazabicyclo[2.2.2]octane (DABCO) (480 g, 2.0 eq) was then introduced, and the reaction mixture was stirred for 30 minutes. A solution of iodo ester (7 in Scheme 1) (1024.8 g, 2.0 eq) in DMF (1200 mL) was added drop wise over a period of 1 hour. An additional 1 equiv. of DABCO (258 g) was added and the reaction mixture was stirred for another hour. The reaction mixture was quenched with cold water (12 L), stirred for 15 minutes, and extracted with ethyl acetate (2×6 L). The combined organic layers was washed with brine (2×3 L), dried over anhydrous sodium sulfate (100 g) and concentrated under reduced pressure. The crude product (840 g) was stirred in methanol (1200 mL) and maintained at 0-5° C. for 30 minutes. The solid precipitate was filtered and washed with methanol (200 mL), to give isopropyl (Z)-3-(3-(3-isopropoxy-5-(trifluoromethyl)phenyl)-1H-1,2,4-triazol-1-yl)acrylate (8 in Scheme 1) as a white solid (550 g, 65.0%). Purity: 87.34% (HPLC); $^1$H NMR (300 MHz, CDCl$_3$) δ: 1.30 (d, 6H, J=6.0 Hz), 5.12 (m, 1H), 5.73 (d, 1H, J=10.8 Hz), 7.24 (d, 1H, J=10.8 Hz), 7.91 (s, 1H), 8.58 (s, 2H), 9.70 (s, 1H). Cis-isomer: Trans-isomer ratio is 83:8.

Isopropyl (Z)-3-(3-(3-isopropoxy-5-(trifluoromethyl)phenyl)-1H-1,2,4-triazol-1-yl)acrylate (8 in Scheme 1) (125 g, 1 eq.) was added in THF (1.25 L) at room temperature. The reaction mixture was cooled to 0° C. and an ice cold lithium hydroxide solution (66.58 g in 1.25 L water) was added over a period of 30 minutes. The reaction temperature was slowly raised to 25° C., at which temperature it was stirred for 3 hours. The reaction mixture was quenched with ice cold water (385 mL) and stirred for 30 minutes. The pH was adjusted to 1-2 with dilute hydrochloric acid (30%, 400 mL), and the reaction mixture was extracted with ethyl acetate (3×625 mL). The combined organic layers were washed with brine (650 mL), dried over anhydrous sodium sulfate (12.5 g) and concentrated under reduced pressure at 30-35° C. Hexane was added to the crude product and stirred for 30 minutes. The solid precipitate was filtered and washed with hexane (250 mL), and dried under reduced pressure at room temperature for 3-4 hours. (Z)-3-(3-(3-isopropoxy-5-(trifluoromethyl)phenyl)-1H-1,2,4-triazol-1-yl)acrylic acid (9 in Scheme 1) was isolated as a white powder (92.8 g, 84.36%). Purity: 93% (HPLC); $^1$H NMR (300 MHz, DMSO-d6) δ: 5.98 (d, 1H, J=10.2 Hz), 7.48 (d, 1H, J=10.2 Hz), 8.2 (s, 1H), 8.50-8.54 (m, 2H), 9.39 (s, 1H).

(Z)-3-(3-(3-isopropoxy-5-(trifluoromethyl)phenyl)-1H-1,2,4-triazol-1-yl)acrylic acid (9 in Scheme 1) (100 g, 289.67 mmol) was dissolved in dichloromethane (5.0 L) and cooled to −10° C. 5-Hydroxymethyl-pyrimidine (38.66 g, 347.60 mmol) was added, followed by the dropwise addition of 50% propylphosphonic anhydride (T$_3$P) in ethyl acetate (258.6 mL, 434.50 mmol) at −10° C. Triethylamine (81 mL, 579.34 mmol) was then added dropwise followed by 4-dimethylaminopyridine (DMAP) (1.79 g, 14.48 mmol), and the reaction mixture was stirred at −10° C. for 2.5 hours, transferred into iced water, extracted with dichloromethane, purified by silica gel chromatography, and recrystallized using isopropanol to afford pyrimidin-5-ylmethyl (Z)-3-(3-(3-isopropoxy-5-(trifluoromethyl)phenyl)-1H-1,2,4-triazol-1-yl)acrylate (1 in Scheme 1). Yield (23%). $^1$H NMR (400 MHz, DMSO-d$_6$) δ9.73 (s, 1H), 9.25 (s, 1H), 8.84 (s, 2H), 7.98 (s, 1H), 7.84 (s, 1H), 7.38 (d, J=10.8 Hz, 1H). 7.20 (s, 1H), 5.77 (d, J=10.8 Hz, 1H), 5.29 (s, 2H), 4.68-4.75 (m, 1H), 1.39 (d, J=6 Hz, 6H). LCMS: m/z 434.33 [M+H]$^+$, $t_R$=3.34 min.

EXAMPLE 11

Evaluation of the Effects of Topical Application of Compound 4 on Wound Healing Processes in Pig For the purposes of this example, and its associated figures, Compound 4 refers to Compound C-3 (from Table 1C) in dimethylsulfoxide (DMSO) (e.g., 0.1%, 0.02%, 0.0067% DMSO in water).

The effects of Compound 4 on skin wound healing were studied in healthy pigs using multiple longitudinal full thickness skin incisions in two rows alongside the spine. A pig was subjected to the wounding procedure in which twenty full thickness longitudinal skin incisions (ten pairs) were made that were approximately 25 mm±3 mm in length and 8 mm to 20 mm deep. Variations in wound size were due to differences in skin thickness and the anatomy of the area. Each pair of incisions was located at the same distance from the dorsum midline. All wounds on the left side of the animal were treated with Compound 4 and wounds on the right side were treated with vehicle controls. Wounds were treated daily by topical application of Compound 4 at a concentration of 1 μM or 3 μM, formulated in either 0.02% or 0.0067% DMSO. On the day of surgery, the pig was anesthetized using ketamine, xylazin, diazepam and isoflurane. The hair on the dorsum thorax and abdomen was carefully cut using an Oster® clipper machine (blade size 30) and 20 individual regions of 4 cm$^2$ each were marked in two rows (10 regions per row). Ten pairs of 2.5 cm full thickness longitudinal skin incisions were made using #11 scalpel blade, 4 cm from either side of the dorsum midline.

Wound treatment was performed using a gauze pad soaked in 2 mL of the dosing solution and applied on the wound for 1 minute or, when placed on a scab, until the scab and the wound edges completely absorbed the treatment. Approximately 1 mL of the solution was delivered to the wound. Absorption was considered complete when liquid no longer moves out of wound. The study duration was 19 days. Several hours after wounding, due to skin elasticity and activity of the animals, the incisions took elliptical shapes. At this stage, the widest area of the wound was measured and determined as baseline wound width. Wound healing evaluation was made by measuring the widest area of the wound. During the experiment, wounds were photo-documented and morphological analysis was performed. At the end of the experiment (19 days after wounding), pigs were sacrificed by administration of anesthetic and potassium chloride. Wound morphology was assessed, wound widths were measured and biopsies of wound area were harvested and fixed for further analysis. Following fixation, wound biopsies were photo-documented using high resolution digital camera FinePix S700 and biopsies of the wound area subjected to histopathological analysis. Assessment of wound healing was performed in a paired manner—where each wound treated with Compound 4 was directly compared to the control wound at the same anatomical location at other side of the dorsum midline. This paired assessment of healing is crucial in terms of objective assessment and objective comparison of treated wounds to non-treated because of variability associated with a degree of vascularization and blood circulation in the skin at different areas of the pig's back. Wounds located in the front area near the neck display far better healing properties than wounds located on the rear back.

TABLE 8A

Study Groups.

| Group | Number of wounds | Test Article | Dose | Route of Administration | Schedule |
|---|---|---|---|---|---|
| 1 | 5 front wounds on the right side | 0.02% DMSO in water | 1 mL | Topical | Daily |
| 2 | 5 rear wounds on the right side | 0.0067% DMSO in water | 1 mL | Topical | Daily |
| 3 | 5 front wounds on the left side | CMPD 4 in 0.02% DMSO | 3 μM in 1 ml | Topical | Daily |
| 4 | 5 rear wounds on the left side | CMPD 4 in 0.0067% DMSO | 1 μM in 1 ml | Topical | Daily |

Compound 4 was dissolved in DMSO to make a stock solution of 15 mM in 100% DMSO. Dilutions in water for injection were performed to achieve working solutions of 3 μM and 1 μM Compound 4 for dosing. Dosing solutions were prepared fresh each day.

On day 5 post-wounding, wound width and wound length were measured and a morphological assessment of the wounds was performed. Initial wound measurements were not performed because, following initial skin incision elliptical wounds are formed within 12-24 hours after wounding and continue to increase in size for at least 3-5 days. From day 5, wound size in the pig model is stabilized. Wound width and wound length measurements are presented in Table 8B. Wound morphology data is presented in Table 8C. Scab status was scored as: (+) formed, (−) not formed/open wound and (+/−) partially formed/wound still secreting. Swellings were scored as mild (+), moderate (++) and severe (+++). Wounds with only minor, non-significant swellings were scored as +/−. Secretions were scored as mild (+), moderate (++) or severe (+++). Wounds with only minor, non-significant secretions were scored as (+/−).

TABLE 8B

Wound Measurement Data Day 5 Post-wounding.

| Treatment | Group | Width (mm) | Length (mm) |
|---|---|---|---|
| | Group 1 | | |
| 3 μM CMPD 4 in DMSO 0.067% | L1 | 4.5 | 25.32 |
| | L2 | 5.4 | 30.13 |
| | L3 | 5.2 | 25.82 |
| | L4 | 5.9 | 23.14 |
| | L5 | 8.26 | 36.43 |
| | Average | 5.9 | 28.2 |
| | SD | 1.3 | 4.7 |

TABLE 8B-continued

Wound Measurement Data Day 5 Post-wounding.

| Treatment | Group | Width (mm) | Length (mm) |
|---|---|---|---|
| | Group 2 | | |
| 1 µM CMPD 4 inDMSO | L1 | 3.0 | 29.11 |
| | L2 | 6.30 | 27.57 |
| | L3 | 10.70 | 29.09 |
| | L4 | 8.80 | 33.00 |
| | L5 | 4.20 | 27.74 |
| | Average | 6.6 | 29.3 |
| | SD | 2.8 | 2.0 |
| | Group 3 | | |
| DMSO 0.02% | R1 | 6.3 | 26.34 |
| | R2 | 2.7 | 29.40 |
| | R3 | 7.10 | 26.50 |
| | R4 | 5.07 | 34.99 |
| | R5 | 9.77 | 25.56 |
| | Average | 6.2 | 28.6 |
| | SD | 2.3 | 3.5 |
| | Group 4 | | |
| DMSO 0.067% | R1 | 9.27 | 26.13 |
| | R2 | 8.02 | 29.10 |
| | R3 | 12.50 | 33.58 |
| | R4 | 11.20 | 38.12 |
| | R5 | 5.80 | 30.36 |
| | Average | 9.4 | 31.5 |
| | SD | 2.4 | 4.1 |

TABLE 8C

Wound Morphology Data Day 5 Post-wounding.

| Treatment | Wound Pair | Swelling | Scab | Secretion | Treatment | Swelling | Scab | Secretion |
|---|---|---|---|---|---|---|---|---|
| 3 µM CMPD 4 in 0.02% DMSO | 1 | − | + | − | DMSO 0.02% | +/+ | − | + |
| | 2 | − | + | − | | + | − | + |
| | 3 | − | + | − | | − | − | + |
| | 4 | − | +/− | − | | − | + | − |
| | 5 | − | +/− | + | | + | − | +++ |
| 1 µM CMPD in 0.0067% DMSO | 1 | − | + | − | DMSO 0.0067% | ++ | − | + |
| | 2 | − | +/− | − | | + | − | + |
| | 3 | + | − | − | | ++ | − | + |
| | 4 | +/− | − | + | | + | − | + |
| | 5 | − | + | − | | − | + | + |

On day 5 of the treatment phase, morphological assessment of wounds was performed. Swelling was examined, scored according to the severity in each wound and documented as mild, moderate or severe. Wounds which exhibited moderate and severe swelling were presented as a percentage of total wounds in the experimental group. Secretion was examined and scored in a binary mode: a wound that exhibited minimal secretion was considered positive and a wound without any detectable secretion was considered negative for this parameter. Wounds that exhibited secretions (positive for this parameter) were presented as a percentage of total wounds in the experimental group. A scab was considered as completely formed when a continuous layer of the hard dry, reddish, dark yellow or brown formation covered the entire wound area and was strongly attached to the wound bed and, therefore, provided a continuous and strong barrier between the external environment and wounded tissues. Scab formation was examined and scored in a binary mode: wounds that exhibited a completely formed scab which was dry and strong were considered as positive and wounds without a scab or with scabs at an earlier stage were considered as negative for this parameter. Wounds with a completely formed scab were presented as a percentage of total wounds per experimental group.

On day 5, pigs were anaesthetized and photo-documentation of the wounds was performed using FinePix S700 camera. All wounds treated with Compound 4 and their appropriate controls were done in a way that allowed paired comparison of wounds on the same anatomical location. Scale bar=approximately 2.5 cm. N=20 wounds.

Figure 9A:
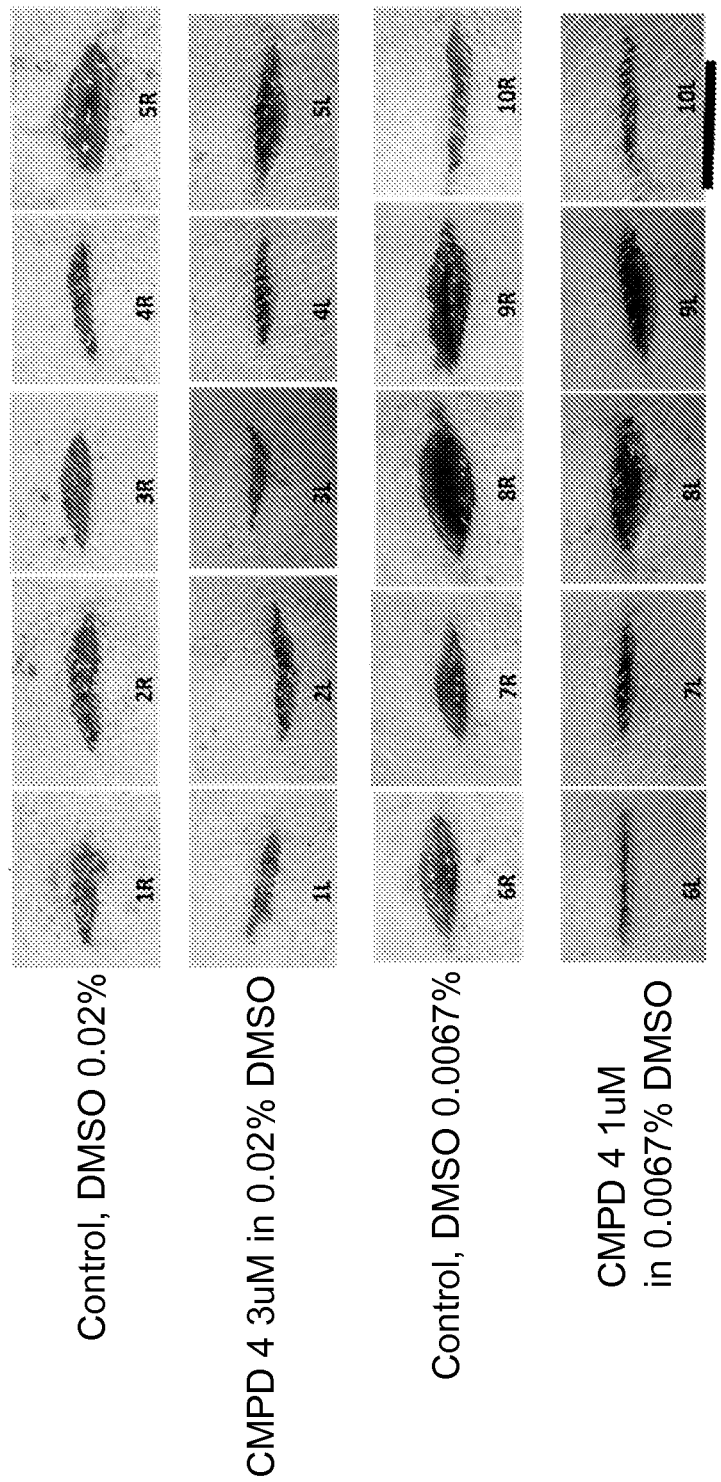
FIG. 9A shows the morphology of wounds treated with DMSO or Compound 4 on Day 5 post-wounding in a pig model (scale bar represents approximately 2.5 cm).

Swelling and secretion are part of excessive inflammatory response that might cause a delay in tissue repair and induce unaesthetic scarring. FIG. 9A depicts that treatment with Compound 4 attenuated the inflammatory response. No abnormal swelling and minimal secretion were observed in the wounds treated with Compound 4. In contrast, high levels of secretion and swelling indicative of an excessive inflammatory response was observed in saline-treated wounds. In wounds treated with Compound 4, 100% of the wounds formed scabs, whereas in saline treated wounds only 20% of wounds displayed scabbing.

On days 12 and 19 post-wounding, wound measurements were taken. Wound length and wound width measurements from day 12 post-wounding are presented in Table 8D. Wound length and wound width measurements as well as scab and swelling observations from day 19 post-wounding are presented in Table 8E. Initial wound measurements were not performed because, following initial skin incision, elliptical wounds are formed within 12-24 hours after wounding and continue to increase in size for at least 3-5 days. From day 5, wound size in the pig model is stabilized. "NA" indicates complete healing. Binary assessment of the scab status was performed: +indicates intact scab, − indicates uneventfully detached scab. Swelling was scored as described above with respect to Table 8C.

TABLE 8D

Wound Measurement Data Day 12 Post-wounding.

| Treatment | Group | Width (mm) | Length (mm) |
|---|---|---|---|
| | Group 1 | | |
| 3 µM CMPD 4 in 0.02% DMSO/H$_2$O | L1 | 1.8 | 9.7 |
| | L2 | 5.3 | 21.7 |
| | L3 | 2.6 | 14.1 |
| | L4 | 5.4 | 18.4 |
| | L5 | 5.8 | 12.6 |
| | Average | 4.18 | 15.3 |
| | SD | 1.6 | 4.3 |
| | Group 2 | | |
| 1 µM CMPD 4 in 0.0067% DMSO/H$_2$O | L1 | 1.8 | 7.16 |
| | L2 | 5.9 | 18.3 |
| | L3 | 10.7 | 20 |
| | L4 | 10.8 | 23.2 |
| | L5 | 3.8 | 16.4 |
| | Average | 6.6 | 17.0 |
| | SD | 3.6 | 5.4 |
| | Group 3 | | |
| Control 0.02% DMSO/H$_2$O | R1 | 5.6 | 18.9 |
| | R2 | 6.9 | 24.4 |
| | R3 | 6.7 | 22.3 |
| | R4 | 4 | 23.5 |
| | R5 | 9.2 | 22.6 |
| | Average | 6.48 | 22.34 |
| | SD | 1.7 | 1.9 |
| | Group 4 | | |
| Control 0.067% DMSO/H$_2$O | R1 | 6.4 | 19.5 |
| | R2 | 9.3 | 22.8 |
| | R3 | 11.2 | 21.8 |
| | R4 | 11.8 | 31.4 |
| | R5 | 5.2 | 24 |
| | Average | 8.78 | 23.9 |
| | SD | 2.6 | 4.03 |

TABLE 8E

Wound Measurement Data Day 19 Post-wounding.

| Wound No. | Wound Width | Wound Length | Scar Width | Scar Length | Scab | Swelling |
|---|---|---|---|---|---|---|
| Controls: DMSO, 0.02%, 0.067% | | | | | | |
| R1 | NA | NA | 2.8 | 20.2 | + | − |
| R2 | 3.1 | 8.07 | — | — | − | − |
| R3 | NA | NA | 1.90 | 17.6 | + | − |
| R4 | NA | NA | 2.76 | 21.2 | + | − |
| R5 | 2.9 | 9.8 | — | — | + | +/− |
| R6 | 3.56 | 6.1 | — | — | + | + |
| R7 | 3.61 | 9.06 | — | — | − | +/− |
| R8 | 5.46 | 12.56 | — | — | + | + |
| R9 | 6.98 | 11.87 | — | — | + | + |
| R10 | NA | NA | 2.80 | 16.26 | + | +/− |
| Average | 4.9 | 9.6 | 2.6 | 18.8 | | |
| SD | 1.42 | 2.56 | 0.17 | 1.81 | | |
| CMPD4: 3 µM, 1 µM | | | | | | |
| L1 | NA | NA | 1.8 | 22.5 | − | − |
| L2 | NA | NA | 2.3 | 22 | − | − |
| L3 | NA | NA | 1.15 | 21 | − | − |
| L4 | NA | NA | 1.9 | 18 | − | − |
| L5 | NA | NA | 3.5 | 21 | − | − |
| L6 | NA | NA | 1.8 | 17.2 | + | − |
| L7 | NA | NA | 3.6 | 17.8 | + | +/− |
| L8 | 5.5 | 7.6 | — | — | − | + |
| L9 | 5.1 | 8.4 | — | — | − | +/− |
| L10 | NA | NA | 2.0 | 21.2 | + | − |
| Average | 5.3 | 8.0 | 2.5 | 18.7 | | |
| SD | 0.2 | 0.4 | 0.8 | 1.8 | | |

Table 8E shows that 60% of the control wounds exhibited swelling at the wound area on day 19 post-wounding, while only 30% of the Compound 4-treated wounds exhibited swelling at the wound area on day 19 post-wounding.

Figure 9B:
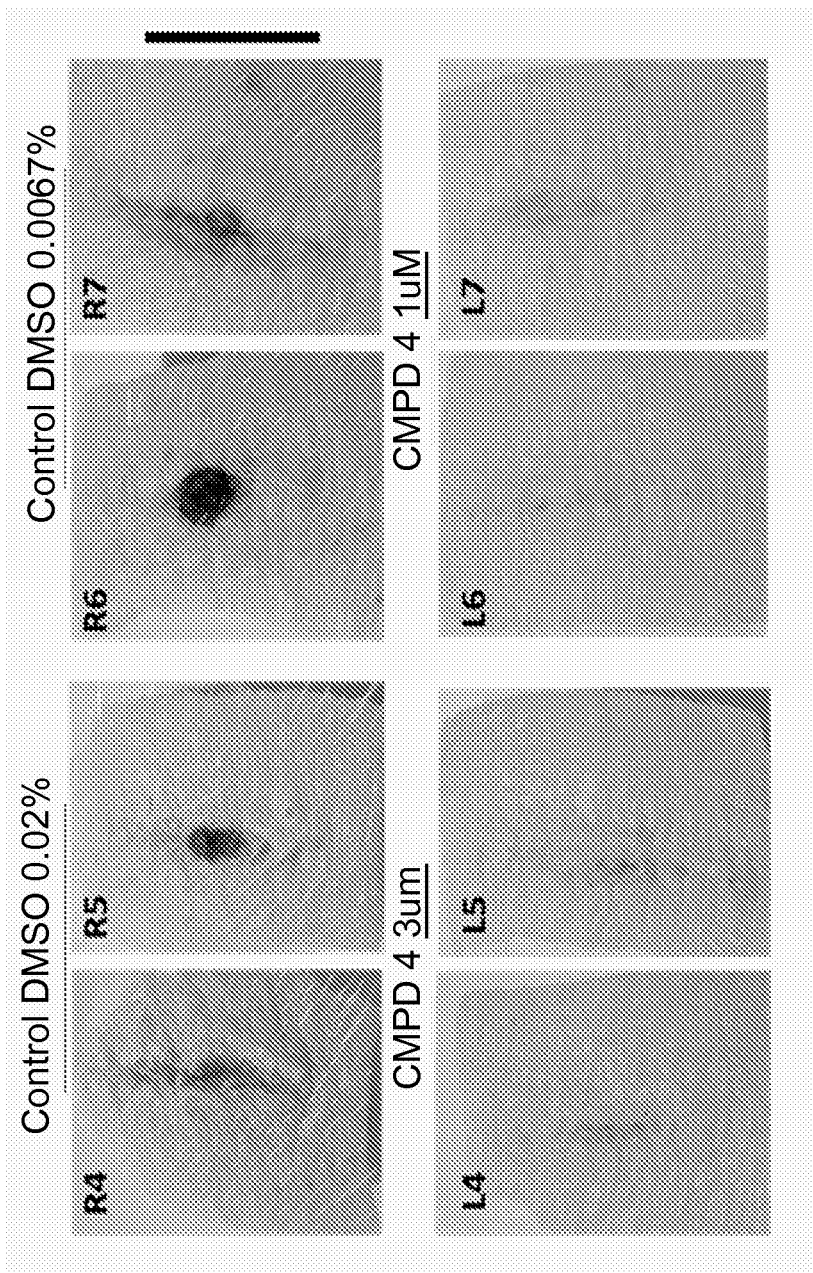
FIG. 9B shows the aesthetics of selected wounds treated with DMSO or Compound 4 on Day 19 post-wounding in a pig model.

On day 19 post-wounding, wound areas were harvested together with healthy skin areas near the wound, and were fixed and subjected to morphological assessment. Wound photo-documentation was performed using macro resolution of digital camera FinePix S700. The results of the photo-documentation are depicted in FIG. 9B.

Figure 9C:
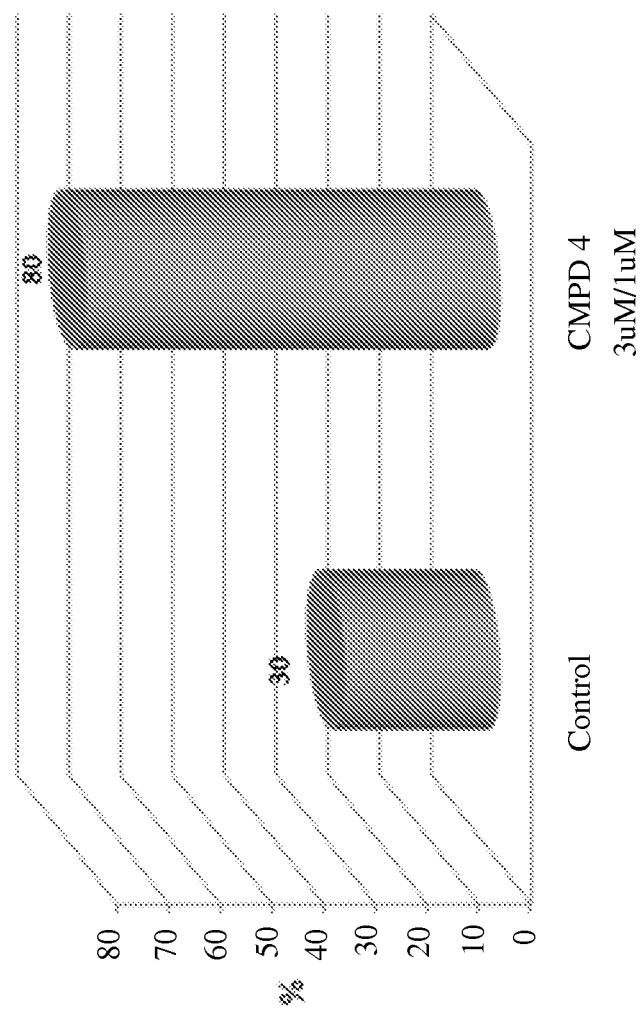
FIG. 9C is a bar graph, and shows the percentage of control and Compound 4-treated wounds that exhibited complete closure by day 19 post-wounding in a pig model.

On day 19 post-wounding, morphological assessment of complete wound closure was performed. Wounds were considered completely closed when scab was detached and when scab detachment process did not cause damage to the newly formed epidermis. Closed wounds were counted and presented as a percentage of total wounds per group. All wounds in control groups, DMSO 0.02% and DMSO 0.0067%, and all wounds in treated groups, 3 µM Compound 4 and 1 µM Compound 4, were combined and assessed together as control and treated. The data are presented in FIG. 9C.

Figure 9D:
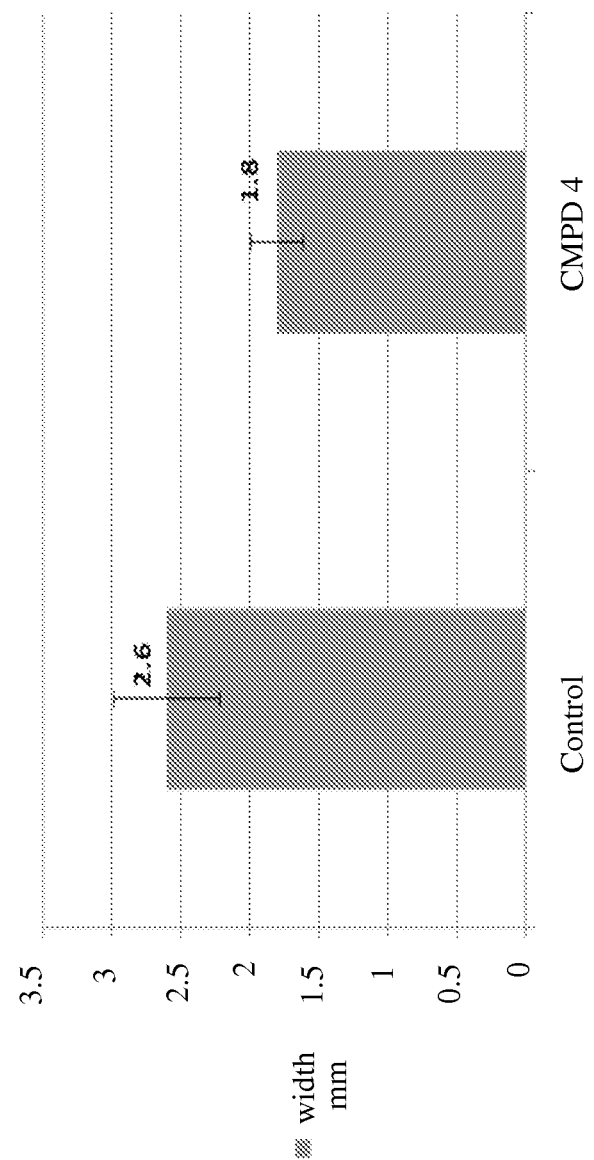
FIG. 9D is a bar graph, and shows scar width of control and Compound 4-treated wounds on day 19 post-wounding in a pig model.
Figure 9E:
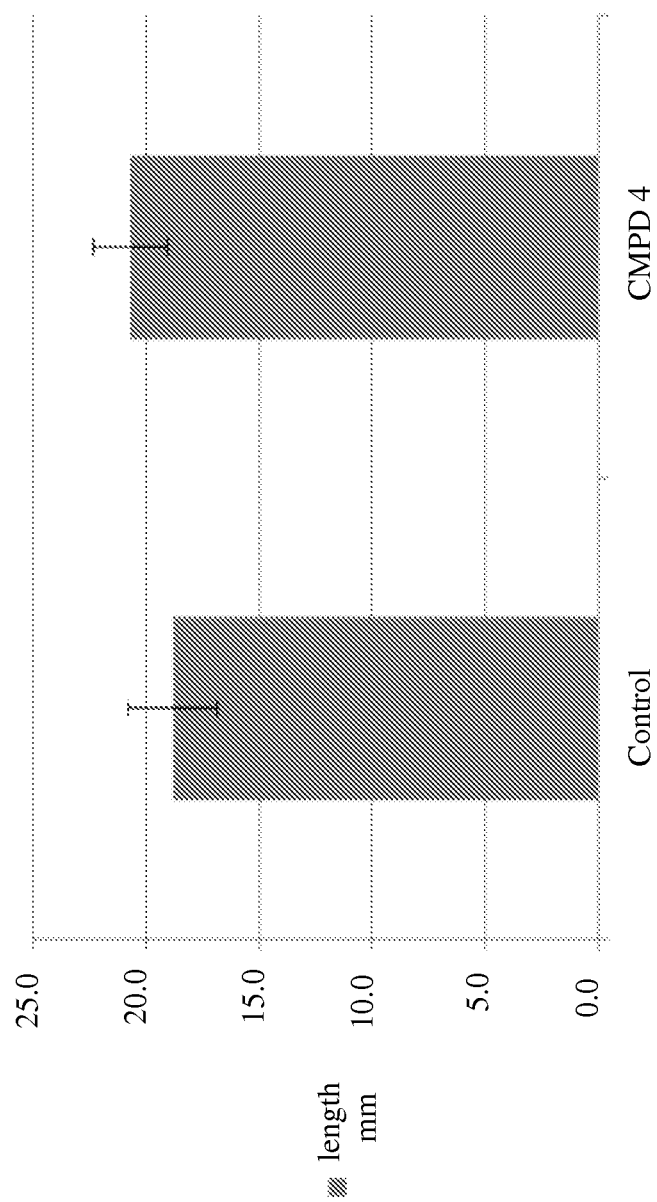
FIG. 9E is a bar graph, and shows scar length of control and Compound 4-treated wounds on day 19 post-wounding in a pig model.
Figure 10A:
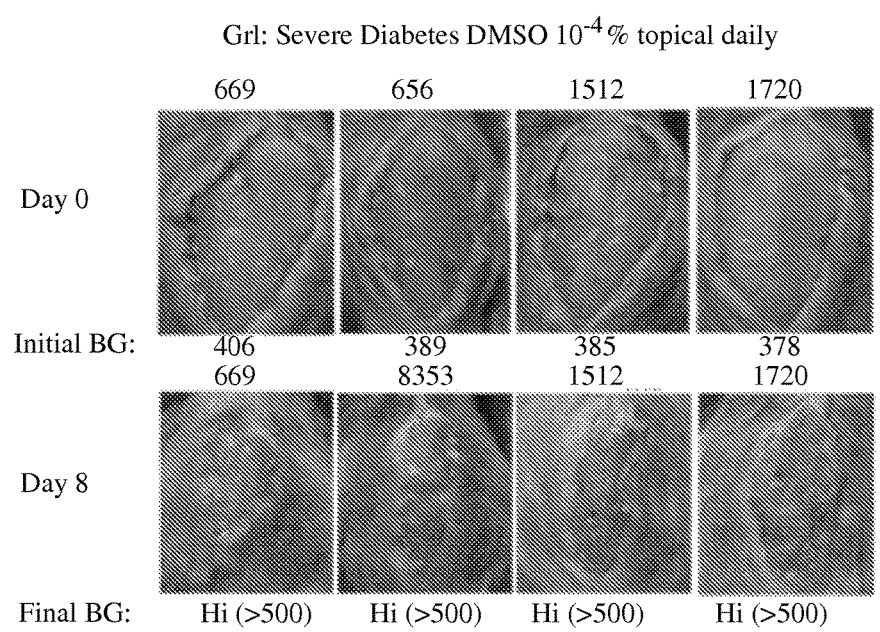
FIG. 10A are images of wounds in mice with severe diabetes treated with DMSO or Compound 4 taken on Day 0 and Day 8 post-wounding (scale bar represents 1 cm).
Figure 10A:
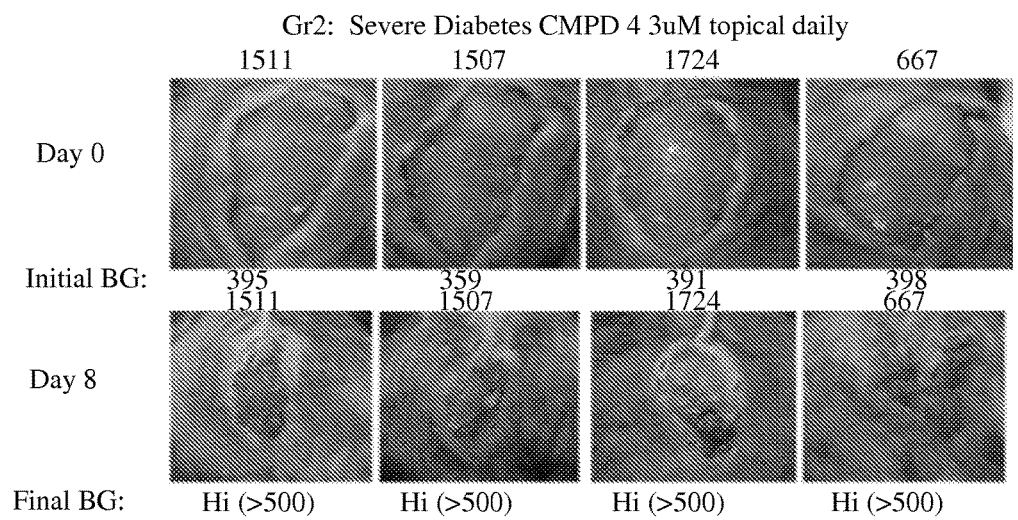
Figure 10B:
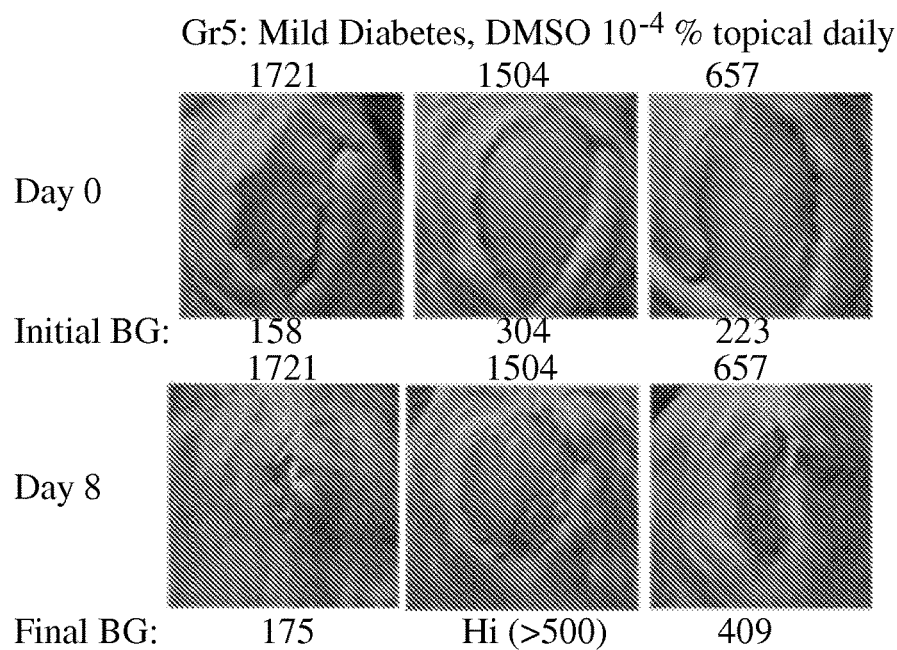
FIG. 10B are images of wounds in mice with moderate diabetes treated with DMSO or Compound 4 taken on Day 0 and Day 8 post-wounding (scale bar represents 1 cm).
Figure 10B:
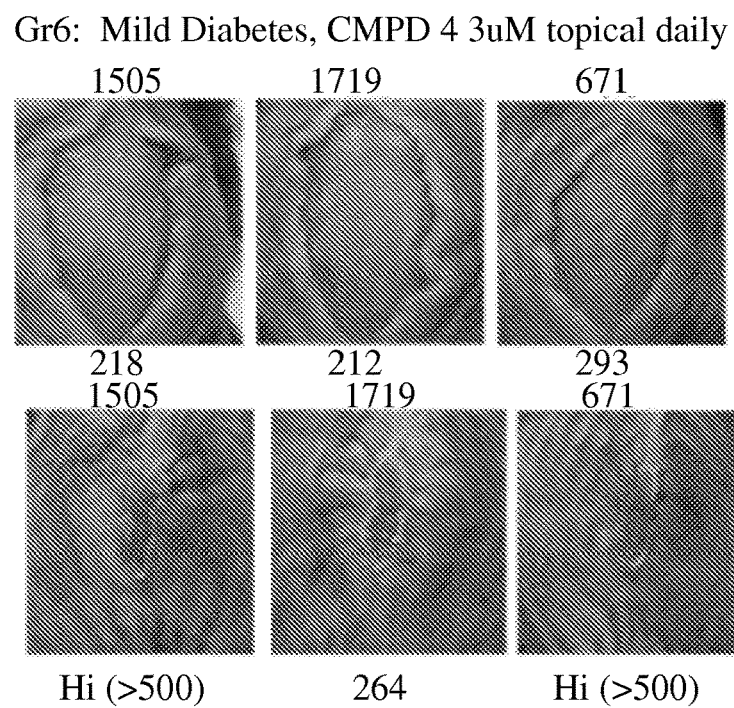

Scar size was also assessed on day 19 post-wounding. For wounds that morphologically exhibited complete healing (including scab detachment), scar size was measured. Since assessment in pig wound healing model has to be paired, only those wound pairs that displayed complete healing with both control and treated wounds are presented in the graph. All wounds in control groups, DMSO 0.02% and DMSO 0.0067%, and all wounds in treated groups, 3 µM Compound 4 and 1 µM Compound 4, were combined and assessed together as control and treated. The data are presented in FIG. 9D and FIG. 9E. 4 treated and 4 control wounds. N=8 wounds, 4 wound pairs.

A histological assessment was also made on day 19 post-wounding. A summary of the histological assessment is presented in Table 8F. Wounds were scored according to the wound healing histological index. The healing of dermis was considered advanced when both edges were observed in the same microscope field (100×). Inflammation was scored as mild (+), moderate (++) or severe (+++). Only severe inflammation was considered negative. Adhesions were scored as none, mild, moderate and severe. Only severe and moderate adhesions were considered negative.

TABLE 8F

Histological Assessment of Wounds Day 19 Post-wounding.

| Wound No. | Treatment | Epidermal Closure | Epidermal Migration | Dermal Closure | Granulation Tissue | Inflammation | Adhesion |
|---|---|---|---|---|---|---|---|
| L1 | CMPD 4 | + | + | + | + | − | − |
| L2 | 3 µM in | + | + | + | + | − | − |
| L3 | DMSO | + | + | + | + | + | − |
| L4 | topical | + | + | + | + | + | − |
| L5 | daily | + | + | + | + | ++ | + |
| L6 | CMPD 4 | + | + | + | + | ++ | − |
| L7 | 1 µM in | + | + | + | + | ++ | + |
| L8 | DMSO, | + | + | − | + | ++ | + |
| L9 | topical daily | +/− reopened | + | − | + | +++ | + |
| L10 |  | + | + | + | + | + | − |
| R1 | Control | + | + | + | + | − | − |
| R2 | DMSO | + | + | + | + | + | − |
| R3 | (topical | + | + | + | + | + | − |
| R4 | daily) | + | + | + | + | + | + |
| R5 |  | + | + | − | + | +++ | + |
| R6 |  | + | + | − | + | +++ | ++ |
| R7 |  | + | + | − | −/+ | +++ | +++ |
| R8 |  | + | + | − | + | ++ | ++ |
| R9 |  | + | + | − | + | +++ | + |
| R10 |  | +/− reopened | + | + | + | + | + |

Table 8F shows that 40% of the control wounds exhibited severe inflammation at the wound area on day 19 post-wounding, while only 10% of the Compound 4-treated wounds exhibited severe inflammation at the wound area on day 19 post-wounding. In addition, only 50% of the control wounds exhibited dermal healing at day 19 post-wounding, whereas 80% of the Compound 4-treated wounds exhibited dermal healing at day 19 post-wounding. 70% of control wounds displayed an adhesion of any type and 30% of control wounds displayed a moderate or severe adhesion at day 19 post-wounding, while just 40% of Compound 4-treated wounds displayed an adhesion of any type and 0% of Compound 4-treated wounds displayed a moderate or severe adhesion at day 19 post-wounding.

Compound 4 accelerated wound healing in a dose- and time-dependent manner. Compound 4 decreased the size of wounds during the inflammation phase by decreasing early excessive inflammation, promoting clot formation, and stimulating epidermal migration. Compound 4 increased epidermal closure, dermal closure and granulation maturation during the proliferation phase, while preserving the physiological properties of the tissue relative to control. Treatment with Compound 4 induced timely scab detachment with reduced scar formation, normal adhesion and granulation maturation in the wound bed during the remodeling phase. All animals that participated in the experiment tolerated the treatment well, showing no significant change in weight, and experienced normal ingestion and habitus. No adverse events were observed during the experimental phase.

EXAMPLE 12

Evaluation of the Effects of Topical Administration of Compound 4 on Skin Wound Healing in Diabetic Mice For the purposes of this example, and its associated figures, Compound 4 refers to Compound C-3 (from Table 1C) in dimethylsulfoxide (DMSO) (e.g., 0.1%, 0.02%, 0.0067% DMSO in water).

The effects of topically applied Compound 4 were evaluated on skin wound healing in chemically induced streptozotocin (STZ) diabetic mice using a longitudinal full thickness skin incision wound model. Prior to induction of the experiment, 10-11 mice per group (total 31 mice) were injected with three concentrations of STZ (200, 180 and 160 mg/kg body weight per day) to induce hyperglycemia. On day 6 post-STZ injection, there were enough animals with severe diabetes (blood glucose 350-500 mg/dl and polyuria) to form experimental groups for the pilot wound healing study. Animals with severe diabetes exhibited increased weight loss and thin skin without normal subcutaneous fat tissue. On day 7 following STZ injection, the surviving mice were randomized and introduced into the wound healing study. Experimental groups were randomized according to the severity of hyperglycemia (mild: 160-220 mg/dl glucose; severe: 350-500**mg/dl glucose), and subjected to the wounding procedure. Mice that were resistant to STZ (non-diabetic by day 6 post-injection) were subjected to wounding as well and considered as a reference group. Approximately 20 mm±3 mm longitudinal skin incisions were performed using a scalpel blade on the backs (parallel to backbone) of mice anesthetized with isoflurane. The duration of the wound healing phase was 8 days. Longitudinal skin incisions were treated daily with either 0.2 mL of 3 µM Compound 4 in 0.0001 w/v DMSO or vehicle alone in accordance with the study groups outlined in Table 9A. Wound healing parameters were then monitored. At the end of the experiment, 8 days post-wounding, the mice were sacrificed, wound widths were measured, pictures were taken and biopsies of the wound area were collected and subjected to histological analysis.

TABLE 9A

Study Groups.

| Group | Description | Number of Mice | Test Article | Dose | Route of Administration | Schedule |
|---|---|---|---|---|---|---|
| 1 | Severe Diabetes Blood Glucose >350 mg/dl | 8 | 0.0001 w/v DMSO in water | 0.2 mL | Topical | Daily |
| 2 | Severe Diabetes Blood Glucose >350 mg/dl | 9 | Compound 4 in vehicle | 3 μM in 0.2 mL | Topical | Daily |
| 3 | Mild Diabetes Blood Glucose 160-220 mg/dl | 3 | 0.0001 w/v DMSO in water | 0.2 mL | Topical | Daily |
| 4 | Mild Diabetes Blood Glucose 160-220 mg/dl | 3 | Compound 4 in vehicle | 3 μM in 0.2 mL | Topical | Daily |
| 5 | Non-diabetic Blood Glucose <160 mg/dl | 3 | Compound 4 in vehicle | 3 μM in 0.2 mL | Topical | Daily |
| 6 | Non-diabetic Blood Glucose <160 mg/dl | 3 | 0.0001 w/v DMSO in water | 0.2 mL | Topical | Daily |

Epidermal closure was considered complete when newly formed epidermis covered the entire wound area. Wounds were considered to have advanced epidermal migration toward sealing of the wound gap, when both epidermal edges were observed in ×100 magnification field of microscope. General epidermal migratory potential was considered positive (+) when newly formed epidermal edges displayed proper directed migration, even if the migration was just starting. Migratory epidermal edges in the group were counted and presented as a percentage of the total number of epidermal edges (twice the number of wounds in the group). In wounds that exhibited complete epidermal closure, both epidermal edges were considered migratory (+/+).

Non-migratory and hyperplastic epidermal edges in the group were counted and presented as a percentage of the total number of epidermal edges. When the epidermal edge appeared thicker than the normal epidermis at healthy skin areas and when such an epidermal edge did not exhibit migration toward sealing the wound gap, it was considered hyperplastic and non-migratory.

Dermal closure was assessed by examining the eosin stained healthy dermis and newly formed dermal edges at the wound gap. Wounds with both dermal edges visible at ×100 magnification field of the microscope (×10 lens) were considered to be at an advanced stage of dermal healing (indicated as +); wounds in which both dermal edges were visible at ×40 magnification field (×4 lens) (BX41 Olympus or Axiovert 25, Zeiss) were considered to be at a less advanced stage (indicated as (−(×4))). If the wound was too wide that it was impossible to see both dermal edges or the same field at ×40 magnification, the wound was considered as having negative dermal closure (−). The number of wounds with advanced dermal closure (+) was presented as a percentage of the total wounds in the experimental group.

Areas with granulation tissue at the wound gap were documented and presented as a percentage of the total wound gap area. When more than 40% of the wound gap displayed granulation tissue, a wound was considered positive for this parameter. The results are calculated as a percentage of the total wounds per group.

Inflammation was considered as severe/excessive when all four parameters were observed as following: 1) high abundance of white blood cells (WBC) at the wound gap (greater than 200 cells in the ×100 field); 2) a high ratio WBC/red blood cell (RBC) in the blood vessels; 3) a high abundance of WBC near blood vessels and within the endothelial wall of blood vessels (tissue infiltration); and 4) abscesses at different stages of formation at the wound area.

Adhesions at the wound gap were scored when the wound gap exhibited other tissue such as skeletal muscles or extensive lymphoid tissues instead of granulation tissue. Adhesions were scored in accordance with a mild (+), moderate (++) and severe (+++) scale. N=14. The data is summarized as the number of assessed events per group and as a percentage out of the total number of wounds in the group that meet each wound healing assessment parameter.

Overall, Compound 4 at a dosage of 3 μM induced healing of the epidermis by affecting several critical healing parameters. The results of the histological assessment of wounds in mice with severe diabetes (blood glucose greater than 350 mg/dl, defined as severe diabetes in terms of wound healing impairment) are summarized in Table 9B. At the end of the treatment phase (on day 8 post-wounding), mice were sacrificed and the wounds as well as the surrounding skin areas were harvested. Histological sections were prepared and tissue specimens stained with hematoxylin and eosin (H & E) stain. Assessment of wound healing status was performed.

TABLE 9B

Histological Assessment in Mice with Severe Diabetes.
EXP # 004 - Histological Assesment According to Initial Study Groups

| N° | Treatment | # Mouse | BG mg/% | Epidermis Closure | Epidermis Migration | Epidermis Hyperplasia | Dermis Closure | Wound Gap % Granulation | Wound Gap Inflammation | Adhesion Muscle | Adhesion Lymphoid |
|---|---|---|---|---|---|---|---|---|---|---|---|
| 1 | Severe | 669 | 500 | − | +/− | +/− | −(×4) | <40 | severe | + | − |
| 2 | Diabetes | 656 | 500 | − | −/− | +/+ | −(×4) | <40 | severe | + | − |
| 3 | Control | 1512 | 500 | − | −/+ | +/+ | −(×4) | <40 | severe | + | − |

TABLE 9B-continued

Histological Assessment in Mice with Severe Diabetes.
EXP # 004 - Histological Assesment According to Initial Study Groups

| N° | Treatment | # Mouse | BG mg/% | Epidermis Closure | Migration | Hyperplasia | Dermis Closure | % Granulation | Inflammation | Adhesion Muscle | Lymphoid |
|---|---|---|---|---|---|---|---|---|---|---|---|
| 4 | | 1720 | 500 | + | −/− | +/+ | − | <40 | moderate | + | − |
| 5 | | 1504 | 500 | − | −/− | +/+ | − | <40 | severe | ++ | − |
| 6 | | 657 | 409 | − | −/− | +/+ | −(x4) | <40 | severe | + | − |
| | # of events per group | | | 0 | 2 | 11 | 0 | 0 | 5 | 0 | 0 |
| | % of total per group | | | 0% | 17% | 92% | 0% | 0% | 83% | | |
| 1 | Severe | 1511 | 500 | − | −/− | +/+ | −(x4) | <40 | severe | + | − |
| 2 | Diabetes | 1507 | 500 | −(x10) | +/− | +/− | −(x4) | <40 | moderate | + | − |
| 3 | CMPD 4 | 1724 | 500 | − | −/− | +/+ | −(x4) | <40 | severe | ++ | − |
| 4 | 3 µM | 667 | 500 | − | −/+ | +/− | −(x4) | 40> | severe | ++ | − |
| 5 | | 1709 | 364 | + | +/+ | +/+ | + | 40> | severe | + | − |
| 6 | | 1517 | 490 | + | +/+ | +/+ | + | 40> | severe | + | − |
| 7 | | 1505 | 500 | −(x10) | +/+ | +/− | −(x4) | <40 | mild | + | − |
| 8 | | 671 | 500 | −(x10) | −/+ | +/− | −(x4) | 40> | severe | − | − |
| | # of events per group | | | 2 | 10 | 12 | 2 | 4 | 6 | 0 | 0 |
| | % of total per group | | | 25% | 63% | 75% | 25% | 50% | 75% | | |

Complete epidermal closure (+) was achieved in 25% of Compound 4-treated wounds and an additional 37% of Compound 4-treated wounds displayed progress toward epidermal closure. In three out of eight wounds, the epidermis was observed in the fixed field of the microscope when using ×100 magnification. In the control group, no epidermal closure and no progress towards epidermal closure was detected.

Epidermal migration, including initiation of epidermal migration, was observed in 63% of Compound 4-treated wounds compared to only 17% of the vehicle-treated wounds.

Newly formed epidermal edges were hyperplastic in 75% of the Compound 4-treated wounds compared to 92% in control wounds. In the Compound 4-treated groups, some edges of the epidermis were hyperplastic but still displayed migratory potential (observed as properly directed migration towards sealing of the wound gap). In comparison to the Compound 4-treated group, the control group showed increased hyperplasia, which resulted in a decreased migratory potential compared to Compound 4-treated wounds.

For animals in the Compound 4-treated group, 25% of wounds displayed advanced dermal closure (+) and 75% of the wounds displayed some dermal healing capacity (both edges of dermis were observed at ×40 magnification). In contrast, there were no wounds in the vehicle control group with advanced dermal closure. Moreover, 33% of the control wounds were exceptionally wide (−) with no signs of dermal healing and only 67% displayed some dermal healing capacity (−(×4) magnification).

All wounds displayed reduced healing capacity at the wound gap. However, excessive inflammation was attenuated in the Compound 4-treated wounds (75% compared to 83% in the vehicle controls). More stable granulation tissue was detected at the wound gap of Compound 4-treated animals; in 50% of the wounds, more than 40% of early granulation tissue was formed. In the control group, not a single animal was able to form up to 40% of granulation tissue.

Photo-documentation of the wounds was performed on day 0 and day 8 post-wounding in diabetic C57BL mice using a digital camera (FinePix S700). The results of the photo-documentation are shown in FIGS. 11A-11D. Scale bar=1 cm. Experimental groups are presented in accordance with the severity of hyperglycemia, Initial Blood Glucose (BG), taken on the day of photo-docuementation. N=14.

EXAMPLE 13

Treatment of Wounds with Compound 4 in a Hydrogel Formulation in a Preclinical Ischemic Wound Porcine Model For the purposes of this example, and its associated figures, Compound 4 refers to Compound C-3 (from Table 1C) in dimethylsulfoxide (DMSO) (e.g., 0.1%, 0.02%, 0.0067% DMSO in water).

The efficacy of Compound 4 in a hydrogel formulation was measured on wound outcomes in a preclinical ischemic wound porcine model. This model mimics chronic diabetic ulcers. Upon arrival, two 75-pound domestic white pigs were allowed to acclimate for several days prior to the initiation of the study. Prior to surgery, the dorsal region of the pigs was shaved and the skin was surgically prepared with alternating BETADINE® and alcohol scrubs. The pigs were anesthetized using 2.5 mL telazol intramuscularly and maintained with isoflurane during the length of the procedure. The animals were fully monitored during the entire length of the procedure. Bipedicle skin flaps were created using parallel incisions measuring 15×5 cm. The dermal flap was elevated from the underlying subcutaneous tissue and pre-sized (for the incision length) medical grade sterilized 0.01-inch-thick silicon sheets were placed underneath the flap to prevent re-adherence and reperfusion of the flap from the underlying tissue. The skin flap incisions and silicon sheet were sutured into position using 3-O Ethilon continuous sutures. Ischemia of the flap tissue was verified by laser Doppler imaging of blood flow. Once the bipedical skin flaps were completed, a full thickness excision wound was created in the middle of each flap using a 12 mm disposable biopsy punch. The flap incisions were dressed with a surgical grade VAC drape and VeTrap and Elastikon adhesive wrapping, which covered the entire flap, except the area of the 12 mm biopsy wound. Pigs were treated with Compound 4 either daily or biweekly at a dosage of 3 µM or 10 µM in a 2% thermal hydrogel that gelled upon contact with the pig's body. The first treatment application was slowly dispersed onto the wound. Subsequent treatments were applied by injecting the drug into the hydrogel plug. In addition, there were a series of 6 injections (50 μL/injection) with Compound 4 in vehicle directly into the surrounding tissues to look for signs of necrosis. No signs of necrosis were observed. The total concentration of Compound 4 used for all treatments was either 3 μM or 10 μM. All wounds on the right side of the animal were treated with Compound 4 and wounds on the left side were treated with vehicle controls in hydrogel. Each pair of wounds was located at the same distance from the dorsum midline. The dressing was changed every 3 days, and any accumulating wound fluid was drained. The ischemic wounds were digitally imaged for collection of wound closure data. During designated time points, the entire wound tissue was harvested for tissue analyses (histological). After the completion of the experiments, the pigs were euthanized and full thickness wound-edge tissue end biopsies were collected using a 16 mm sterile biopsy punch for histological analyses.

Figure 11A:
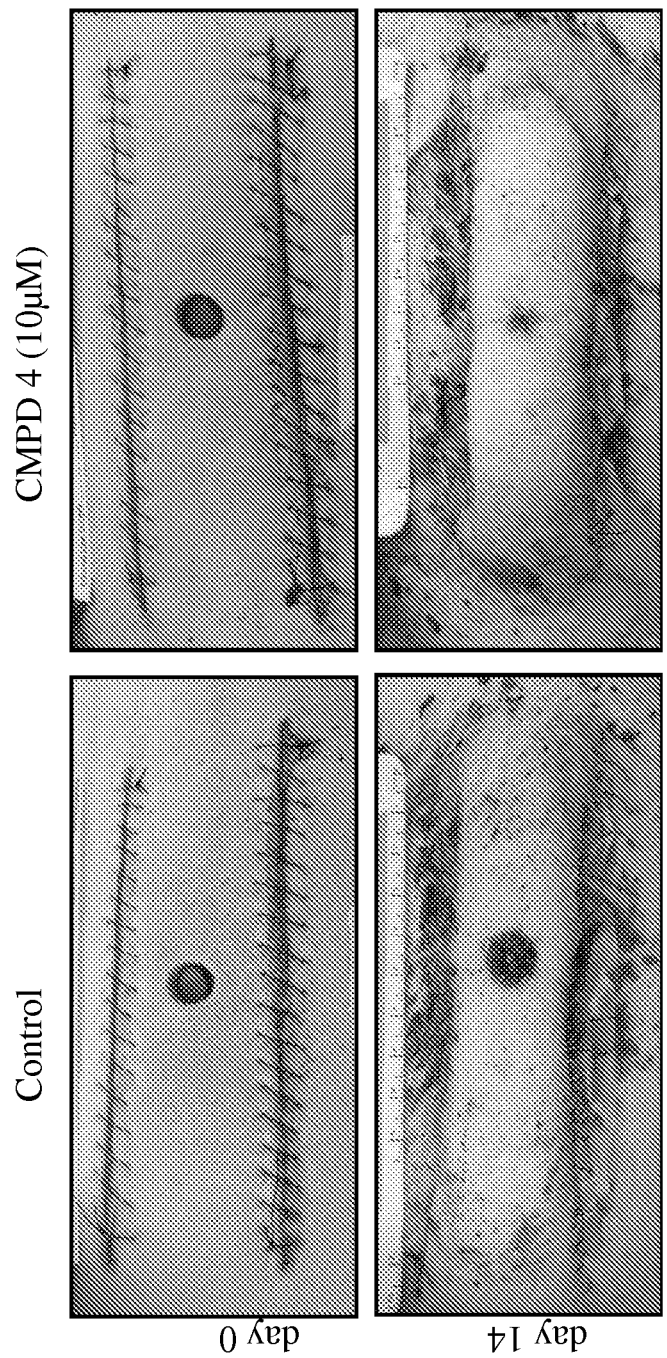
FIG. 11A are images of wounds in a pig treated biweekly with vehicle control or with 10 μM Compound 4.
Figure 11B:
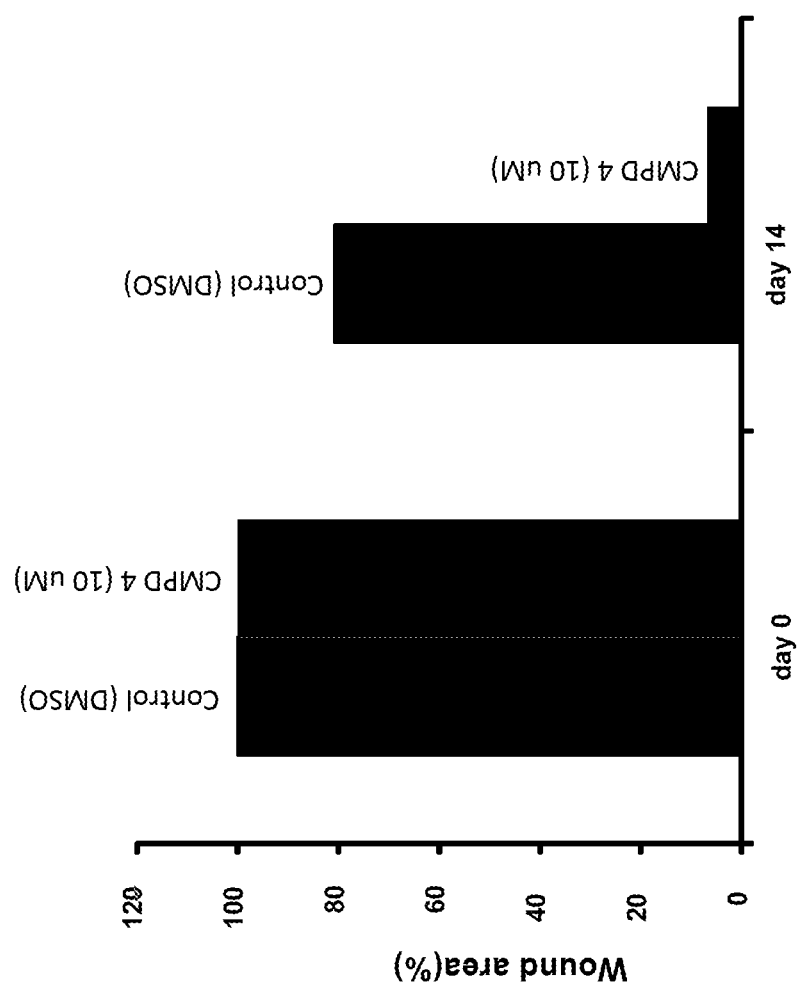
FIG. 11B is a bar graph of wound area (as a percentage of control) at day 0 and day 14 post-wounding, and shows the wound area of a wound in a pig treated biweekly with vehicle control or with 10 μM Compound 4, as calculated by surface plenimetry.

FIG. 11A are digital images of a control wound and a wound treated with Compound 4 at 10 μM biweekly for 14 days on day 0 and day 14 post-wounding. Wounds were photographed using a Cannon S110 digital camera with electro-focus and 5.2-26.0 mm lens. A ruler was captured in the photographs near the wound border for scale adjustments. The photos were uploaded in Image J software to calculate the wound area. The ruler photographed on the image was used to calibrate scale then freehand tracing around the wound was performed. Based on surface plenimetry, the area of the Compound 4-treated wound was smaller compared to the area of the vehicle-treated wound at Day 14. The calculated surface wound area and volume was less in the Compound 4-treated wound compared to the control wound. The calculated areas for the control wound and the Compound 4-treated wound on day 0 and day 14 are graphed in FIG. 11B.

Laser Speckle Perfusion Imaging (LSI) is a tissue perfusion mapping technique based on the principle of speckle patterns of light formed when laser light passes through the moving blood particle into the blood stream. The vessel region is blurred because of motion and creates a contrast between the vessel and outer tissue. The blurred microvessels are color-coded to generate perfusion maps. Perfusion maps were acquired on all time points of wounds treated with vehicle or 10 μM Compound 4, and average perfusion calculations were performed during post-processing using PimSoft v1.4 software. The wound edge and wound bed tissue regions that were chosen as regions of interest (ROI) and time of interest (TOI) were selected from the real time graphs. Mean and standard deviation of perfusion data were obtained from the selected TOI perfusion data.

Figure 12A:
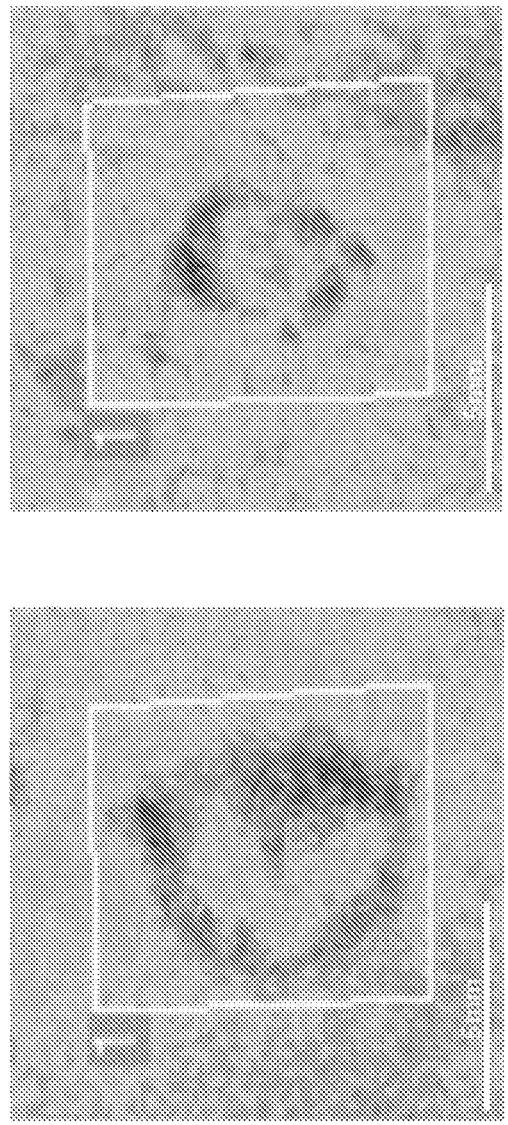
FIG. 12A are images obtained from laser speckle perfusion imaging (LSI) of wounds in a pig treated biweekly with vehicle control or with 10 μM Compound 4 (scale bar represents 5 mm).
Figure 12B:
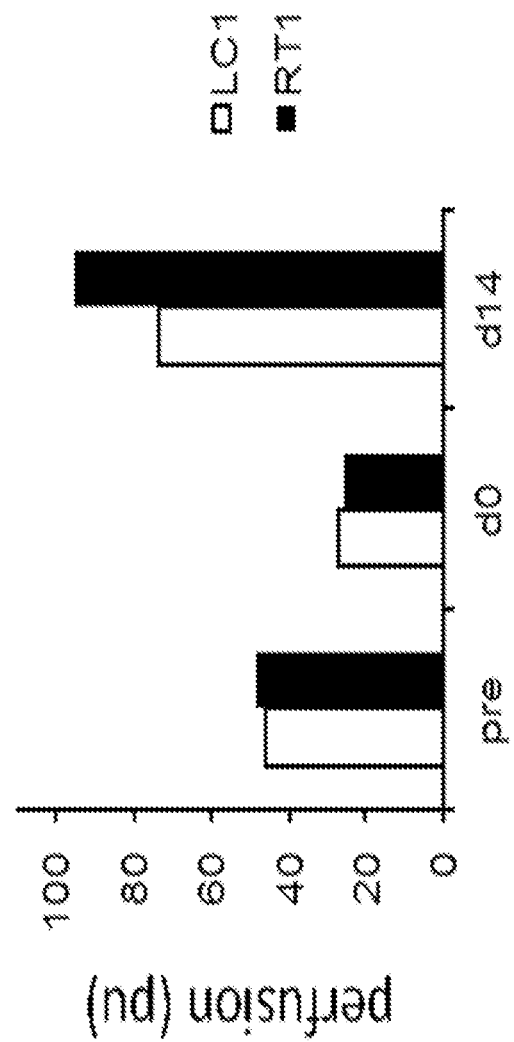
FIG. 12B is a bar graph of perfusion pre-wounding (pre) and at Day 0 (d0) and Day 14 (d14) post-wounding in wounds in a pig treated biweekly with vehicle control (LC1) or 10 μM Compound 4 (RT1), and shows a higher perfusion level in Compound 4-treated wounds compared to vehicle control-treated wounds at Day 14 post-wounding.

FIG. 12A shows the results of LSI. FIG. 12B is a bar graph, and shows the calculated perfusion for vehicle control (LC1) and Compound 4-treated wounds (RT1) pre-wounding and on Day 0 and Day 14 post-wounding. Comparison of Day 14 laser speckle flowmetry shows larger wound perimeters for vehicle control compared to Compound 4-treated wounds. Standardized quantification of blood flow shows higher perfusion level in Compound 4 treated wounds compared to vehicle control wounds on Day 14, indicating a more advanced stage of healing.

Figure 13:
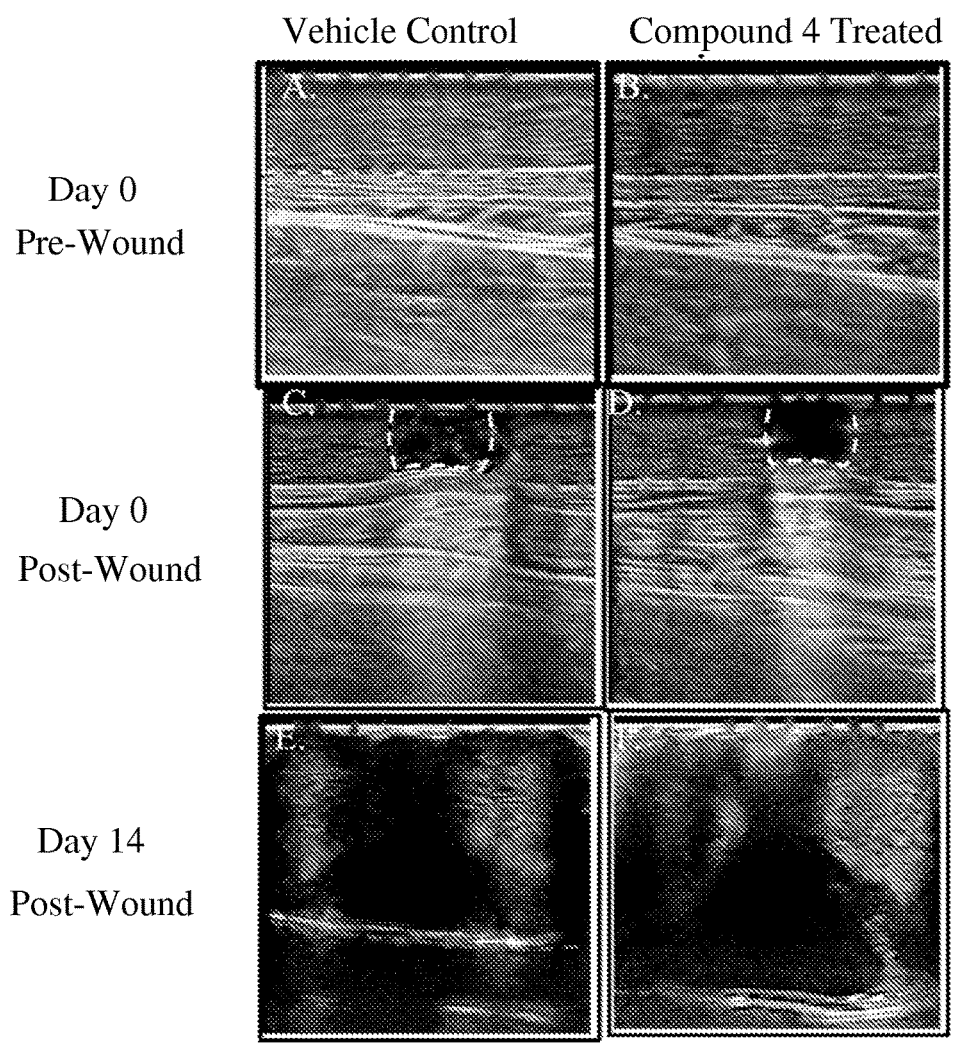
FIG. 13 is images obtained from B-mode ultrasound imaging of wounds in a pig treated biweekly with vehicle control or 10 μM Compound 4 pre-wounding and on Day 0 and Day 14 post-wounding.

B-mode ultrasound imaging of wound depth was performed on wounds treated biweekly with Compound 4 at 10 μM on Day 0, pre-wounding and post-wounding and Day 14 post wounding. The results of B-mode ultrasound imaging are depicted in FIG. 13. Briefly, noblus video-clips of the whole axial wound scan were recorded using linear array probe of frequency ranging from 13-18 MHz. Ultrasound conducting gel was used to obtain quality images using B-mode. Before recording videos, the tissue harmonic imaging mode was turned on and the gain and focus were adjusted to adjust image quality. Once the image quality was optimized, the video was recorded while gently sliding the probe head across the wound surface with enough gel contact. From the video recorded, central time frames were chosen to measure the wound depth. Normal skin images were used to measure baseline skin thickness. The skin-adipose border layer was observed brightest in the image. This border was used as an anatomical landmark to measure the wound depth and skin thickness. Ultrasound imaging reveals the structure of resting skin. The horizontal dashed line marks the end of skin thickness, measured as 7 mm in depth in the day 0 pre-wound images. Ultrasound imaging depicting the lack of skin tissue at the wound site is denoted by the vertical white dashed line in the Day 0 post-wounding images. The horizontal dashed line below the wound marks upward bulging of subcutaneous tissue. Day 14 ultrasound imaging revealed more efficient healing across the thickness of the skin for Compound 4-treated wounds compared to vehicle-treated wounds. The lowering of the horizontal dashed line below the wound in the Compound 4-treated wound in the Day 14 post-wounding image may be caused by pressure generated by the healing tissue.

Figure 14:
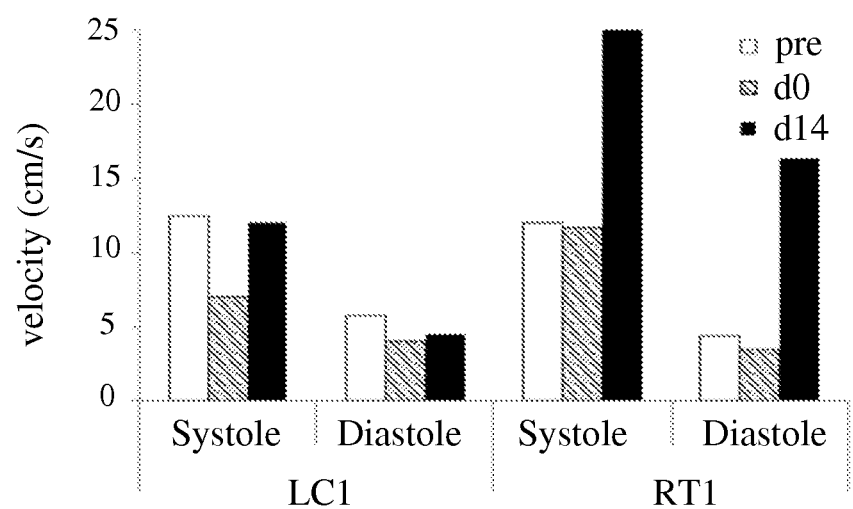
FIG. 14 is a bar graph of systole and diastole velocity (cm/s) of pulse flow through blood vessels feeding wounded tissue treated biweekly with vehicle control (LC1) or 10 μM Compound 4 (RT1) pre-wounding (pre) and at Day 0 (d0) and Day 14 (d14) post-wounding.

Doppler velocity measurements of blood vessels feeding the wounded tissue in wounds treated biweekly with 10 μM Compound 4 were also made. Pulse wave color Doppler allows for the capture of blood velocity profiles from color flow images. Sample volume selector was placed on the blood vessels obtained on the color flow video to record real-time velocity profiles. Post-acquisition, the velocity of the blood flow at systole (profile peaks) and diastole (profile troughs) were measured from these velocity profiles. Vessel diameters were measured first as an identifier of similar blood vessels in the desired area for all time points to be consistent with measuring similar blood vessels. Three peaks and troughs were chosen to measure velocity from which mean and standard deviation were calculated. The difference between the diastole and systole represents the pulse flow velocity. Both vehicle- and Compound 4-treated frames at the pre-wounding time point look comparable. On day 14, pulse velocity, a marker of blood vessel function, is higher in the Compound 4-treated frames than in the vehicle control. These results indicate a more advanced blood vessel function in treated wounds compared to untreated controls. The results of the Doppler velocity measurements are graphed in FIG. 14. LC1: Vehicle Control, RT1: Compound 4, 10 μM.

Figure 15:
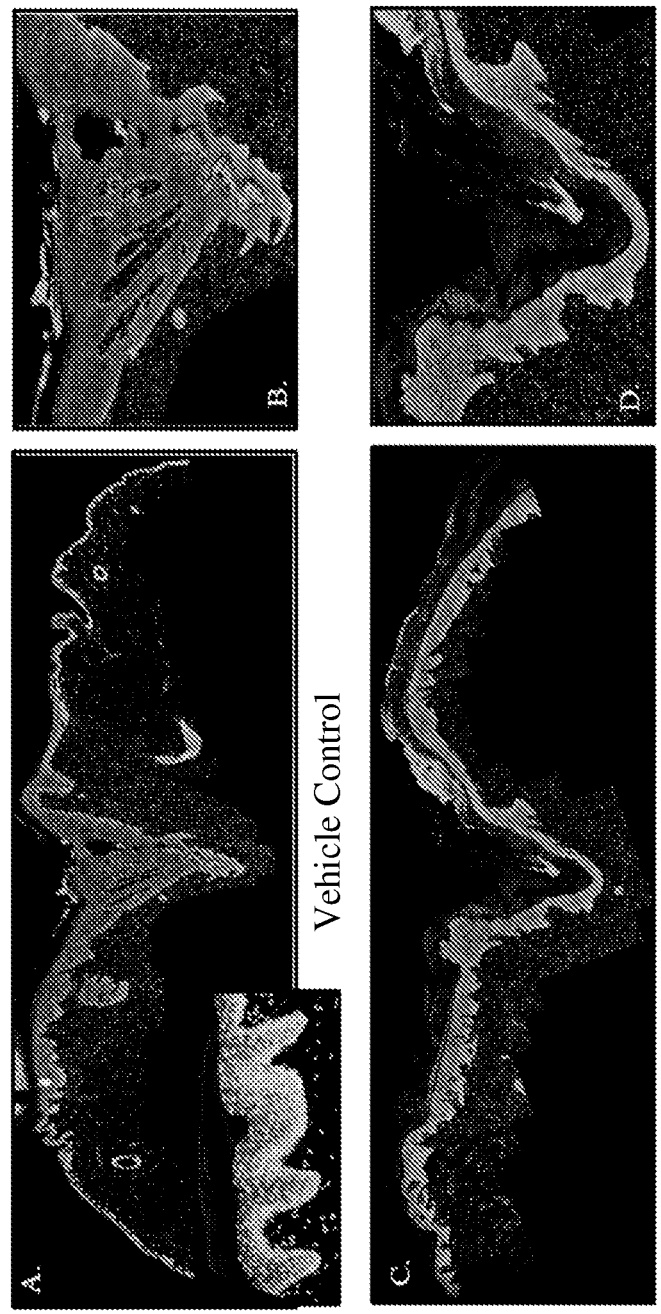
FIG. 15 are immunofluorescence images of wounds treated biweekly with vehicle control or 10 μM Compound 4 taken on Day 14 post-wounding in a pig.

Immunofluorescence images of a Day 14 wound treated with Compound 4 at 10 μM was stained with keratin-14 antibody. On completion of the study (Day 14), full thickness wound-edge tissue point biopsies were collected using a 16 mm sterile biopsy punch for histological analyses. Formalin-fixed paraffin-embedded wound-edge specimens were sectioned and deparaffinized. Immunohistochemical staining was performed using primary antibody: anti-keratin 14 antibody (1:600) after heat-induced epitope retrieval when necessary. Fluorescence detection and counterstaining were performed using Alexa Fluor 488 or 568 secondary antibody (1:200). K-14 (keratinocyte) staining showed a more mature phase of healing in the Compound 4-treated wound (panels B and D of FIG. 15) compared to the vehicle control-treated wound (panels A and C of FIG. 15). Hyper-proliferating epithelium featuring long rete ridges indicates an earlier phase of healing in vehicle control-treated wounds compared to Compound 4-treated wounds, where rete ridges become shorter and look more similar to those observd in the intact part of the skin.

Figure 16:
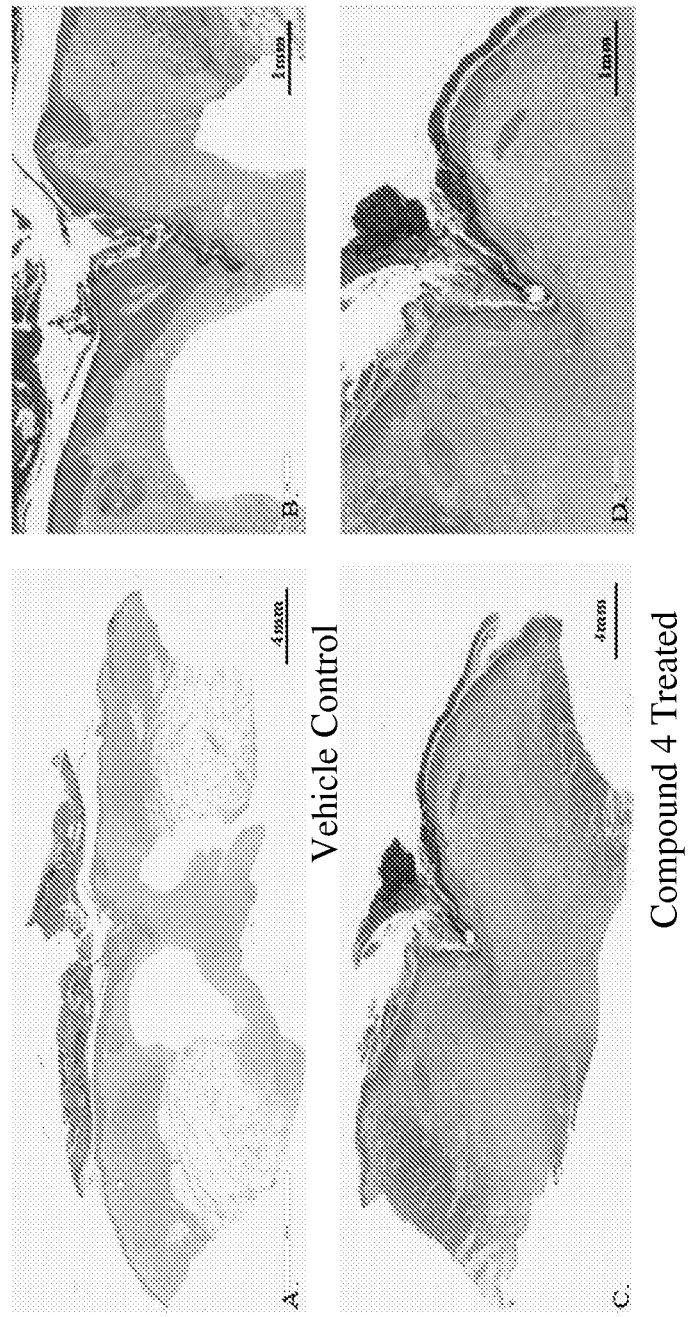
FIG. 16 are hematoxylin and eosin wound epithelialization images of wounds treated biweekly with vehicle control or 10 μM Compound 4 taken on Day 14 post-wounding in a pig.

Wound epithelialization of H&E-stained wounds was documented on Day 14 post-wounding. On completion of the study (Day 14), full thickness wound-edge tissue point biopsies were collected using a 16 mm sterile biopsy punch for histological analyses. Formalin-fixed paraffin-embedded wound-edge specimens were sectioned, deparaffinized and stained with H&E. H&E staining shows a more mature phase of healing in wounds treated with Compound 4 (panels B and D in FIG. 16) compared to wounds treated with vehicle controls (panels A and C in FIG. 16). Hyperproliferating epitelium featuring long rete ridges indicates an earlier phase of healing in Compound 4-treated compared to control-treated wounds, where rete ridges become shorter and look more similar to those observed in the intact part of the skin.

In conclusion, the efficacy of Compound 4 in a hydrogel formulation was measured on wound outcomes in a preclinical ischemic wound porcine model. Pigs were treated with Compound 4 either daily or biweekly at a dosage of 3 µM or 10 µM in a 2% thermal hydrogel. Digital images and measured area of wounds treated biweekly with Compound 4 at 10 µM biweekly for 14 days showed decreased wound area compared to vehicle control-treated wounds.

LSI on Day 14 in wounds treated biweekly with Compound 4 (10 µM) showed larger wound perimeters for vehicle control-treated compared to Compound 4-treated wounds. Standardized quantification of blood flow shows higher perfusion levels in Compound 4-treated wounds compared to vehicle control wounds on Day 14, indicating a more advanced stage of healing in the Compound 4-treated wounds.

B-mode ultrasound imaging of wound depth measurements in wounds treated biweekly with Compound 4 at 10 µM on Day 0, pre-wounding and post-wounding, and Day 14 post wounding revealed more efficient healing across the thickness of the skin for Compound 4-treated wounds compared to vehicle-treated wounds.

At day 14 post-wounding, pulse velocity, a marker of blood vessel function was higher in frames corresponding to wounds treated with Compound 4 at 10 µM than in frames corresponding to the vehicle control-treated wounds. These results indicate a more advanced blood vessel function in treated wounds compared to untreated controls.

H&E staining and keratin 14 immunofluorescence images of Day 14 wounds treated with Compound 4 at 10 µM showed a more mature phase of healing in Compound 4-treated wounds compared to vehicle control-treated wounds.

EXAMPLE 14

Treatment of Human Dermal Fibroblasts with Compound 4 Increases in Vitro Fibroblast to Myofibroblast Differentiation For the purposes of this example, and its associated figures, Compound 4 refers to Compound C-3 (from Table 1C) in dimethylsulfoxide (DMSO) (e.g., 0.1%, 0.02%, 0.0067% DMSO in water).

The ability of Compound 4 to induce the myofibroblast differentiation was tested by adding Compound 4 (10, 100, 1000, and 2000 nM and respective DMSO controls) for 4 days to human dermal fibroblast cultures in the absence of exogenous TGF-β1 (2 nM). Myofibroblast differentiation was quantitatively assessed by densitometry of Western blots and immunofluorescence for the contractile myofibroblast marker α-SMA and ED-A fibronectin (ED-A FN). Western blots were performed with whole cell extracts using antibodies against α-SMA (42 kDA), vimentin (58 kDa), ED-A FN (220 kDa) and vinculin (116 kDa). The intermediate filament protein vimentin served as loading control. Band intensities were quantified with densitometry from three independent blots. Furthermore, the percentage of cells forming α-SMA-positive stress fibers was determined using automatic image analysis of immunofluorescence images (α-SMA/DAPI) over at least 10 low-power image fields per condition. At least three independent experiments were performed per test.

Figure 17A:
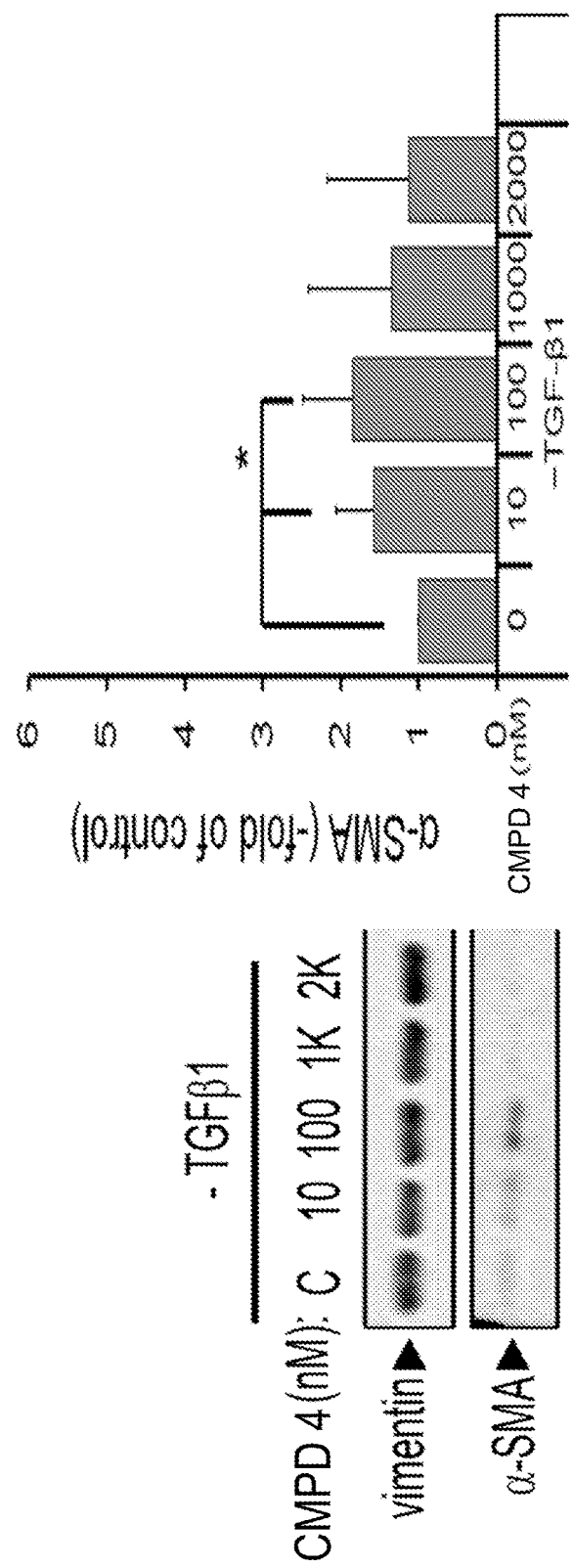
FIG. 17A is an image of a Western blot against vimentin and α-SMA and a graph of the level of α-SMA as a function of the concentration of Compound 4 in the absence of TGF-β1. The graph represents the quantification by densitometric analysis of the Western blot against vimentin and α-SMA.
Figure 17B:
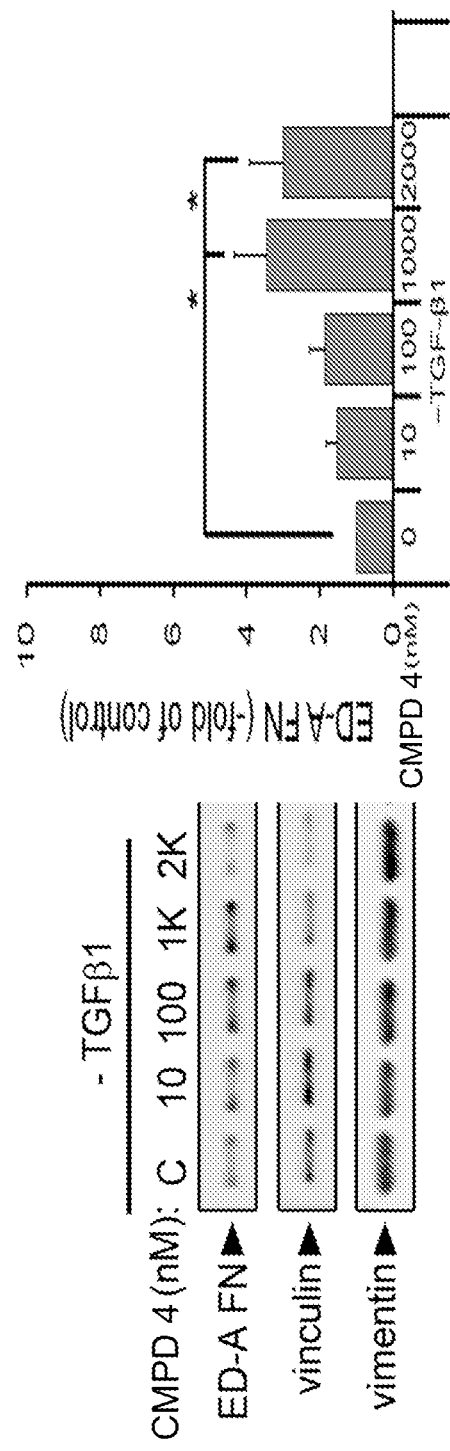
FIG. 17B is an image of a Western blot against ED-A FN, vinculin and vimentin and a graph of the level of ED-A FN as a function of the concentration of Compound 4 in the absence of TGF-β1. The graph represents the quantification by densitometric analysis of the Western blot against ED-A FN, vinculin and vimentin.

FIGS. 17A and 17B are images of a Western blot and graphs resulting from densitometric analyses of three Western blots. Average values±standard deviation are displayed. The asterisks indictes $p \leq 0.5$, Student's t-test.

Western blot assessment and quantification demonstrated that Compound 4 at concentrations of 10 and 100 nM increased the expression of α-SMA independently of TGF-β1 (1.6 and 1.8-fold, respectively). At 1000 and 2000 nM, α-SMA was comparable to control levels. These results were confirmed by immunofluorescence staining for α-SMA (not shown). The percentage of human dermal fibroblasts expressing α-SMA in stress fibers in control conditions was 6±1% in the absence of TGF-β1. This percentage increased with Compound 4 treatment to 10±2% (10 nM) and 12±2% (100 nM). Staining intensity for α-SMA in stress fibers of individual human dermal fibroblasts was highest in presence of 100 nM Compound 4.

ED-A FN is the splice variant of cellular fibronectin that is frequently associated with myofibroblast development. In the absence of added TGF-β1, expression of ED-A FN increased with increasing concentrations of Compound 4, as shown by Western blotting (FIG. 17B) and immunofluorescence staining (not shown). Highest expression levels of ED-A FN were obtained at 1000 nM Compound 4 (2.3-fold), and then saturated.

In dermal fibroblasts with low baseline myofibroblast differentiation, Compound 4 has an inducing effect on α-SMA and ED-A FN expression levels.

EXAMPLE 15

Treatment of Human Dermal Fibroblasts with Compound 4 Increases in Vitro Contraction of Human Dermal Fibroblasts For the purposes of this example, and its associated figures, Compound 4 refers to Compound C-3 (from Table 1C) in dimethylsulfoxide (DMSO) (e.g., 0.1%, 0.02%, 0.0067% DMSO in water).

The effects of Compound 4 on myofibroblast function were examined using a two dimensional contractile "wrinkling" assay. Contraction of a collagenous extracellular matrix (ECM) is one of the main outcomes of myofibroblast activities in normal wound healing and is substantially impaired in chronic wounds. Two-dimensional contraction tests were performed using a 96-well automated cell contraction "wrinkling" assay that quantifies the percentage of contractile cells in a given population. Compound 4 was added at 10, 100, and 1000 nM and respective DMSO controls to human dermal fibroblasts cultured in standard culture plates.

Cells were then passaged to wrinkling substrates in the respective medium condition and assessed for contraction after another day. To quantify wrinkles, images were taken over at least ten random regions of interest per condition. Using an in-house developed algorithm, the surface covered by wrinkles was quantified and normalized to the number of cells in the field and expressed as percentage of control. One major advantage of using wrinkling substrates over 3D collagen contraction assays is the independence of the results from cell proliferation. Contraction is assessed with single cell resolution at the culture population level. At least three independent experiments were performed per test. Shown are mean values±standard deviation.

Figure 18:
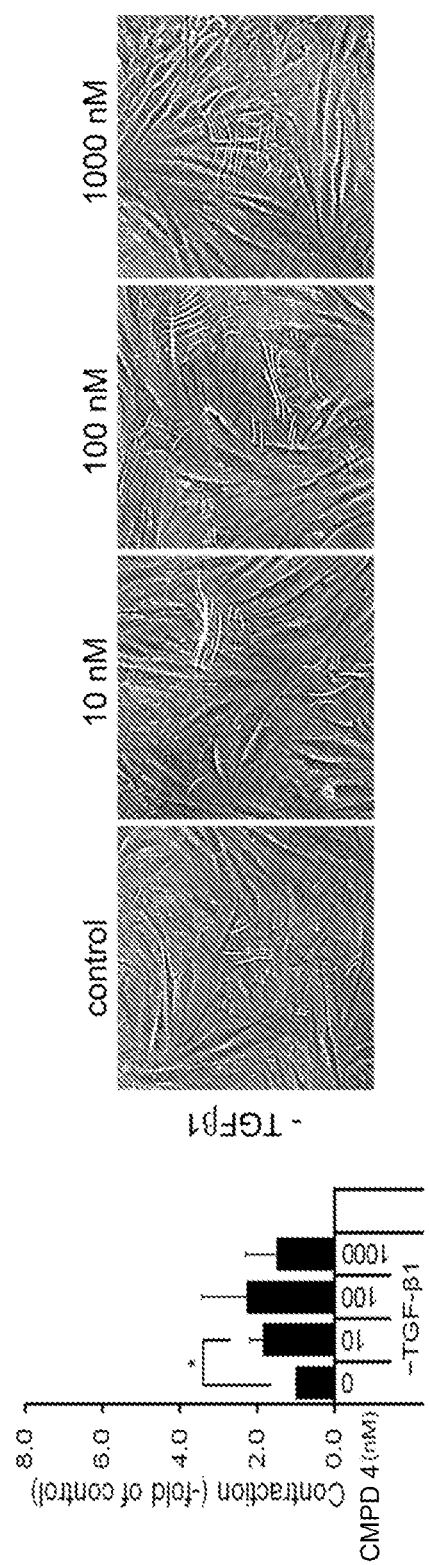
FIG. 18 is a graph of contraction of human dermal fibroblasts as a function of the concentration of Compound 4 and images of human dermal fibroblasts cultured for four days in the presence of the indicated concentrations of Compound 4 in the absence of TGF-β1. The graph represents the quantification of the images.
Figure 19A:
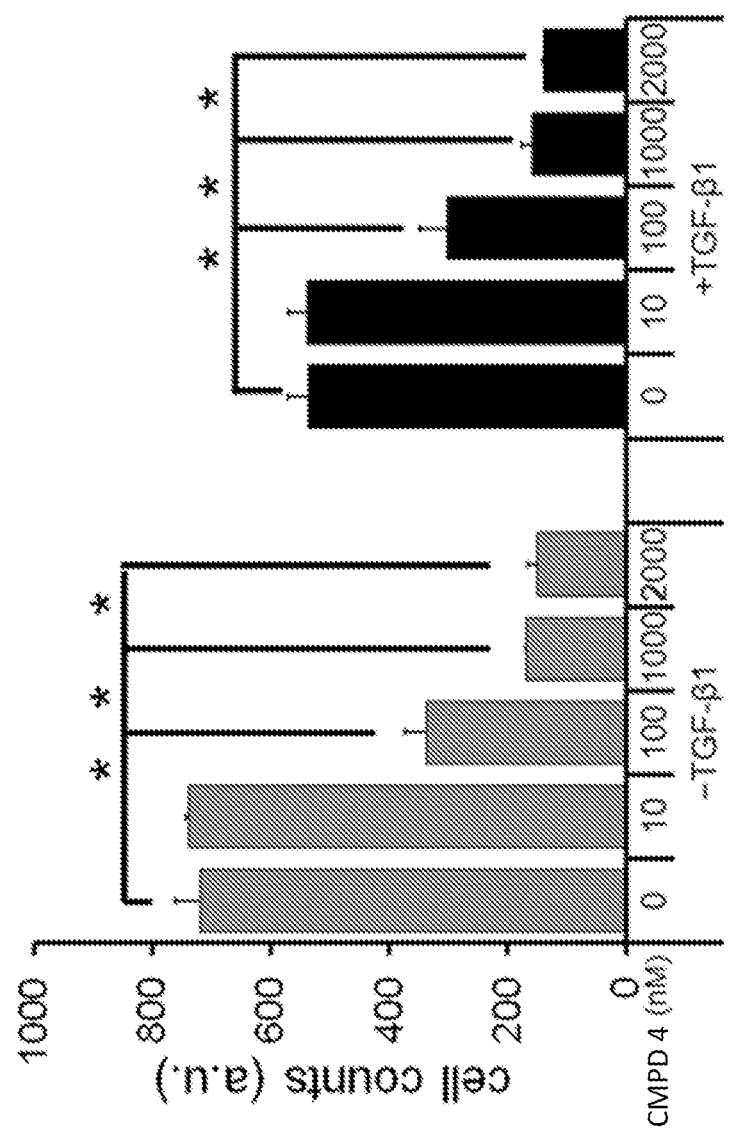
FIG. 19A is a graph of human dermal fibroblast counts (absorbance units, a.u.) as a function of the concentration of Compound 4 in the presence or absence of TGF-β1, and shows that increasing concentrations of Compound 4 reduces human dermal fibroblast counts after 4 day of culture in the presence of absence of TGF-β1.
Figure 19B:
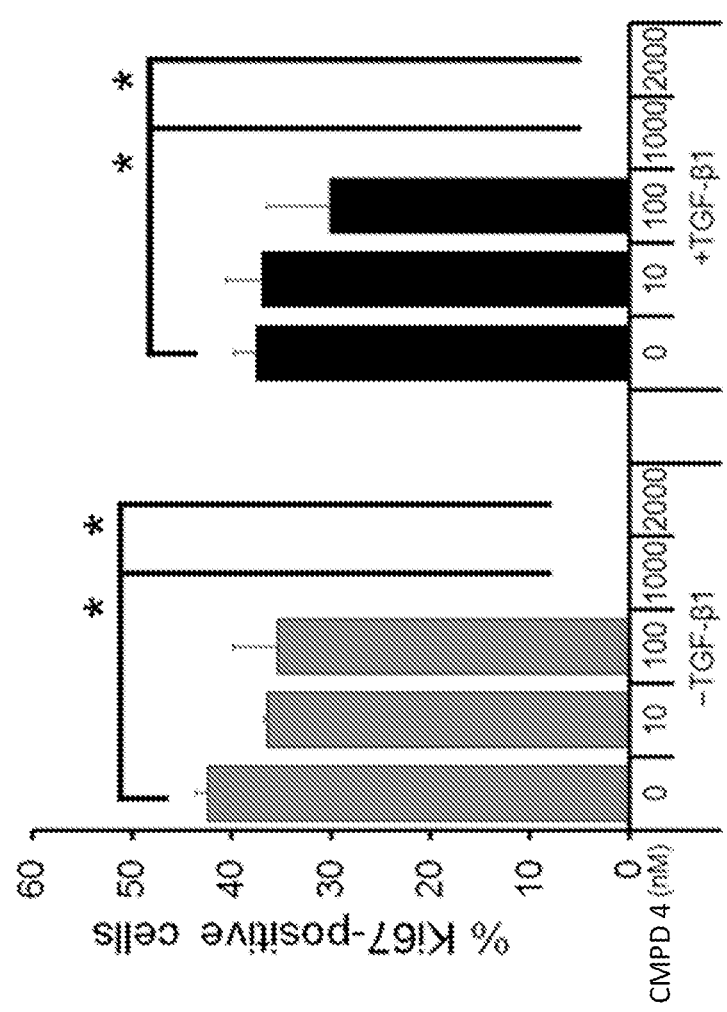
FIG. 19B is a graph of Ki67-positive human dermal fibroblasts as a function of the concentration of Compound 4 in the presence or absence of TGF-β1, and shows that increasing concentrations of Compound 4 reduce the number of fibroblasts in a proliferating state.
Figure 19C:
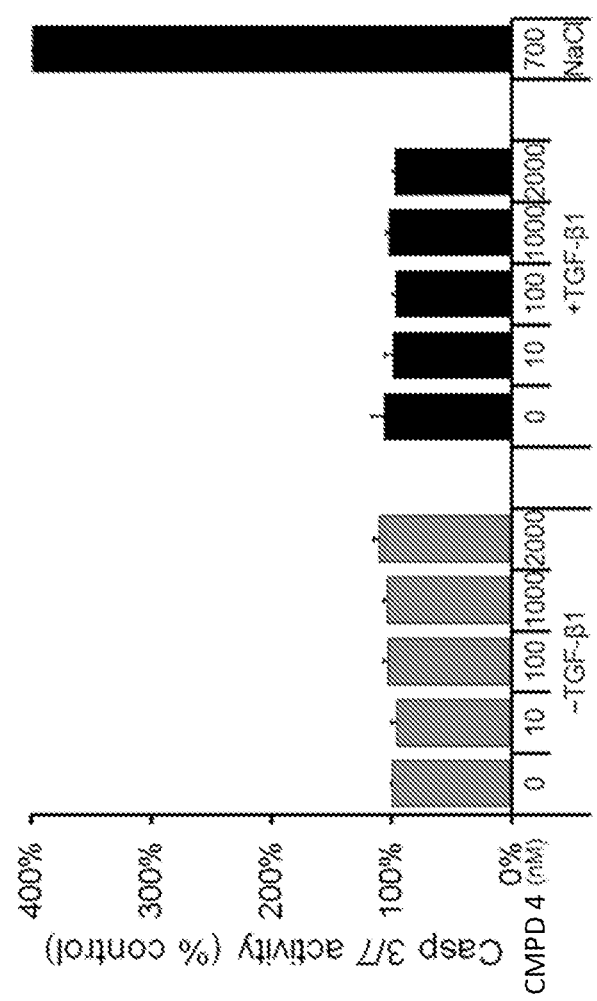
FIG. 19C is a graph of caspase 3/7 activity (as a percentage of control) in human dermal fibroblasts at 24 hours as a function of the concentration of Compound 4 in the presence or absence of TGF-β1, and shows that Compound 4 did not induce apoptosis in the fibroblasts.

Human dermal fibroblasts were cultured for 4 days in the presence of Compound 4 (10, 100, and 1000 nM), added once at the beginning of the culture period without TGFβ1. Cells were then passaged onto wrinkling silicone substrates and cultured in the same media for twenty four hours. Cell contraction leads to wrinkling of the substrate surface that is visible as white lines perpendicular to the cell axis. Images from one representative of three similarly performed experiments are shown in FIG. 18. Also shown in FIG. 18 is a graph of contraction calculated from images taken over four image fields per well and at least three wells per experimental condition. Contraction was calculated as surface covered by wrinkles normalized to cell number (quantified by live nuclear staining) and expressed as percentage of control. Shown are mean values±standard error of measurement (SEM) from three independent experiments with three wells and four images per well.

When Compound 4 was added without the addition of TGF-β1, there was increased human dermal fibroblast contraction with increasing concentrations of Compound 4. Statistical significance was reached at 10 nM Compound 4 (2.0-fold of control) and maximum contraction level was reached at 100 nM Compound 4.

EXAMPLE 16

Treatment of Human Dermal Fibroblasts with Compound 4 Increases in Vitro Reduces Human Dermal Fibroblast Proliferation without Affecting Apoptosis For the purposes of this example, and its associated figures, Compound 4 refers to Compound C-3 (from Table 1C) in dimethylsulfoxide (DMSO) (e.g., 0.1%, 0.02%, 0.0067% DMSO in water).

The effects of Compound 4 on proliferation and apoptosis were examined in human dermal fibroblasts. Human dermal fibroblasts were cultured for 4 days in the presence of Compound 4 at concentrations of 10, 100, 1000, and 2000 nM and respective DMSO controls (only highest concentration DMSO control is shown in the results). Compound 4 was added once at the beginning of the culture period either in the absence or presence of exogenous pro-fibrotic TGF-β1. After 4 days, cells were washed three times with serum-free medium and processed for immunofluorescence and Western blotting according to standard procedures. Cell proliferation was determined by cell counts and immunolocalization of the proliferation indicator Ki67 in the cell's nucleus. Apoptosis was quantified using a luminescence-based readout of active Caspase 3/7 (Promega).

Human dermal fibroblasts were cultured for 4 days in the presence of Compound 4 (10, 100, 1000, and 2000 nM), added once at the beginning of the culture period, with or without TGFβ1. Cell numbers were determined from nuclei counts, performed on at least 10 low-power fluorescence images. Proliferative cells were determined by calculating the percentage of Ki67-positive nuclei of all nuclei. Quantifications were automated using the particle analysis function in Fiji (ImageJ). Apoptosis was quantified using a luminescence-based readout of active Caspase 3/7. Positive control for apoptosis was treatment with 700 mM NaCl to induce hyperosmotic shock. Averages±standard deviation (SD) from three independent experiments are displayed. *p≤0.05, Student's t-test, compared with controls. The results are depicted in FIGS. 20A-20C.

FIGS. 20A-20C show that Compound 4 reduces human dermal fibroblast numbers by decreasing proliferation parameters. Compound 4 at concentrations of 100 nM and higher significantly decreased (about 2-fold) human dermal fibroblast cell counts after 4 days of culture in the presence and absence of TGF-β1 (FIG. 20A). The addition of Compound 4 at 1000 and 2000 nM completely eliminated cells in a proliferative state, indicated by the absence of Ki67-positive nuclei with and without TGF-β1 treatment (FIG. 20B). Apoptotic figures above control levels were not observed in any of the tested conditions (see FIG. 20C).

EXAMPLE 17

Treatment of Pig Wounds with Compound 4 Increased Myofibroblast Formation in Vivo For the purposes of this example, and its associated figures, Compound 4 refers to Compound C-3 (from Table 1C) in dimethylsulfoxide (DMSO) (e.g., 0.1%, 0.02%, 0.0067% DMSO in water).

Paraffin sections from day 12 and 19 biopsy tissue extracted from full thickness excision pig wounds that were stained with anti-smooth muscle alpha-actin (SMAA) antibody (20 paraffin sections from each of the following treatments: control and treated 12 and 19 day granulation tissue). At least 5 sections per treatment were analyzed for SMAA immunostaining. SMAA immunostaining in superficial and deep dermis of wound margins and in granulation tissue was assessed semi-quantitatively on a four-graded scale: 0=no positive staining, 1=weak, 2=moderate, and 3=abundant. The results are presented in Table 10A.

TABLE 10A

Semi-quantitative Analysis of Myofibroblast Number of Day 12 Wounds.

| | Compound 4 3 μM Wounds | Compound 4 1 μM Wounds | Control Wounds | Control Skin |
|---|---|---|---|---|
| | 3 | 3 | 1 | 0 |
| | 3 | 3 | 1 | 0 |
| | 2 | 3 | 1 | 0 |
| | 2 | 3 | 1 | 0 |
| | 2 | | 1 | 0 |
| | 2 | | 1 | 0 |
| | 3 | | 1 | 0 |
| | 3 | | 1 | |
| Ave. | 2.5 | 3 | 1 | 0 |

Table 10A shows that paraffin embedded sections of Compound 4-treated pig wounds on day 12 showed an increased number of myofibroblasts in the granulation tissue compared to control wounds. These results suggest that Compound 4 promotes earlier formation and function of myofibroblasts during wound healing. This enhanced temporal appearance of myofibroblasts correlates with previous results showing that Compound 4 enhances wound closure in day 12 wounds. There was no difference between treatment groups at 1 μM and 3 μM Compound 4.

Analysis of biopsy granulation tissue from wounds on Day 19 show that treatment with Compound 4 reduces the number of myofibroblasts compared to control wounds. This data is presented in Table 10B.

TABLE 10B

Semi-quantitative Analysis of Myofibroblast Number on Day 19 Wounds.

| | Compound 4 3 μM-0.02% DMSO Wounds | Compound 4 1 μM-0.0067% DMSO Wounds | 0.02% DMSO Control Wounds | 0.0067% DMSO Control Wounds |
|---|---|---|---|---|
| | 1 | 1 | 3 | 3 |
| | 1 | 1 | 3 | 3 |
| | 1 | 1 | 2 | 3 |
| | 1 | 1 | 2 | 3 |
| | 1 | | 3 | 2 |
| | 1 | | 3 | 2 |
| | 1 | | | |
| | 1 | | | |
| Ave | 1 | 1 | 2.7 | 2.7 |

Additional examination of Compound 4-treated wounds showed accelerated completely healed and formed scar tissue. The reduced number of myofibroblasts would be expected if wounds were already closed and scar tissue was forming. In addition, control wounds had significantly more myofibroblasts at Day 19 than Day 12; consistent with them still contracting the wound. These results suggest that Compound 4 is enhancing the temporal progression of wound healing and closure.

Together these results strongly suggest that Compound 4 is enhancing the temporal appearance of functional myofibroblasts, resulting in earlier wound closure, scar formation, and loss of myofibroblasts than in control wounds.

EXAMPLE 18

Synthesis of Pyrazin-2-Ylmethyl (Z)-3-(3-(3-Isopropdxy-5-(Trifluoromethyl)Phenyl)-1h-1,2,4-Triazol-1-Yl)Acrylate (Compound 130 In Table 1A).

Compound 130 was prepared in accordance with the synthetic procedure outlined in EXAMPLE 10 for Compound 129 using the appropriate reagents. $^1$H NMR (400 MHz, DMSO-d$_6$) δ9.24 (s, 1H), 8.70 (d, J=1 Hz, 1H). 8.63-8.59 (m, 2H), 7.79 (s, 1H), 7.71 (s, 1H), 7.60 (d, J=10 Hz, 1H), 7.34 (s, 1H), 6.14 (d, J=10 Hz, 1H), 5.39 (s, 2H), 4.85-4.76 (m, 1H). 1.32 (d, J=6Hz, 6H). LCMS: m/z 434.1 [M+H]$^+$, t$_R$=1.83 min.

EXAMPLE 19

Assays

Certain compounds of the invention were tested in various assays.

Inhibition of Nuclear Export

The inhibition of CRM1 mediated nuclear export by compounds of the invention can be determined in a RevGFP assay.

Rev is a protein from human immunodeficiency virus type 1 (HIV-1) and contains a nuclear export signal (NES) in its C-terminal domain and a nuclear localization signal (NLS) in its N-terminal domain. Nuclear export of Rev protein is dependent on the classical NES/CRM1 pathway (Neville et al, 1997, Kau et al, 2003). Nuclear accumulation of Rev is observed in cells treated with specific inhibitors of CRM1, such as LMB (Kau et al, 2003). In this assay, U2OS-RevGFP cells are seeded onto clear-bottom, black, 384-well plates the day before the experiment. Compounds are serially diluted 1:2 starting from 40 μM in a separate 384-well plate in DMEM, and then transferred onto cells. Cells are incubated with compound for approximately 1 hr before fixation with 3.7% formaldehyde and nuclei staining with Hoechst 33258. The amount of GFP in cell nuclei is measured and compound IC$_{50S}$ are determined (Kau et al, 2003).

MTT Cell Proliferation Assay

The MTT cell proliferation assay was used to study the cytotoxic properties of certain compounds. The assay was performed according to the method described by Roche Molecular Biochemicals, with minor modifications. The assay is based on the cleavage of the tetrazolium salt, MTT, in the presence of an electron-coupling reagent. The water-insoluble formazan salt produced must be solubilized in an additional step. Cells grown in a 96-well tissue culture plate were incubated with the MTT solution for approximately 4 hours. After this incubation period, a water-insoluble formazan dye formed. After solubilization, the formazan dye was quantitated using a scanning multi-well spectrophotometer (ELISA reader). The absorbance revealed directly correlates to the cell number. The cells were seeded at 5,000-10,000 cells in each well of 96-well plate in 100 μL of fresh culture medium and were allowed to attach overnight. The stock solutions of the compounds were diluted in 100 μL cell culture medium to obtain eight concentrations of each test compound, ranging from 1 nM to 30 μM. After incubation for approximately 64-72 hours, 20 μL of CellTiter 96 Aqueous One Solution Reagent (Promega, G358B) was added to each well and the plate was returned to the incubator (37° C.; 5% CO$_2$) until an absolute OD of 1.5 was reached for the control cells. All optical densities were measured at 490 nm using a Vmax Kinetic Microplate Reader (Molecular Devices). In most cases, the assay was performed in duplicate and the results were presented as a mean percent inhibition to the negative control±SE. The following formula was used to calculate the percent of inhibition: Inhibition (%)=(1−(OD$_c$/OD))×100.

Certain compounds were tested against MM1.S cells. The MM1S cell line was established from the peripheral blood of a human multiple myeloma patient.

The results of the MTT assay are reported in Table 11.

TABLE 11

MTT Assay Results for Compounds 252 and 260

| Compound No. | IC$_{50}$ MM1.S (μM) |
|---|---|
| 129 | 0.02 |
| 130 | 0.004 |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:
1. A method of promoting wound healing in a subject in need thereof, the method comprising administering to the subject a therapeutically effective amount of a compound represented by any one of the structural formulas selected from:
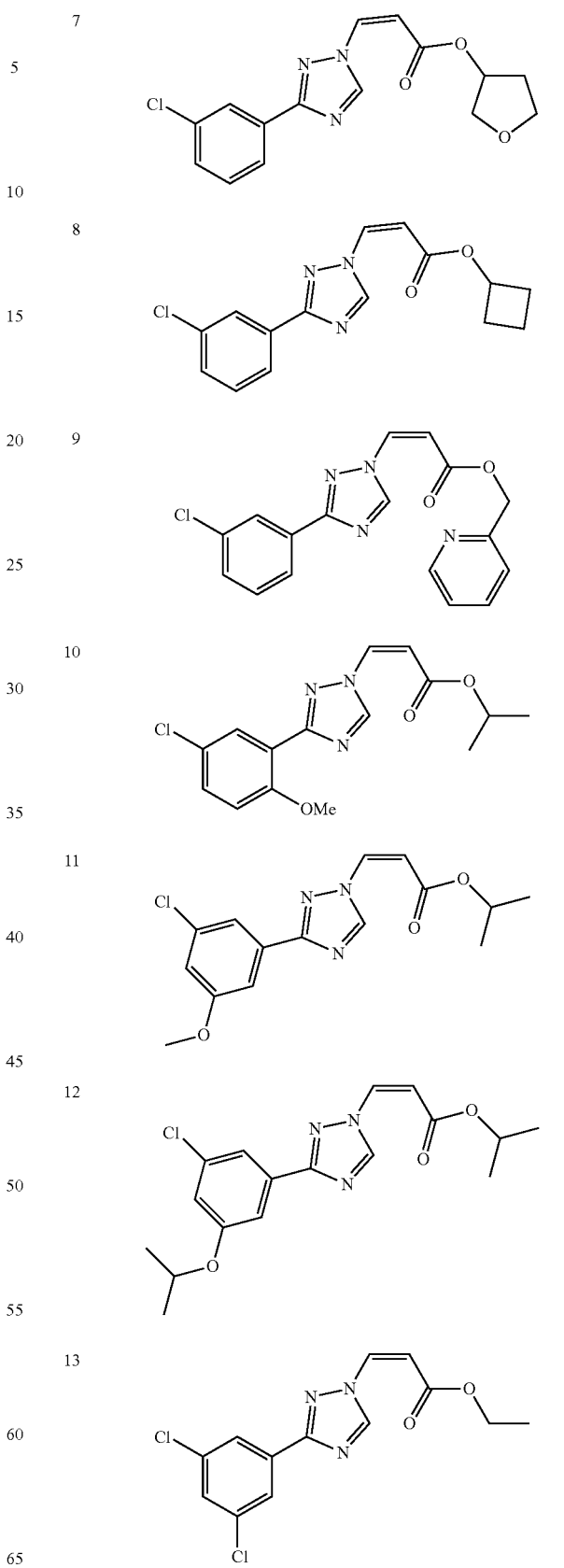

| 195 -continued | 196 -continued |
|---|---|
| 14 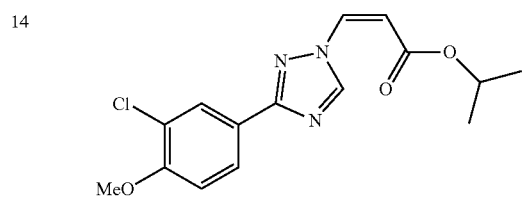 | 20 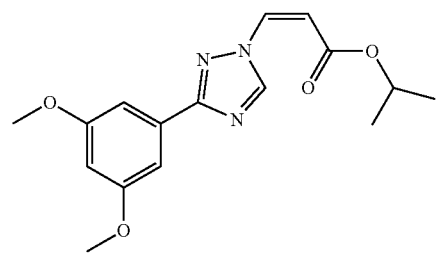 [SMILES: COc1cc(OC)cc(-c2ncn(/C=C\C(=O)OC(C)C)n2)c1] |
| 15 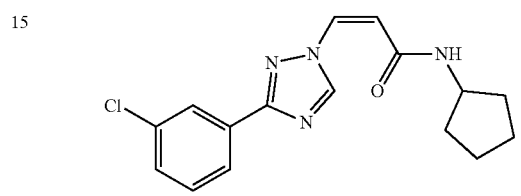 | 21 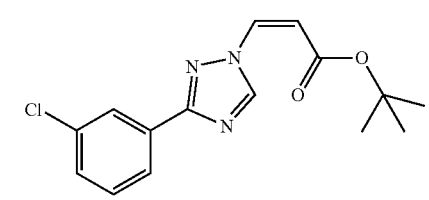 [SMILES: CC(C)(C)OC(=O)/C=C\n1cnc(-c2cccc(Cl)c2)n1] |
| 16 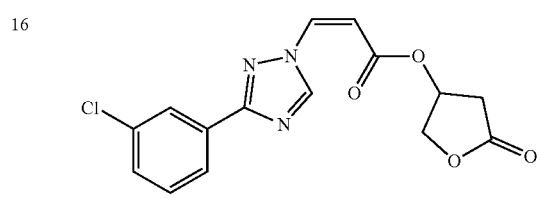 | 22 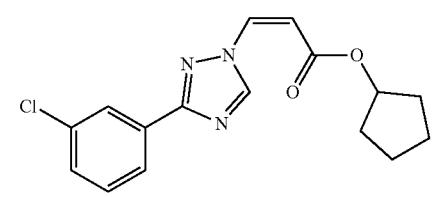 [SMILES: O=C(/C=C\n1cnc(-c2cccc(Cl)c2)n1)OC1CCCC1] |
| 17 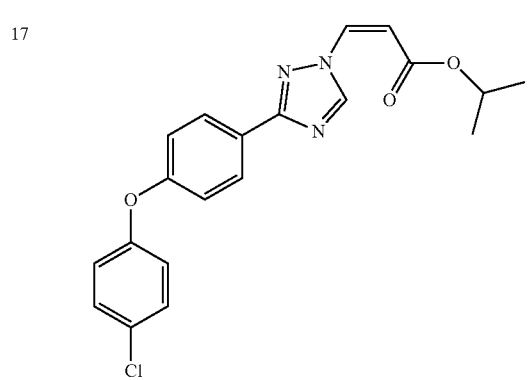 | 23 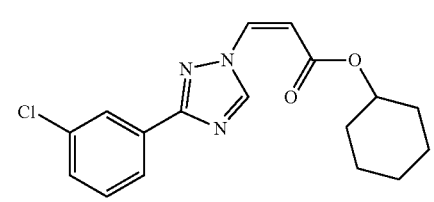 [SMILES: O=C(/C=C\n1cnc(-c2cccc(Cl)c2)n1)OC1CCCCC1] |
| | 24 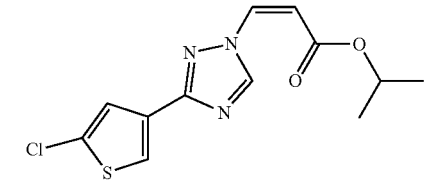 [SMILES: CC(C)OC(=O)/C=C\n1cnc(-c2csc(Cl)c2)n1] |
| 18 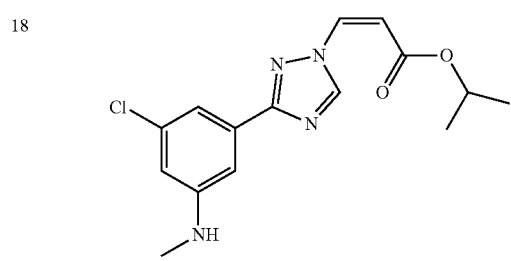 | 25 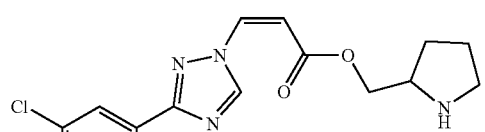 |
| 19 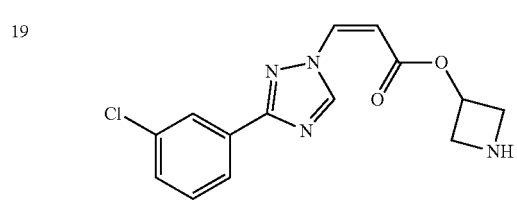 | 26 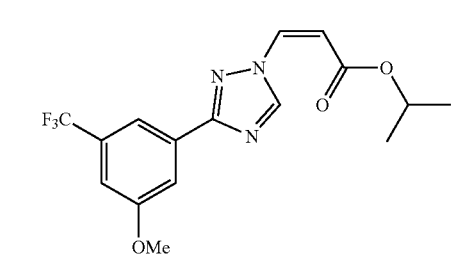 [SMILES: COc1cc(-c2ncn(/C=C\C(=O)OC(C)C)n2)cc(C(F)(F)F)c1] |

| | |
|---|---|
| 27 | 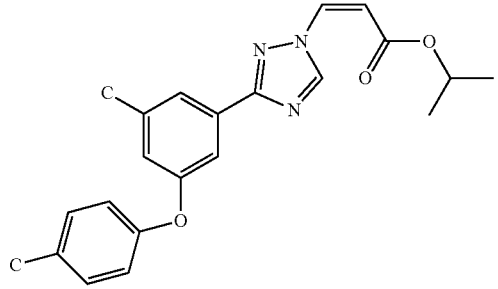 [SMILES: Cc1ccc(Oc2cc(C)cc(-c3ncn(/C=C\C(=O)OC(C)C)n3)c2)cc1] |
| 28 | 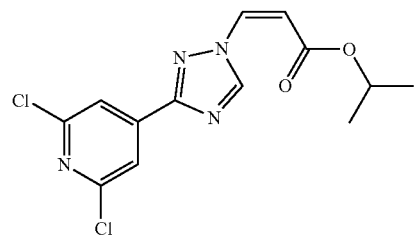 [SMILES: CC(C)OC(=O)/C=C\n1cnc(-c2cc(Cl)nc(Cl)c2)n1] |
| 29 | 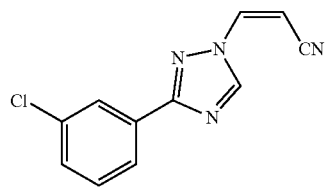 [SMILES: N#C/C=C\n1cnc(-c2cccc(Cl)c2)n1] |
| 30 | 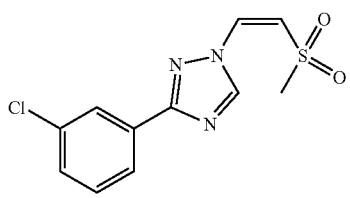 [SMILES: CS(=O)(=O)/C=C\n1cnc(-c2cccc(Cl)c2)n1] |
| 31 | 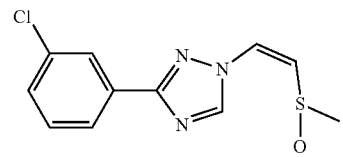 |
| 32 | 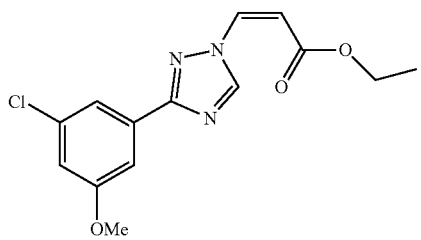 [SMILES: CCOC(=O)/C=C\n1cnc(-c2cc(Cl)cc(OC)c2)n1] |
| 33 | 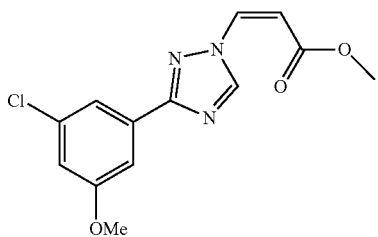 [SMILES: COC(=O)/C=C\n1cnc(-c2cc(Cl)cc(OC)c2)n1] |
| 34 | 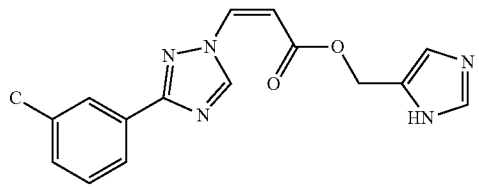 [SMILES: Cc1cccc(-c2ncn(/C=C\C(=O)OCc3cnc[nH]3)n2)c1] |
| 35 | 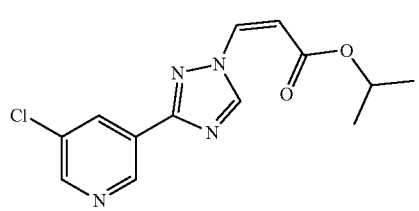 [SMILES: CC(C)OC(=O)/C=C\n1cnc(-c2cncc(Cl)c2)n1] |
| 36 | 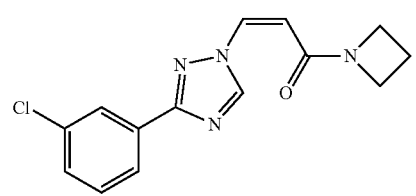 [SMILES: O=C(/C=C\n1cnc(-c2cccc(Cl)c2)n1)N1CCC1] |
| 37 | 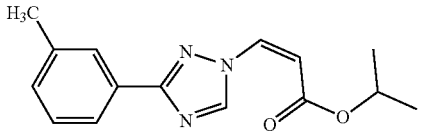 [SMILES: Cc1cccc(-c2ncn(/C=C\C(=O)OC(C)C)n2)c1] |
| 38 | 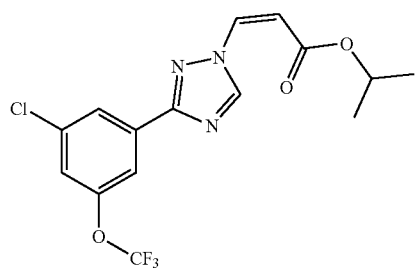 [SMILES: CC(C)OC(=O)/C=C\n1cnc(-c2cc(Cl)cc(OC(F)(F)F)c2)n1] |
| 39 | 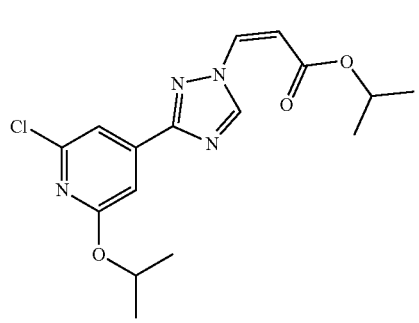 [SMILES: CC(C)OC(=O)/C=C\n1cnc(-c2cc(Cl)nc(OC(C)C)c2)n1] |
| 40 | 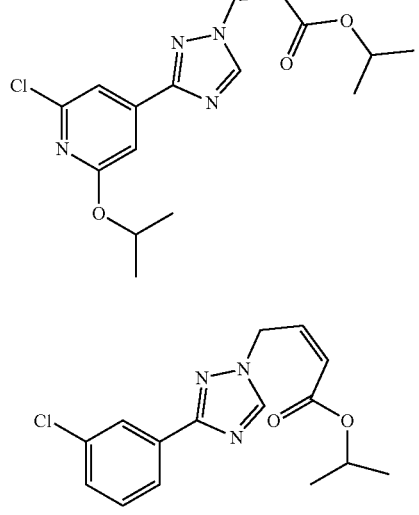 |

| 41 | 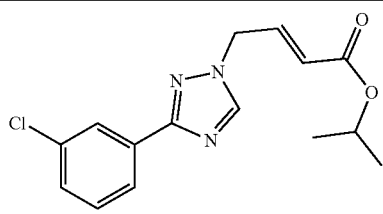 | 46 | 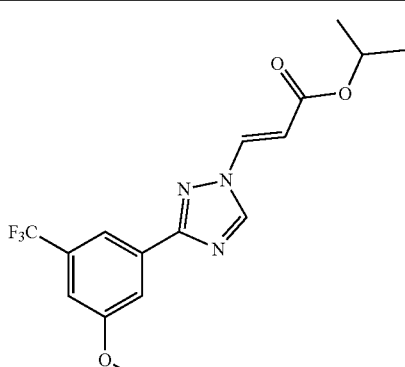 |
| 42 | 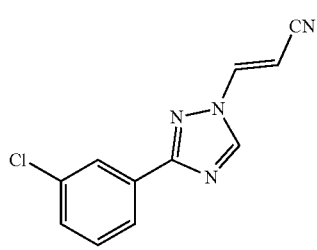 [SMILES: N#C/C=C/n1cnc(-c2cccc(Cl)c2)n1] | | |
| 43 | 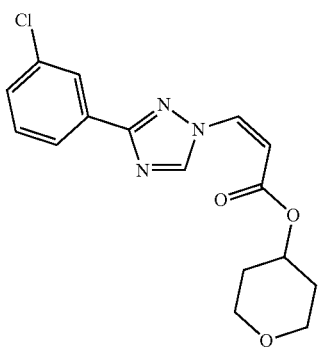 [SMILES: O=C(/C=C\n1cnc(-c2cccc(Cl)c2)n1)OC1CCOCC1] | 47 |  |
| | | 48 | 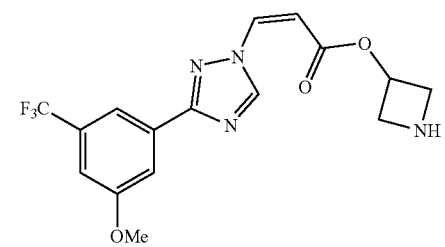 |
| 44 | 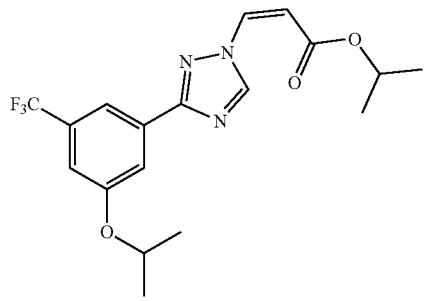 [SMILES: CC(C)OC(=O)/C=C\n1cnc(-c2cc(OC(C)C)cc(C(F)(F)F)c2)n1] | 49 | 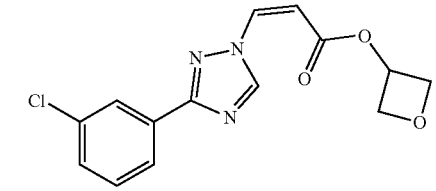 |
| 45 | 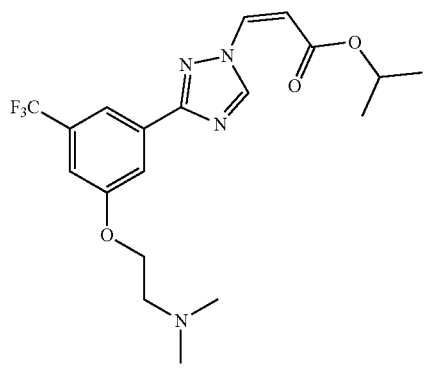 [SMILES: CC(C)OC(=O)/C=C\n1cnc(-c2cc(OCCN(C)C)cc(C(F)(F)F)c2)n1] | 50 | 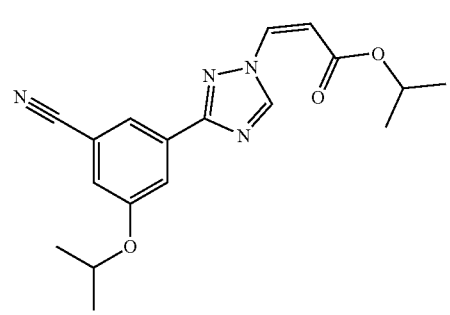 [SMILES: CC(C)OC(=O)/C=C\n1cnc(-c2cc(C#N)cc(OC(C)C)c2)n1] |

| | |
|---|---|
| 51 | 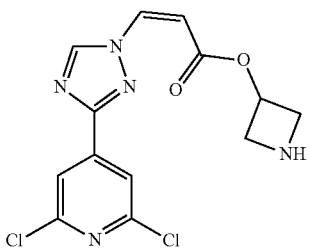 [SMILES: O=C(/C=C\n1cnc(-c2cc(Cl)nc(Cl)c2)n1)OC1CNC1] |
| 52 | 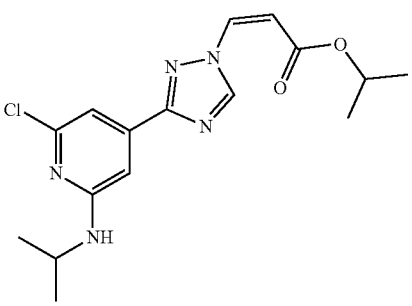 [SMILES: CC(C)Nc1cc(-c2ncn(/C=C\C(=O)OC(C)C)n2)cc(Cl)n1] |
| 53 | 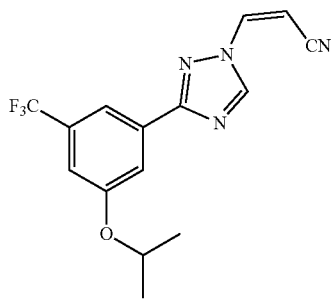 [SMILES: CC(C)Oc1cc(-c2ncn(/C=C\C#N)n2)cc(C(F)(F)F)c1] |
| 54 | 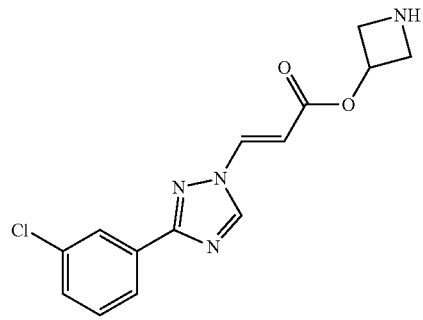 [SMILES: O=C(/C=C/n1cnc(-c2cccc(Cl)c2)n1)OC1CNC1] |
| 55 | 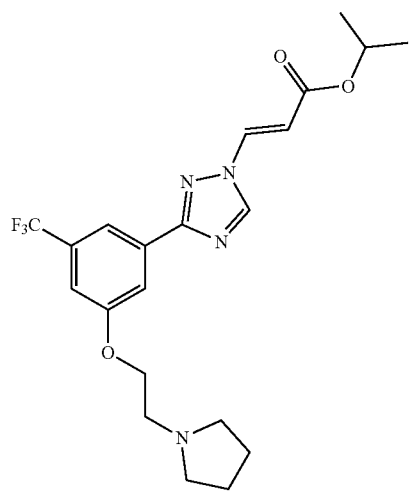 [SMILES: CC(C)OC(=O)/C=C/n1cnc(-c2cc(OCCN3CCCC3)cc(C(F)(F)F)c2)n1] |
| 56 | 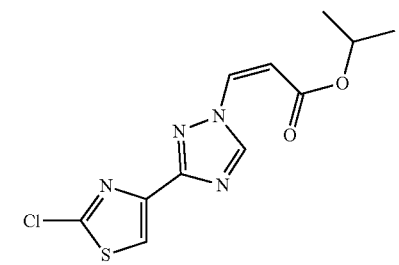 [SMILES: CC(C)OC(=O)/C=C\n1cnc(-c2csc(Cl)n2)n1] |
| 57 | 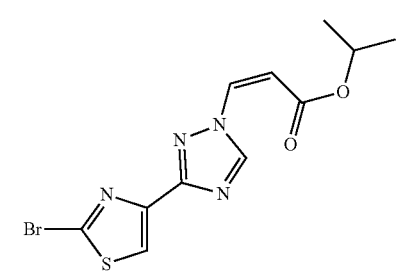 |
| 58 | 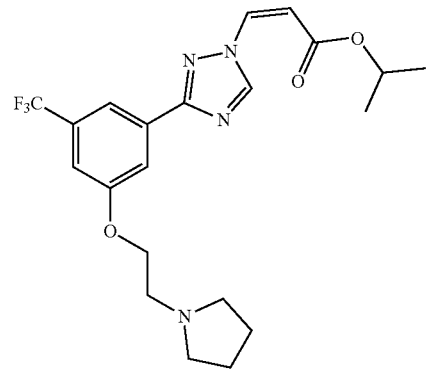 [SMILES: CC(C)OC(=O)/C=C\n1cnc(-c2cc(OCCN3CCCC3)cc(C(F)(F)F)c2)n1] |

| | |
|---|---|
| 59 | 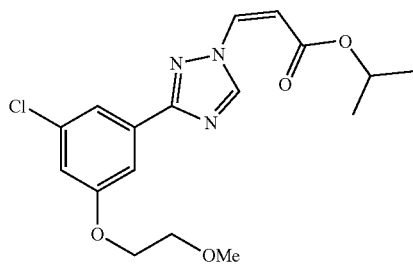 [SMILES: COCCOc1cc(Cl)cc(-c2ncn(/C=C\C(=O)OC(C)C)n2)c1] |
| 60 | 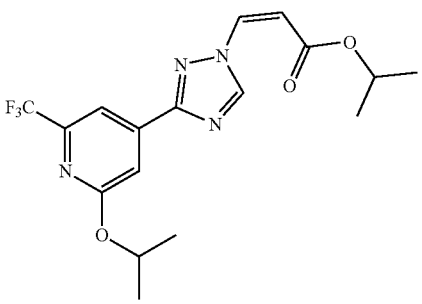 |
| 61 | 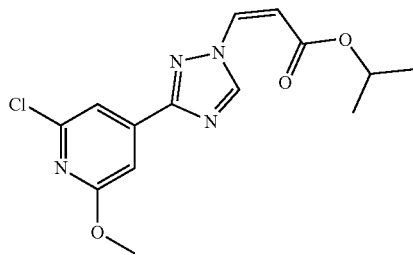 [SMILES: COc1cc(-c2ncn(/C=C\C(=O)OC(C)C)n2)cc(Cl)n1] |
| 62 | 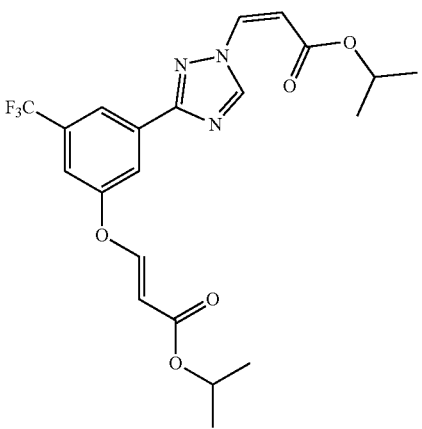 [SMILES: CC(C)OC(=O)/C=C\n1cnc(-c2cc(O/C=C/C(=O)OC(C)C)cc(C(F)(F)F)c2)n1] |
| 63 | 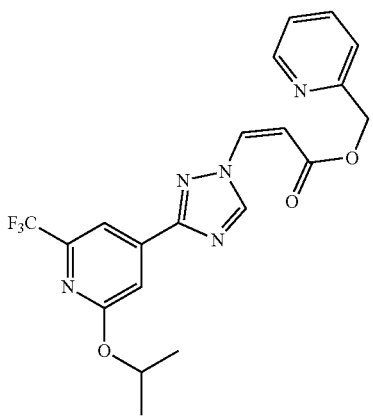 [SMILES: CC(C)Oc1cc(-c2ncn(/C=C\C(=O)OCc3ccccn3)n2)cc(C(F)(F)F)n1] |
| 64 | 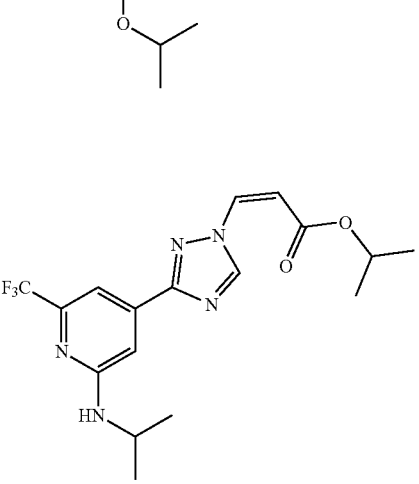 |
| 65 | 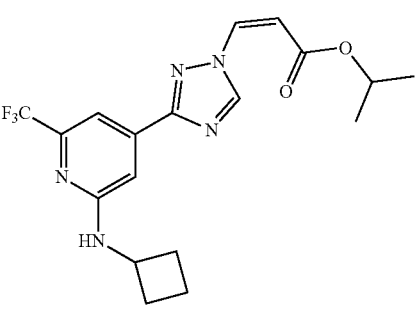 [SMILES: CC(C)OC(=O)/C=C\n1cnc(-c2cc(NC3CCC3)nc(C(F)(F)F)c2)n1] |
| 66 | |

| 67 | 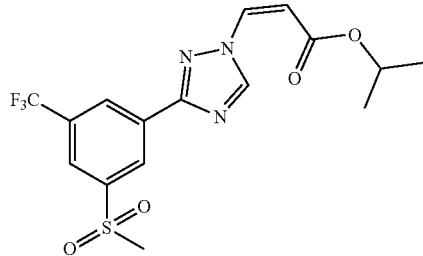 [SMILES: CC(C)OC(=O)/C=C\n1cnc(-c2cc(C(F)(F)F)cc(S(C)(=O)=O)c2)n1] | 73 | 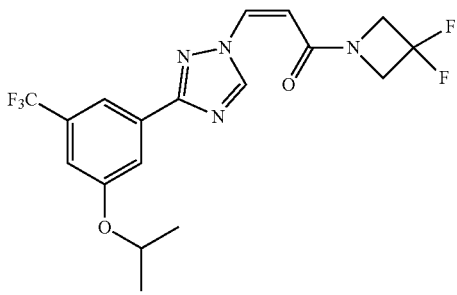 [SMILES: CC(C)Oc1cc(-c2ncn(/C=C\C(=O)N3CC(F)(F)C3)n2)cc(C(F)(F)F)c1] |
| --- | --- | --- | --- |
| 68 | 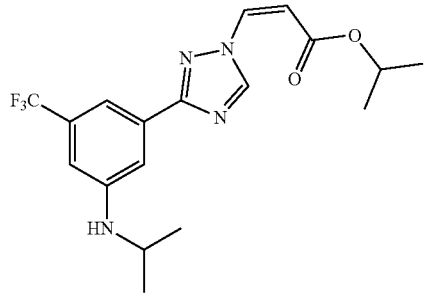 | 74 | 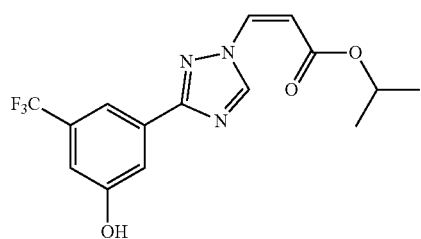 [SMILES: CC(C)OC(=O)/C=C\n1cnc(-c2cc(O)cc(C(F)(F)F)c2)n1] |
| 69 | 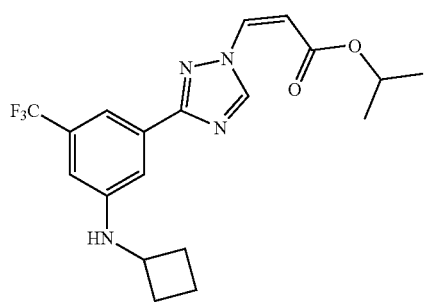 | 75 | 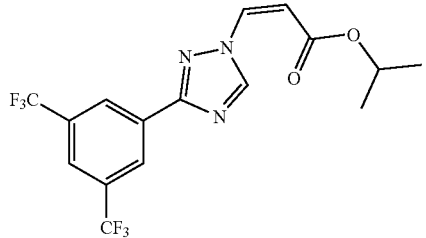 [SMILES: CC(C)OC(=O)/C=C\n1cnc(-c2cc(C(F)(F)F)cc(C(F)(F)F)c2)n1] |
| 70 | 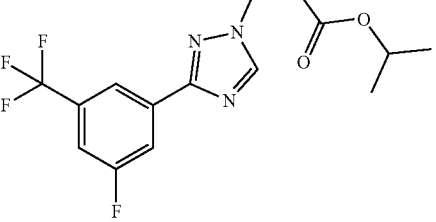 | 76 | 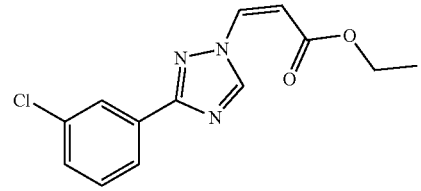 [SMILES: CCOC(=O)/C=C\n1cnc(-c2cccc(Cl)c2)n1] |
| 71 | 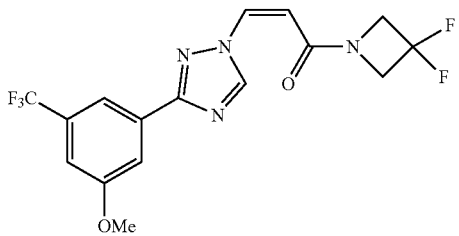 | 77 | 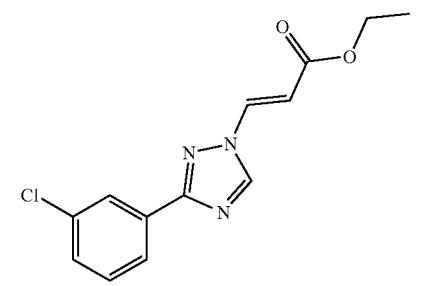 [SMILES: CCOC(=O)/C=C/n1cnc(-c2cccc(Cl)c2)n1] |
| 72 | 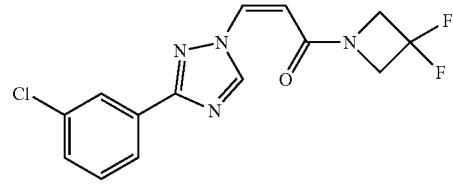 | 78 | 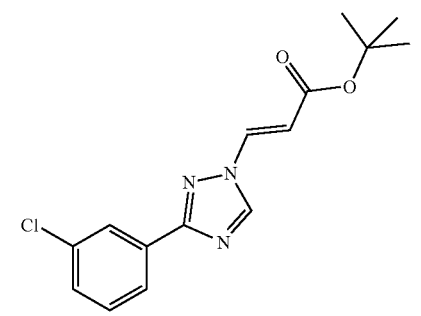 [SMILES: CC(C)(C)OC(=O)/C=C/n1cnc(-c2cccc(Cl)c2)n1] |

| 207 -continued | 208 -continued |
|---|---|
| 79 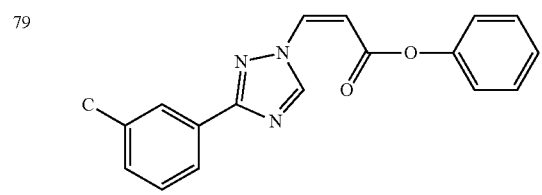 | 86 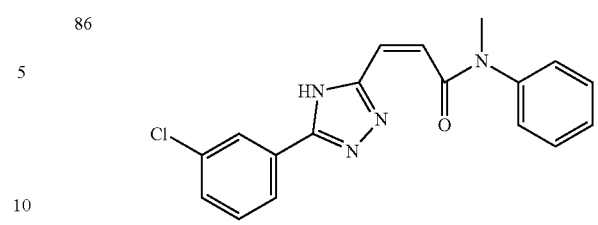 |
| 80 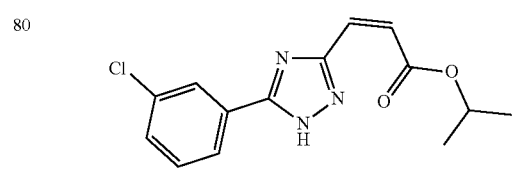 | 87 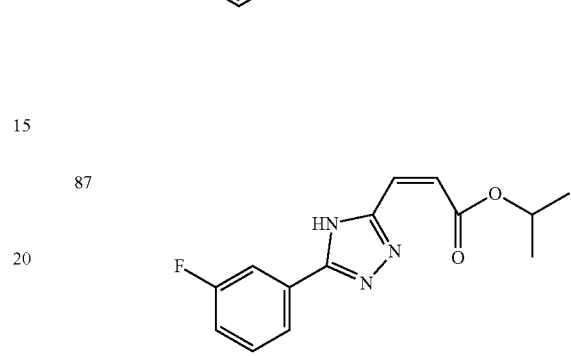 |
| 81 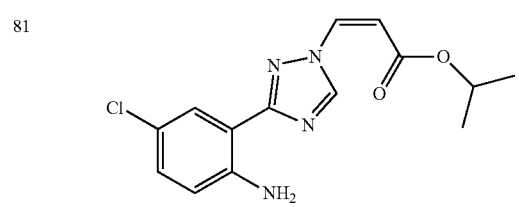 | |
| 82 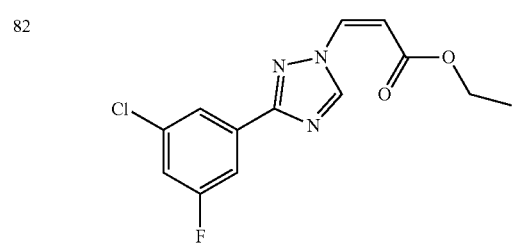 | 88 |
| 83 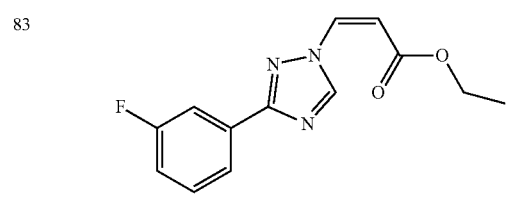 | 89 |
| 84 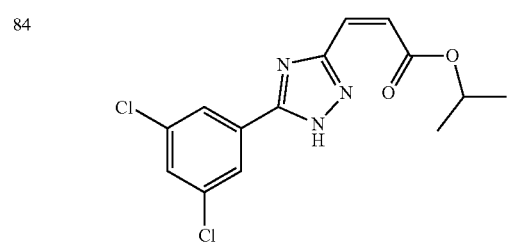 | 90 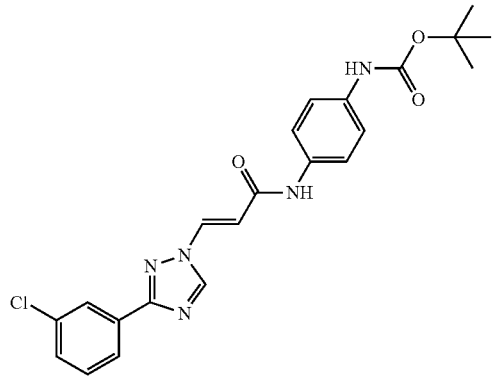 [SMILES: CC(C)(C)OC(=O)Nc1ccc(NC(=O)/C=C/n2cnc(-c3cccc(Cl)c3)n2)cc1] |
| 85 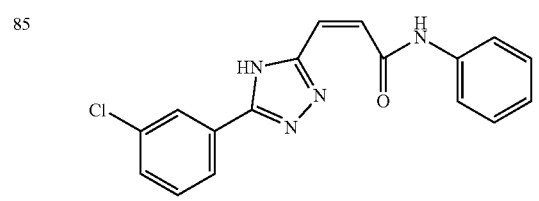 | |

| 92 | 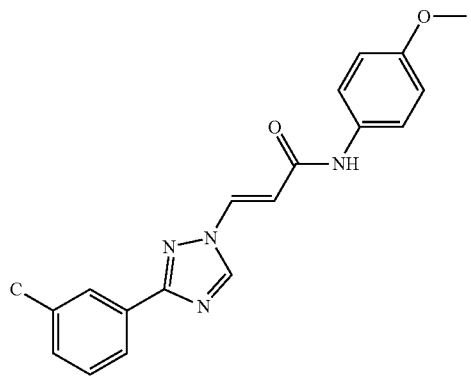 |
|---|---|
| 93 | 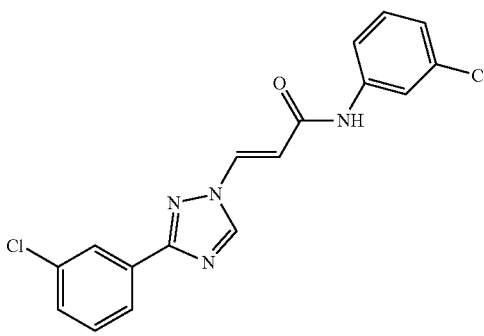 [SMILES: O=C(/C=C/n1cnc(-c2cccc(Cl)c2)n1)Nc1cccc(Cl)c1] |
| 94 | 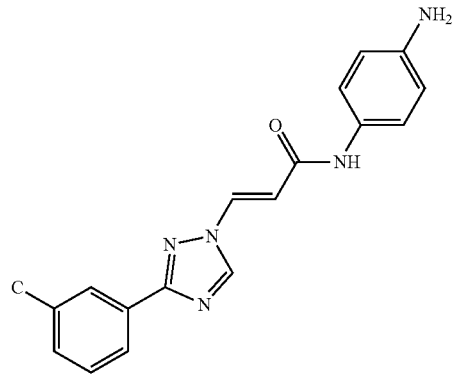 [SMILES: Cc1cccc(-c2ncn(/C=C/C(=O)Nc3ccc(N)cc3)n2)c1] |
| 95 |  |
| 96 | 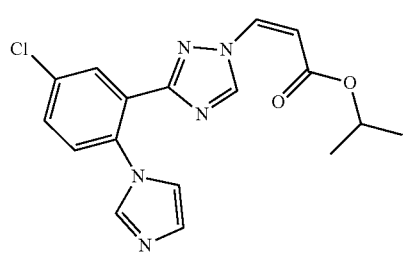 [SMILES: CC(C)OC(=O)/C=C\n1cnc(-c2cc(Cl)ccc2-n2ccnc2)n1] |
| 97 | 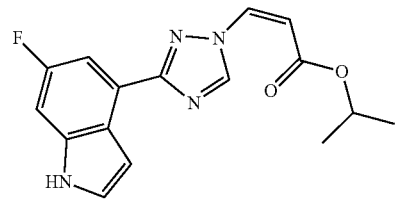 [SMILES: CC(C)OC(=O)/C=C\n1cnc(-c2cc(F)cc3[nH]ccc23)n1] |
|---|---|
| 98 | 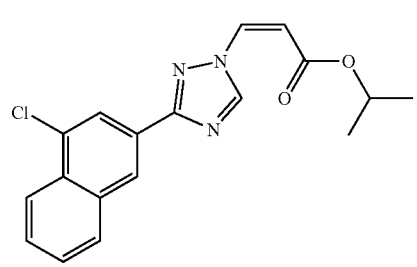 [SMILES: CC(C)OC(=O)/C=C\n1cnc(-c2cc(Cl)c3ccccc3c2)n1] |
| 99 | 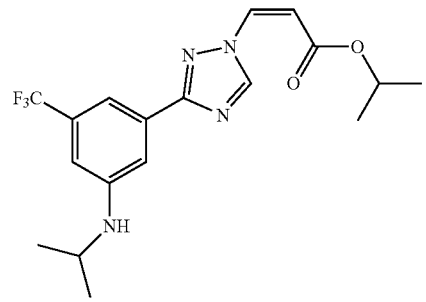 [SMILES: CC(C)Nc1cc(-c2ncn(/C=C\C(=O)OC(C)C)n2)cc(C(F)(F)F)c1] |
| 100 | 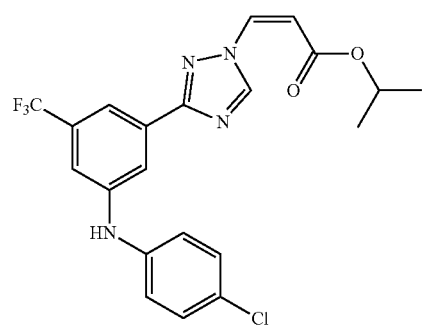 [SMILES: CC(C)OC(=O)/C=C\n1cnc(-c2cc(Nc3ccc(Cl)cc3)cc(C(F)(F)F)c2)n1] |
| 101 | 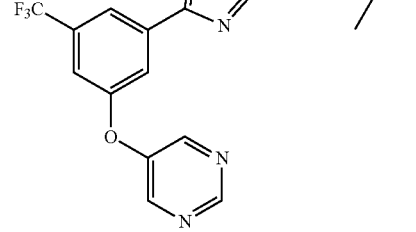 |

| 102 | 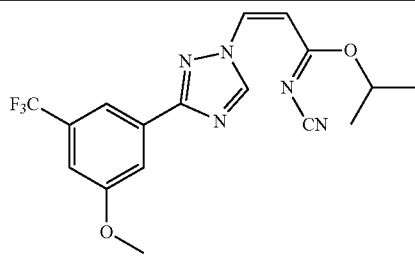 |
| 103 | 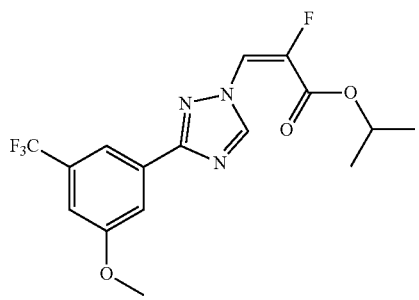 [SMILES: COc1cc(-c2ncn(/C=C(/F)C(=O)OC(C)C)n2)cc(C(F)(F)F)c1] |
| 104 | 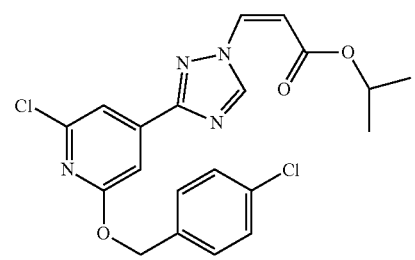 [SMILES: CC(C)OC(=O)/C=C\n1cnc(-c2cc(Cl)nc(OCc3ccc(Cl)cc3)c2)n1] |
| 105 | 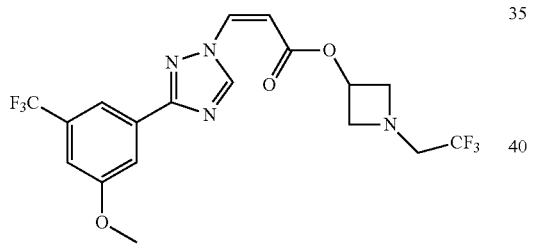 |
| 106 | 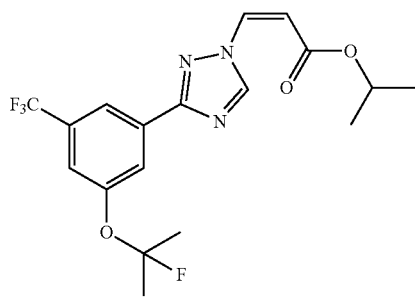 [SMILES: CC(C)OC(=O)/C=C\n1cnc(-c2cc(OC(C)(C)F)cc(C(F)(F)F)c2)n1] |
| 107 | 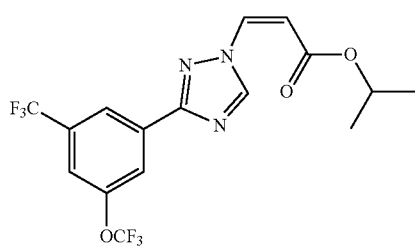 [SMILES: CC(C)OC(=O)/C=C\n1cnc(-c2cc(OC(F)(F)F)cc(C(F)(F)F)c2)n1] |
| 108 | 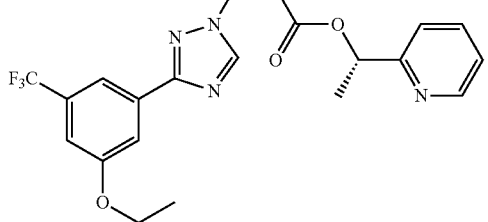 |
| 109 | 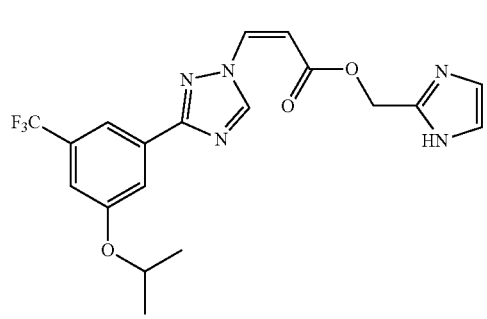 [SMILES: CC(C)Oc1cc(-c2ncn(/C=C\C(=O)OCc3ncc[nH]3)n2)cc(C(F)(F)F)c1] |
| 110 | 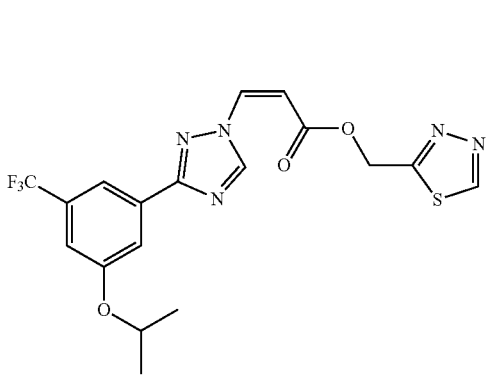 [SMILES: CC(C)Oc1cc(-c2ncn(/C=C\C(=O)OCc3nncs3)n2)cc(C(F)(F)F)c1] |
| 111 | 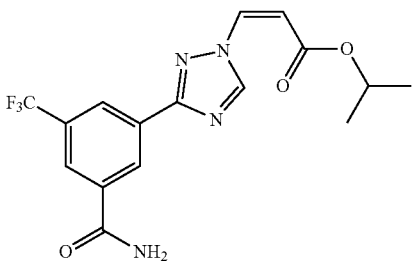 [SMILES: CC(C)OC(=O)/C=C\n1cnc(-c2cc(C(N)=O)cc(C(F)(F)F)c2)n1] |
| 112 | 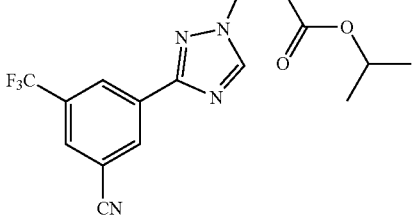 |

| | |
|---|---|
| 113 | 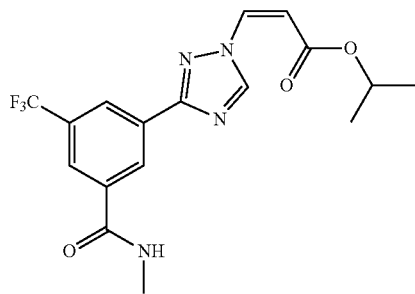 [SMILES: CNC(=O)c1cc(-c2ncn(/C=C\C(=O)OC(C)C)n2)cc(C(F)(F)F)c1] |
| 114 | 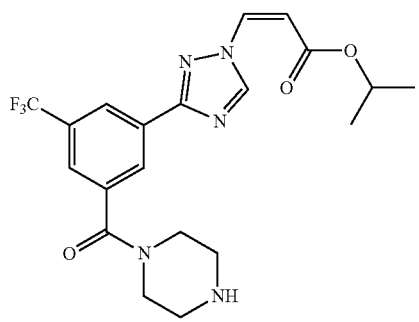 [SMILES: CC(C)OC(=O)/C=C\n1cnc(-c2cc(C(=O)N3CCNCC3)cc(C(F)(F)F)c2)n1] |
| 115 | 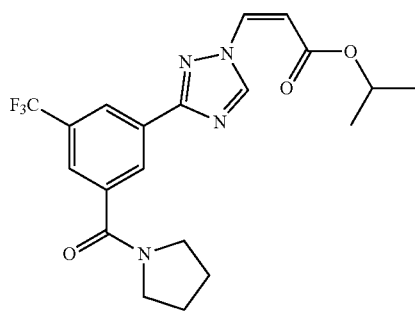 [SMILES: CC(C)OC(=O)/C=C\n1cnc(-c2cc(C(=O)N3CCCC3)cc(C(F)(F)F)c2)n1] |
| 116 | 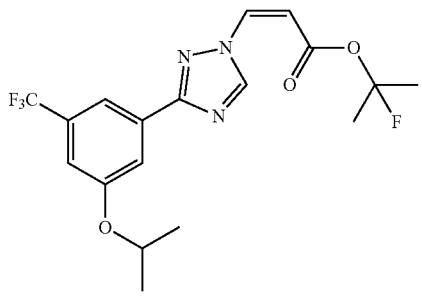 [SMILES: CC(C)Oc1cc(-c2ncn(/C=C\C(=O)OC(C)(C)F)n2)cc(C(F)(F)F)c1] |
| 117 | 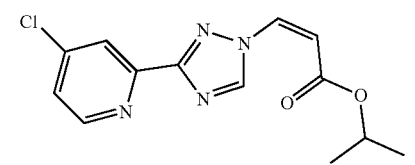 [SMILES: CC(C)OC(=O)/C=C\n1cnc(-c2cc(Cl)ccn2)n1] |
| | |
|---|---|
| 118 | 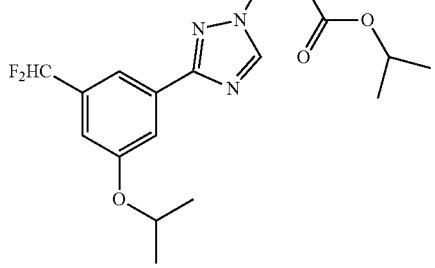 |
| 119 | 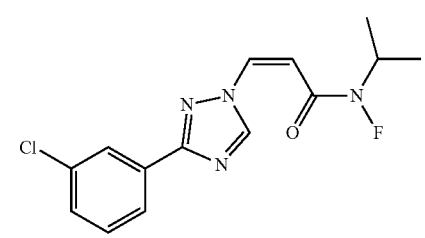 [SMILES: CC(C)N(F)C(=O)/C=C\n1cnc(-c2cccc(Cl)c2)n1] |
| 120 | 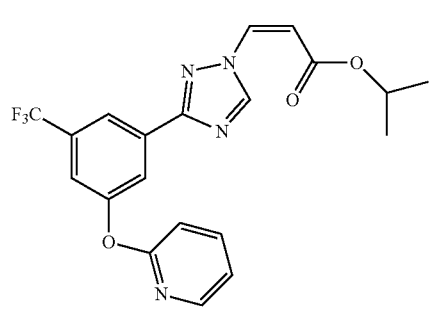 [SMILES: CC(C)OC(=O)/C=C\n1cnc(-c2cc(Oc3ccccn3)cc(C(F)(F)F)c2)n1] |
| 121 | 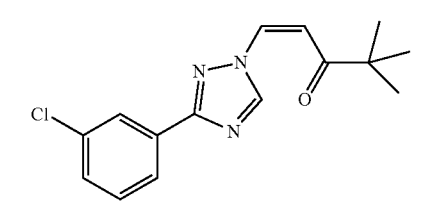 [SMILES: CC(C)(C)C(=O)/C=C\n1cnc(-c2cccc(Cl)c2)n1] |
| 122 | 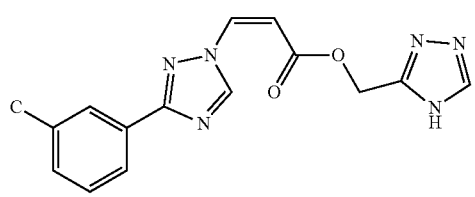 [SMILES: Cc1cccc(-c2ncn(/C=C\C(=O)OCc3nnc[nH]3)n2)c1] |
| 123 | 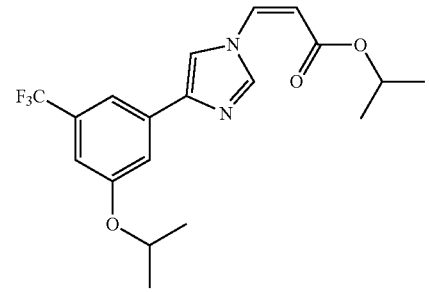 |

-continued

| | |
|---|---|
| 124 | 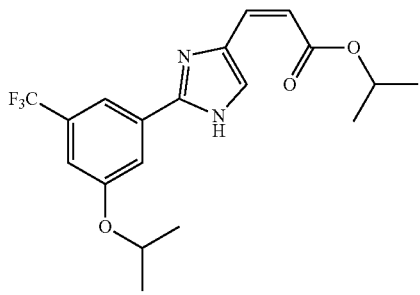 |
| 125 | 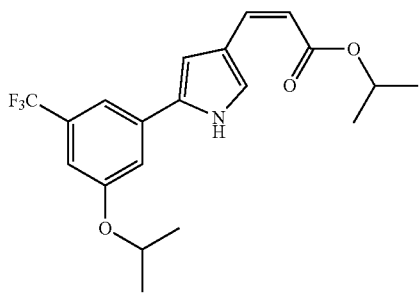 [SMILES: CC(C)OC(=O)/C=C\c1c[nH]c(-c2cc(OC(C)C)cc(C(F)(F)F)c2)n1] |
| 126 | 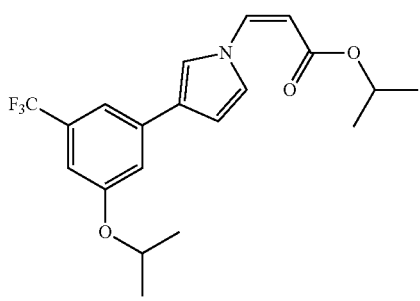 [SMILES: CC(C)OC(=O)/C=C\n1ccc(-c2cc(OC(C)C)cc(C(F)(F)F)c2)c1] |
| 127 | 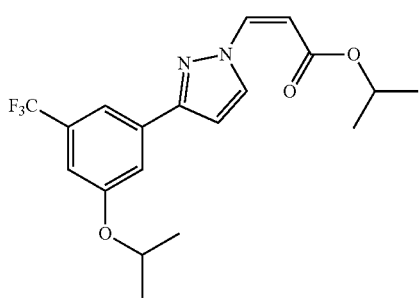 [SMILES: CC(C)OC(=O)/C=C\n1ccc(-c2cc(OC(C)C)cc(C(F)(F)F)c2)n1] |
| 128 | 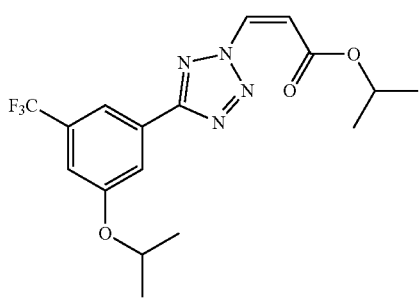 [SMILES: CC(C)OC(=O)/C=C\n1nnc(-c2cc(OC(C)C)cc(C(F)(F)F)c2)n1] |

-continued

| | |
|---|---|
| 129 | 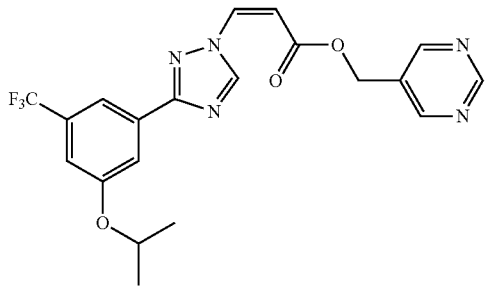 [SMILES: CC(C)Oc1cc(-c2ncn(/C=C\C(=O)OCc3cnccn3)n2)cc(C(F)(F)F)c1] |
| 130 | 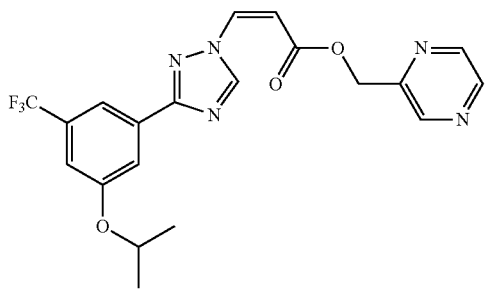 |

| Example | Name |
|---|---|
| 1 | (Z)-3-[3-(3-Chloro-phenyl)-[1,2,4]-triazol-1-yl]-acrylic acid isopropyl ester |
| 2 | (E)-3-[3-(3-Chloro-phenyl)-[1,2,4]-triazol-1-yl]-acrylic acid isopropyl ester |
| 3 | (Z)-isopropyl 3-(3-(4-chlorophenyl)-1H-1,2,4-triazol-1-yl)acrylate |
| 4 | (Z)-isopropyl 3-(3-(2-fluoro-[1,1'-biphenyl]-4-yl)-1H-1,2,4-triazol-1-yl)acrylate |
| 5 | (Z)-isopropyl 3-(3-(3-(trifluoromethyl)phenyl)-1H-1,2,4-triazol-1-yl)acrylate |
| 6 | (Z)-isopropyl 3-(3-(3,4-dichlorophenyl)-1H-1,2,4-triazol-1-yl)acrylate |
| 7 | (Z)-tetrahydrofuran-3-yl 3-(3-(3-chlorophenyl)-1H-1,2,4-triazol-1-yl)acrylate |
| 8 | (Z)-cyclobutyl 3-(3-(3-chlorophenyl)-1H-1,2,4-triazol-1-yl)acrylate |
| 9 | (Z)-pyridin-2-ylmethyl 3-(3-(3-chlorophenyl)-1H-1,2,4-triazol-1-yl)acrylate |
| 10 | (Z)-isopropyl 3-(3-(5-chloro-2-methoxyphenyl)-1H-1,2,4-triazol-1-yl)acrylate |
| 11 | (Z)-isopropyl 3-(3-(3-chloro-5-methoxyphenyl)-1H-1,2,4-triazol-1-yl)acrylate |
| 12 | (Z)-isopropyl 3-(3-(3-chloro-5-isopropoxyphenyl)-1H-1,2,4-triazol-1-yl)acrylate |
| 13 | (Z)-3-[3-(3,5-Dichloro-phenyl)-[1,2,4]triazol-1-yl]-acrylic acid ethyl ester |
| 14 | (Z)-isopropyl 3-(3-(3-chloro-4-methoxyphenyl)-1H-1,2,4-triazol-1-yl)acrylate |
| 15 | (Z)-3-(3-(3-chlorophenyl)-1H-1,2,4-triazol-1-yl)-N-cyclopentylacrylamide |
| 16 | (Z)-5-oxotetrahydrofuran-3-yl 3-(3-(3-chlorophenyl)-1H-1,2,4-triazol-1-yl)acrylate |
| 17 | (Z)-isopropyl 3-(3-(4-(4-chlorophenoxy)phenyl)-1H-1,2,4-triazol-1-yl)acrylate |
| 18 | (Z)-isopropyl 3-(3-(3-chloro-5-(methylamino)phenyl)-1H-1,2,4-triazol-1-yl)acrylate |
| 19 | (Z)-azetidin-3-yl 3-(3-(3-chlorophenyl)-1H-1,2,4-triazol-1-yl)acrylate |
| 20 | (Z)-isopropyl 3-(3-(3,5-dimethoxyphenyl)-1H-1,2,4-triazol-1-yl)acrylate |
| 21 | (Z)-tert-butyl 3-(3-(3-chlorophenyl)-1H-1,2,4-triazol-1-yl)acrylate |
| 22 | (Z)-cyclopentyl 3-(3-(3-chlorophenyl)-1H-1,2,4-triazol-1-yl)acrylate |
| 23 | (Z)-cyclohexyl 3-(3-(3-chlorophenyl)-1H-1,2,4-triazol-1-yl)acrylate |
| 24 | (Z)-isopropyl 3-(3-(5-chlorothiophen-3-yl)-1H-1,2,4-triazol-1-yl)acrylate |

| # | Compound |
|---|---|
| 25 | (Z)-pyrrolidin-2-ylmethyl 3-(3-(3-chlorophenyl)-1H-1,2,4-triazol-1-yl)acrylate |
| 26 | (Z)-isopropyl 3-(3-(3-methoxy-5-(trifluoromethyl)phenyl)-1H-1,2,4-triazol-1-yl)acrylate |
| 27 | (Z)-isopropyl 3-(3-(3-chloro-5-(4-chlorophenoxy)phenyl)-1H-1,2,4-triazol-1-yl)acrylate |
| 28 | (Z)-isopropyl 3-(3-(2,6-dichlorophenyl)-4-yl)-1H-1,2,4-triazol-1-yl)acrylate |
| 29 | (Z)-3-(3-(3-chlorophenyl)-1H-1,2,4-triazol-1-yl)acrylonitrile |
| 30 | (Z)-3-(3-chlorophenyl)-1-(2-(methylsulfonyl)vinyl)-1H-1,2,4-triazole |
| 31 | (Z)-ethyl 3-(3-(3-chloro-5-methoxyphenyl)-1H-1,2,4-triazol-1-yl)acrylate |
| 32 | (Z)-methyl 3-(3-(3-chloro-5-methoxyphenyl)-1H-1,2,4-triazol-1-yl)acrylate |
| 33 | (Z)-methyl 3-(3-(3-chloro-5-methoxyphenyl)-1H-1,2,4-triazol-1-yl)acrylate |
| 34 | (Z)-(1H-imidazol-5-yl)methyl 3-(3-(3-chlorophenyl)-1H-1,2,4-triazol-1-yl)acrylate |
| 35 | (Z)-isopropyl 3-(3-(5-chloropyridin-3-yl)-1H-1,2,4-triazol-1-yl)acrylate |
| 36 | (Z)-1-(azetidin-1-yl)-3-(3-(3-chlorophenyl)-1H-1,2,4-triazol-1-yl)prop-2-en-1-one |
| 37 | (Z)-isopropyl 3-(3-(m-tolyl)-1H-1,2,4-triazol-1-yl)acrylate |
| 38 | (Z)-isopropyl 3-(3-(3-chloro-5-(trifluoromethyl)phenyl)-1H-1,2,4-triazol-1-yl)acrylate |
| 39 | (Z)-isopropyl 3-(3-(2-chloro-6-isopropoxypyridin-4-yl)-1H-1,2,4-triazol-1-yl)acrylate |
| 40 | (Z)-isopropyl 4-(3-(3-chlorophenyl)-1H-1,2,4-triazol-1-yl)but-2-enoate |
| 41 | (E)-isopropyl 4-(3-(3-chlorophenyl)-1H-1,2,4-triazol-1-yl)but-2-enoate |
| 42 | (E)-3-(3-(3-chlorophenyl)-1H-1,2,4-triazol-1-yl)acrylonitrile |
| 43 | (Z)-tetrahydro-2H-pyran-4-yl 3-(3-(3-chlorophenyl)-1H-1,2,4-triazol-1-yl)acrylate |
| 44 | (Z)-isopropyl 3-(3-(3-isopropoxy-5-(trifluoromethyl)phenyl)-1H-1,2,4-triazol-1-yl)acrylate |
| 45 | (Z)-isopropyl 3-(3-(3-(2-(dimethylamino)ethoxy)-5-(trifluoromethyl)phenyl)-1H-1,2,4-triazol-1-yl)acrylate |
| 46 | (E)-isopropyl 3-(3-(3-(2-dimethylamino)ethoxy)-5-(trifluoromethyl)phenyl)-1H-1,2,4-triazol-1-yl)acrylate |
| 47 | (Z)-3-(3-chlorophenyl)-1-(3,3,3-trifluoroprop-1-en-1-yl)-1H-1,2,4-triazole |
| 48 | (Z)-azetidin-3-yl 3-(3-(3-methoxy-5-(trifluoromethyl)phenyl)-1H-1,2,4-triazol-1-yl)acrylate |
| 49 | (Z)-oxetan-3-yl 3-(3-(3-chlorophenyl)-1H-1,2,4-triazol-1-yl)acrylate |
| 50 | (Z)-isopropyl 3-(3-(3-cyano-5-isopropoxyphenyl)-1H-1,2,4-triazol-1-yl)acrylate |
| 51 | (Z)-azetidin-3-yl 3-(3-(2,6-dichloropyridin-4-yl)-1H-1,2,4-triazol-1-yl)acrylate |
| 52 | (Z)-isopropyl 3-(3-(2-chloro-6-(isopropylamino)pyridin-4-yl)-1H-1,2,4-triazol-1-yl)acrylate |
| 53 | (Z)-3-(3-(3-isopropoxy-5-(trifluoromethyl)phenyl)-1H-1,2,4-triazol-1-yl)acrylonitrile |
| 54 | (E)-azetidin-3-yl 3-(3-(3-chlorophenyl)-1H-1,2,4-triazol-1-yl)acrylate |
| 55 | (E)-isopropyl 3-(3-(2-(pyrrolidin-1-yl)ethoxy)-5-(trifluoromethyl)phenyl)-1H-1,2,4-triazol-1-yl)acrylate |
| 56 | (Z)-isopropyl 3-(3-(2-chlorothiazol-4-yl)-1H-1,2,4-triazol-1-yl)acrylate |
| 57 | (Z)-isopropyl 3-(3-(2-bromothiazol-4-yl)-1H-1,2,4-triazol-1-yl)acrylate |
| 58 | (Z)-isopropyl 3-(3-(3-(2-(pyrrolidin-1-yl)ethoxy)-5-(trifluoromethyl)phenyl)-1H-1,2,4-triazol-1-yl)acrylate |
| 59 | (Z)-isopropyl 3-(3-(3-chloro-5-(2-methoxyethoxy)phenyl)-1H-1,2,4-triazol-1-yl)acrylate |
| 60 | (Z)-isopropyl 3-(3-(2-isopropoxy-6-(trifluoromethyl)pyridin-4-yl)-1H-1,2,4-triazol-1-yl)acrylate |
| 61 | (Z)-isopropyl 3-(3-(2-chloro-6-methoxypyridin-4-yl)-1H-1,2,4-triazol-1-yl)acrylate |
| 62 | (E)-isopropyl 3-(3-(1-((Z)-3-isopropoxy-3-oxoprop-1-en-1-yl)-1H-1,2,4-triazol-3-yl)-5-(trifluoromethyl)phenoxy)acrylate |
| 63 | (Z)-pyridin-2-ylmethyl 3-(3-(2-isopropoxy-6-(trifluoromethyl)pyridin-4-yl)-1H-1,2,4-triazol-1-yl)acrylate |
| 64 | (Z)-pyridin-2-ylmethyl 3-(3-(3-isopropoxy-5-(trifluoromethyl)phenyl)-1H-1,2,4-triazol-1-yl)acrylate |
| 65 | (Z)-isopropyl 3-(3-(2-(isopropylamino)-6-(trifluoromethyl)pyridin-4-yl)-1H-1,2,4-triazol-1-yl)acrylate |
| 66 | (Z)-isopropyl 3-(3-(2-(cyclobutylamino)-6-(trifluoromethyl)pyridin-4-yl)-1H-1,2,4-triazol-1-yl)acrylate |
| 67 | (Z)-isopropyl 3-(3-(3-(methylsulfonyl)-5-(trifluoromethyl)phenyl)-1H-1,2,4-triazol-1-yl)acrylate |
| 68 | (Z)-isopropyl 3-(3-(3-(isopropylamino)-5-(trifluoromethyl)phenyl)-1H-1,2,4-triazol-1-yl)acrylate |
| 69 | (Z)-isopropyl 3-(3-(3-(cyclobutylamino)-5-(trifluoromethyl)phenyl)-1H-1,2,4-triazol-1-yl)acrylate |
| 70 | (Z)-isopropyl 3-(3-(3-fluoro-5-(trifluoromethyl)phenyl)-1H-1,2,4-triazol-1-yl)acrylate |
| 71 | (Z)-1-(3,3-difluoroazetidin-1-yl)-3-(3-(3-methoxy-5-(trifluoromethyl)phenyl)-1H-1,2,4-triazol-1-yl)prop-2-en-1-one |
| 72 | (Z)-3-(3-(3-chlorophenyl)-1H-1,2,4-triazol-1-yl)-1-(3,3-difluoroazetidin-1-yl)prop-2-en-1-one |
| 73 | (Z)-1-(3,3-difluoroazetidin-1-yl)-3-(3-(3-isopropoxy-5-(trifluoromethyl)phenyl)-1H-1,2,4-triazol-1-yl)prop-2-en-1-one |
| 74 | (Z)-isopropyl 3-(3-(3-hydroxy-5-(trifluoromethyl)phenyl)-1H-1,2,4-triazol-1-yl)acrylate |
| 75 | (Z)-isopropyl 3-(3-(3,5-bis(trifluoromethyl)phenyl)-1H-1,2,4-triazol-1-yl)acrylate |
| 76 | (Z)-3-[3-(3-Chloro-phenyl)-[1,2,4]-triazol-1-yl]-acrylic acid ethyl ester |
| 77 | (E)-3-[3-(3-Chloro-phenyl)-[1,2,4]-triazol-1-yl]-acrylic acid ethyl ester |
| 78 | (E)-3-[3-(3-Chloro-phenyl)-[1,2,4]-triazol-1-yl]-acrylic acid tert-butyl ester |
| 79 | (Z)-3-[3-(3-Chloro-phenyl)-[1,2,4]triazol-1-yl]-acrylic acid phenyl ester |
| 80 | (Z)-3-[5-(3-Chloro-phenyl)-1H-[1,2,4]triazol-3-yl]-acrylic acid isopropyl ester |
| 81 | 3-[3-(2-Amino-5-chloro-phenyl)-[1,2,4]triazol-1-yl]-acrylic acid isopropyl ester |
| 82 | 3-[3-(3-Chloro-5-fluoro-phenyl)-[1,2,4]triazol-1-yl]-acrylic acid ethyl ester |
| 83 | 3-[3-(3-Fluoro-phenyl)-[1,2,4]triazol-1-yl]-acrylic acid ethyl ester |
| 84 | (Z)-isopropyl 3-(5-(3,5-dichlorophenyl)-1H-1,2,4-triazol-3-yl)acrylate |
| 85 | (Z)-3-(5-(3-chlorophenyl)-4H-1,2,4-triazol-3-yl)-N-phenylacrylamide |
| 86 | (Z)-3-(5-(3-chlorophenyl)-4H-1,2,4-triazol-3-yl)-N-methyl-N-phenylacrylamide |
| 87 | (Z)-isopropyl 3-(5-(3-fluorophenyl)-4H-1,2,4-triazol-3-yl)acrylate |
| 88 | (Z)-ethyl 3-(3-(3,5-dichlorophenyl)-1H-1,2,4-triazol-1-yl)acrylate |
| 89 | (Z)-ethyl 3-(3-(3,5-difluorophenyl)-1H-1,2,4-triazol-1-yl)acrylate |
| 90 | (E)-tert-butyl (4-(3-(3-(3-chlorophenyl)-1H-1,2,4-triazol-1-yl)acrylamido)phenyl)carbamate |
| 92 | (E)-3-(3-(3-chlorophenyl)-1H-1,2,4-triazol-1-yl)-N-(4-methoxyphenyl)acrylamide |
| 93 | (E)-N-(3 Chloro-phenyl)-3-[3-(3-chloro-phenyl)-[1,2,4]-triazol-1-yl]-acryl amide |
| 94 | (E)-N-(4-Amino-phenyl)-3-[3-(3-chloro-phenyl)-[1,2,4]-triazol-1-yl]-acryl amide |
| 95 | 3-[5-(3-Chloro-phenyl)-1H-[1,2,4]triazol-3-yl]-N-isopropyl-N-methyl-acrylamide |
| 96 | (Z)-isopropyl 3-(3-(5-chloro-2-(1H-imidazol-1-yl)phenyl)-1H-1,2,4-triazol-1-yl)acrylate |
| 97 | (Z)-isopropyl 3-(3-(6-fluoro-1H-indol-4-yl)-1H-1,2,4-triazol-1-yl)acrylate |
| 98 | (Z)-isopropyl 3-(3-(4-chloronaphthalen-2-yl)-1H-1,2,4-triazol-1-yl)acrylate |
| 99 | (Z)-isopropyl 3-(3-(3-(isopropylamino)-5-(trifluoromethyl)phenyl)-1H-1,2,4-triazol-1-yl)acrylate |
| 100 | (Z)-isopropyl 3-(3-(3-((4-chlorophenyl)amino)-5-(trifluoromethyl)phenyl)-1H-1,2,4-triazol-1-yl)acrylate |
| 101 | (Z)-isopropyl 3-(3-(3-(pyrimidin-5-yloxy)-5-(trifluoromethyl)phenyl)-1H-1,2,4-triazol-1-yl)acrylate |
| 102 | (1Z,2Z)-isopropyl N-cyano-3-(3-(3-methoxy-5-(trifluoromethyl)phenyl)-1H-1,2,4-triazol-1-yl)acrylimidate |

-continued

| | |
|---|---|
| 103 | (E)-isopropyl 2-fluoro-3-(3-(3-methoxy-5-(trifluoromethyl)phenyl)-1H-1,2,4-triazol-1-yl)acrylate |
| 104 | (Z)-isopropyl 3-(3-(2-chloro-6-((4-chlorobenzyl)oxy)pyridin-4-yl)-1H-1,2,4-triazol-1-yl)acrylate |
| 105 | (Z)-1-(2,2,2-trifluoroethyl)azetidin-3-yl 3-(3-(3-methoxy-5-(trifluoromethyl)phenyl)-1H-1,2,4-triazol-1-yl)acrylate |
| 106 | (Z)-isopropyl 3-(3-(3-((2-fluoropropan-2-yl)oxy)-5-(trifluoromethyl)phenyl)-1H-1,2,4-triazol-1-yl)acrylate |
| 107 | (Z)-isopropyl 3-(3-(3-(trifluoromethoxy)-5-(trifluoromethyl)phenyl)-1H-1,2,4-triazol-1-yl)acrylate |
| 108 | (S,Z)-1-(pyridin-2-yl)ethyl 3-(3-(3-isopropoxy-5-(trifluoromethyl)phenyl)-1H-1,2,4-triazol-1-yl)acrylate |
| 109 | (Z)-(1H-imidazol-2-yl)methyl 3-(3-(3-isopropoxy-5-(trifluoromethyl)phenyl)-1H-1,2,4-triazol-1-yl)acrylate |
| 110 | (Z)-(1,3,4-thiadiazol-2-yl)methyl 3-(3-(3-isopropoxy-5-(trifluoromethyl)phenyl)-1H-1,2,4-triazol-1-yl)acrylate |
| 111 | (Z)-isopropyl 3-(3-(3-carbamoyl-5-(trifluoromethyl)phenyl)-1H-1,2,4-triazol-1-yl)acrylate |
| 112 | (Z)-isopropyl 3-(3-(3-cyano-5-(trifluoromethyl)phenyl)-1H-1,2,4-triazol-1-yl)acrylate |
| 113 | (Z)-isopropyl 3-(3-(3-(methylcarbamoyl)-5-(trifluoromethyl)phenyl)-1H-1,2,4-triazol-1-yl)acrylate |
| 114 | (Z)-isopropyl 3-(3-(3-(piperazine-1-carbonyl)-5-(trifluoromethyl)phenyl)-1H-1,2,4-triazol-1-yl)acrylate |
| 115 | (Z)-isopropyl 3-(3-(3-(pyrrolidine-1-carbonyl)-5-(trifluoromethyl)phenyl)-1H-1,2,4-triazol-1-yl)acrylate |
| 116 | (Z)-2-fluoropropan-2-yl 3-(3-(3-isopropoxy-5-(trifluoromethyl)phenyl)-1H-1,2,4-triazol-1-yl)acrylate |
| 117 | (Z)-isopropyl 3-(3-(4-chloropyridin-2-yl)-1H-1,2,4-triazol-1-yl)acrylate |
| 118 | (Z)-isopropyl 3-(3-(3-(difluoromethyl)-5-isopropoxyphenyl)-1H-1,2,4-triazol-1-yl)acrylate |
| 119 | (Z)-3-(3-(3-chlorophenyl)-1H-1,2,4-triazol-1-yl)-N-fluoro-N-isopropylacrylamide |
| 120 | (Z)-isopropyl 3-(3-(3-(pyridin-2-yloxy)-5-(trifluoromethyl)phenyl)-1H-1,2,4-triazol-1-yl)acrylate |
| 121 | (Z)-1-(3-(3-chlorophenyl)-1H-1,2,4-triazol-1-yl)-4,4-dimethylpent-1-en-3-one |
| 122 | (Z)-(4H-1,2,4-triazol-3-yl)methyl 3-(3-(3-chlorophenyl)-1H-1,2,4-triazol-1-yl)acrylate |
| 123 | (Z)-isopropyl 3-(4-(3-isopropoxy-5-(trifluoromethyl)phenyl)-1H-imidazol-1-yl)acrylate |
| 124 | (Z)-isopropyl 3-(2-(3-isopropoxy-5-(trifluoromethyl)phenyl)-1H-imidazole-4-yl)acrylate |
| 125 | (Z)-isopropyl 3-(5-(3-isopropoxy-5-(trifluoromethyl)phenyl)-1H-pyrrol-3-yl)acrylate |
| 126 | (Z)-isopropyl 3-(3-(3-isopropoxy-5-(trifluoromethyl)phenyl)-1H-pyrrol-1-yl)acrylate |
| 127 | (Z)-isopropyl 3-(3-(3-isopropoxy-5-(trifluoromethyl)phenyl)-1H-pyrazol-1-yl)acrylate |
| 128 | (Z)-isopropyl 3-(5-(3-isopropoxy-5-(trifluoromethyl)phenyl)-2H-tetrazol-2-yl)acrylate |
| 129 | (Z)-pyrimidin-5-ylmethyl 3-(3-(3-isopropoxy-5-(trifluoromethyl)phenyl)-1H-1,2,4-triazol-1-yl)acrylate |
| 130 | pyrazin-2-ylmethyl (Z)-3-(3-(3-isopropoxy-5-(trifluoromethyl)phenyl)-1H-1,2,4-triazol-1-yl)acrylate |

| Compound | Structure |
|---|---|
| B-1 | 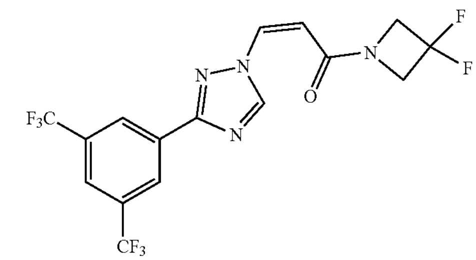 [SMILES: O=C(/C=C\n1cnc(-c2cc(C(F)(F)F)cc(C(F)(F)F)c2)n1)N1CC(F)(F)C1] |
| B-2 | 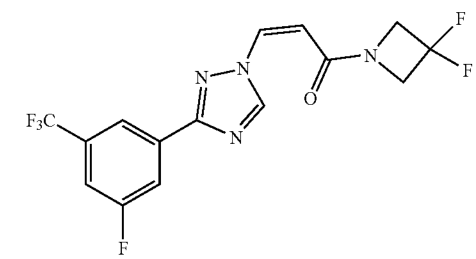 [SMILES: O=C(/C=C\n1cnc(-c2cc(F)cc(C(F)(F)F)c2)n1)N1CC(F)(F)C1] |
| B-3 | 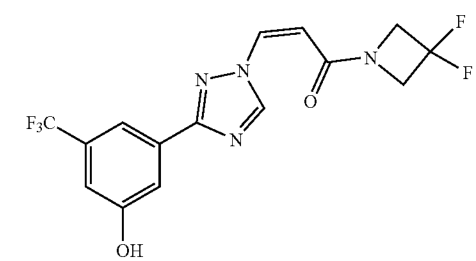 [SMILES: O=C(/C=C\n1cnc(-c2cc(O)cc(C(F)(F)F)c2)n1)N1CC(F)(F)C1] |
| B-4 | 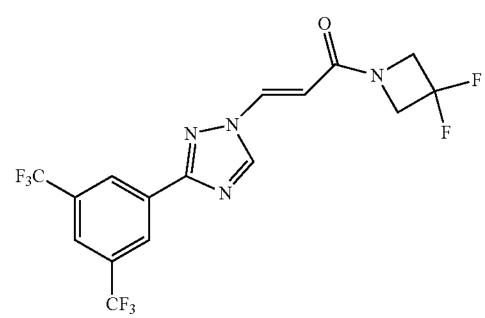 [SMILES: O=C(/C=C/n1cnc(-c2cc(C(F)(F)F)cc(C(F)(F)F)c2)n1)N1CC(F)(F)C1] |
| B-5 | 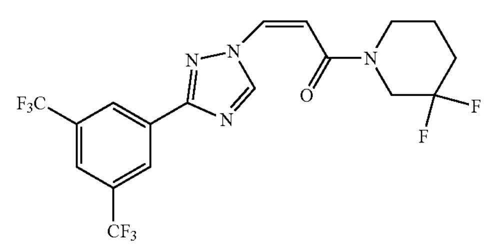 [SMILES: O=C(/C=C\n1cnc(-c2cc(C(F)(F)F)cc(C(F)(F)F)c2)n1)N1CCCC(F)(F)C1] |
| B-6 | 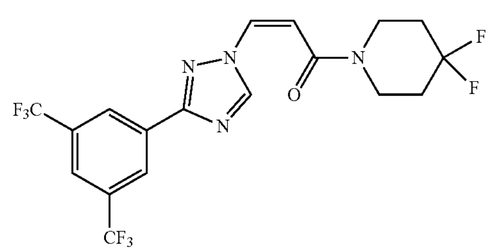 [SMILES: O=C(/C=C\n1cnc(-c2cc(C(F)(F)F)cc(C(F)(F)F)c2)n1)N1CCC(F)(F)CC1] |

-continued
B-7
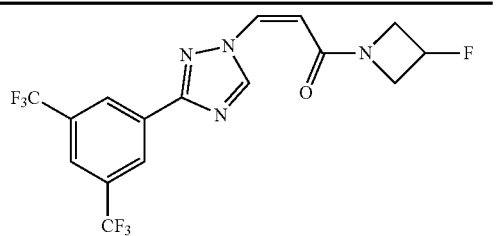
B-13
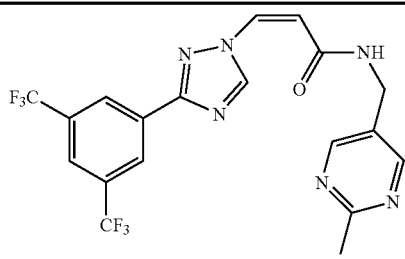
B-8
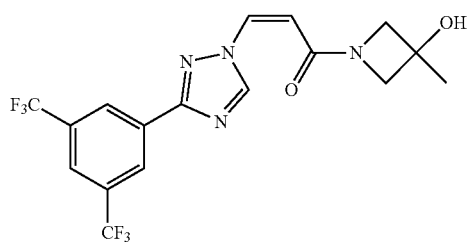 [SMILES: CC1(O)CN(C(=O)/C=C\n2cnc(-c3cc(C(F)(F)F)cc(C(F)(F)F)c3)n2)C1]
B-14
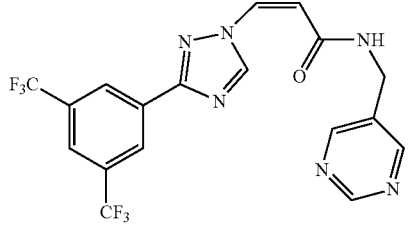
B-9
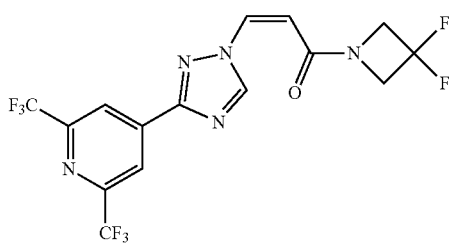 [SMILES: O=C(/C=C\n1cnc(-c2cc(C(F)(F)F)nc(C(F)(F)F)c2)n1)N1CC(F)(F)C1]
B-15
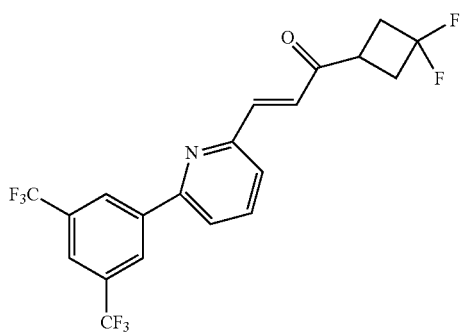
B-10
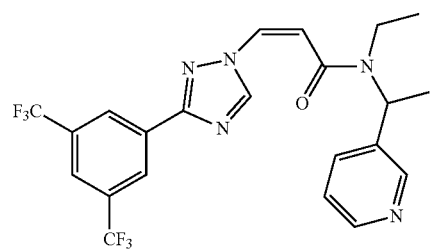 [SMILES: CCN(C(=O)/C=C\n1cnc(-c2cc(C(F)(F)F)cc(C(F)(F)F)c2)n1)C(C)c1cccnc1]
B-16
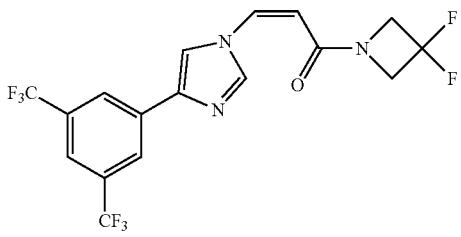
B-11
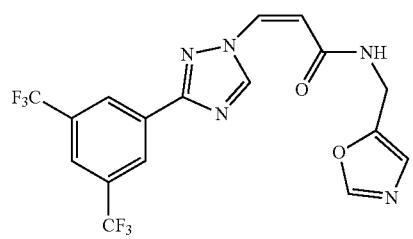 [SMILES: O=C(/C=C\n1cnc(-c2cc(C(F)(F)F)cc(C(F)(F)F)c2)n1)NCc1cnco1]
B-17
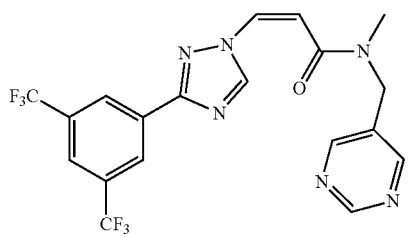
B-12
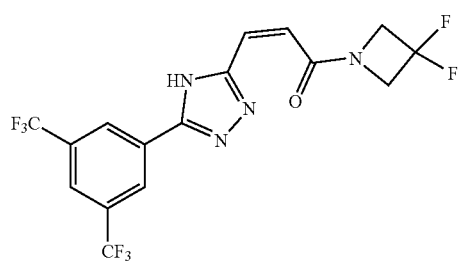 [SMILES: O=C(/C=C\c1nnc(-c2cc(C(F)(F)F)cc(C(F)(F)F)c2)[nH]1)N1CC(F)(F)C1]
B-18
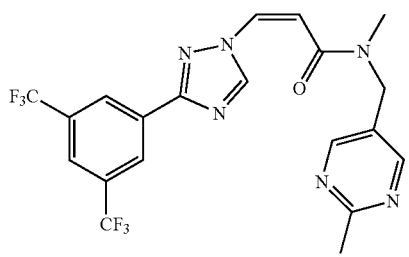 [SMILES: Cc1ncc(CN(C)C(=O)/C=C\n2cnc(-c3cc(C(F)(F)F)cc(C(F)(F)F)c3)n2)cn1]

| | |
|---|---|
| B-19 | 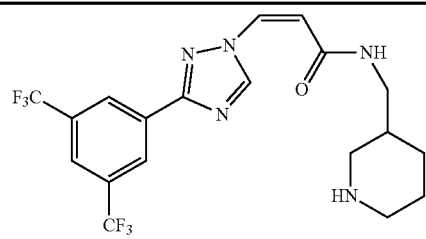 |
| B-20 | 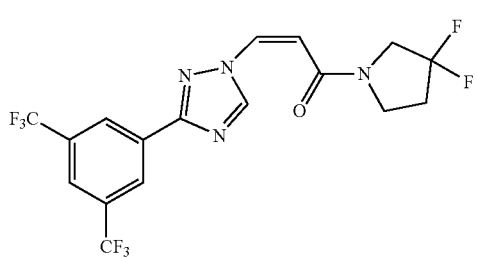 [SMILES: O=C(/C=C\n1cnc(-c2cc(C(F)(F)F)cc(C(F)(F)F)c2)n1)N1CCC(F)(F)C1] |
| B-21 | 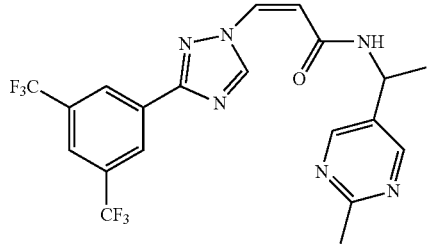 [SMILES: Cc1ncc(C(C)NC(=O)/C=C\n2cnc(-c3cc(C(F)(F)F)cc(C(F)(F)F)c3)n2)cn1] |
| B-22 | 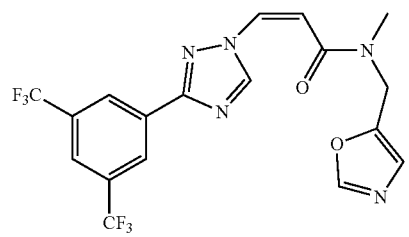 [SMILES: CN(Cc1cnco1)C(=O)/C=C\n1cnc(-c2cc(C(F)(F)F)cc(C(F)(F)F)c2)n1] |
| B-23 | 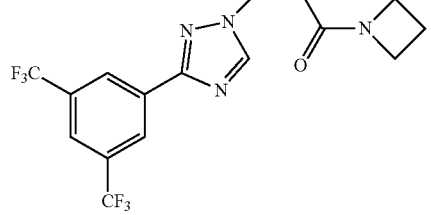 |
| B-24 | 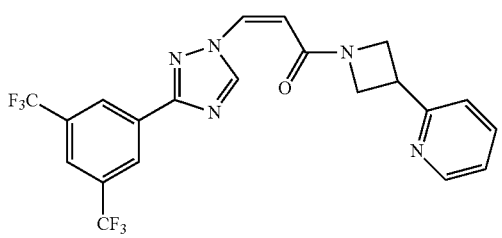 [SMILES: O=C(/C=C\n1cnc(-c2cc(C(F)(F)F)cc(C(F)(F)F)c2)n1)N1CC(c2ccccn2)C1] |
| B-25 | 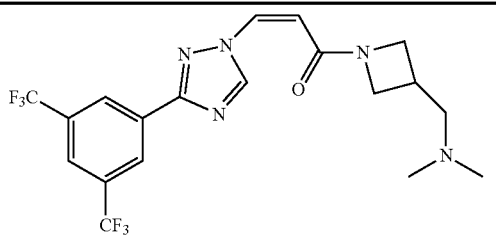 |
| B-26 | 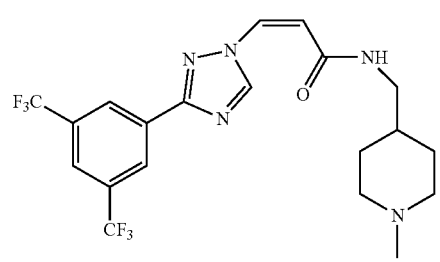 [SMILES: CN1CCC(CNC(=O)/C=C\n2cnc(-c3cc(C(F)(F)F)cc(C(F)(F)F)c3)n2)CC1] |
| B-27 | 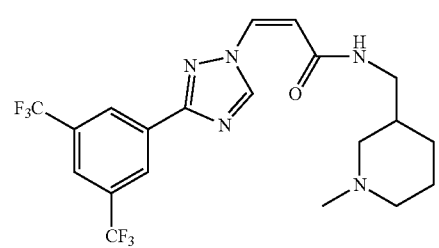 [SMILES: CN1CCCC(CNC(=O)/C=C\n2cnc(-c3cc(C(F)(F)F)cc(C(F)(F)F)c3)n2)C1] |
| B-28 | 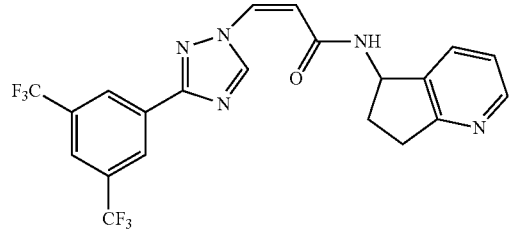 [SMILES: O=C(/C=C\n1cnc(-c2cc(C(F)(F)F)cc(C(F)(F)F)c2)n1)NC1CCc2ncccc21] |
| B-29 | 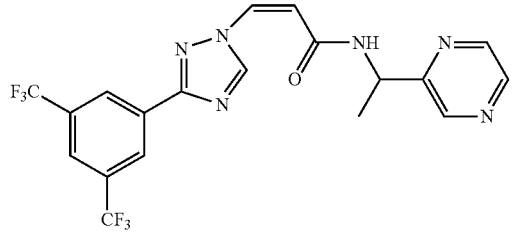 [SMILES: CC(NC(=O)/C=C\n1cnc(-c2cc(C(F)(F)F)cc(C(F)(F)F)c2)n1)c1cnccn1] |
| B-30 | 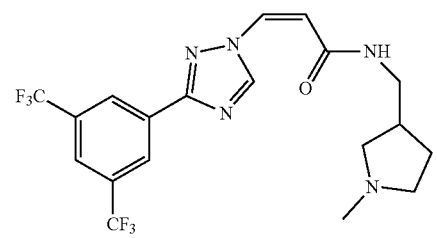 [SMILES: CN1CCC(CNC(=O)/C=C\n2cnc(-c3cc(C(F)(F)F)cc(C(F)(F)F)c3)n2)C1] |

-continued
B-31 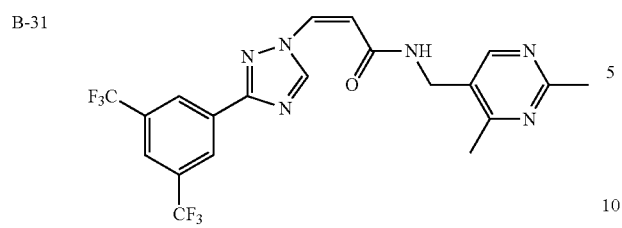
B-32 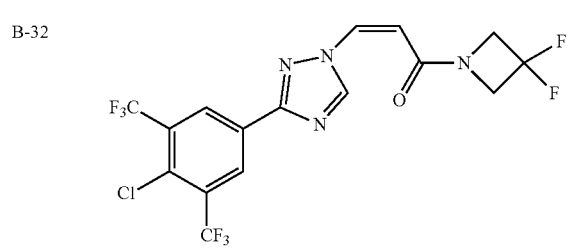
B-33 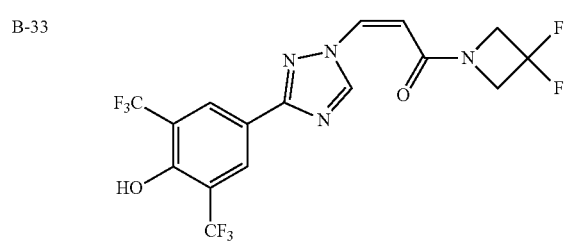
B-34 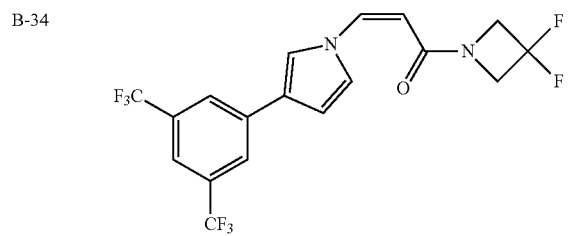
B-35 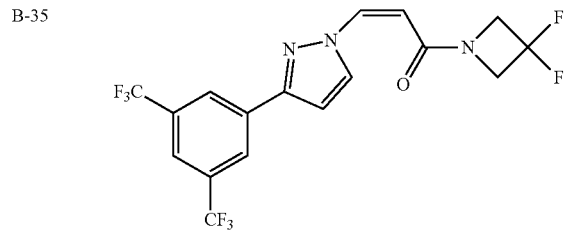
B-36 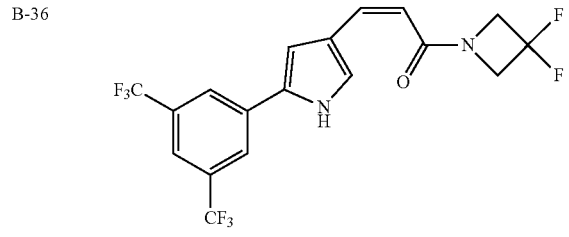
-continued
B-37 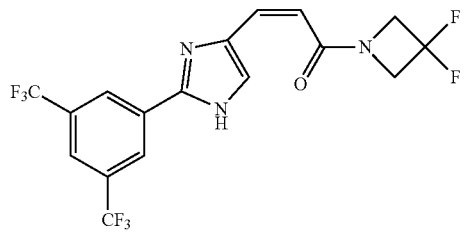 [SMILES: O=C(/C=C\c1c[nH]c(-c2cc(C(F)(F)F)cc(C(F)(F)F)c2)n1)N1CC(F)(F)C1]
B-38 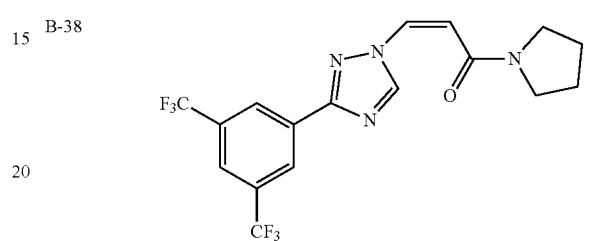
B-39 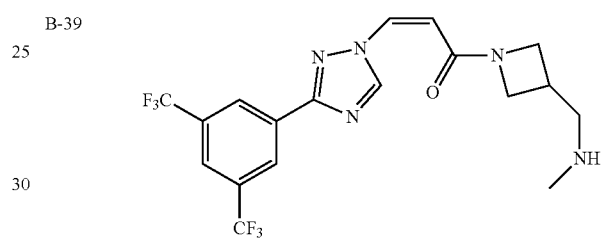
B-40 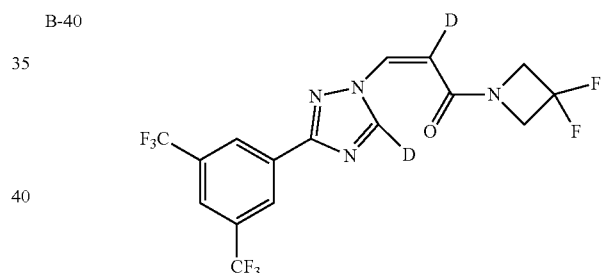
B-41 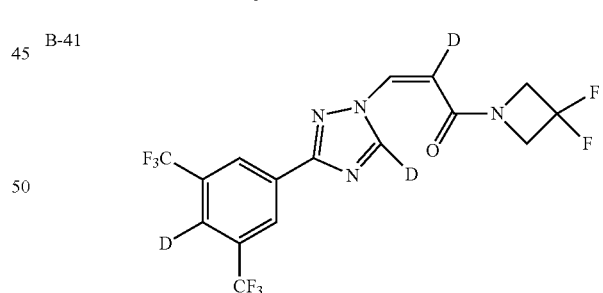
B-42 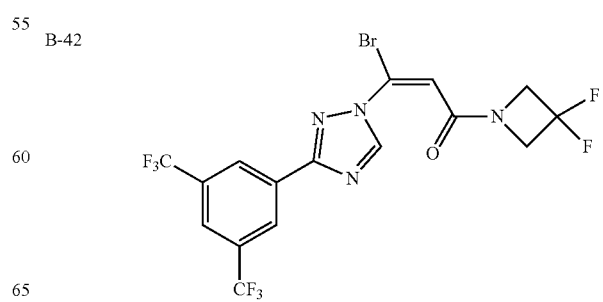

B-43 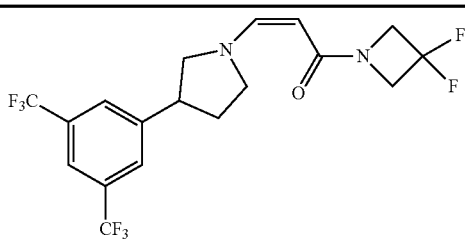
B-44 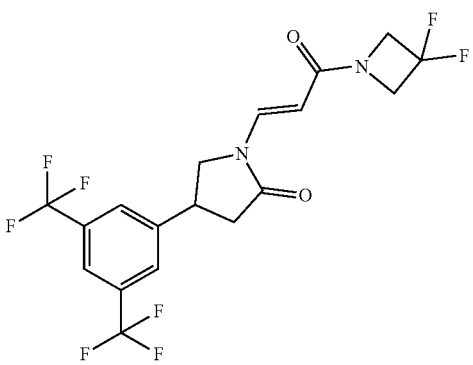 [SMILES: O=C1CC(c2cc(C(F)(F)F)cc(C(F)(F)F)c2)CN1/C=C/C(=O)N1CC(F)(F)C1]
B-45 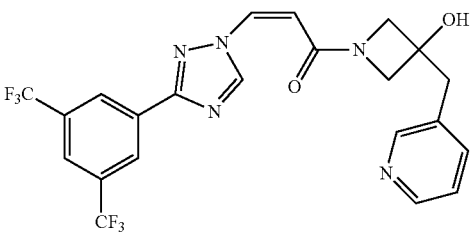 [SMILES: O=C(/C=C\n1cnc(-c2cc(C(F)(F)F)cc(C(F)(F)F)c2)n1)N1CC(O)(Cc2cccnc2)C1]
B-46 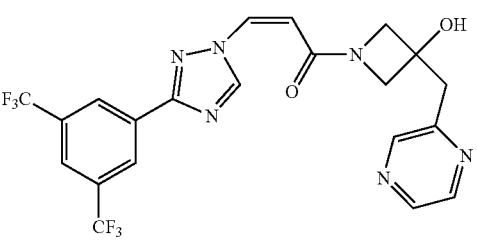 [SMILES: O=C(/C=C\n1cnc(-c2cc(C(F)(F)F)cc(C(F)(F)F)c2)n1)N1CC(O)(Cc2cnccn2)C1]
B-47 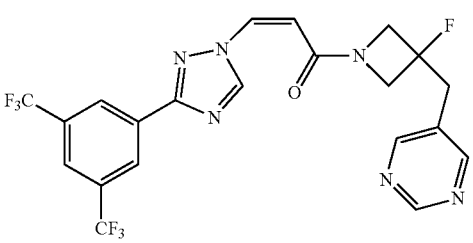
B-48 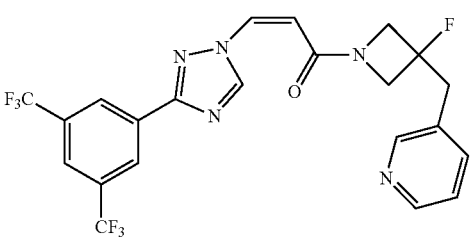 [SMILES: O=C(/C=C\n1cnc(-c2cc(C(F)(F)F)cc(C(F)(F)F)c2)n1)N1CC(F)(Cc2cccnc2)C1]
B-49 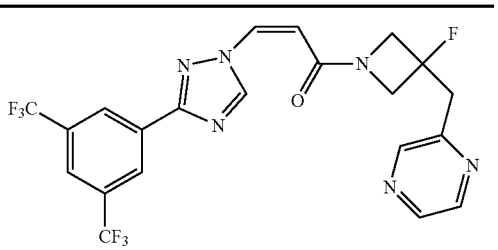
B-50 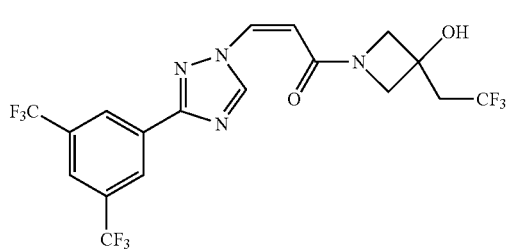 [SMILES: O=C(/C=C\n1cnc(-c2cc(C(F)(F)F)cc(C(F)(F)F)c2)n1)N1CC(O)(CC(F)(F)F)C1]
B-51 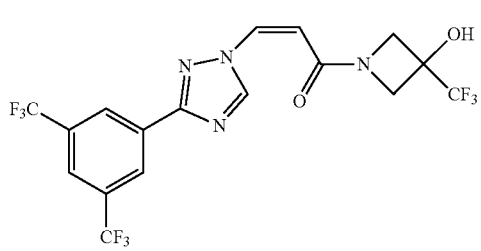 [SMILES: O=C(/C=C\n1cnc(-c2cc(C(F)(F)F)cc(C(F)(F)F)c2)n1)N1CC(O)(C(F)(F)F)C1]
B-52 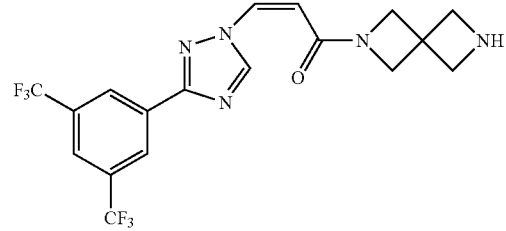 [SMILES: O=C(/C=C\n1cnc(-c2cc(C(F)(F)F)cc(C(F)(F)F)c2)n1)N1CC2(CNC2)C1]
B-53 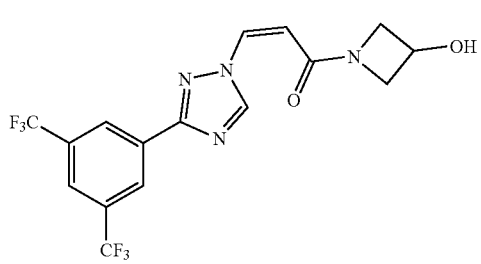
B-54 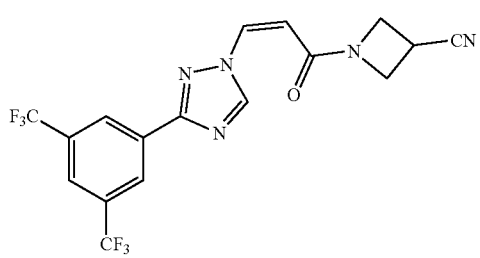 [SMILES: O=C(/C=C\n1cnc(-c2cc(C(F)(F)F)cc(C(F)(F)F)c2)n1)N1CC(O)C1]

-continued
B-55
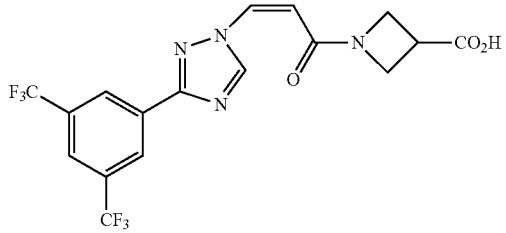 [SMILES: O=C(O)C1CN(C(=O)/C=C\n2cnc(-c3cc(C(F)(F)F)cc(C(F)(F)F)c3)n2)C1]
B-56
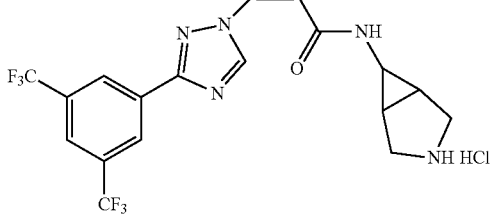
B-57
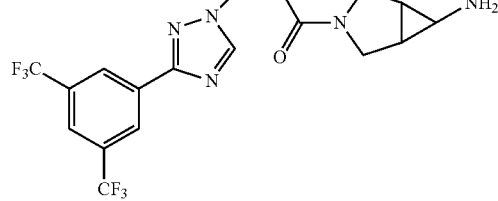
B-58
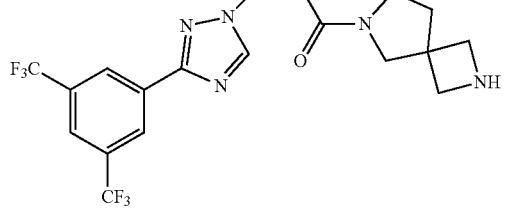
B-59
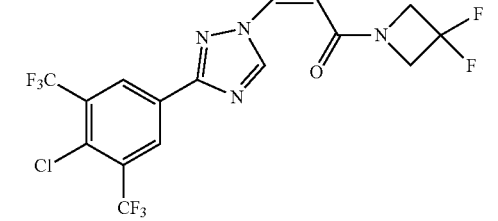
B-60
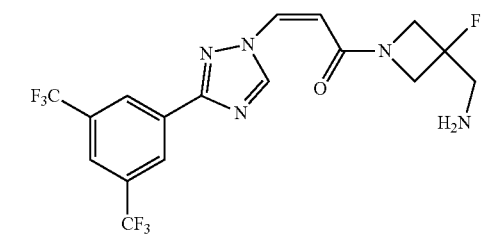 [SMILES: NCC1(F)CN(C(=O)/C=C\n2cnc(-c3cc(C(F)(F)F)cc(C(F)(F)F)c3)n2)C1]
-continued
B-61
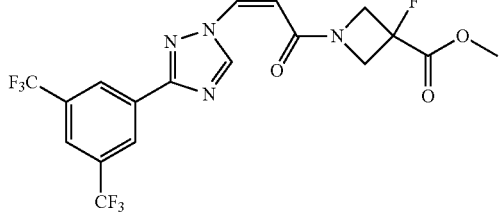
B-62
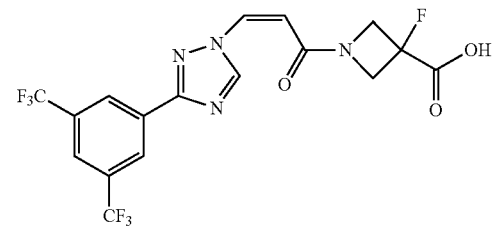 [SMILES: O=C(/C=C\n1cnc(-c2cc(C(F)(F)F)cc(C(F)(F)F)c2)n1)N1CC(F)(C(=O)O)C1]
B-63
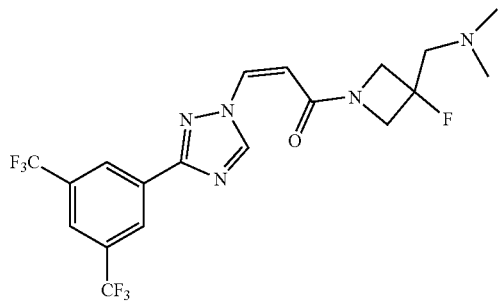 [SMILES: CN(C)CC1(F)CN(C(=O)/C=C\n2cnc(-c3cc(C(F)(F)F)cc(C(F)(F)F)c3)n2)C1]
B-64
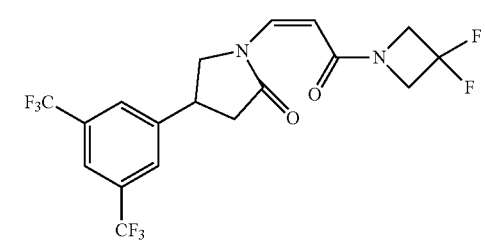 [SMILES: O=C1CC(c2cc(C(F)(F)F)cc(C(F)(F)F)c2)CN1/C=C\C(=O)N1CC(F)(F)C1]
B-65
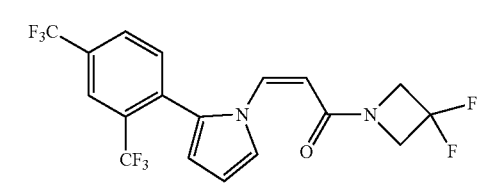 [SMILES: O=C(/C=C\n1cccc1-c1ccc(C(F)(F)F)cc1C(F)(F)F)N1CC(F)(F)C1]
B-66
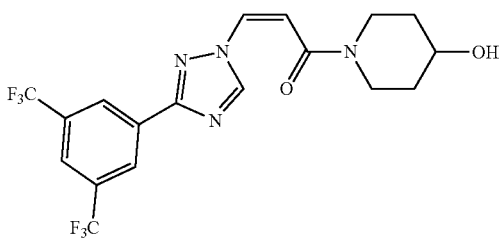 [SMILES: O=C(/C=C\n1cnc(-c2cc(C(F)(F)F)cc(C(F)(F)F)c2)n1)N1CCC(O)CC1]

B-67

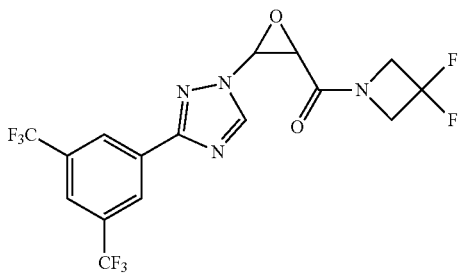 [SMILES: O=C(C1OC1n1cnc(-c2cc(C(F)(F)F)cc(C(F)(F)F)c2)n1)N1CC(F)(F)C1]

B-68

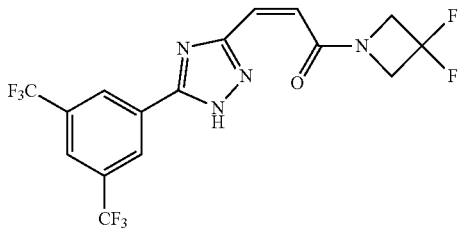 [SMILES: O=C(/C=C\c1n[nH]c(-c2cc(C(F)(F)F)cc(C(F)(F)F)c2)n1)N1CC(F)(F)C1]

B-69

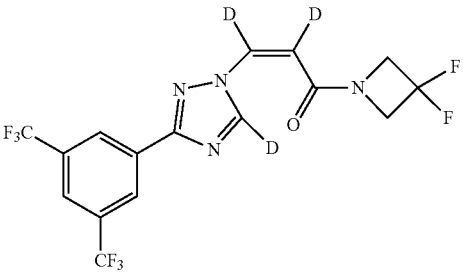 [SMILES: [2H]/C(C(=O)N1CC(F)(F)C1)=C(\[2H])n1nc(-c2cc(C(F)(F)F)cc(C(F)(F)F)c2)nc1[2H]]

| Compound | Name |
|---|---|
| B-1 | (Z)-3-(3-(3,5-bis(trifluoromethyl)phenyl)-1H-1,2,4-triazol-1-yl)-1-(3,3-difluoroazetidin-1-yl)prop-2-en-1-one |
| B-2 | (Z)-1-(3,3-difluoroazetidin-1-yl)-3-(3-(3-fluoro-5-(trifluoromethyl)phenyl)-1H-1,2,4-triazol-1-yl)prop-2-en-1-one |
| B-3 | (Z)-1-(3,3-difluoroazetidin-1-yl)-3-(3-(3-hydroxy-5-(trifluoromethyl)phenyl)-1H-1,2,4-triazol-1-yl)prop-2-en-1-one |
| B-4 | (E)-3-(3-(3,5-bis(trifluoromethyl)phenyl)-1H-1,2,4-triazol-1-yl)-1-(3,3-difluoroazetidin-1-yl)prop-2-en-1-one |
| B-5 | (Z)-3-(3-(3,5-bis(trifluoromethyl)phenyl)-1H-1,2,4-triazol-1-yl)-1-(3,3-difluoropiperidin-1-yl)prop-2-en-1-one |
| B-6 | (Z)-3-(3-(3,5-bis(trifluoromethyl)phenyl)-1H-1,2,4-triazol-1-yl)-1-(4,4-difluoropiperidin-1-yl)prop-2-en-1-one |
| B-7 | (Z)-3-(3-(3,5-bis(trifluoromethyl)phenyl)-1H-1,2,4-triazol-1-yl)-1-(3-fluoroazetidin-1-yl)prop-2-en-1-one |
| B-8 | (Z)-3-(3-(3,5-bis(trifluoromethyl)phenyl)-1H-1,2,4-triazol-1-yl)-1-(3-hydroxy-3-methylazetidin-1-yl)prop-2-en-1-one |
| B-9 | (Z)-3-(3-(2,6-bis(trifluoromethyl)pyridin-4-yl)-1H-1,2,4-triazol-1-yl)-1-(3,3-difluoroazetidin-1-yl)prop-2-en-1-one |
| B-10 | (Z)-3-(3-(3,5-bis(trifluoromethyl)phenyl)-1H-1,2,4-triazol-1-yl)-N-ethyl-N-(1-(pyridin-3-yl)ethyl)acrylamide |
| B-11 | (Z)-3-(3-(3,5-bis(trifluoromethyl)phenyl)-1H-1,2,4-triazol-1-yl)-N-(oxazol-5-ylmethyl)acrylamide |
| B-12 | (Z)-3-(5-(3,5-bis(trifluoromethyl)phenyl)-4H-1,2,4-triazol-3-yl)-1-(3,3-difluoroazetidin-1-yl)prop-2-en-1-one |
| B-13 | (Z)-3-(3-(3,5-bis(trifluoromethyl)phenyl)-1H-1,2,4-triazol-1-yl)-N-((2-methylpyrimidin-5-yl)methyl)acrylamide |
| B-14 | (Z)-3-(3-(3,5-bis(trifluoromethyl)phenyl)-1H-1,2,4-triazol-1-yl)-N-(pyrimidin-5-ylmethyl)acrylamide |
| B-15 | (E)-3-(6-(3,5-bis(trifluoromethyl)phenyl)pyridin-2-yl)-1-(3,3-difluorocyclobutyl)prop-2-en-1-one |
| B-16 | (Z)-3-(4-(3,5-bis(trifluoromethyl)phenyl)-1H-imidazol-1-yl)-1-(3,3-difluoroazetidin-1-yl)prop-2-en-1-one |
| B-17 | (Z)-3-(3-(3,5-bis(trifluoromethyl)phenyl)-1H-1,2,4-triazol-1-yl)-N-methyl-N-(pyrimidin-5-ylmethyl)acrylamide |
| B-18 | (Z)-3-(3-(3,5-bis(trifluoromethyl)phenyl)-1H-1,2,4-triazol-1-yl)-N-methyl-N-((2-methylpyrimidin-5-yl)methyl)acrylamide |
| B-19 | (Z)-3-(3-(3,5-bis(trifluoromethyl)phenyl)-1H-1,2,4-triazol-1-yl)-N-(piperidin-3-ylmethyl)acrylamide |
| B-20 | (Z)-3-(3-(3,5-bis(trifluoromethyl)phenyl)-1H-1,2,4-triazol-1-yl)-1-(3,3-difluoropyrrolidin-1-yl)prop-2-en-1-one |
| B-21 | (Z)-3-(3-(3,5-bis(trifluoromethyl)phenyl)-1H-1,2,4-triazol-1-yl)-N-(1-(2-methylpyrimidin-5-yl)ethyl)acrylamide |
| B-22 | (Z)-3-(3-(3,5-bis(trifluoromethyl)phenyl)-1H-1,2,4-triazol-1-yl)-N-methyl-N-(oxazol-5-ylmethyl)acrylamide |
| B-23 | (Z)-1-(azetidin-1-yl)-3-(3-(3,5-bis(trifluoromethyl)phenyl)-1H-1,2,4-triazol-1-yl)prop-2-en-1-one |
| B-24 | (Z)-3-(3-(3,5-bis(trifluoromethyl)phenyl)-1H-1,2,4-triazol-1-yl)-1-(3-(pyridin-2-yl)azetidin-1-yl)prop-2-en-1-one |
| B-25 | (Z)-3-(3-(3,5-bis(trifluoromethyl)phenyl)-1H-1,2,4-triazol-1-yl)-1-(3-((dimethylamino)methyl)azetidin-1-yl)prop-2-en-1-one |
| B-26 | (Z)-3-(3-(3,5-bis(trifluoromethyl)phenyl)-1H-1,2,4-triazol-1-yl)-N-((1-methylpiperidin-4-yl)methyl)acrylamide |
| B-27 | (Z)-3-(3-(3,5-bis(trifluoromethyl)phenyl)-1H-1,2,4-triazol-1-yl)-N-((1-methylpiperidin-3-yl)methyl)acrylamide |
| B-28 | (Z)-3-(3-(3,5-bis(trifluoromethyl)phenyl)-1H-1,2,4-triazol-1-yl)-N-(6,7-dihydro-5H-cyclopenta[b]pyridin-5-yl)acrylamide |
| B-29 | (Z)-3-(3-(3,5-bis(trifluoromethyl)phenyl)-1H-1,2,4-triazol-1-yl)-N-(1-(pyrazin-2-yl)ethyl)acrylamide |
| B-30 | (Z)-3-(3-(3,5-bis(trifluoromethyl)phenyl)-1H-1,2,4-triazol-1-yl)-N-((1-methylpyrrolidin-3-yl)methyl)acrylamide |
| B-31 | (Z)-3-(3-(3,5-bis(trifluoromethyl)phenyl)-1H-1,2,4-triazol-1-yl)-N-((2,4-dimethylpyrimidin-5-yl)methyl)acrylamide |
| B-32 | (Z)-3-(3-(4-chloro-3,5-bis(trifluoromethyl)phenyl)-1H-1,2,4-triazol-1-yl)-1-(3,3-difluoroazetidin-1-yl)prop-2-en-1-one |
| B-33 | (Z)-1-(3,3-difluoroazetidin-1-yl)-3-(3-(4-hydroxy-3,5-bis(trifluoromethyl)phenyl)-1H-1,2,4-triazol-1-yl)prop-2-en-1-one |
| B-34 | (Z)-3-(3-(3,5-bis(trifluoromethyl)phenyl)-1H-pyrrol-1-yl)-1-(3,3-difluoroazetidin-1-yl)prop-2-en-1-one |
| B-35 | (Z)-3-(3-(3,5-bis(trifluoromethyl)phenyl)-1H-pyrazol-1-yl)-1-(3,3-difluoroazetidin-1-yl)prop-2-en-1-one |
| B-36 | (Z)-3-(5-(3,5-bis(trifluoromethyl)phenyl)-1H-pyrrol-3-yl)-1-(3,3-difluoroazetidin-1-yl)prop-2-en-1-one |
| B-37 | (Z)-3-(2-(3,5-bis(trifluoromethyl)phenyl)-1H-imidazol-4-yl)-1-(3,3-difluoroazetidin-1-yl)prop-2-en-1-one |
| B-38 | (Z)-3-(3-(3,5-bis(trifluoromethyl)phenyl)-1H-1,2,4-triazol-1-yl)-1-(pyrrolidin-1-yl)prop-2-en-1-one |
| B-39 | (Z)-3-(3-(3,5-bis(trifluoromethyl)phenyl)-1H-1,2,4-triazol-1-yl)-1-(3-((methylamino)methyl)azetidin-1-yl)prop-2-en-1-one |
| B-40 | D2-(Z)-3-(3-(3,5-bis(trifluoromethyl)phenyl)-1H-1,2,4-triazol-1-yl)-1-(3,3-difluoroazetidin-1-yl)prop-2-en-1-one |
| B-41 | D3-(Z)-3-(3-(3,5-bis(trifluoromethyl)phenyl)-1H-1,2,4-triazol-1-yl)-1-(3,3-difluoroazetidin-1-yl)prop-2-en-1-one |
| B-42 | (E)-3-(3-(3,5-bis(trifluoromethyl)phenyl)-1H-1,2,4-triazol-1-yl)-3-bromo-1-(3,3-difluoroazetidin-1-yl)prop-2-en-1-one |
| B-43 | 3-(3-(3,5-bis(trifluoromethyl)phenyl)pyrrolidin-1-yl)-1-(3,3-difluoroazetidin-1-yl)propan-1-one |
| B-44 | (E)-4-(3,5-bis(trifluoromethyl)phenyl)-1-(3-(3,3-difluoroazetidin-1-yl)-3-oxoprop-1-en-1-yl)pyrrolidin-2-one |
| B-45 | (Z)-3-(3-(3,5-bis(trifluoromethyl)phenyl)-1H-1,2,4-triazol-1-yl)-1-(3-hydroxy-3-(pyridin-3-ylmethyl)azetidin-1-yl)prop-2-en-1-one |
| B-46 | (Z)-3-(3-(3,5-bis(trifluoromethyl)phenyl)-1H-1,2,4-triazol-1-yl)-1-(3-hydroxy-3-(pyrazin-2-ylmethyl)azetidin-1-yl)prop-2-en-1-one |
| B-47 | (Z)-3-(3-(3,5-bis(trifluoromethyl)phenyl)-1H-1,2,4-triazol-1-yl)-1-(3-fluoro-3-(pyrimidin-5-ylmethyl)azetidin-1-yl)prop-2-en-1-one |
| B-48 | (Z)-3-(3-(3,5-bis(trifluoromethyl)phenyl)-1H-1,2,4-triazol-1-yl)-1-(3-fluoro-3-(pyridin-3-ylmethyl)azetidin-1-yl)prop-2-en-1-one |
| B-49 | (Z)-3-(3-(3,5-bis(trifluoromethyl)phenyl)-1H-1,2,4-triazol-1-yl)-1-(3-fluoro-3-(pyrazin-2-ylmethyl)azetidin-1-yl)prop-2-en-1-one |
| B-50 | (Z)-3-(3-(3,5-bis(trifluoromethyl)phenyl)-1H-1,2,4-triazol-1-yl)-1-(3-hydroxy-3-(2,2,2-trifluoroethyl)azetidin-1-yl)prop-2-en-1-one |
| B-51 | (Z)-3-(3-(3,5-bis(trifluoromethyl)phenyl)-1H-1,2,4-triazol-1-yl)-1-(3-hydroxy-3-(trifluoromethyl)azetidin-1-yl)prop-2-en-1-one |
| B-52 | (Z)-3-(3-(3,5-bis(trifluoromethyl)phenyl)-1H-1,2,4-triazol-1-yl)-1-(2,6-diazaspiro[3.3]heptan-2-yl)prop-2-en-1-one |
| B-53 | (Z)-1-(3-(3-(3,5-bis(trifluoromethyl)phenyl)-1H-1,2,4-triazol-1-yl)acryloyl)azetidine-3-carbonitrile |
| B-54 | (Z)-1-(3-(3-(3,5-bis(trifluoromethyl)phenyl)-1H-1,2,4-triazol-1-yl)acryloyl)azetidine-3-carbonitrile |
| B-55 | (Z)-1-(3-(3-(3,5-bis(trifluoromethyl)phenyl)-1H-1,2,4-triazol-1-yl)acryloyl)azetidine-3-carboxylic acid |
| B-56 | (Z)-N-(3-azabicyclo[3.1.0]hexan-6-yl)-3-(3-(3,5-bis(trifluoromethyl)phenyl)-1H-1,2,4-triazol-1-yl)acrylamide |
| B-57 | (Z)-N-(3-aminobicyclo[3.1.0]hexan-6-yl)-3-(3-(3,5-bis(trifluoromethyl)phenyl)-1H-1,2,4-triazol-1-yl)acrylamide |
| B-58 | (Z)-N-(2,6-diazaspiro[3.4]octan-6-ylmethyl)-3-(3-(3,5-bis(trifluoromethyl)phenyl)-1H-1,2,4-triazol-1-yl)acrylamide |

-continued

| Cmpd. No. | Name |
|---|---|
| B-59 | (Z)-3-(3-(4-chloro-3,5-bis(trifluoromethyl)phenyl)-1H-1,2,4-triazol-1-yl)-1-(3,3-difluoroazetidin-1-yl)prop-2-en-1-one |
| B-60 | (Z)-1-(3-(aminomethyl)-3-fluoroazetidin-1-yl)-3-(3-(3,5-bis(trifluoromethyl)phenyl)-1H-1,2,4-triazol-1-yl)prop-2-en-1-one |
| B-61 | (Z)-3-(3-(3,5-bis(trifluoromethyl)phenyl)-1H-1,2,4-triazol-1-yl)-1-(3-fluoro-3-(2-methoxyacetyl)azetidin-1-yl)prop-2-en-1-one |
| B-62 | (Z)-3-(3-(3,5-bis(trifluoromethyl)phenyl)-1H-1,2,4-triazol-1-yl)-1-(3-fluoro-3-(2-hydroxyacetyl)azetidin-1-yl)prop-2-en-1-one |
| B-63 | (Z)-3-(3-(3,5-bis(trifluoromethyl)phenyl)-1H-1,2,4-triazol-1-yl)-1-(3-((dimethylamino)methyl)-3-fluoroazetidin-1-yl)prop-2-en-1-one |
| B-64 | (Z)-4-(3,5-bis(trifluoromethyl)phenyl)-1-(3-(3,3-difluoroazetidin-1-yl)-3-oxoprop-1-en-1-yl)pyrrolidin-2-one |
| B-65 | (Z)-3-(2-(2,4-bis(trifluoromethyl)phenyl)-1H-pyrrol-1-yl)-1-(3,3-difluoroazetidin-1-yl)prop-2-en-1-one |
| B-66 | (Z)-3-(3-(3,5-bis(trifluoromethyl)phenyl)-1H-1,2,4-triazol-1-yl)-1-(4-hydroxypiperidin-1-yl)prop-2-en-1-one |
| B-67 | (3-(3,5-bis(trifluoromethyl)phenyl)-1H-1,2,4-triazol-1-yl)oxiran-2-yl)(3,3-difluoroazetidin-1-yl)methanone |
| B-68 | (Z)-3-(5-(3,5-bis(trifluoromethyl)phenyl)-1H-1,2,4-triazol-3-yl)-1-(3,3-difluoroazetidin-1-yl)prop-2-en-1-one |
| B-69 | D3-(Z)-3-(3-(3,5-bis(trifluoromethyl)phenyl)-1H-1,2,4-triazol-1-yl)-1-(3,3-difluoroazetidin-1-yl)prop-2-en-1-one |

| Cmpd. No. | Structure |
|---|---|
| C-3 | |
| C-4 | |
| C-5 | |
| C-6 | |
| C-7 | 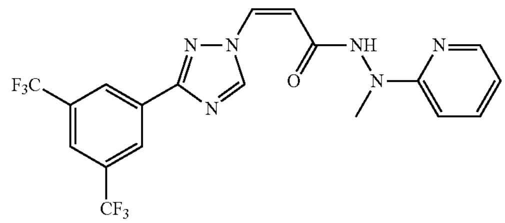 [SMILES: CN(NC(=O)/C=C\n1cnc(-c2cc(C(F)(F)F)cc(C(F)(F)F)c2)n1)c1ccccn1] |
| C-8 | 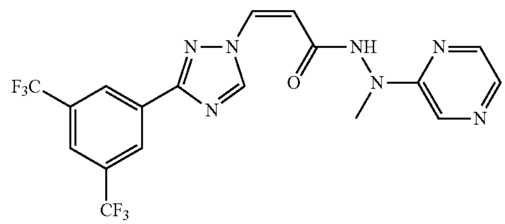 [SMILES: CN(NC(=O)/C=C\n1cnc(-c2cc(C(F)(F)F)cc(C(F)(F)F)c2)n1)c1cnccn1] |
| C-9 | 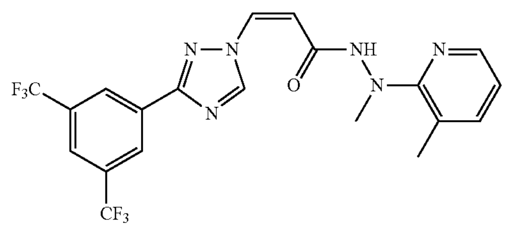 [SMILES: Cc1cccnc1N(C)NC(=O)/C=C\n1cnc(-c2cc(C(F)(F)F)cc(C(F)(F)F)c2)n1] |
| C-10 | 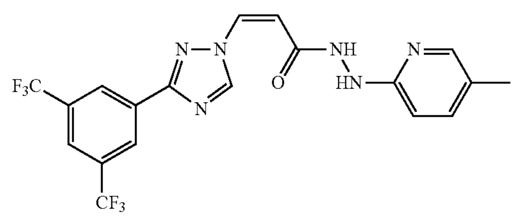 [SMILES: Cc1ccc(NNC(=O)/C=C\n2cnc(-c3cc(C(F)(F)F)cc(C(F)(F)F)c3)n2)nc1] |
| C-11 | 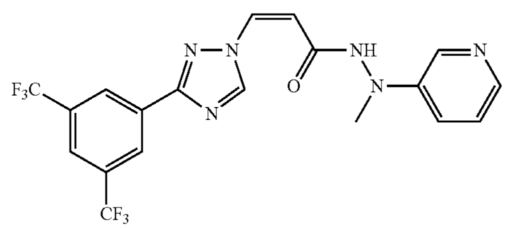 [SMILES: CN(NC(=O)/C=C\n1cnc(-c2cc(C(F)(F)F)cc(C(F)(F)F)c2)n1)c1cccnc1] |
| C-12 | 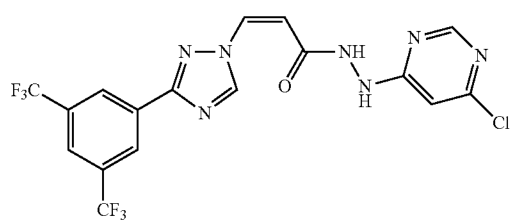 [SMILES: O=C(/C=C\n1cnc(-c2cc(C(F)(F)F)cc(C(F)(F)F)c2)n1)NNc1cc(Cl)ncn1] |
| C-13 | 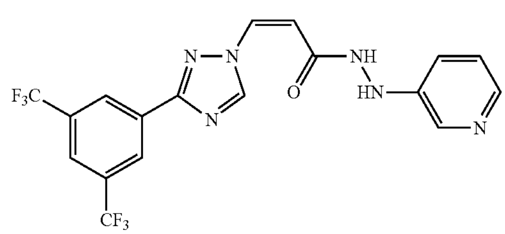 [SMILES: O=C(/C=C\n1cnc(-c2cc(C(F)(F)F)cc(C(F)(F)F)c2)n1)NNc1cccnc1] |

-continued

| Cmpd. No. | Structure |
|---|---|
| C-14 | 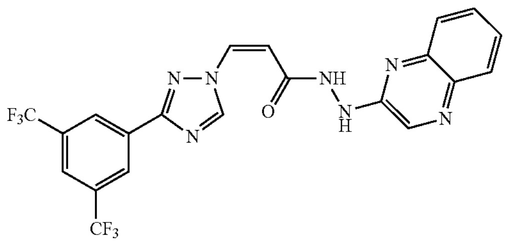 [SMILES: O=C(/C=C\n1cnc(-c2cc(C(F)(F)F)cc(C(F)(F)F)c2)n1)NNc1cnc2ccccc2n1] |
| C-15 | 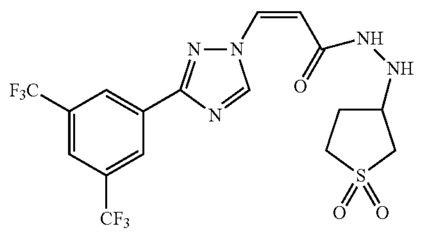 [SMILES: O=C(/C=C\n1cnc(-c2cc(C(F)(F)F)cc(C(F)(F)F)c2)n1)NNC1CCS(=O)(=O)C1] |
| C-16 | 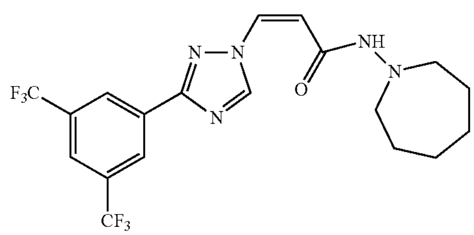 [SMILES: O=C(/C=C\n1cnc(-c2cc(C(F)(F)F)cc(C(F)(F)F)c2)n1)NN1CCCCCC1] |
| C-17 | 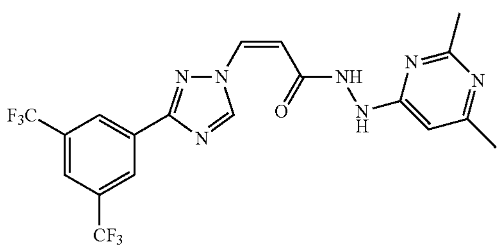 [SMILES: Cc1cc(NNC(=O)/C=C\n2cnc(-c3cc(C(F)(F)F)cc(C(F)(F)F)c3)n2)nc(C)n1] |
| C-18 | 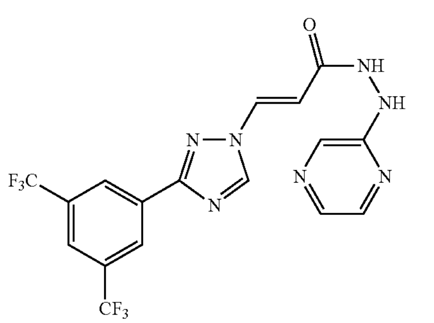 [SMILES: O=C(/C=C/n1cnc(-c2cc(C(F)(F)F)cc(C(F)(F)F)c2)n1)NNc1cnccn1] |
| C-19 | 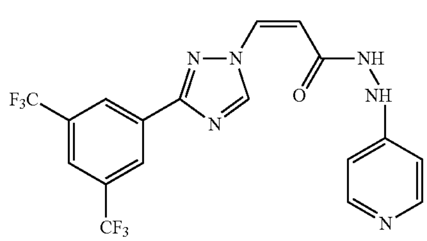 [SMILES: O=C(/C=C\n1cnc(-c2cc(C(F)(F)F)cc(C(F)(F)F)c2)n1)NNc1ccncc1] |

-continued

| Cmpd. No. | Structure |
|---|---|
| C-20 | |
| C-21 | |
| C-22 | |
| C-23 | |
| C-24 | |
| C-25 | |

| Cmpd. No. | Structure |
|---|---|
| C-26 | 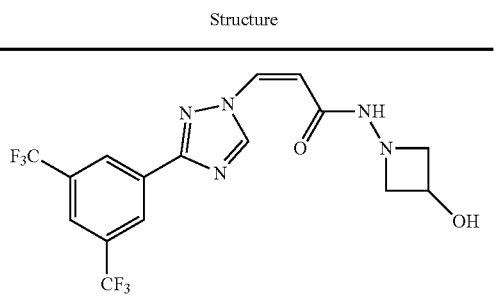 |
| Compound | Structure |
|---|---|
| D-1 | 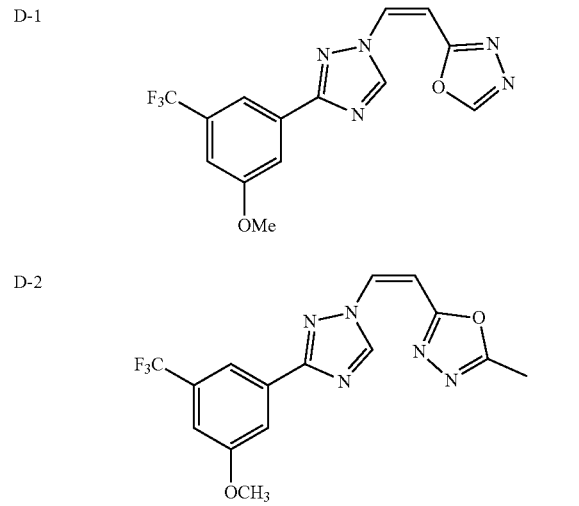 |
| D-2 | |
| D-3 | |
| D-4 | 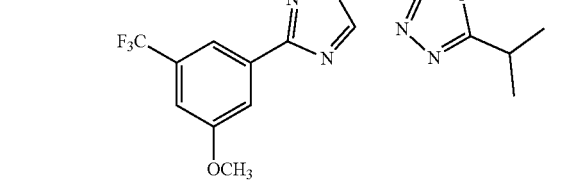 |
| Compound | Structure |
|---|---|
| D-5 | 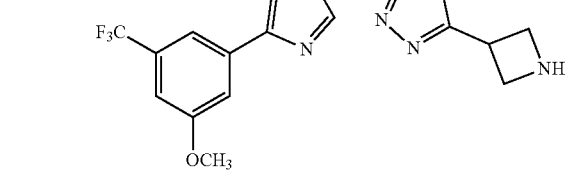 |
| D-6 | 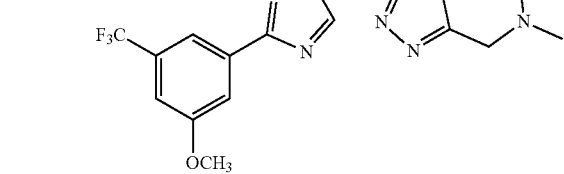 |
| D-7 | 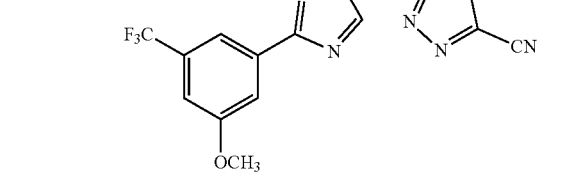 |
| D-8 | 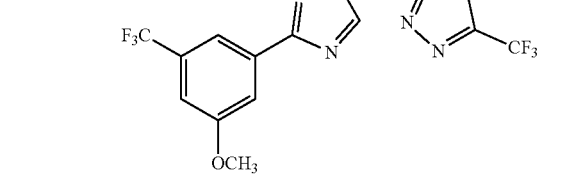 |
| D-9 | 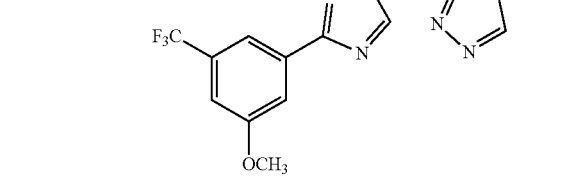 |
| D-10 | 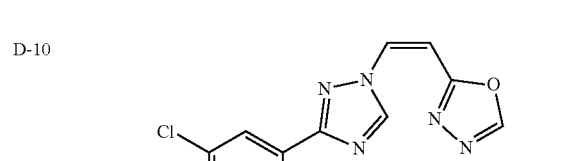 |

| | |
|---|---|
| D-11 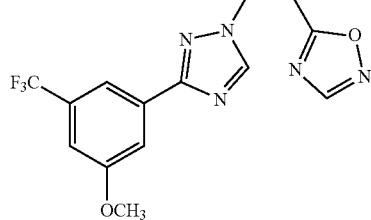 | D-17 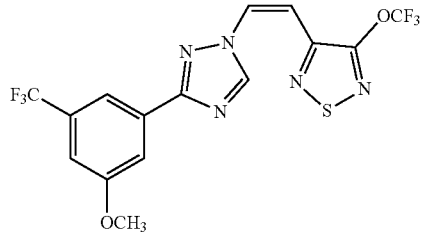 |
| D-12 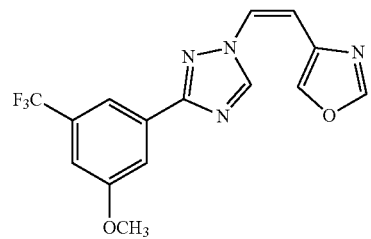 [SMILES: COc1cc(-c2ncn(/C=C\c3cocn3)n2)cc(C(F)(F)F)c1] | D-18 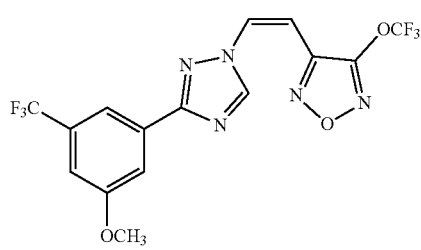 |
| D-13 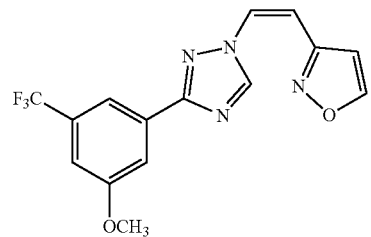 [SMILES: COc1cc(-c2ncn(/C=C\c3ccon3)n2)cc(C(F)(F)F)c1] | D-19 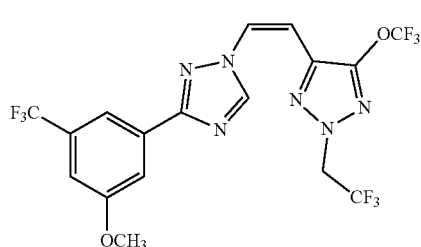 |
| D-14 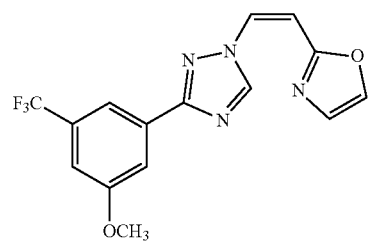 [SMILES: COc1cc(-c2ncn(/C=C\c3ncco3)n2)cc(C(F)(F)F)c1] | D-20 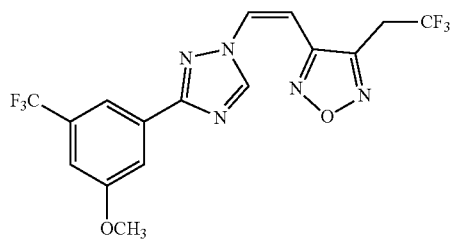 |
| D-15 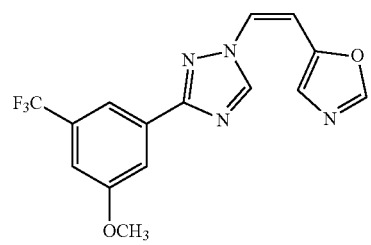 [SMILES: COc1cc(-c2ncn(/C=C\c3cnco3)n2)cc(C(F)(F)F)c1] | D-21 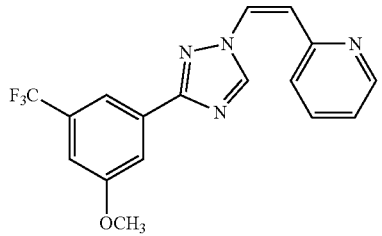 |
| D-16 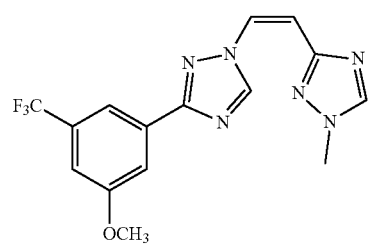 [SMILES: COc1cc(-c2ncn(/C=C\c3ncn(C)n3)n2)cc(C(F)(F)F)c1] | D-22 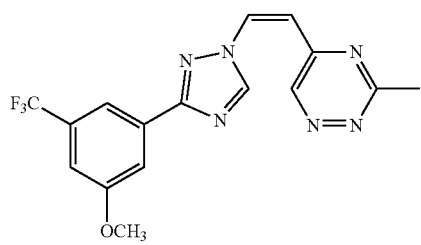 [SMILES: COc1cc(-c2ncn(/C=C\c3cnnc(C)n3)n2)cc(C(F)(F)F)c1] |

D-23 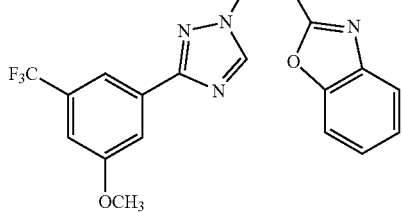
D-24 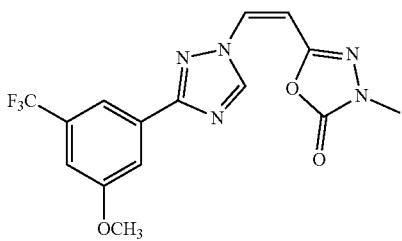 [SMILES: COc1cc(-c2ncn(/C=C\c3nn(C)c(=O)o3)n2)cc(C(F)(F)F)c1]
D-25 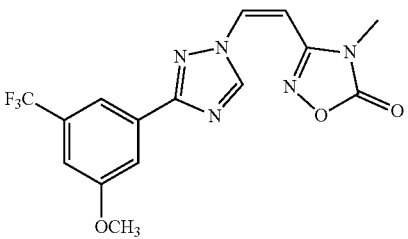 [SMILES: COc1cc(-c2ncn(/C=C\c3noc(=O)n3C)n2)cc(C(F)(F)F)c1]
D-26 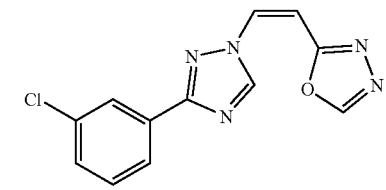 [SMILES: Clc1cccc(-c2ncn(/C=C\c3nnco3)n2)c1]
D-27 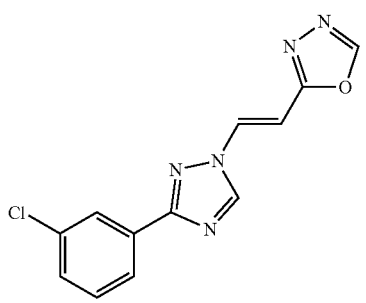 [SMILES: Clc1cccc(-c2ncn(/C=C/c3nnco3)n2)c1]
D-28 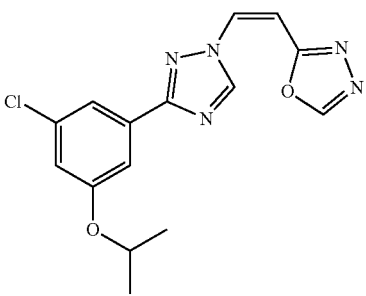 [SMILES: CC(C)Oc1cc(Cl)cc(-c2ncn(/C=C\c3nnco3)n2)c1]
D-29 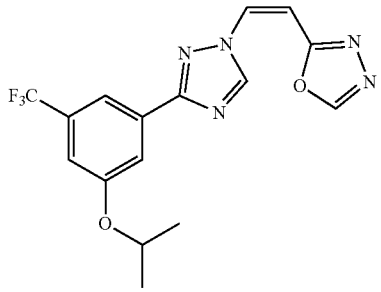 [SMILES: CC(C)Oc1cc(-c2ncn(/C=C\c3nnco3)n2)cc(C(F)(F)F)c1]
D-30 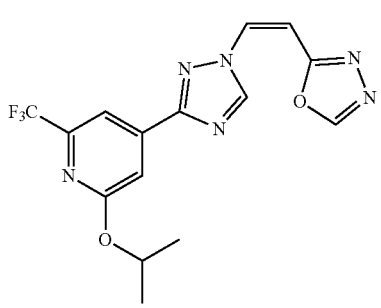 [SMILES: CC(C)Oc1cc(-c2ncn(/C=C\c3nnco3)n2)cc(C(F)(F)F)n1]
D-31 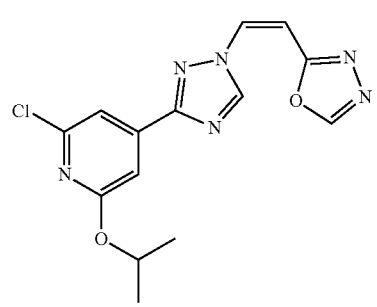 [SMILES: CC(C)Oc1cc(-c2ncn(/C=C\c3nnco3)n2)cc(Cl)n1]
D-32 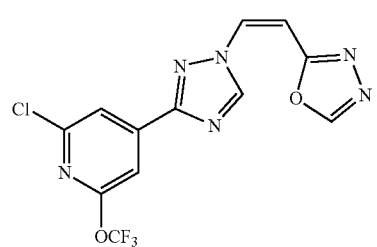 [SMILES: FC(F)(F)Oc1cc(-c2ncn(/C=C\c3nnco3)n2)cc(Cl)n1]
D-33 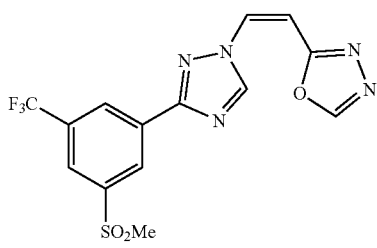 [SMILES: CS(=O)(=O)c1cc(-c2ncn(/C=C\c3nnco3)n2)cc(C(F)(F)F)c1]
D-34 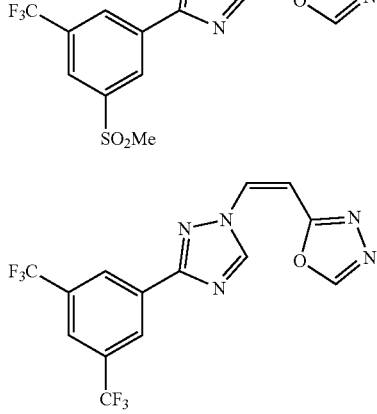

-continued

| Compound | | |
|---|---|---|
| D-35 | 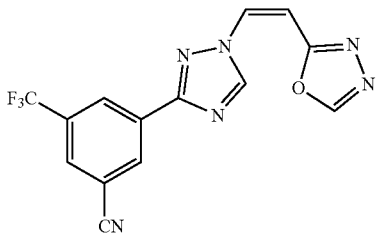 [SMILES: N#Cc1cc(-c2ncn(/C=C\c3nnco3)n2)cc(C(F)(F)F)c1] | |
| D-36 | 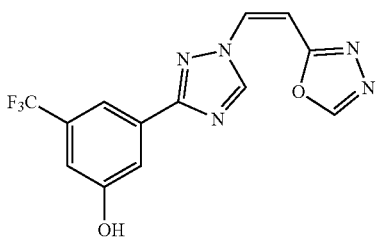 [SMILES: Oc1cc(-c2ncn(/C=C\c3nnco3)n2)cc(C(F)(F)F)c1] | |
| D-37 | 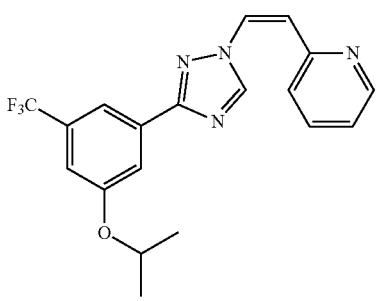 [SMILES: CC(C)Oc1cc(-c2ncn(/C=C\c3ccccn3)n2)cc(C(F)(F)F)c1] | |
| D-38 | 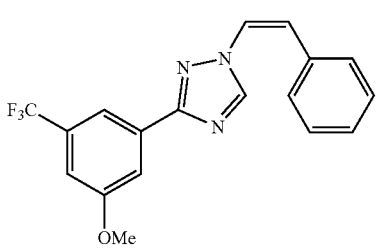 [SMILES: COc1cc(-c2ncn(/C=C\c3ccccc3)n2)cc(C(F)(F)F)c1] | |
| D-39 | 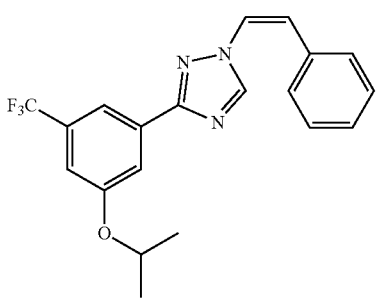 [SMILES: CC(C)Oc1cc(-c2ncn(/C=C\c3ccccc3)n2)cc(C(F)(F)F)c1] | |

| Compound | Name |
|---|---|
| D-1 | (Z)-2-(2-(3-(3-methoxy-5-(trifluoromethyl)phenyl)-1H-1,2,4-triazol-1-yl)vinyl)-1,3,4-oxadiazole |
| D-2 | (Z)-2-(2-(3-(3-methoxy-5-(trifluoromethyl)phenyl)-1H-1,2,4-triazol-1-yl)vinyl)-5-methyl-1,3,4-oxadiazole |
| D-3 | (Z)-2-isopropyl-5-(2-(3-(3-methoxy-5-(trifluoromethyl)phenyl)-1H-1,2,4-triazol-1-yl)vinyl)-1,3,4-oxadiazole |
| D-4 | (Z)-2-cyclopentyl-5-(2-(3-(3-methoxy-5-(trifluoromethyl)phenyl)-1H-1,2,4-triazol-1-yl)vinyl)-1,3,4-oxadiazole |
| D-5 | (Z)-2-(azetidin-3-yl)-5-(2-(3-(3-methoxy-5-(trifluoromethyl)phenyl)-1H-1,2,4-triazol-1-yl)vinyl)-1,3,4-oxadiazole |
| D-6 | (Z)-1-(5-(2-(3-(3-methoxy-5-(trifluoromethyl)phenyl)-1H-1,2,4-triazol-1-yl)vinyl)-1,3,4-oxadiazol-2-yl)-N,N-dimethylmethanamine |
| D-7 | (Z)-5-(2-(3-(3-methoxy-5-(trifluoromethyl)phenyl)-1H-1,2,4-triazol-1-yl)vinyl)-1,3,4-oxadiazole-2-carbonitrile |
| D-8 | (Z)-2-(2-(3-(3-methoxy-5-(trifluoromethyl)phenyl)-1H-1,2,4-triazol-1-yl)vinyl)-5-(trifluoromethyl)-1,3,4-oxadiazole |
| D-9 | (Z)-2-(2-(3-(2-methoxy-6-(trifluoromethyl)pyridin-4-yl)-1H-1,2,4-triazol-1-yl)vinyl)-1,3,4-oxadiazole |
| D-10 | (Z)-2-(2-(3-(2-chloro-6-methoxypyridin-4-yl)-1H-1,2,4-triazol-1-yl)vinyl)-1,3,4-oxadiazole |
| D-11 | (Z)-5-(2-(3-(3-methoxy-5-(trifluoromethyl)phenyl)-1H-1,2,4-triazol-1-yl)vinyl)-1,2,4-oxadiazole |
| D-12 | (Z)-4-(2-(3-(3-methoxy-5-(trifluoromethyl)phenyl)-1H-1,2,4-triazol-1-yl)vinyl)oxazole |
| D-13 | (Z)-3-(2-(3-(3-methoxy-5-(trifluoromethyl)phenyl)-1H-1,2,4-triazol-1-yl)vinyl)isoxazole |
| D-14 | (Z)-2-(2-(3-(3-methoxy-5-(trifluoromethyl)phenyl)-1H-1,2,4-triazol-1-yl)vinyl)oxazole |
| D-15 | (Z)-5-(2-(3-(3-methoxy-5-(trifluoromethyl)phenyl)-1H-1,2,4-triazol-1-yl)vinyl)oxazole |
| D-16 | (Z)-3-(3-methoxy-5-(trifluoromethyl)phenyl)-1-(2-(1-methyl-1H-1,2,4-triazol-3-yl)vinyl)-1H-1,2,4-triazole |
| D-17 | (Z)-3-(2-(3-(3-methoxy-5-(trifluoromethyl)phenyl)-1H-1,2,4-triazol-1-yl)vinyl)-4-(trifluoromethoxy)-1,2,5-thiadiazole |
| D-18 | (Z)-3-(2-(3-(3-methoxy-5-(trifluoromethyl)phenyl)-1H-1,2,4-triazol-1-yl)vinyl)-4-(trifluoromethoxy)-1,2,5-oxadiazole |
| D-19 | (Z)-4-(2-(3-(3-methoxy-5-(trifluoromethyl)phenyl)-1H-1,2,4-triazol-1-yl)vinyl)-2-(2,2,2-trifluoroethyl)-5-(trifluoromethoxy)-2H-1,2,3-triazole |
| D-20 | (Z)-3-(2-(3-(3-methoxy-5-(trifluoromethyl)phenyl)-1H-1,2,4-triazol-1-yl)vinyl)-4-(2,2,2-trifluoroethyl)-1,2,5-oxadiazole |
| D-21 | (Z)-2-(2-(3-(3-methoxy-5-(trifluoromethyl)phenyl)-1H-1,2,4-triazol-1-yl)vinyl)pyridine |
| D-22 | (Z)-5-(2-(3-(3-methoxy-5-(trifluoromethyl)phenyl)-1H-1,2,4-triazol-1-yl)vinyl)-3-methyl-1,2,4-triazine |
| D-23 | (Z)-2-(2-(3-(3-methoxy-5-(trifluoromethyl)phenyl)-1H-1,2,4-triazol-1-yl)vinyl)benzo[d]oxazole |
| D-24 | (Z)-5-(2-(3-(3-methoxy-5-(trifluoromethyl)phenyl)-1H-1,2,4-triazol-1-yl)vinyl)-3-methyl-1,3,4-oxadiazol-2(3H)-one |
| D-25 | (Z)-3-(2-(3-(3-methoxy-5-(trifluoromethyl)phenyl)-1H-1,2,4-triazol-1-yl)vinyl)-4-methyl-1,2,4-oxadiazol-5(4H)-one |
| D-26 | (Z)-2-(2-(3-(3-chlorophenyl)-1H-1,2,4-triazol-1-yl)vinyl)-1,3,4-oxadiazole |
| D-27 | (E)-2-(2-(3-(3-methoxy-5-(trifluoromethyl)phenyl)-1H-1,2,4-triazol-1-yl)vinyl)-1,3,4-oxadiazole |
| D-28 | (Z)-2-(2-(3-(3-chloro-5-isopropoxyphenyl)-1H-1,2,4-triazol-1-yl)vinyl)-1,3,4-oxadiazole |
| D-29 | (Z)-2-(2-(3-(3-isopropoxy-5-(trifluoromethyl)phenyl)-1H-1,2,4-triazol-1-yl)vinyl)-1,3,4-oxadiazole |
| D-30 | (Z)-2-(2-(3-(2-isopropoxy-6-(trifluoromethyl)pyridin-4-yl)-1H-1,2,4-triazol-1-yl)vinyl)-1,3,4-oxadiazole |
| D-31 | (Z)-2-(2-(3-(2-chloro-6-isopropoxypyridin-4-yl)-1H-1,2,4-triazol-1-yl)vinyl)-1,3,4-oxadiazole |
| D-32 | (Z)-2-(2-(3-(2-chloro-6-(trifluoromethoxy)pyridin-4-yl)-1H-1,2,4-triazol-1-yl)vinyl)-1,3,4-oxadiazole |
| D-33 | (Z)-2-(2-(3-(3-(methylsulfonyl)-5-(trifluoromethyl)phenyl)-1H-1,2,4-triazol-1-yl)vinyl)-1,3,4-oxadiazole |
| D-34 | (Z)-2-(2-(3-(3,5-bis(trifluoromethyl)phenyl)-1H-1,2,4-triazol-1-yl)vinyl)-1,3,4-oxadiazole |
| D-35 | (Z)-3-(1-(2-(1,3,4-oxadiazol-2-yl)vinyl)-1H-1,2,4-triazol-3-yl)-5-(trifluoromethyl)benzonitrile |
| D-36 | (Z)-3-(1-(2-(1,3,4-oxadiazol-2-yl)vinyl)-1H-1,2,4-triazol-3-yl)-5-(trifluoromethyl)phenol |
| D-37 | (Z)-2-(2-(3-(3-isopropoxy-5-(trifluoromethyl)phenyl)-1H-1,2,4-triazol-1-yl)vinyl)pyridine |
| D-38 | (Z)-3-(3-methoxy-5-(trifluoromethyl)phenyl)-1-styryl-1H-1,2,4-triazole |
| D-39 | (Z)-3-(3-isopropoxy-5-(trifluoromethyl)phenyl)-1-styryl-1H-1,2,4-triazole, | or a pharmaceutically acceptable salt thereof.

2. The method of claim 1, wherein the compound is represented by the following structural formula:

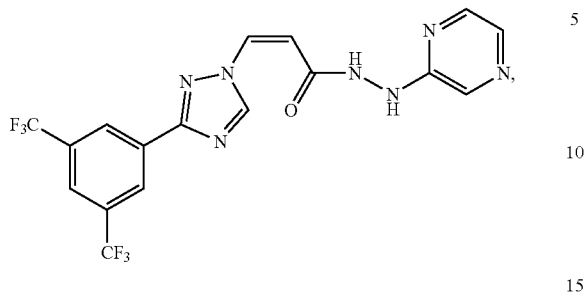

or a pharmaceutically acceptable salt thereof.

3. The method of claim 1, wherein the wound is a surface wound, a surgical wound, an internal wound, a chronic wound, or an ulcer.

4. The method of claim 1, wherein the wound is selected from the group consisting of an incised wound, an open wound, a surgical wound, a diabetic lesion, a pressure sore, a bedsore, and a condition related to diabetes or poor circulation.

5. The method of claim 1, wherein the wound is an acute wound.

6. A method of reducing scar formation during wound healing in a subject in need thereof, the method comprising administering to the subject a therapeutically effective amount of a compound of claim 1, or a pharmaceutically acceptable salt thereof.

* * * * *